US008372623B2

(12) United States Patent
Meyer

(10) Patent No.: US 8,372,623 B2
(45) Date of Patent: Feb. 12, 2013

(54) COMPOSITIONS AND METHODS FOR ALTERING ALPHA- AND BETA-TOCOTRIENOL CONTENT USING MULTIPLE TRANSGENES

(75) Inventor: Knut Meyer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/523,997

(22) Filed: Jun. 15, 2012

(65) Prior Publication Data

US 2012/0252124 A1 Oct. 4, 2012

Related U.S. Application Data

(60) Continuation of application No. 13/005,369, filed on Jan. 12, 2011, now Pat. No. 8,293,976, which is a division of application No. 12/240,434, filed on Sep. 29, 2008, now Pat. No. 7,893,324.

(60) Provisional application No. 60/977,495, filed on Oct. 4, 2007.

(51) Int. Cl.
*A01H 1/00* (2006.01)
*C07H 21/04* (2006.01)
*C07K 14/415* (2006.01)
*C12N 15/00* (2006.01)

(52) U.S. Cl. ...... 435/243; 435/6.1; 435/468; 435/252.3; 435/320.1; 435/183; 435/471; 536/23.1; 536/23.6; 800/278; 800/295; 530/370

(58) Field of Classification Search .................. 435/6.1, 435/69.1, 468, 183, 419, 320.1, 471, 243; 530/370; 536/23.2, 23.6, 24.1; 800/278, 800/295

See application file for complete search history.

(56) References Cited

U.S. PATENT DOCUMENTS

2003/0154513 A1 8/2003 Van Enennaam et al.
2004/0034886 A1 2/2004 Cahoon et al.
2004/0266862 A1 12/2004 Wolf et al.
2007/0199096 A1 8/2007 Meyer

FOREIGN PATENT DOCUMENTS

WO WO 99/04622 2/1999
WO WO 00/32757 6/2000
WO WO 00/72862 12/2000
WO WO 03/034812 5/2003
WO WO 03/082899 10/2003
WO WO 2005/002358 1/2005
WO WO 2007/059077 5/2007

OTHER PUBLICATIONS

Bertoli et al., Characterization of Chilean Hazelnut (*Gevuina avellana* Mol) Seed Oil, JAOCS, 1998, vol. 75:1037-1040.

J. S. Bonvehi et al., Liquid Chromatographic Determination of Tocopherols and Tocoppherols in Vegtable Oils, Formulated Preparations, and Biscuits, J. AOAC Intl., 2000, vol.83:627-634.

Cahoon et al., Metabolic Redesign of Vitamin E Biosynthesis in Plants for Tocotrienol Production and Increased Antioxidant Content, Nat. Biotechnol., 2003, vol. 21:1082-1087.

Cheng et al., Highly Divergent Methyltransferases Catalyze a Conserved Reaction in Tocopherol and Plastoquinone Synthesis in Cyanobacteria and Photosynthetic Eukaryotes, Plant Cell, 2003, vol. 15:2343-2356.

C. L. Emmons et al., Antioxidant Capacity of Oat (*Avena sativa* L.) Extracts. 2. In Vitro Antioxidant Activity and Contents of Phenolic and Tocol Antioxidants, J. Agric. Food Chem., 1999, vol. 47:4894-4898.

N. Frega et al., Identification and Estimation of Tocotrienols in the Annatto Lipid Fraction by Gas Chromatography-Mass Spectrometry, J. Amer. Oil. Chem. Soc., 1998, vol. 75:1723-1728.

F. D. Goffman et al., Relationship Between Fatty Acid Profile and Vitamin E Content in Maize Hybrids (*Zea mays* L.), J. Agric. Food Chem., 2001, vol. 49:4990-4994.

F. D. Gunstone et al., The Lipid Handbook, 2nd Edition, 1994, pp. 129-131.

A. Kamal-Eldi et al., Normal-Phase High-Performance Liquid Chromatography of Tocopherols and Tocotrienols, Comparison of Different Chromatographic Columns, J. Chromatogr., 2000, vol. 881:217-227.

Karunanandaa et al., Metabolically Engineered Oilseed Crops With Enhanced Seed Tocopherol, Metab. Eng., 2005, vol. 7:384-400.

A. J. Kinney, Development of Genetically Engineered Soybean Oils for Food Applications, J. Food Lipids, 1996, vol. 3:273-292.

Kiyose et al., Distribution and Metabolism of Tocopherols and Tocotrienols in Vivo, J. Clin. Biochem. Nutr. 2004, vol. 35:47-52.

Packer et al., Molecular Aspects of X-Tocotrienol Antioxidant Action and Cell Signalling, J. Nutr., 2001, vol. 131:369-373.

M. Podda et al., Simultaneous Determination of Tissue Tocopherols, Tocotrienols, Ubiquinols, and Ubiquinones, J. Lipid Res., 1996, vol. 37:893-901.

Sarmishtha, D.E., et al., Natural Dietary Agents Can Protect Against DMBA Genotoxicity in Lymphocytes as Revealed by Single Cell Gel Electrophoresis Assay, Teratogenesis Carcinogenesis and Mutagenesis, 2003, Supplement 1:71-78.

E. A. Serbinova et al. Antioxidant Properties of X-Tocopherol and X-Tocotrienol, Meth. Enzymol., 1994, vol. 234:354-366.

Soll et al., Tocopherol and Plastoquinone Synthesis in Spinach Chloroplasts Subfractions, Arch. Biochem. Biophys., 1980, vol. 204:544-550.

Theriault et al., Tocotrienol: A Review of Its Therapeutic Potential, Clin. Biochem., 1999, vol. 32:309-319.

Qureshii et al., The Structure of an Inhibitor of Cholesterol Biosynthesis Isolated From Barley J. Biol. Chem., 1986, vol. 261:10544-10550.

Van Eenennaam et al., Engineering Vitamin E Content: From *Arabidopsis* Mutant to Soy Oil, Plant Cell, 2003, vol. 15:3007-3019.

(Continued)

*Primary Examiner* — Phuong Bui

(57) ABSTRACT

Preparation and use of isolated nucleic acids useful in altering the oil phenotype of plants are described. Isolated nucleic acids and their encoded polypeptides are described that alter the content of alpha-tocotrienol, beta-tocotrienol, or both, in transformed seeds and oil obtained from the transformed seeds. Expression cassettes, host cells and transformed plants are described that contain the foregoing nucleic acids.

3 Claims, 6 Drawing Sheets

OTHER PUBLICATIONS

National Center for Biotechnology Information General Identifier No. 66732623, May 31, 2005, Y. Hu et al., Cloning of Gamma Tocopherol Methyltransferase Gene in *Lotus corniculatus* var. *japonicus*, Accession No. AAY52459.

National Center for Biotechnology Information General Identifier No. 62126056, Apr. 6, 2005, Y. Hu et al., Cloning Gamma-Tocopherol Methyltransferase Gene in Glycine Max, Accession No. AY960126.

National Center for Biotechnology Information General Identifier No. 50911846, Nov. 9, 2004, Accession No. XM_46733.1.

National Center for Biotechnology Information General Identifier No. 27448217, Jan. 1, 2003, Q. Ouyang et al., Gamma-Tocopherol Methyltransferase, Accession No. AF381248.

National Center for Biotechnology Information General Identifier No. 17224291, Dec. 2, 2001, K. H. Kim et al., Cloning of *Perilla* Gamma-Tocopherol Methyltransferase, Accession No. AF213481.

National Center for Biotechnology Information General Identifier No. 4106537, Jan. 26, 2006, D. Shintani et al., Elevating the Vitamin E Content of Plants Through Metabolic Engineering, Accession No. AF104220.

National Center for Biotechnology Information General Identifier No. 62115030, Apr. 5, 2005, Y. Hu et al., Cloning Gamma-Tocopherol Methyltransferase Gene in *Medicago truncaluta*, Accession No. AY962639.

National Center for Biotechnology Information General Identifier No. 61657537, Apr. 15, 2005, G. Galvez-Valdivieso et al., Cloning and Characterization of Gamma-Tocopherol Methyltransferase From the Unicellular Alga *Chlamydomonas reinhardtii*, Accesion No. AJ884948.

National Center for Biotechnology Information General Identifier No. 16331764, Jul. 17, 2008, T. Kaneko et al., Sequence Analysis of the Genome of the Unicellular Cyanobacterium *Synechocystis* Sp. Strain PCC6803. II. Sequence Determination of the Entire Genome and Assignment of Potential-Coding Regions, Accession No. NP_442492.

National Center for Biotechnology Information General Identifier No. 17130893, Dec. 21, 2007, T. Kaneko et al., Complete Genomic Sequence of the Filamentous Nitrogen-Fixing Cyanobacterium *Anabaena* Sp. Strain PCC 7120, Accession No. BAB73502.

National Center for Biotechnology Information General Identifier No. 37522659, Jul. 23, 2008, Y. Nakamura et al., Complete Genome Structure of *Gloeobacter violaceus* PCC 7421, A Cyanobacterium That Lacks Thylakoids, Accession No. NP_926036.

National Center for Biotechnology Information, Accession No. Q2XV86, Dec. 20, 2005.

Norris et al., A_GENESEQ_200912 Database, Acc. No. ADD19073, WO2003034812, Published May 1, 2003, Result 8.

Zhang, et al., A_GENESEQ_200912 Database, Acc. No. AOF66142, CN1807608, Published Jul. 26, 2006.

FIG. 3A

Multiple Alignment of VTE3 Polypeptides

```
   ............................................................ Consensus #1
            10        20        30        40        50        60
 1 --MASAMLNGAESLKLTRG-L---APK-----GLGFSGSNFP-RLGIVSTYRCSK---AA SEQ ID NO-54.pro
 1 --MASLMLNGAITFPKGLG-----SP--V----SNLHARSIP-RPTLLSVTRTSTP--RL SEQ ID NO-61.pro
 1 --MASSMLTGAENLKLIRG-I---SPNGLGFLGSDVHGKHFP-KLGLVSWSRNYR---LK SEQ ID NO-62.pro
 1 --MTSSMLYGAENLAIIRGRV---AANGLGFNGSELNGRKFPLKVNLACGNSISRG--KT SEQ ID NO-63.pro
 1 --MASSMLNGAESFTLIRG-V---TERRVDFFGSGEHGKHLS-NLGLAFSVRISRP--GT SEQ ID NO-64.pro
 1 --MGSVMISGTEKITI-RT-I---TGNGLGFTGSDLHGKNFE-RVSFAATTSAKVPNFRS SEQ ID NO-65.pro
 1 MAMASTYAPGGGARALAQGRCRVRGEAGLGFLGPSKAAG-LERPIALALARRMSSP-VAV SEQ ID NO-66.pro
 1 ------------------------------------------------------------ SEQ ID NO-67.pro
 1 ------------------------------------------------------------ SEQ ID NO-68.pro
 1 ------------------------------------------------------------ SEQ ID NO-69.pro
 1 ------------------------------------------------------------ SEQ ID NO-70.pro

   ...............RP....RFIQHKKEA.WFYRFLSI.YDH.INPGHWTEDMR..ALE Consensus #1
            70        80        90       100       110       120
46 PMAPKCS----LSASRPASQPRFIQHKKEAFWFYRFLSIVYDHIINPGHWTEDMRDEALE SEQ ID NO-54.pro
45 SVATRCSSSS-VSSSRPSAQPRFIQHKKEAYWFYRFLSIVYDHVINPGHWTEDMRDDALE SEQ ID NO-61.pro
51 TLKARCN----ASVSRPASQIRFIQHKKEAFWFYRFLSIVYDHIINPGHWTEDMRDDALE SEQ ID NO-62.pro
54 LVVPKCS----VSLTRPASQPRFIQHKKEAFWFYRFLSIVYDHVINPGHWTEDMRDEALE SEQ ID NO-63.pro
52 TMAPKCG----LSASRPASQPRFIQHKKEAFWFYRFLSIIYDHVINPGHWTEDMRNDALE SEQ ID NO-64.pro
53 IVVPKCS----VSASRPSSQPRFIQHKKEAFWFYRFLSIVYDHVINPGHWTEDMRDDALE SEQ ID NO-65.pro
59 GARLRCAASSSPAAARPATAPRFIQHKKEAFWFYRFLSIVYDHVINPGHWTEDMRDDALE SEQ ID NO-66.pro
 1 ---------------RPSAQPRFIQHKKEAYWFYRFLSIVYDHVINPGHWTEDMRDDALE SEQ ID NO-67.pro
 1 --VPKCS----VSASRPSSQPRFIQHKKEAFWFYRFLSIVYDHVINPGHWTEDMRDDALE SEQ ID NO-68.pro
 1 --RLRCAASSSPAAARPATAPRFIQHKKEAFWFYRFLSIVYDHVINPGHWTEDMRDDALE SEQ ID NO-69.pro
 1 --APKCS----LSASRPASQPRFIQHKKEAFWFYRFLSIVYDHIINPGHWTEDMRDEALE SEQ ID NO-70.pro
```

FIG. 3B

Multiple Alignment of VTE3 Polypeptides

```
    PADL......VVDVGGGTGFTTLGIVK.V...NVT.LDQSPHQL.KA..KE.LK...I.E Consensus #1
            130       140       150       160       170       180
102 PADLSDRNMIVVDVGGGTGFTTLGIVKHVDAKNVTILDQSPHQLAKAKQKEPLKDCKIIE SEQ ID NO-54.pro
104 PADLSHPDMRVVDVGGGTGFTTLGIVKTVKAKNVTTLDQSPHQLAKAKQKEPLKECKIVE SEQ ID NO-61.pro
107 PADLNDRNLVVVDVGGGTGFTTLGIVKHVDAKNVTLLDQSPHQLAKAKNKEPLKDCRIIE SEQ ID NO-62.pro
110 PADLYSRNMLVVDVGGGTGFTTLGIVKSVDAKNVTILDQSPHQLAKAKQKEPLKECKIIE SEQ ID NO-63.pro
108 PADLNNRNMIVVDVGGGTGFTTLGIVKHVDAKNVTILDQSPHQLAKAKQKEPLKECRIIE SEQ ID NO-64.pro
109 PADLNDRNMIVVDVGGGTGFTTLGIVKHVDAKNVTILDQSPHQLAKAKQKEPLKECKIIE SEQ ID NO-65.pro
119 PADLFSRELTVVDVGGGTGFTTLGIVKHVNPENVIILDQSPHQLDKARQKEALKGVTIME SEQ ID NO-66.pro
46  PADLSHPDMRVVDVGGGTGFTTLGIVKTVKAKNVTILDQSPHQLAKAKQKEPLKECKIVE SEQ ID NO-67.pro
55  PADLNDRNMIVVDVGGGTGFTTLGIVKHVDAKNVTILDQSPHQLAKAKQKEPLKECKIIE SEQ ID NO-68.pro
59  PADLFSRELTVVDVGGGTGFTTLGIVKHVNPENVTILDQSPHQLDKARQKEALKGVTIME SEQ ID NO-69.pro
55  PADLSDRNMIVVDVGGGTGFTTLGIVKHVDAKNVTILDQSPHQLAKAKQKEPLKDCKIIE SEQ ID NO-70.pro

    GDAEDLPF.TD..DRY.SAGSIEYWP.PQRGI.EAYRVL..GG.AC.IGPVYPT.WLSRF Consensus #1
            190       200       210       220       230       240
162 GDAEDLPFRTDYADRYVSAGSIEYWPDPQRGITEAYRVLKLGGKACLIGPVYPTFWLSRF SEQ ID NO-54.pro
164 GDAEDLPFPTDYADRYVSAGSIEYWPDPQRGIKEAYRVLKIGGKACLIGPVYPTFWLSRF SEQ ID NO-61.pro
167 GDAEDLPFPTDYADRYVSAGSIEYWPEPQRGIKEAYRVLKQGGKACMIGPVYPTFWLSRF SEQ ID NO-62.pro
170 GDAEDLPFKTDYADRYISAGSIEYWPEPQRGIKEAYRVLKIGGKACVIGPVYPTHWLSRF SEQ ID NO-63.pro
168 GDAEDLPFRTDYADRYVSAGSIEYWPDPQRGIKEAYRVLKLGGKACLIGPVYPTFWLSRF SEQ ID NO-64.pro
169 GDAEDLPFRTDYADRYVSAGSIEYWPDPQRGIKEAYRVLKLGGKACLIGPVYPTFWLSRF SEQ ID NO-65.pro
179 GDAEDLPFPTDSFDRYISAGSIEYWPDPQRGIKEAYRVLRFGGLACVIGPVYPTFWLSRF SEQ ID NO-66.pro
106 GDAEDLPFPTDYADRYVSAGSIEYWPDPQRGIKEAYRVLKIGGKACLIGPVYPTFWLSRF SEQ ID NO-67.pro
115 GDAEDLPFRTDYADRYVSAGSIEYWPDPQRGIKEAYRVLKLGGKACLIGPVYPTFWLSRF SEQ ID NO-68.pro
119 GDAEDLPFPTDSFDRYISAGSIEYWPDPQRGIKEAYRVLRFGGLACVIGPVYPTFWLSRF SEQ ID NO-69.pro
115 GDAEDLPFRTDYADRYVSAGSIEYWPDPQRGITEAYRVLKLGGKACLIGPVYPTFWLSRF SEQ ID NO-70.pro
```

Multiple Alignment of VTE3 Polypeptides

FIG. 4
Percent Sequence Identity Between VTE3 Polypeptides

Percent Identity

Divergence

| | 1 | 2 | 3 | 4 | 5 | 6 | 7 | 8 | 9 | 10 | 11 | | |
|---|---|---|---|---|---|---|---|---|---|---|---|---|---|
| 1 | | 80.7 | 83.0 | 81.8 | 86.0 | 84.7 | 73.1 | 88.9 | 92.4 | 80.2 | 100.0 | 1 | SEQ ID NO-54.pro |
| 2 | 22.3 | | 76.9 | 78.1 | 79.3 | 81.7 | 72.3 | 100.0 | 89.6 | 79.4 | 87.8 | 2 | SEQ ID NO-61.pro |
| 3 | 19.4 | 27.7 | | 81.2 | 83.8 | 82.3 | 72.9 | 84.6 | 89.2 | 79.9 | 88.5 | 3 | SEQ ID NO-62.pro |
| 4 | 20.9 | 25.9 | 21.7 | | 80.4 | 83.2 | 72.2 | 87.1 | 90.3 | 80.6 | 89.6 | 4 | SEQ ID NO-63.pro |
| 5 | 15.6 | 24.2 | 18.3 | 22.8 | | 83.2 | 73.2 | 87.1 | 92.0 | 80.9 | 92.0 | 5 | SEQ ID NO-64.pro |
| 6 | 17.1 | 21.1 | 20.2 | 19.0 | 19.0 | | 70.9 | 90.7 | 100.0 | 79.5 | 92.4 | 6 | SEQ ID NO-65.pro |
| 7 | 33.4 | 34.5 | 33.7 | 34.7 | 33.1 | 36.8 | | 81.4 | 79.5 | 100.0 | 80.2 | 7 | SEQ ID NO-66.pro |
| 8 | 12.1 | 0.0 | 17.3 | 14.2 | 14.2 | 10.0 | 21.5 | | 90.7 | 81.4 | 88.9 | 8 | SEQ ID NO-67.pro |
| 9 | 8.1 | 11.2 | 11.6 | 10.4 | 8.5 | 0.0 | 24.0 | 10.0 | | 79.5 | 92.4 | 9 | SEQ ID NO-68.pro |
| 10 | 23.0 | 24.2 | 23.5 | 22.6 | 22.1 | 24.0 | 0.0 | 21.5 | 24.0 | | 80.2 | 10 | SEQ ID NO-69.pro |
| 11 | 0.0 | 13.3 | 12.5 | 11.2 | 8.5 | 8.1 | 23.0 | 12.1 | 8.1 | 23.0 | | 11 | SEQ ID NO-70.pro |
| | 1 | 2 | 3 | 4 | 5 | 6 | 7 | 8 | 9 | 10 | 11 | | |

COMPOSITIONS AND METHODS FOR ALTERING ALPHA- AND BETA-TOCOTRIENOL CONTENT USING MULTIPLE TRANSGENES

CROSS-REFERENCE TO RELATED APPLICATIONS

This application is a continuation application of U.S. application No. 13/005,369, filed Jan. 12, 2011 and issued on Oct. 23, 2012 as U.S. Pat. No. 8,293,976, which is a divisional application of U.S. application Ser. No. 12/240,434, filed Sep. 29, 2008 and issued on Feb. 22, 2011 as U.S. Pat. No. 7,893,324, which claims the benefit of U.S. Provisional Application No. 60/977,495, filed Oct. 4, 2007, the entire disclosure of which is herein incorporated by reference.

FIELD OF INVENTION

The field of the invention relates to plant breeding and molecular biology, and particularly to alteration of oil phenotype in plants through the use of nucleic acid fragments encoding homogentisate geranylgeranyl transferase, gamma-tocopherol methyltransferase (VTE4) and 2-methyl-6-phytylbenzoquinol methyltransferase (VTE3).

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 400523SEQLIST.txt, created on Jan. 12, 2011, and having a size of 251 kilobytes and is filed concurrently with the specification. The sequence listing contained in this ASCII formatted document is part of the specification and is herein incorporated by reference in its entirety.

BACKGROUND OF THE INVENTION

Tocotrienols are vitamin E-related compounds whose occurrence in plants is limited primarily to the seeds and fruits of most monocot species (e.g., palm, wheat, rice and barley). Tocotrienols are structurally similar to tocopherols, including alpha-tocopherol which is a form of vitamin E. Tocopherols occur ubiquitously in the plant kingdom as well as in photosynthetic microbes such as *Synechocystis*.

Tocotrienols and tocopherols both contain a chromanol head group that is linked to a hydrocarbon side chain. The only structural difference between these molecules is the presence of three double bonds in the hydrocarbon side chain of tocotrienols. This difference is related to the biosynthetic origins of the side chains. Tocopherol side chains are derived from phytyl-pyrophosphate (PP), and the tocotrienol side chains are believed to be derived from geranylgeranyl-PP, see FIG. 1 and FIG. 2, respectively (Soll et al. (1980) *Arch. Biochem. Biophys.* 204:544-550).

At least four forms or molecular species of tocopherols and tocotrienols occur in nature: alpha, beta, gamma and delta ($\alpha$, $\beta$, $\gamma$ and $\delta$, respectively). These molecular species contain different numbers of methyl groups that are bound to the aromatic portion of the chromanol head. Like tocopherols, tocotrienols are potent lipid-soluble antioxidants and therefore have considerable nutritive value in human and animal diets (Packer et al. (2001) *J. Nutr.* 131:369 S-373S). In addition, tocotrienols are believed to have therapeutic properties including a demonstrated ability to down regulate cholesterol biosynthesis (Theriault et al. (1999) *Clin. Biochem.* 32:309-319; Qureshii et al. (1986) *J. Biol. Chem.* 261:10544-10550).

The first committed step in the tocopherol biosynthetic pathway is the prenylation of homogentisic acid with phytyl-diphosphate to form 2-methyl-6-phytylbenzoquinol (MPBQ). Two distinct methyltransferase enzymes catalyze methylations of the aromatic moiety of tocopherols (VTE3 and VTE4). 2-methyl-6-phytylbenzoquinol methyltransferase (VTE3) acts on the tocopherol intermediate MPBQ prior to cyclization. Cyclization of the product of the first methylation reaction (2,3-dimethyl-5-phytylbenzoquinol) with tocopherol cyclase (VTE1) provides gamma-tocopherol. Gamma-tocopherol is further methylated to alpha-tocopherol by the second methyltransferase enzyme of tocopherol biosynthesis, gamma-tocopherol methyltransferase (VTE4). The same enzyme methylates delta-tocopherol thereby generating beta-tocopherol.

It has been speculated that the first committed step in the biosynthesis of tocotrienols involves the condensation of geranylgeranyl-PP and homogentisate to form 2-methyl-6-geranylgeranylbenzoquinol (Soll et al. (1980) *Arch. Biochem. Biophys.* 204:544-550). The enzyme that catalyzes this reaction can thus be functionally described as a homogentisate geranylgeranyl transferase (HGGT). After cyclization and an initial methylation, the last step of tocotrienol production would require the methylation of gamma-tocotrienol to alpha-tocotrienol or delta-tocotrienol to beta-tocotrienol.

Functional identification of genes or cDNAs encoding homogentisate geranylgeranyl transferase (HGGT) and gamma-tocopherol methyltransferase polypeptides has been reported. The use of these nucleic acids in combination to manipulate the biosynthesis of the nutritionally important tocotrienols, such as alpha- and beta-tocotrienol, in plants, seeds and microbial hosts has been reported in US Patent Publication US-2007-0199096-A1.

SUMMARY OF THE INVENTION

Compositions and methods for the alteration of the alpha- and beta-tocotrienol content and composition of plants are provided. The compositions comprise nucleotide molecules comprising nucleotide sequences for HGGT, gamma-tocopherol methyltransferase and 2-methyl-6-phytylbenzoquinol methyltransferase. The compositions can be used to transform plants to manipulate the synthetic pathway for tocol compounds.

The present invention includes:

In one embodiment, a transformed plant comprising in its genome: (a) a first recombinant nucleic acid molecule comprising at least one regulatory sequence operably linked to at least one nucleotide sequence selected from the group consisting of: (i) a nucleotide sequence encoding a polypeptide having gamma-tocopherol methyltransferase activity; (ii) a nucleotide sequence set forth in SEQ ID NOs: 11, 13, 15, 17, 19, 21, 23, 25, 27, 29, 31, 33, 35, 37 or 39; (iii) a nucleotide sequence encoding the amino acid sequence set forth in SEQ ID NOs: 12, 14, 16, 18, 20, 22, 24, 26, 28, 30, 32, 34, 36, 38 or 40; (iv) a nucleotide sequence having at least 80% sequence identity to the nucleotide sequence set forth in any one of (i)-(iii), wherein the nucleotide sequence encodes a polypeptide having gamma-tocopherol methyltransferase activity; and (v) a nucleotide sequence that is fully complementary to the nucleotide sequence of any one of (i)-(iv); (b) a second recombinant nucleic acid molecule comprising at least one regulatory sequence operably linked to at least one nucleotide sequence selected from the group consisting of: (vi) a nucleotide sequence encoding a polypeptide having homogentisate geranylgeranyl transferase activity; (vii) a nucleotide sequence set forth in SEQ ID NOs: 1, 3, 5, 7, or 9; (viii) a nucleotide sequence encoding the amino acid sequence set forth in SEQ ID NOs: 2, 4, 6, 8, or 10; (ix) a nucleotide sequence having at least 80% sequence identity to the nucleotide sequence set forth in any one of (vi)-(viii), wherein the nucleotide sequence encodes a polypeptide having homogentisate geranylgeranyl transferase activity; and (x) a nucleotide sequence that is fully complementary to the nucleotide sequence of any one of (vi)-(ix); and (c) a third recombinant nucleic acid molecule comprising at least one regulatory sequence operably linked to at least one nucleotide sequence selected from the group consisting of: (xi) a nucleotide sequence encoding a polypeptide having 2-methyl-6-phytylbenzoquinol methyltransferase activity; (xii) a nucleotide sequence set forth in SEQ ID NO:53; (xiii) a nucleotide sequence encoding the amino acid sequence set forth in SEQ ID NOs: 54, 61, 62, 63, 64, 65, 66, 67, 68, 69 or 70; (xiv) a nucleotide sequence having at least 80% sequence identity to the nucleotide sequence set forth in any one of (xi)-(xii), wherein the nucleotide sequence encodes a polypeptide having 2-methyl-6-phytylbenzoquinol methyltransferase activity; (xv) a nucleotide sequence encoding a polypeptide having 2-methyl-6-phytylbenzoquinol methyltransferase activity, wherein the amino acid sequence of the polypeptide has at least 95% sequence identity to the amino acid sequence set forth in SEQ ID NOs: 54, 61, 62, 63, 64, 65, 66, 67, 68, 69 or 70; and (xvi) a nucleotide sequence that is fully complementary to the nucleotide sequence of any one of (xi)-(xv); wherein the first recombinant nucleic acid molecule, the second recombinant nucleic acid molecule and the third recombinant nucleic acid molecule are stably incorporated into the genome of the transformed plant.

In another embodiment, a transformed plant comprising in its genome at least one recombinant nucleic acid molecule selected from the group consisting of the first recombinant nucleic acid molecule, the second recombinant nucleic acid molecule and the third recombinant nucleic acid molecule of above, wherein the at least one recombinant nucleic acid molecule is stably incorporated into the genome of the transformed plant.

In another embodiment, the transformed plant may be a monocot selected from the group consisting of maize, wheat, rice, sorghum, barley, millet and rye.

In another embodiment, the transformed plant may be a dicot selected from the group consisting of soybean, *Brassica* sp., alfalfa, safflower, sunflower, cotton, peanut, canola, *Arabidopsis*, tobacco and potato.

In another embodiment, the at least one regulatory sequence of the first, second or third recombinant nucleic acid molecule comprises at least one promoter selected from the group consisting of seed-preferred, constitutive, chemically regulated, tissue-preferred, and developmentally regulated promoters.

In another embodiment, the invention includes seed of the transformed plant, wherein said seed comprises in its genome the first recombinant nucleic acid molecule, the second recombinant nucleic acid molecule and the third recombinant nucleic acid molecule.

In another embodiment, the transformed plant of the invention produces a seed with an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, the invention includes a method of increasing the level of alpha-tocotrienol, beta-tocotrienol, or both, in a plant, comprising stably incorporating into a plant genome: (a) a first recombinant nucleic acid molecule comprising at least one regulatory sequence operably linked to at least one nucleotide sequence selected from the group consisting of: (i) a nucleotide sequence encoding a polypeptide having gamma-tocopherol methyltransferase activity; (ii) a nucleotide sequence set forth in SEQ ID NOs: 11, 13, 15, 17, 19, 21, 23, 25, 27, 29, 31, 33, 35, 37 or 39; (iii) a nucleotide sequence encoding the amino acid sequence set forth in SEQ ID NOs: 12, 14, 16, 18, 20, 22, 24, 26, 28, 30, 32, 34, 36, 38 or 40; (iv) a nucleotide sequence having at least 80% sequence identity to the nucleotide sequence set forth in any one of (i)-(iii), wherein the nucleotide sequence encodes a polypeptide having gamma-tocopherol methyltransferase activity; and (v) a nucleotide sequence that is complementary to the nucleotide sequence of any one of (i)-(iv); (b) a second recombinant nucleic acid molecule comprising at least one regulatory sequence operably linked to at least one nucleotide sequence selected from the group consisting of: (vi) a nucleotide sequence encoding a polypeptide having homogentisate geranylgeranyl transferase activity; (vii) a nucleotide sequence set forth in SEQ ID NOs: 1, 3, 5, 7, or 9; (viii) a nucleotide sequence encoding the amino acid sequence set forth in SEQ ID NOs: 2, 4, 6, 8, or 10; (ix) a nucleotide sequence having at least 80% sequence identity to the nucleotide sequence set forth in any one of (vi)-(viii), wherein the nucleotide sequence encodes a polypeptide having homogentisate geranylgeranyl transferase activity; and (x) a nucleotide sequence that is complementary to the nucleotide sequence of any one of (vi)-(ix); and (c) a third recombinant nucleic acid molecule comprising at least one regulatory sequence operably linked to at least one nucleotide sequence selected from the group consisting of: (xi) a nucleotide sequence encoding a polypeptide having 2-methyl-6-phytylbenzoquinol methyltransferase activity; (xii) a nucleotide sequence set forth in SEQ ID NO:53; (xiii) a nucleotide sequence encoding the amino acid sequence set forth in SEQ ID NOs: 54, 61, 62, 63, 64, 65, 66, 67, 68, 69 or 70; (xiv) a nucleotide sequence having at least 80% sequence identity to the nucleotide sequence set forth in any one of (xi)-(xii), wherein the nucleotide sequence encodes a polypeptide having 2-methyl-6-phytylbenzoquinol methyltransferase activity; (xv) a nucleotide sequence encoding a polypeptide having 2-methyl-6-phytylbenzoquinol methyltransferase activity, wherein the amino acid sequence of the polypeptide has at least 95% sequence identity to the amino acid sequence set forth in SEQ ID NOs: 54, 61, 62, 63, 64, 65, 66, 67, 68, 69 or 70; and (xvi) a nucleotide sequence that is fully complementary to the nucleotide sequence of any one of (xi)-(xv); and selecting a transformed plant that has an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, a method in which the first, second and third recombinant nucleic acid molecules are incorporated into the plant genome by co-transformation of a plant cell.

In another embodiment, a method in which at least one of said first, second or third recombinant nucleic acid molecules is incorporated into the plant genome by re-transformation of a transformed plant cell, wherein said transformed plant cell comprises at least one of said first, second or third recombinant nucleic acid molecules.

In another embodiment, a method in which at least one of said first, second or third recombinant nucleic acid molecule is incorporated into the plant genome by breeding.

In another embodiment, a method in which the at least one regulatory sequence of the first, second or third recombinant nucleic acid molecule comprises at least one promoter selected from the group consisting of seed-preferred, constitutive, chemically regulated, tissue-preferred, and developmentally regulated promoters.

In another embodiment, the invention includes methods for transforming plants and plants cells to change the oil content therein comprising transforming a plant with one to three nucleotide sequences alone or in any combination of two or three nucleotide sequences. The method comprises; (a) obtaining a first plant comprising in its genome a first recombinant nucleic acid molecule comprising at least one regulatory sequence operably linked to a nucleotide sequence encoding a polypeptide having gamma-tocopherol methyltransferase activity; and (b) crossing the transgenic plant of step (a) with a second plant comprising in its genome a second recombinant nucleic acid molecule comprising at least one regulatory sequence operably linked to a nucleotide sequence encoding a polypeptide having homogentisate geranylgeranyl transferase activity; (c) crossing the transgenic plant of step (b) with a third plant comprising in its genome a third recombinant nucleic acid molecule comprising at least one regulatory sequence operably linked to a nucleotide sequence encoding a polypeptide having 2-methyl-6-phytylbenzoquinol methyltransferase activity; (d) obtaining a progeny plant from said step (c) crossing, wherein said progeny plant comprises in its genome the first recombinant nucleic acid molecule, the second recombinant nucleic acid molecule and the third recombinant nucleic acid molecule, and wherein said progeny plant exhibits an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, a method of increasing the level of alpha-tocotrienol, beta-tocotrienol, or both, in a plant, comprising: (a) obtaining a first transformed plant comprising in its genome a first recombinant nucleic acid molecule comprising at least one regulatory sequence operably linked to at least one nucleotide sequence selected from the group consisting of: (i) a nucleotide sequence encoding a polypeptide having gamma-tocopherol methyltransferase activity; (ii) a nucleotide sequence set forth in SEQ ID NOs: 11, 13, 15, 17, 19, 21, 23, 25, 27, 29, 31, 33, 35, 37 or 39; (iii) a nucleotide sequence encoding the amino acid sequence set forth in SEQ ID NOs: 12, 14, 16, 18, 20, 22, 24, 26, 28, 30, 32, 34, 36, 38 or 40; (iv) a nucleotide sequence having at least 80% sequence identity to the entire coding sequence of the nucleotide sequence set forth in any one or (i)-(iii), wherein the nucleotide sequence encodes a polypeptide having gamma-tocopherol methyltransferase activity; and (v) a nucleotide sequence that is complementary to the nucleotide sequence of any one of (i)-(iv); (b) crossing the transformed plant of step (a) with a second transformed plant comprising within its genome a second recombinant nucleic acid molecule comprising at least one regulatory sequence operably linked to at least one nucleotide sequence selected from the group consisting of: (vi) a nucleotide sequence encoding a polypeptide having homogentisate geranylgeranyl transferase activity; (vii) a nucleotide sequence set forth in SEQ ID NOs: 1, 3, 5, 7 or 9; (viii) a nucleotide sequence encoding the amino acid sequence set forth in SEQ ID NOs: 2, 4, 6, 8 or 10; (ix) a nucleotide sequence having at least 80% sequence identity to the entire coding sequence of the nucleotide sequence set forth in (vi)-(viii), wherein the nucleotide sequence encodes a polypeptide having homogentisate geranylgeranyl transferase activity; and (x) a nucleotide sequence that is complementary to the nucleotide sequence of any one of (vi)-(ix); and (c) crossing the transformed plant of step (b) with a third transformed plant comprising within its genome a third recombinant nucleic acid molecule comprising at least one regulatory sequence operably linked to at least one nucleotide sequence selected from the group consisting of: (xi) a nucleotide sequence encoding a polypeptide having 2-methyl-6-phytylbenzoquinol methyltransferase activity; (xii) a nucleotide sequence set forth in SEQ ID NO:53; (xiii) a nucleotide sequence encoding the amino acid sequence set forth in SEQ ID NOs: 54 or 70; (xiv) a nucleotide sequence having at least 80% sequence identity to the nucleotide sequence set forth in any one of (xi)-(xii), wherein the nucleotide sequence encodes a polypeptide having 2-methyl-6-phytylbenzoquinol methyltransferase activity; (xv) a nucleotide sequence encoding a polypeptide having 2-methyl-6-phytylbenzoquinol methyltransferase activity, wherein the amino acid sequence of the polypeptide has at least 95% sequence identity to the amino acid sequence set forth in SEQ ID NOs: 54, 61, 62, 63, 64, 65, 66, 67, 68, 69 or 70; and (xvi) a nucleotide sequence that is fully complementary to the nucleotide sequence of any one of (xi)-(xv); and selecting a progeny plant from said step (c) crossing, wherein said progeny plant comprises in its genome the first recombinant nucleic acid molecule, the second recombinant nucleic acid molecule and the third recombinant nucleic acid molecule, and wherein said progeny plant exhibits an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, any of the methods of the invention wherein the plant is a monocot is selected from the group consisting of maize, wheat, rice, sorghum, barley, millet and rye.

In another embodiment, any of the methods of the invention wherein the plant is a dicot is selected from the group consisting of soybean, *Brassica* sp., alfalfa, safflower, sunflower, cotton, peanut, canola, *Arabidopsis*, tobacco and potato.

In another embodiment, the invention includes transformed seed or byproducts of any of the transformed plants of the invention.

In another embodiment, the transformed seed of the invention has an alpha-tocotrienol level of at least 20 parts per million (ppm).

In another embodiment, the transformed seed of the invention contains alpha-tocotrienol in an amount of at least 20% of total tocopherol and tocotrienol content in the transformed seed.

In another embodiment, the transformed seed of the invention has an alpha-tocotrienol content of at least 70% of total combined tocopherol and tocotrienol content in the transformed seed.

In another embodiment, the transformed seed of the invention contains a combined level of alpha-tocotrienol and alpha-tocopherol of at least 95% of total tocopherol and tocotrienol content in the transformed seed.

In another embodiment, a method of improving the tissue quality of an animal, comprising feeding the animal the transformed seed of the invention.

In another embodiment, the tissue is meat and the quality of the meat is measured by at least one criteria selected from the group consisting of increased pH, improved food color, improved oxidative stability, increased shelf life and reduced purge.

In another embodiment, the animal is a ruminant, preferably cattle.

In another embodiment, the animal is a non-ruminant, preferably swine or poultry.

In another embodiment, an isolated polynucleotide comprising SEQ ID NO:57.

In another embodiment, an isolated polynucleotide comprising: (a) a nucleotide sequence encoding a polypeptide having 2-methyl-6-phytylbenzoquinol methyltransferase activity, wherein the polypeptide has an amino acid sequence of at least 95% sequence identity, based on the Clustal W method of alignment, when compared to SEQ ID NO:54 or 70, or (b) a complement of the nucleotide sequence, wherein the complement and the nucleotide sequence consist of the same number of nucleotides and are 100% complementary. The amino acid sequence of the polypeptide preferably comprises SEQ ID NO:54 or 70. The nucleotide sequence preferably comprises SEQ ID NO:53.

In another embodiment, the present invention includes a vector comprising any of the isolated polynucleotides of the present invention.

In another embodiment, the present invention includes a recombinant DNA construct comprising any of the isolated polynucleotides of the present invention operably linked to at least one regulatory sequence.

In another embodiment, the present invention concerns a method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterium.

In another embodiment, the present invention includes a method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

In another embodiment, an isolated polypeptide having 2-methyl-6-phytylbenzoquinol methyltransferase activity, wherein the polypeptide has an amino acid sequence of at least 95% sequence identity, based on the Clustal W method of alignment, when compared to one of SEQ ID NO:54 or 70. The amino acid sequence of the polypeptide preferably comprises SEQ ID NO:54 or 70.

In another embodiment, a method for isolating a polypeptide having 2-methyl-6-phytylbenzoquinol methyltransferase activity comprising isolating the polypeptide from a cell or culture medium of the cell, wherein the cell comprises a recombinant DNA construct comprising the polynucleotide of the invention operably linked to at least one regulatory sequence.

In another embodiment, a method of altering the level of expression of a 2-methyl-6-phytylbenzoquinol methyltransferase in a host cell comprising: (a) transforming a host cell with the recombinant DNA construct of the invention; and (b) growing the transformed host cell under conditions that are suitable for expression of the recombinant DNA construct wherein expression of the recombinant DNA construct results in production of altered levels of the 2-methyl-6-phytylbenzoquinol methyltransferase in the transformed host cell.

BRIEF DESCRIPTION OF THE DRAWINGS AND SEQUENCE LISTING

The invention can be more fully understood from the following detailed description and the accompanying drawings and Sequence Listing which form a part of this application.

Figure 1:
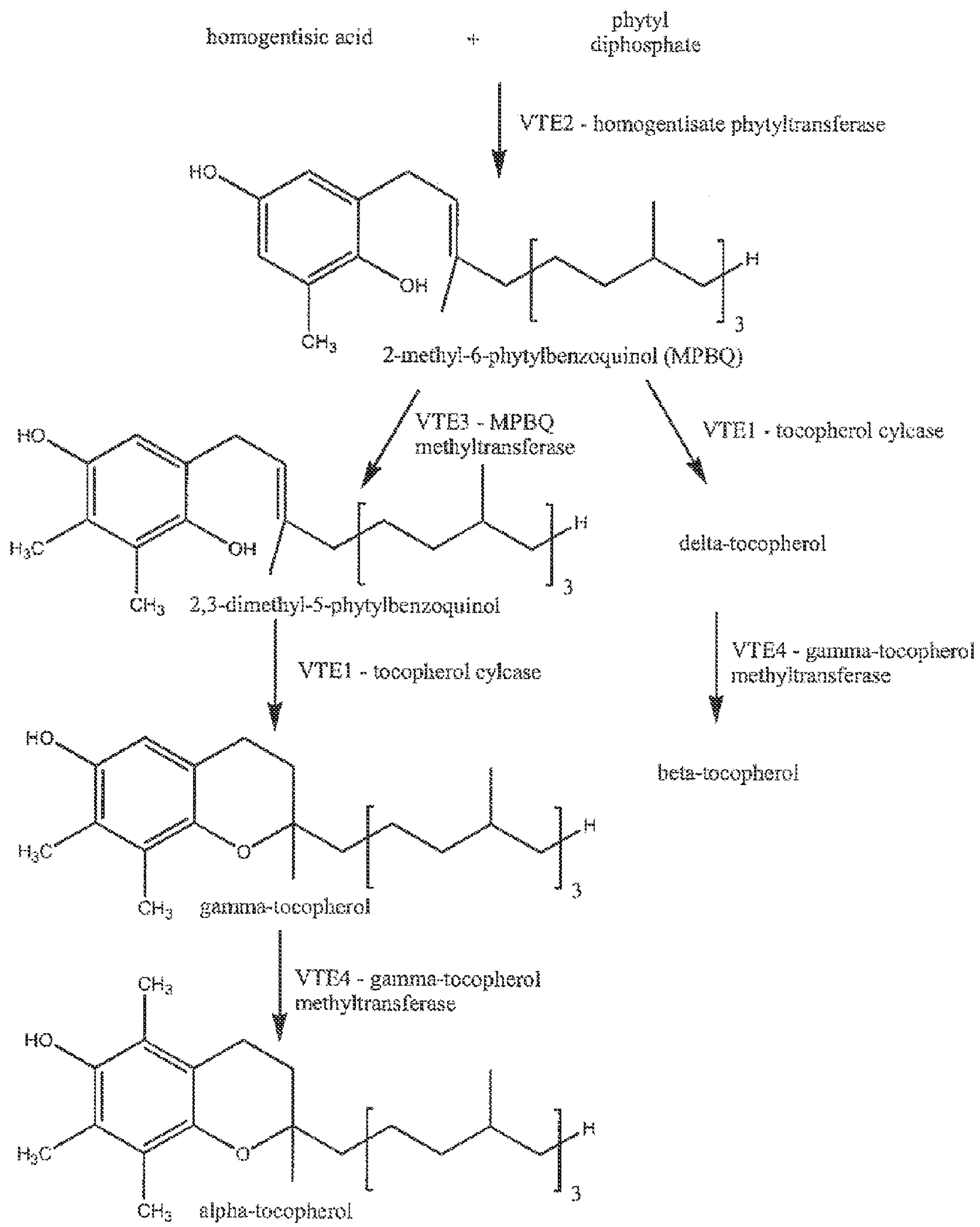
FIG. 1 is a schematic depiction of the tocopherol biosynthetic pathway.
Figure 2:
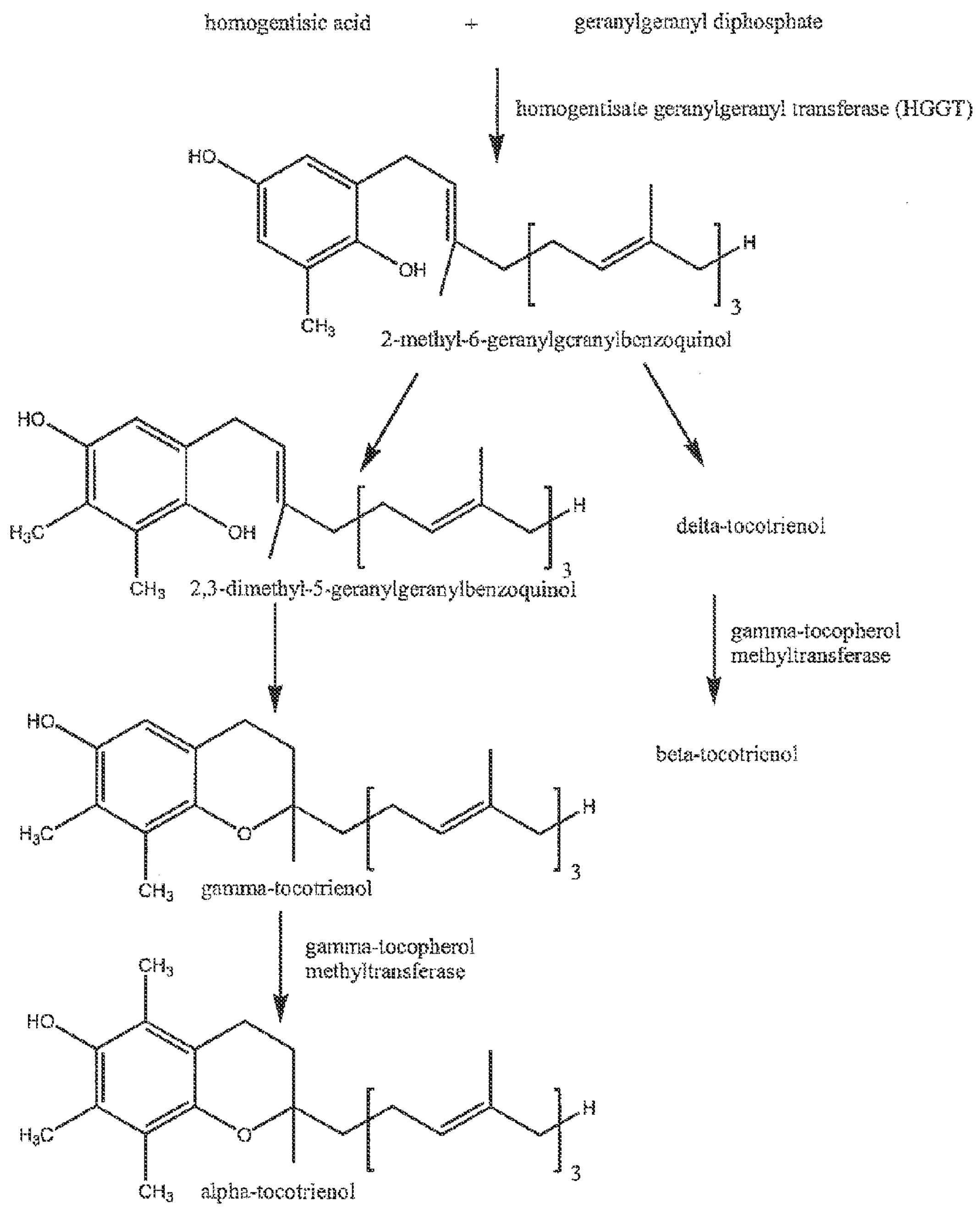
FIG. 2 is a schematic depiction of the tocotrienol biosynthetic pathway.
Figure 3C:
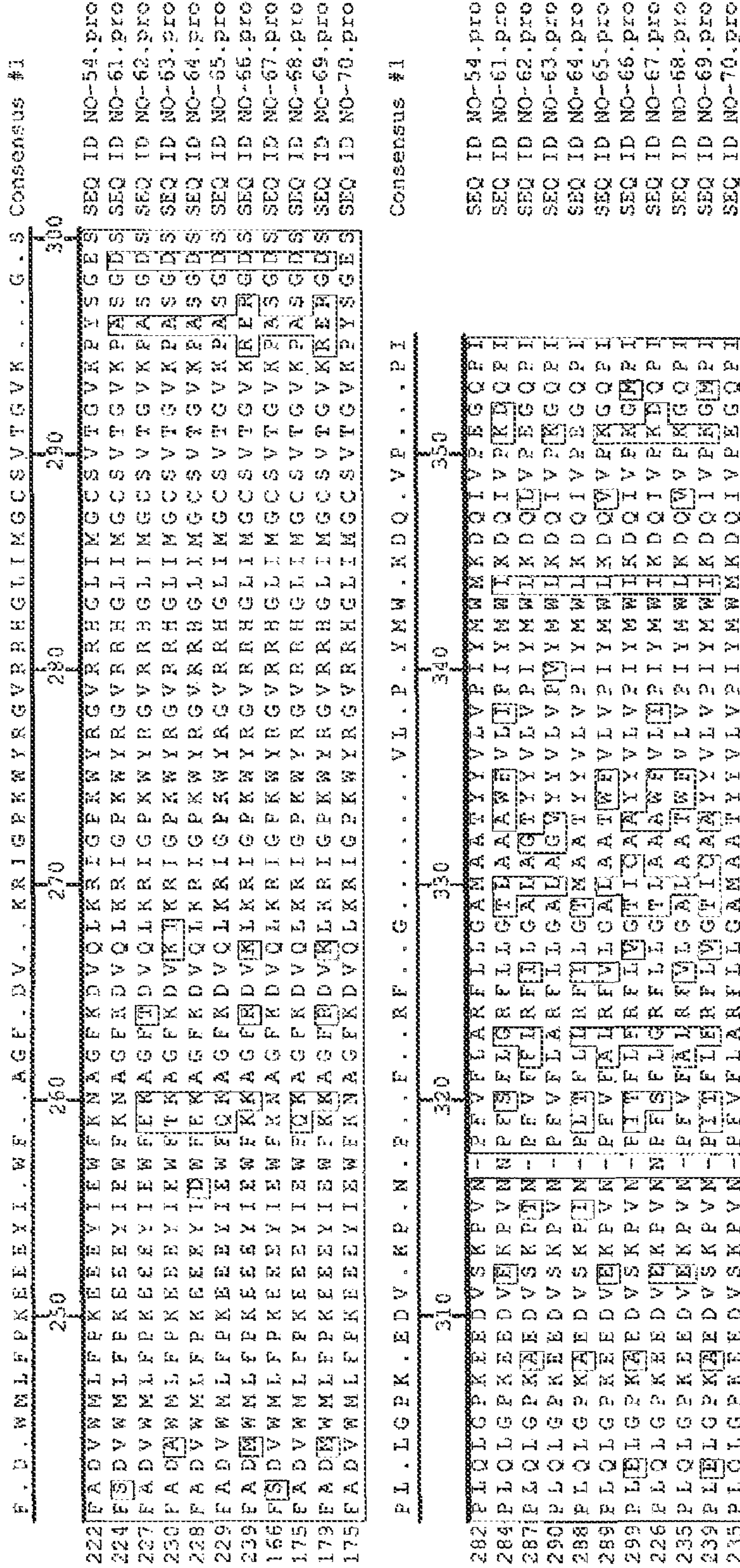

FIG. 3A-3C show a multiple alignment of the 2-methyl-6-phytylbenzoquinol methyltransferase polypeptides of SEQ ID NOs: 54, 61, 62, 63, 64, 65, 66, 67, 68, 69 and 70. The multiple alignment was assembled using the Clustal W method of alignment with the default parameters. Residues that match SEQ ID NO:54 exactly are enclosed in a box. Above the alignment is shown a consensus sequence. A residue is shown in the consensus sequence when all residues at that position are identical.

FIG. 4 shows the percent sequence identity and divergence for each pair of polypeptides from the multiple alignment of FIG. 3A-3C.

DETAILED DESCRIPTION OF THE INVENTION

Unless defined otherwise, all technical and scientific terms used herein have the same meaning as commonly understood by one of ordinary skill in the art to which this invention belongs.

Many modifications and other embodiments of the invention set forth herein will come to mind to one skilled in the art to which this invention pertains, having the benefit of the teachings presented in the descriptions and the drawings herein. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The articles "a" and "an" are used herein to refer to one or more than one (i.e., to at least one) of the grammatical object of the article. By way of example, "an element" means one or more than one element.

The combination of HGGT, gamma-tocopherol methyltransferase and 2-methyl-6-phytylbenzoquinol methyltransferase polynucleotides may be used in plants, plant cells, yeast, and microbes to alter the tocols, such as tocotrienols, produced in the cells via the production of the respective enzymes from each polynucleotide. The instant invention shows, inter alia, that the combination of HGGT, gamma-tocopherol methyltransferase and 2-methyl-6-phytylbenzoquinol methyltransferase polynucleotides, more specifically producing the enzymes they encode, may be used to significantly increase the content of vitamin E-related antioxidants, specifically alpha- and beta-tocotrienol, in edible tissues of vegetable, fruit, and agronomic crop plants, including grains which include but are not limited to maize and soybean seed. The changes in vitamin-E antioxidant content will also be reflected in the oil obtained from these plants, grains and seeds. The use of polynucleotides encoding HGGT and gamma-tocopherol methyltransferase is described in U.S. Patent Application Publication No. 2007-0199096, which is herein incorporated by reference.

The invention includes compositions and methods for altering tocols. The compositions and methods find use in improving the antioxidant quality of grain for use as food for humans and feed for livestock. Furthermore, the tocols can be extracted, purified or further altered via processing.

As used herein, "grain" means the mature seed produced by commercial growers for purposes other than reproducing the species and/or immature seed as an integral part of whole plant maize harvested for silage. As used herein, grain includes plant parts commonly categorized as a fruit, nut or vegetable.

As used herein, "wild-type" refers to untransformed organisms and descendants of untransformed organisms.

The molecular formula of a chemical may be presented in various formats. For example, the terms "$ZnSO_4.7H_2O$", "$ZnSO_4.7H_2O$", "$ZnSO_4.7H_2O$", and "$ZnSO_4.7H_2O$" are used interchangeably herein.

The term "tocol" refers generally to any of the tocopherol and tocotrienol molecular species (e.g., α-, β-, γ-, and δ-) that are known to occur in biological systems. The term "tocol content" refers to the total amount of tocopherol and tocotrienol in a whole plant, tissue, or cell or in a microbial host. The term "tocol composition" refers both to the ratio of the various tocols produced in any given biological system and to characteristics, such as antioxidant activity, of any one tocol compound. When the alteration of tocols is taught or claimed herein, such alteration can be to tocol content and/or tocol composition. When an increase of tocols is taught or claimed herein, such increase refers to an increase of tocol content and/or an increase of tocol activity.

The term "tocotrienol" refers generally to any of the tocotrienol molecular species (e.g., α, β, γ, and δ) that are known to occur in biological systems. The term "tocotrienol content" refers to the total amount of tocotrienol in a whole plant, tissue, or cell or in a microbial host. The term "tocotrienol composition" refers both to the ratio of the various tocotrienols produced in any given biological system and to characteristics, such as antioxidant activity, of any one tocotrienol compound. When the alteration of a tocotrienol is taught or claimed herein, such alteration can be to tocotrienol content and/or tocotrienol composition. When an increase of tocotrienols is taught or claimed herein, such increase refers to an increase of tocotrienol content and/or an increase of tocotrienol activity.

The term "homogentisate phytyltransferase" or "HPT" refers to the enzyme that catalyzes the condensation of homogentisate (or homogentisic acid) and phytyl pyrophosphate (or phytyl diphosphate). This reaction is believed to be the committed step in tocopherol biosynthesis. Other names that have been used to refer to this enzyme include "homogentisate phytyl pyrophosphate prenyltransferase" and "homogentisate phytyl diphosphate prenyltransferase". The shortened version phytyl/prenyl transferase is also used.

The terms "homogentisate geranylgeranyl transferase" and "HGGT", which are used interchangeably herein, refer to the enzyme that catalyzes the condensation of homogentisate (or homogentisic acid) and geranylgeranyl pyrophosphate (or geranylgeranyl diphosphate). This reaction is an important step in tocotrienol biosynthesis and can result in the alteration of the tocol content and/or composition. HGGT enzymes may include, but are not limited to, those shown in Table 1.

TABLE 1

Homogentisate Geranylgeranyl Transferase Enzymes

| Protein | Clone Designation | SEQ ID NO: (Nucleotide) | SEQ ID NO: (Amino Acid) |
|---|---|---|---|
| barley homogentisate geranylgeranyl transferase | bdl2c.pk006.o2 | 1 | 2 |
| wheat homogentisate geranylgeranyl transferase | wdk2c.pk012.f2:cgs | 3 | 4 |
| rice homogentisate geranylgeranyl transferase | rds1c.pk007.m9 | 5 | 6 |
| maize homogentisate geranylgeranyl transferase | cco1n.pk087.l17:cgs | 7 | 8 |
| maize homogentisate geranylgeranyl transferase | p0058.chpbj67r:fis | 9 | 10 |

The terms "gamma-tocopherol methyltransferase", "γ-TMT", "GTMT" and "VTE4", which are used herein, refer to the enzyme that catalyzes the methylation of gamma- and delta-tocopherol to alpha- and beta-tocopherol, respectively, and to the methylation of gamma- and delta-tocotrienol to alpha- and beta-tocotrienol, respectively. This reaction is an important step in tocotrienol biosynthesis and can result in the alteration of the tocol content and/or composition. Gamma-tocopherol methyltransferase enzymes may include, but are not limited to, those shown in Table 2.

TABLE 2

Gamma-Tocopherol Methyltransferase Enzymes

| Protein | Clone Designation or GenBank Accession No. | SEQ ID NO: (Nucleotide) | SEQ ID NO: (Amino Acid) |
|---|---|---|---|
| Soybean gamma-tocopherol Methyltransferase | sah1c.pk004.g2 | 11 | 12 |
| Soybean gamma-tocopherol Methyltransferase | sah1c.pk001.k8:fis | 13 | 14 |
| maize gamma-tocopherol methyltransferase | p0060.coran49r:fis | 15 | 16 |
| wheat gamma-tocopherol methyltransferase | wr1.pk0077.f1:fis | 17 | 18 |
| *lotus corniculatus* gamma-tocopherol methyltransferase | GenBank Accession No. DQ13360 | 19 | 20 |
| soybean gamma-tocopherol methyltransferase | GenBank Accession No. AY960126 | 21 | 22 |
| rice gamma-tocopherol methyltransferase | GenBank Accession No. XM467331 | 23 | 24 |
| *Brassica* gamma-tocopherol Methyltransferase | GenBank Accession No. AF381248 | 25 | 26 |
| *Perilla frutescens* gamma-tocopherol methyltransferase | GenBank Accession No. AF213481 | 27 | 28 |
| *Arabidopsis thaliana* gamma-tocopherol methyltransferase | GenBank Accession No. AF104220 | 29 | 30 |
| *Medicago truncatula* gamma-tocopherol Methyltransferase | GenBank Accession No. AY962639 | 31 | 32 |
| *Chlamydomonas* gamma-tocopherol methyltransferase | GenBank Accession No. AJ884948 | 33 | 34 |
| *Synechocystis* gamma-tocopherol methyltransferase | GenBank Accession No. NP_442492 | 35 | 36 |
| *Anabaena* gamma-tocopherol Methyltransferase | GenBank Accession No. BAB73502 | 37 | 38 |
| *Gloeobacter violaceus* gamma-tocopherol methyltransferase | GenBank Accession No. NP_926036 | 39 | 40 |

Limited information regarding enzymes catalyzing methylations of gamma- and delta-tocotrienol is available. U.S. Application No. 2003154513 discloses sequences derived from cotton, maize and the cyanobacteria *Anabaena*. These sequences show similarity to gamma-tocopherol methyltransferase genes from *Arabidopsis* (PCT Publication No. WO 99/04622) and soybean (PCT Publication No. WO 00/032757). The heterologously expressed enzyme from maize, a moncotyledoneous plant, showed almost equal activity with tocopherol and tocotrienol substrates. On the other hand, gamma-tocopherol methyltransferase orthologs from the dicotyledoneous plant cotton or blue-green algae showed only trace activities with tocotrienol substrates.

The terms "2-methyl-6-phytylbenzoquinol methyltransferase", "VTE3" and "MPBQMT", which are used interchangeably herein, refer to the enzyme that catalyzes the methylation of 2-methyl-6-phytylbenzoquinol (MPBQ) prior to cyclization. This reaction is an important step in tocotrienol biosynthesis and can result in the alteration of the tocol content and/or composition. 2-methyl-6-phytylbenzoquinol methyltransferase enzymes may include, but are not limited to, those shown in Table 3. The amino acid sequence of the enzyme in which the putative transit peptide has been removed is designated as "mature".

TABLE 3

2-Methyl-6-Phytylbenzoquinol Methyltransferase Enzymes

| Clone Name, NCBI GI No. or Patent Reference | Plant | SEQ ID NO |
|---|---|---|
| fds1n.pk003.e5 (FIS) | *Momordica charantia* | 54 |
| GI No. 108385436 | *Arabidopsis* | 61 |
| GI No. 157348021 | Grape | 62 |
| GI No. 80971672 | Sunflower | 63 |
| US2007061916 | Cotton | 64 |
| WO2003034812 | Soybean | 65 |
| WO2003034812 | Corn | 66 |
| GI No. 108385436-derived | *Arabidopsis* (mature) | 67 |
| WO2003034812 | Soybean (mature) | 68 |
| WO2003034812 | Corn (mature) | 69 |

The VTE3 (vitamin E defective) locus in *Arabidopsis* has been isolated and characterized, and encodes the *Arabidopsis* 2-methyl-6-phytylbenzoquinol methyltransferase (Cheng et al. 2003 Plant Cell 15:2343-2356). Recombinant DNA constructs encoding the *Arabidopsis* VTE3 and VTE4 polypeptides have been co-expressed in transgenic soybean (Van Eenennaam et al. 2003 Plant Cell 15:3007-3019).

The present invention concerns an isolated polynucleotide comprising a nucleotide sequence encoding a 2-methyl-6-phytylbenzoquinol methyltransferase polypeptide having at least 95% identity, based on the Clustal W method of alignment, when compared to SEQ ID NO:54 or 70.

The invention includes the use of the combination of HGGT, gamma-tocopherol methyltransferase and 2-methyl-6-phytylbenzoquinol methyltransferase enzymes to significantly increase the content of vitamin E-related antioxidants, specifically alpha- and beta-tocotrienol, in organisms including plants and microorganisms. The invention is not limited to the disclosed embodiments, but encompasses all enzymes which include these activities.

This invention also includes to the isolated complement of such polynucleotides, wherein the complement and the polynucleotide consist of the same number of nucleotides, and the nucleotide sequences of the complement and the polynucleotide have 100% complementarity.

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

In another embodiment, the present invention concerns a 2-methyl-6-phytylbenzoquinol methyltransferase polypeptide having an amino acid sequence that is at least 95% identical, based on the Clustal W method of alignment, to a polypeptide of SEQ ID NO:54 or 70.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of tocol content and/or composition in those cells.

The invention provides isolated nucleotide molecules comprising the combination of nucleotide sequences encoding HGGT, gamma-tocopherol methyltransferase and 2-methyl-6-phytylbenzoquinol methyltransferase. Also provided are isolated polypeptides encoded by such nucleotide sequences. The nucleotide sequences find use in methods for altering alpha- and beta-tocotrienols in a biological system such as a plant. The methods include improving the antioxidant activity of grain, altering tocotrienols in a plant or part thereof, and improving tocols in a host. The methods comprise transforming a plant or host with at least one nucleotide construct comprising at least a portion of at least one nucleotide sequence encoding HGGT, at least a portion of at least one nucleotide sequence encoding gamma-tocopherol methyltransferase and at least a portion of at least one nucleotide sequence encoding 2-methyl-6-phytylbenzoquinol methyltransferase. If desired, the nucleotide construct may additionally comprise at least one operably linked regulatory sequence that drives expression in the plant of interest. Such a nucleotide construct can be used to increase the expression of HGGT, gamma-tocopherol methyltransferase and 2-methyl-6-phytylbenzoquinol methyltransferase.

Also provided are novel compositions of seed and extracted oils. Seed and extracted oils are provided that have unexpectanly high levels of alpha-tocotrienol, beta-tocotrienol, or both. Seed or oil with high levels of alpha-tocotrienol have better bioavailabilty of alpha-tocotrienol as compared to other tocotrienol species (Kiyose et al. (2004) *J. Clin. Biochem. Nutr.* 35(1):47-52, entitiled—Distribution and metabolism of tocopherols and tocotrienols in vivo).

Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 4.

TABLE 4

Generalized Steps for Soybean Oil and By-product Production

| Process Step | Process | Impurities Removed and/or By-Products Obtained |
|---|---|---|
| # 1 | soybean seed | |
| # 2 | oil extraction | Meal |
| # 3 | degumming | Lecithin |
| # 4 | alkali or physical refining | gums, free fatty acids, pigments |
| # 5 | water washing | Soap |
| # 6 | bleaching | color, soap, metal |
| # 7 | (hydrogenation) | |
| # 8 | (winterization) | Stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995).

Among the many applications of improved tocols, tocotrienols and antioxidant activity are improved storage of grain, improved stability of oil extracted from grain, benefits to humans consuming the grain, improved meat quality from animals consuming the grain, and the production of novel tocols or tocotrienols for cosmetic, industrial and/or nutraceutical use (U.S. Application No. 2004266862; Karunanandaa et al. (2005) *Metab. Eng.* 7:384-400). It is also known that the presence of tocols in plant vegetative green tissue such as leaf tissue is necessary to protect the plant from the photo-oxidative damage induced directly and indirectly by the production of free oxygen radicals in the chloroplast during oxygenic photosynthesis. It is therefore likely that ectopic expression of tocotrienols in green plant tissue, such as leaf tissue, in addition to the normal tocopherol content of the leaf will lead to an increase ability to withstand such photo-oxidative damage, and thus lead to an increase in the photosynthetic capacity of the plant. This would translate to an increase in harvestable yield for the plant over the entire growing season.

The nucleotide construct of the invention may additionally comprise at least one regulatory sequence that drives expression in a host or plant. Optional regulatory sequences include, for maize, an embryo preferred promoter such as promoters for the 16 kDa and 18 kDa oleosin genes, an endosperm preferred promoter, such as the promoter for the 10 kDa zein gene, and a vegetative promoter such as promoters for ubiquitin genes.

If desired, two or more of such nucleotide sequences may be linked or joined together to form one polynucleotide molecule, and such a polynucleotide may be used to transform a plant. For example, a nucleotide construct comprising a nucleotide sequence encoding an HGGT can be linked with another nucleotide sequence encoding the same or another HGGT. Nucleotide sequences encoding both HGGT and gamma-tocopherol methyltransferase may also be linked in a nucleotide construct. Additionally, nucleotide sequences encoding HGGT, gamma-tocopherol methyltransferase and 2-methyl-6-phytylbenzoquinol methyltransferase may also be linked in a nucleotide construct. Similarly, the three nucleotide sequences can be provided on different nucleotide constructs, and each of the separate nucleotide sequences can be operably linked to at least one regulatory sequence that drives expression in a plant. For example, a construct may be used that increases total HGGT activity and decreases total HPT activity, thereby resulting in shunting the pathway towards the production of tocotrienols and decreased production of tocopherols.

An alternative strategy may also be used. If separate nucleotide constructs are employed for an HGGT nucleotide sequence, a gamma-tocopherol methyltransferase nucleotide sequence and a 2-methyl-6-phytylbenzoquinol methyltransferase nucleotide sequence, three individual plants may be transformed with the nucleotide constructs, and the plants may then be crossed to produce progeny having the desired genotype of HGGT, gamma-tocopherol methyltransferase and 2-methyl-6-phytylbenzoquinol methyltransferase nucleotide sequences (i.e., also referred to as genetic stacks).

Additionally, a construct to down-regulate the geranylgeranyl reductase responsible for producing phytol pyrophosphosphate, one of the precursors for tocopherol biosynthesis, may be linked in cis with a construct to express HGGT. The result of this manipulation would be an increased pool size of geranylgeranyl-pyrophosphate and a corresponding increase of flux into the tocotrienol biosynthetic pathway. Flux into tocotrienols can also be increased by increasing flux of carbon into the shikimate pathway and non-mevalonate pathway of isoprenoid biosynthesis. Specifically, this flux can be accomplished through chloroplast-targeted expression of genes such as bifunctional chorismate mutase-prephenate dehydrogenase (TYRA) (from bacteria) and p-hydroxyphenylpyruvate dioxygenase (HPPD) genes from plants (Karunanandaa et al. (2005) *Metab. Eng.* 7:384-400).

Nucleic acid molecules of the present invention are preferably recombinant nucleic acid molecules (or may also be referred to as recombinant DNA constructs). As used herein, "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

As used herein, "recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant nucleic acid molecule" are used interchangeably herein.

The methods of the present invention can be employed to alter tocols or tocotrienols in any plant or part thereof, and antioxidant activity may thereby be altered. Plants that may be used in the invention include, but are not limited to, field crops (e.g., alfalfa, barley, bean, maize, canola, cotton, flax, pea, rice, rye, safflower, sorghum, oats, millet, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); and fruit and nut crops (e.g., almond, apple, apricot, banana, blackberry, blueberry, cacao, cherry, coconut, cranberry, date, fajoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon) and *Arabidopsis*. Some methods of the invention involve altering the antioxidant levels in grain and other parts of a plant that may be subjected to post-harvest processing. With post-harvest processing, the tocols or tocotrienols so produced can be a valuable source of recovery for millers and other processors.

Grain or vegetable oil derived from transgenic plants containing elevated levels of alpha- and beta-tocotrienol may be fed to livestock and poultry to improve the oxidative stability of meat products. Examples of improvements with practical benefit include increased color stability of fresh beef during retail display and enhanced flavor stability of precooked meat products stored under refrigeration. These and other quality-related improvements may be expected because tocotrienols function as chain-breaking free radical scavengers in muscle tissue, and thus reduce oxidative reactions that degrade meat quality and reduce shelf life.

For example, improved beef quality can be demonstrated by feeding cattle a diet formulated with at least about 300-ppm of total alpha- and beta-tocotrienol obtained from high-tocotrienol transgenic grain or vegetable oil for at least 100 days. For comparison, a group of cattle reared on a standard diet (no additional tocotrienol) under otherwise identical conditions can serve as the control treatment ("control group"). To assess fresh meat color stability, ribeye steaks harvested from each animal are individually packaged in foam trays with PVC overwrap and placed under simulated retail display for seven days. Fresh steak color is subjectively evaluated by trained panelists on a graded scale for visual color intensity and discoloration. Color is also evaluated instrumentally using a HunterLab MiniScan™ Spectrophotometer or similar device to assess the "a* value", which is a measure of the degree of redness. Results of these assays demonstrate that over time steaks from cattle fed a high tocotrienol diet, on average, exhibit better subjective visual scores and higher (i.e., better) a* instrumental values than ribeye steaks from the control group over time. The improvement in color stability extends retail display time and thus reduces the amount of fresh product discounted and discarded due to color deterioration. Other fresh beef products, including ground beef, will also exhibit improved color stability with and thus provide a similar benefit to retailers. (See also WO Publication No. 2005/002358, herein incorporated in its entirety by reference).

Methods for assessing tocopherol content and tocopherol composition (including tocopherol activity) are known in the art. Tocopherol content and composition may be measured by HPLC in combination with fluorescence detection. Such methods are described in numerous literature references (e.g., Kamal-Eldi A., Gorgen S., Pettersson J., Lampi A. M. (2000) *J. Chromatogr. A* 881:217-227; Bonvehi J. S., Coll F. V., Rius I. A. (2000) *J. AOAC Intl.* 83:627-634; Goffman F. D. and Böhme T. (2001) *J. Agric. Food Chem.* 49:4990-4994). Such methods typically involve the resolution of tocopherol molecular species contained in complex mixtures by use of a normal or reverse phase HPLC matrix. Eluted tocopherol molecular species are then detected by fluorescence of the chromanol head group with an excitation wavelength typically in the range of 290 to 295 nm and an emission wavelength typically in the range of 325 to 335 nm. Using this methodology, the composition of a tocopherol mixture can be determined by comparing the retention times of separated molecular species with those of known standards. The content of each tocopherol molecular species can be measured by the relative intensity of its fluorescence emission at the selected wavelength. The absolute amount of each tocopherol species can be determined by measuring the intensity of fluorescence emission relative to that of an internal standard, which is added in a known amount to the tocopherol mixture prior to HPLC analysis. A suitable internal standard can include a tocopherol analog that is not normally found in nature (e.g., 5,7-dimethyltocol) or a naturally occurring tocopherol molecular species that is not present in a given tocopherol mixture. The total tocopherol content of a complex mixture of compounds can be derived by summing the absolute amount of each of the component tocopherol molecular species as determined by HPLC analysis.

Methods for assessing tocotrienol content and tocotrienol composition (including tocotrienol activity) are known in the art. Tocotrienol content and composition may be measured by HPLC using methods described above for the analysis of tocopherol content and composition. Using HPLC techniques described in Example 3 and elsewhere (e.g., Podda M., Weber C., Traber M. G., Packer L. (1996) *J. Lipid Res.* 37:893-901), tocotrienol molecular species can be readily resolved from tocopherol molecular species in a complex mixture. The occurrence and structural identification of tocotrienols in a complex mixture can be determined by gas chromatography-mass spectrometry as described by Frega N., Mozzon M., and Bocci F. (1998) *J. Amer. Oil Chem. Soc.* 75:1723-1728.

In addition, lipophilic antioxidant activity may be measured by assays including the inhibition of the coupled autooxidation of linoleic acid and β-carotene and oxygen radical absorbance capacity (ORAC) as described elsewhere (Serbinova E. A. and Packer L. (1994) *Meth. Enzymol.* 234:354-366; Emmons C. L., Peterson D. M., Paul G. L. (1999) *J. Agric. Food Chem.* 47:4894-4898); Huang D et al (2002) *J. Agric. Food Chem.*). Such methods typically involve measuring the ability of antioxidant compounds (i.e., tocols) in test materials to inhibit the decline of fluorescence of a model substrate (fluorescein, phycoerythrin) induced by a peroxyl radical generator (2',2'-azobis[20amidinopropane]dihydrochloride).

The invention encompasses isolated or substantially purified nucleic acid or polypeptide compositions. An "isolated" or "purified" nucleic acid molecule or polypeptide, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.3 kb or 0.1 kb of nucleotide sequences that naturally flank the nucleic acid molecule in genomic DNA of the cell from which the nucleic acid is derived. A polypeptide that is substantially free of cellular material includes preparations of polypeptide having less than about 30%, 20%, 10%, 5%, (by dry weight) of contaminating polypeptide. When the polypeptide of the invention or biologically active portion thereof is recombinantly produced, preferably culture medium represents less than about 30%, 20%, 10%, 5%, 3% or 1% (by dry weight) of chemical precursors or non-polypeptide-of-interest chemicals.

Fragments and variants of the disclosed nucleotide sequences and polypeptides encoded thereby are also encompassed by the present invention. By "fragment" is intended a portion of the nucleotide sequence or a portion of the amino acid sequence. Functional fragments of a nucleotide sequence may encode polypeptide fragments that retain the biological activity of the native protein and hence HGGT activity and/or gamma-tocopherol methyltransferase activity and/or 2-methyl-6-phytylbenzoquinol methyltransferase activity. Alternatively, fragments of a nucleotide sequence that are useful as hybridization probes generally do not encode polypeptides retaining biological activity. Thus, fragments of a nucleotide sequence may range from at least about 20 nucleotides, about 30 nucleotides, about 50 nucleotides, about 70 nucleotides, about 100 nucleotides, about 150 nucleotides and up to the full-length nucleotide sequence encoding the polypeptides of the invention.

A fragment of a HGGT nucleotide sequence that encodes a biologically active portion of an HGGT polypeptide of the invention will encode at least 15, 25, 30, 50, 75, 100, or 125 contiguous amino acids, or up to the total number of amino acids present in a full-length HGGT polypeptide of the invention (for example, 407, 408, 404, 380 and 361 amino acids for SEQ ID NO:2, 4, 6, 8 and 10, respectively). Fragments of a HGGT nucleotide sequence that are useful as hybridization probes or PCR primers generally need not encode a biologically active portion of an HGGT polypeptide.

Thus, a fragment of an HGGT nucleotide sequence may encode a biologically active portion of an HGGT polypeptide, or it may be a fragment that can be used as a hybridization probe or PCR primer using methods disclosed below. A biologically active portion of an HGGT polypeptide can be prepared by isolating a portion of one of the HGGT nucleotide sequences of the invention, expressing the encoded portion of the HGGT polypeptide (e.g., by recombinant expression in vitro) and assessing the activity of the encoded portion of the HGGT polypeptide.

Nucleic acid molecules that are fragments of an HGGT nucleotide sequence comprise at least 16, 20, 50, 75, 100, 150, 200, 250, 300, 350, 400, 450, 500, 550, 600, 650, or 700 nucleotides, or up to the number of nucleotides present in a full-length HGGT nucleotide sequence disclosed herein (for example, 1457, 1365, 1242, 1730, and 1769 nucleotides for SEQ ID NO:1, 3, 5, 7 and 9, respectively).

Likewise, a fragment of a gamma-tocopherol methyltransferase nucleotide sequence that encodes a biologically active portion of a gamma-tocopherol methyltranferase polypeptide of the invention will encode at least 15, 25, 30, 50, 75, 100, or 125 contiguous amino acids, or up to the total number of amino acids present in a full-length gamma-tocopherol methyltranferase polypeptide of the invention. Fragments of a gamma-tocopherol methyltranferase nucleotide sequence that are useful as hybridization probes or PCR primers generally need not encode a biologically active portion of a gamma-tocopherol methyltransferase polypeptide.

Thus, a fragment of an gamma-tocopherol methyltranferase nucleotide sequence may encode a biologically active portion of an gamma-tocopherol methyltranferase polypeptide, or it may be a fragment that can be used as a hybridization probe or PCR primer using methods disclosed below. A biologically active portion of an gamma-tocopherol methyltranferase polypeptide can be prepared by isolating a portion of one of the gamma-tocopherol methyltranferase nucleotide sequences of the invention, expressing the encoded portion of the gamma-tocopherol methyltranferase polypeptide (e.g., by recombinant expression in vitro) and assessing the activity of the encoded portion of the gamma-tocopherol methyltranferase polypeptide.

Nucleic acid molecules that are fragments of an gamma-tocopherol methyltranferase nucleotide sequence comprise at least 16, 20, 50, 75, 100, 150, 200, 250, 300, 350, 400, 450, 500, 550, 600, 650, or 700 nucleotides, or up to the number of nucleotides present in a full-length gamma-tocopherol methyltranferase nucleotide sequence disclosed herein.

Likewise, a fragment of a 2-methyl-6-phytylbenzoquinol methyltransferase nucleotide sequence that encodes a biologically active portion of a 2-methyl-6-phytylbenzoquinol methyltransferase polypeptide of the invention will encode at least 15, 25, 30, 50, 75, 100, or 125 contiguous amino acids, or up to the total number of amino acids present in a full-length 2-methyl-6-phytylbenzoquinol methyltransferase polypeptide of the invention. Fragments of a 2-methyl-6-phytylbenzoquinol methyltransferase nucleotide sequence that are useful as hybridization probes or PCR primers generally need not encode a biologically active portion of a gamma-tocopherol methyltransferase polypeptide.

Thus, a fragment of a 2-methyl-6-phytylbenzoquinol methyltransferase nucleotide sequence may encode a biologically active portion of a 2-methyl-6-phytylbenzoquinol methyltransferase polypeptide, or it may be a fragment that can be used as a hybridization probe or PCR primer using methods disclosed below. A biologically active portion of a 2-methyl-6-phytylbenzoquinol methyltransferase polypeptide can be prepared by isolating a portion of one of the 2-methyl-6-phytylbenzoquinol methyltransferase nucleotide sequences of the invention, expressing the encoded portion of the 2-methyl-6-phytylbenzoquinol methyltransferase polypeptide (e.g., by recombinant expression in vitro) and assessing the activity of the encoded portion of the 2-methyl-6-phytylbenzoquinol methyltransferase polypeptide.

Nucleic acid molecules that are fragments of an 2-methyl-6-phytylbenzoquinol methyltransferase nucleotide sequence comprise at least 16, 20, 50, 75, 100, 150, 200, 250, 300, 350, 400, 450, 500, 550, 600, 650, or 700 nucleotides, or up to the number of nucleotides present in a full-length 2-methyl-6-phytylbenzoquinol methyltransferase nucleotide sequence disclosed herein.

By "variants" is intended substantially similar sequences. For nucleotide sequences, conservative variants include those sequences that, because of the degeneracy of the genetic code, encode the amino acid sequence of one of the HGGT and/or gamma-tocopherol methyltransferase and/or 2-methyl-6-phytylbenzoquinol methyltransferase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an HGGT and/or gamma-tocopherol methyltransferase and/or 2-methyl-6-phytylbenzoquinol methyltransferase polypeptide of the invention. Generally, variants of a particular nucleotide sequence of the invention will have at least about 80% generally at least about 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" polypeptide is intended a polypeptide derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Variant polypeptides encompassed by the present invention are biologically active, that is they continue to possess the desired biological activity of the native polypeptide, that is, HGGT and/or gamma-tocopherol methyltransferase and/or 2-methyl-6-phytylbenzoquinol methyltransferase activity as described herein. Such variants may result from, for example, genetic polymorphism or from human manipulation. Biologically active variants of a native HGGT and/or gamma-tocopherol methyltransferase and/or 2-methyl-6-phytylbenzoquinol methyltransferase polypeptide of the invention will have at least about 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native polypeptide as determined by sequence alignment programs described elsewhere herein using default parameters. A biologically active variant of a polypeptide of the invention may differ from that polypeptide by as few as 1-15 amino acid residues, as few as 1-10, such as 6-10, as few as 5, as few as 4, 3, 2, or even 1 amino acid residue.

The polypeptides of the invention may be altered in various ways including amino acid substitutions, deletions, truncations, and insertions. Methods for such manipulations are generally known in the art. For example, amino acid sequence variants of the HGGT and/or gamma-tocopherol methyltransferase and/or 2-methyl-6-phytylbenzoquinol methyltransferase polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the polypeptides of the invention encompass both naturally occurring polypeptides as well as variations and modified forms thereof. Such variants will continue to possess the desired HGGT and/or gamma-tocopherol methyltransferase and/or 2-methyl-6-phytylbenzoquinol methyltransferase activity. Preferably, the mutations that will be made in the DNA encoding the variant will not place the sequence out of reading frame and preferably will not create complementary regions that could produce secondary mRNA structure. See, EP Patent Application Publication No. 75,444.

The deletions, insertions, and substitutions of the polypeptide sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays. That is, the activity can be evaluated by assays for HGGT and/or gamma-tocopherol methyltransferase and/or 2-methyl-6-phytylbenzoquinol methyltransferase activity.

Variant nucleotide sequences and polypeptides also encompass sequences and polypeptides derived from a mutagenic and recombinogenic procedure such as DNA shuffling. With such a procedure, one or more different HGGT and/or gamma-tocopherol methyltransferase and/or 2-methyl-6-phytylbenzoquinol methyltransferase coding sequences can be manipulated to create a new HGGT and/or gamma-tocopherol methyltransferase and/or 2-methyl-6-phytylbenzoquinol methyltransferase polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the HGGT polynucleotides of the invention and/or other HGGT genes to obtain a new gene coding for a polypeptide with an improved property of interest, such as an increased $K_m$ in the case of an enzyme. Likewise, using this approach, sequence motifs encoding a domain of interest may be shuffled between the gamma-tocopherol methyltransferase polynucleotides of the invention and/or other gamma-tocopherol methyltransferase genes to obtain a new gene coding for a polypeptide with an improved property of interest, such as an increased $K_m$ in the case of an enzyme. Likewise, using this approach, sequence motifs encoding a domain of interest may be shuffled between 2-methyl-6-phytylbenzoquinol methyltransferase polynucleotides of the invention and/or other 2-methyl-6-phytylbenzoquinol methyltransferase genes to obtain a new gene coding for a polypeptide with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other monocots or dicots. In this manner, methods such as PCR, hybridization, and the like can be used to identify such sequences based on their sequence homology to the sequences set forth herein. Sequences isolated based on their sequence identity to the entire HGGT and/or gamma-tocopherol methyltransferase and/or 2-methyl-6-phytylbenzoquinol methyltransferase nucleotide sequences set forth herein or to fragments thereof are encompassed by the present invention. Such sequences include sequences that are orthologs of the disclosed sequences. By "orthologs" is intended polynucleotides derived from a common ancestral gene and which are found in different species as a result of speciation. Polynucleotides found in different species are considered orthologs when their nucleotide sequences and/or their encoded polypeptide sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

For clarification, "PCR" or "polymerase chain reaction" is a technique for the synthesis of large quantities of specific DNA segments, and consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the HGGT and/or gamma-tocopherol methyltransferase sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire HGGT and/or gamma-tocopherol methyltransferase and/or 2-methyl-6-phytylbenzoquinol methyltransferase sequence disclosed herein, or one or more portions thereof, may be used as a probe capable of specifically hybridizing to corresponding HGGT and/or gamma-tocopherol methyltransferase and/or 2-methyl-6-phytylbenzoquinol methyltransferase sequences and messenger RNAs. To achieve specific hybridization under a variety of conditions, such probes include sequences that are unique among HGGT and/or gamma-tocopherol methyltransferase and/or 2-methyl-6-phytylbenzoquinol methyltransferase sequences and are preferably at least about 10 nucleotides in length, and most preferably at least about 20 nucleotides in length. Such probes may be used to amplify corresponding HGGT and/or gamma-tocopherol methyltransferase and/or 2-methyl-6-phytylbenzoquinol methyltransferase sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated sequences that encode a protein with HGGT and/or gamma-tocopherol methyltransferase and/or 2-methyl-6-phytylbenzoquinol methyltransferase activity and which hybridize under stringent conditions to the HGGT and/or gamma-tocopherol methyltransferase and/or 2-methyl-6-phytylbenzoquinol methyltransferase sequences disclosed herein, or to fragments thereof, are encompassed by the present invention.

Nucleotides (usually found in their T-monophosphate form) are often referred to herein by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R' for purines (A or G), "Y" for pyrimidines (C or T), "K" for G or T, "W" for A or T, "H" for A or C or T, "D" for A or G or T, "M" for A or C, "S" for C or G, "V" for A or C or G, "B" for C or G or T "I" for inosine, and "N" for A, C, G, or T.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988), supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990), supra. BLAST nucleotide searches can be performed with the BLASTN program, score=100, wordlength=12, to obtain nucleotide sequences homologous to a nucleotide sequence encoding a polypeptide of the invention. BLAST polypeptide searches can be performed with the BLASTX program, score=50, wordlength=3, to obtain amino acid sequences homologous to a polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for polypeptides) can be used. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for polypeptide sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

Alternatively, for purposes of the present invention, comparison of nucleotide or polypeptide sequences for determination of percent sequence identity to the HGGT, gamma-tocopherol methyltransferase or 2-methyl-6-phytylbenzoquinol methyltransferase sequences disclosed herein is preferably made using Clustal W found in the MEGALIGN® program of the LASERGENE® bioinformatics computing suite (DNASTAR® Inc., Madison, Wis.), with the following default parameters. The "default parameters" are the parameters pre-set by the manufacturer of the program. For amino acid sequence comparisons, default parameters of Gap Penalty of 10, a Gap Length Penalty of 0.20, a delay divergent sequence of 30%, and a DNA Transition Weight of 0.50 are used for multiple alignments; for pairwise alignments the default parameters are Gap Penalty of 10.0 and Gap Length of 0.10. Alternatively, amino acid sequence comparisons can be made with Clustal V (described by Higgins and Sharp (1989) *CABIOS.* 5:151-153) and found in the MEGALIGN® program of the LASERGENE® bioinformatics computing suite (DNASTAR® Inc., Madison, Wis.). The default parameters of Clustal V for multiple alignments correspond to GAP PENALTY=10 and GAP LENGTH PENALTY=10, while for pairwise alignments they are KTUPLE=1, GAP PENALTY=3, WINDOW=5 and DIAGONALS SAVED=5. After alignment of the sequences, using the Clustal V program, it is possible to obtain a "percent identity" by viewing the "sequence distances" table on the same program. For nucleotide sequence comparisons, a Gap Penalty of 10 and Gap Length Penalty of 10 can be used for multiple alignments and a KTUPLE of 2, Gap Penalty of 5, Window of 4 and Diagonals Saved of 4 can be used for pairwise alignments. Any equivalent program can also be used to determine percent sequence identity. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of polypeptides encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one polypeptide, or at least one RNA, such as, for example, an antisense RNA that is complementary to at least a portion of an mRNA. Typically such a nucleotide construct is comprised of a coding sequence for a polypeptide or an RNA operably linked to 5' and 3' transcriptional regulatory regions. Alternatively, it is also recognized that the methods of the invention may employ a nucleotide construct that is not capable of directing, in a transformed plant, the expression of a polypeptide or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, homologous recombination, chimeric vectors, chimeric mutational vectors, chimeric repair vectors, mixed-duplex oligonucleotides, self-complementary chimeric oligonucleotides, and recombinogenic oligonucleobases. See, U.S. Pat. Nos. 5,565,350; 5,731,181; 5,756,325; 5,760,012; 5,795,972; and 5,871,984; all of which are herein incorporated by reference. See also, PCT Publication No. WO 98/49350, PCT Publication No. WO 99/07865, PCT Publication No. WO 99/25821, PCT Publication No. WO03093428, Jeske et al. (2001) *EMBO* 20:6158-6167, and Beetham et al. (1999) *Proc. Natl. Acad. Sci. USA* 96:8774-8778; herein incorporated by reference.

The HGGT, gamma-tocopherol methyltransferase and 2-methyl-6-phytylbenzoquinol methyltransferase sequences of the invention are provided in expression cassettes for expression in the plant of interest. The cassette(s) will include at least one 5' and 3' regulatory sequences operably linked to a HGGT and/or gamma-tocopherol methyltransferase and/or 2-methyl-6-phytylbenzoquinol methyltransferase nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two polypeptide coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the HGGT and/or gamma-tocopherol methyltransferase and/or 2-methyl-6-phytylbenzoquinol methyltransferase nucleotide sequence to be under the transcriptional regulation of the regulatory regions. The expression cassette may additionally contain selectable marker genes.

The expression cassette will include in the 5'-3' direction of transcription, a transcriptional and translational initiation region, a HGGT and/or gamma-tocopherol methyltransferase and/or 2-methyl-6-phytylbenzoquinol methyltransferase polynucleotide sequence of the invention, and a transcriptional and translational termination region functional in plants. These genes can be added either alone or in combination. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of HGGT and/or gamma-tocopherol methyltransferase and/or 2-methyl-6-phytylbenzoquinol methyltransferase in the plant, plant cell or other host. Thus, the phenotype of the plant, plant cell or other host is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell*

2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, chemically regulated, tissue-preferred, or other promoters for expression in plants.

Such constitutive promoters include, for example, the core promoter of the Rsyn7 promoter and other constitutive promoters disclosed in PCT Publication No. WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemically regulated promoters can be used to modulate the expression of a gene in a plant through the application of an exogenous chemical regulator. Depending upon the objective, the promoter may be a chemical inducible promoter, where application of the chemical induces gene expression, or a chemical repressible promoter, where application of the chemical represses gene expression. Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced HGGT and/or gamma-tocopherol methyltransferase and/or 2-methyl-6-phytylbenzoquinol methyltransferase expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2): 207-218 (soybean root-preferred glutamine synthetase gene); Keller and Baumgartner (1991) *Plant Cell* 3(10):1051-1061 (root-preferred control element in the GRP 1.8 gene of French bean); Sanger et al. (1990) *Plant Mol. Biol.* 14(3):433-443 (root-preferred promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-preferred promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-preferred promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root preferred in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also the promoters found in the following: End1 and End2 (WO 00/12733), Lec1 (WO 2002/42424), Jip1 (WO 2002/42424), EAP1 (U.S. Patent Publication No. 2004/0210043), ODP2 (U.S. Patent Publication No. 2005/0223432); all of which are herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts or other plastids. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The HGGT and/or gamma-tocopherol methyltransferase and/or 2-methyl-6-phytylbenzoquinol methyltransferase polypeptides of the invention can be targeted to specific compartments within the plant cell. Methods for targeting polypeptides to a specific compartment are known in the art. Generally, such methods involve modifying the nucleotide sequence encoding the polypeptide in such a manner as to add or remove specific amino acids from the polypeptide encoded thereby. Such amino acids comprise targeting signals for targeting the polypeptide to a specific compartment such as, for example, a the plastid, the nucleus, the endoplasmic reticulum, the vacuole, the mitochondrion, the peroxisome, the Golgi apparatus, and for secretion from the cell. Targeting sequences for targeting a polypeptide to a specific cellular compartment, or for secretion, are known to those of ordinary skill in the art. Chloroplast-targeting or plastid-targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin B phosphotransferase, as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

Other genes that could serve as selectable or scorable markers in the recovery of transgenic events but that might not be required in the final product would include, but are not limited to: GUS (β-glucoronidase), Jefferson (1987) Plant Mol. Biol. Rep. 5:387); fluorescent proteins, such as, GFP (green florescence protein), YFP (yello florescence protein), RFP (red florescence protein) and CYP (cyan florescence protein), WO 00/34321, WO 00/34526, WO 00/34323, WO 00/34322, WO 00/34318, WO 00/34319, WO 00/34320, WO 00/34325, WO 00/34326, WO 00/34324, Chalfie et al. (1994) Science 263:802; luciferase, Teeri et al. (1989) EMBO J. 8:343; and the maize genes encoding for anthocyanin production, Ludwig et al. (1990) Science 247:449.

The above list of selectable marker genes is not meant to be limiting. Any selectable marker gene can be used in the present invention.

The invention involves transforming host cells with the nucleotide constructs of the invention. Generally, the nucleotide construct will comprise a HGGT nucleotide and/or gamma-tocopherol methyltransferase and/or 2-methyl-6-phytylbenzoquinol methyltransferase sequence of the invention, either a full length sequence or functional fragment thereof, operably linked to a promoter that drives expression in the host cell of interest. Host cells include, but are not limited to: plant cells; animal cells; fungal cells, particularly yeast cells; and bacterial cells.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (PCT Publication No. 00/028058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The nucleotide constructs of the invention may also be introduced into plants by contacting plants with a virus or viral nucleic acids. Generally, such methods involve incorporating a nucleotide construct of the invention within a viral DNA or RNA molecule. It is recognized that a HGGT and/or gamma-tocopherol methyltransferase and/or 2-methyl-6-phytylbenzoquinol methyltransferase of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing nucleotide constructs into plants and expressing a polypeptide encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

As used herein, "transformed plants" include those plants directly transformed as provided herein, as well as plants that have the directly transformed plants in their pedigree and retain the change in genotype, such as the inclusion of the expression cassette, created by the original transformation. The terms "transformed plants" and "transgenic plants" are used interchangeably herein.

The present invention may be used for transformation of any plant species, including, but not limited to, maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, maize, alfalfa, sunflower, *Brassica*, soybean, cotton, safflower, peanut, sorghum, wheat, barley, rice, sorghum, rye, millet, tobacco, etc.), more preferably cereal plants, yet more preferably maize, wheat, barley, rice, sorghum, rye and millet plants.

In some embodiments, the activity of a gene of the invention is reduced or eliminated by transforming a plant cell with an expression cassette expressing a polynucleotide that inhibits the expression of a target gene. The polynucleotide may inhibit the expression of one or more target genes directly, by preventing translation of the target gene messenger RNA, or indirectly, by encoding a polypeptide that inhibits the transcription or translation of a gene encoding the target gene. Methods for inhibiting or eliminating the expression of a gene in a plant are well known in the art, and any such method may be used in the present invention to inhibit the expression of one or more plant genes, such as, HGGT and/or gamma-tocoperol methyltransferase and/or 2-methyl-6-phytylbenzoquinol methyltransferase.

In accordance with the present invention, the expression of a target gene protein is inhibited if the protein level of the target gene is statistically lower than the protein level of the same target gene in a plant that has not been genetically modified or mutagenized to inhibit the expression of that target gene. In particular embodiments of the invention, the protein level of the target gene in a modified plant according to the invention is less than 95%, less than 90%, less than 85%, less than 80%, less than 75%, less than 70%, less than 65%, less than 60%, less than 50%, less than 40%, less than 30%, less than 20%, less than 10%, or less than 5% of the protein level of the same target gene in a plant that is not a mutant or that has not been genetically modified to inhibit the expression of that target gene. The expression level of the target gene may be measured directly, for example, by assaying for the level of target gene expressed in the maize cell or plant, or indirectly, for example, by measuring the activity of the target gene enzyme in the maize cell or plant. The activity of a target gene protein is "eliminated" according to the invention when it is not detectable by at least one assay method described elsewhere herein.

Many methods may be used to reduce or eliminate the activity of a target gene. More than one method may be used to reduce the activity of a single target gene. In addition, combinations of methods may be employed to reduce or eliminate the activity of two or more different target genes. Non-limiting examples of methods of reducing or eliminating the expression of a plant target are given below.

Many techniques for gene silencing are well known to one of skill in the art, including but not limited to knock-outs, such as, by insertion of a transposable element such as Mu (Vicki Chandler, *The Maize Handbook* ch. 118 (Springer-Verlag 1994)), other genetic elements such as a FRT, Lox or other site specific integration site, alteration of the target gene by homologous recombination (Bolon, B. Basic Clin. Pharmacol. Toxicol. 95:4, 12, 154-61 (2004); Matsuda and Alba, A., Methods Mol. Bio. 259:379-90 (2004); Forlino, et. al., J. Biol. Chem. 274:53, 37923-30 (1999), antisense technology (see, e.g., Sheehy et al. (1988) *PNAS* USA 85:8805-8809; and U.S. Pat. Nos. 5,107,065; 5,453,566; and 5,759,829; U.S. Patent Publication No. 20020048814); sense suppression (e.g., U.S. Pat. No. 5,942,657; Flavell et al. (1994) *Proc. Natl. Acad. Sci. USA* 91: 3490-3496; Jorgensen et al. (1996) *Plant Mol. Biol.* 31: 957-973; Johansen and Carrington (2001) *Plant Physiol.* 126: 930-938; Broin et al. (2002) *Plant Cell* 14: 1417-1432; Stoutjesdijk et at (2002) *Plant Physiol.* 129: 1723-1731; Yu et al. (2003) *Phytochemistry* 63: 753-763; and U.S. Pat. Nos. 5,034,323, 5,283,184, and 5,942,657; U.S. Patent Publication No. 20020048814); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS* USA 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al., (1988) *Nature* 334: 585-591, U.S. Pat. No. 4,987,071); hairpin structures (Smith et al. (2000) *Nature* 407:319-320; Waterhouse et al. (1998) *Proc. Natl. Acad. Sci. USA* 95: 13959-13964, Liu et al. (2002) *Plant Physiol.* 129: 1732-1743, Waterhouse and Helliwell (2003) *Nat. Rev. Genet.* 4:29-38; Chuang and Meyerowitz (2000) *Proc. Natl. Acad. Sci. USA* 97: 4985-4990; Stoutjesdijk et al. (2002) *Plant*

*Physiol.* 129: 1723-1731; Panstruga et al. (2003) *Mol. Biol. Rep.* 30: 135-140; Smith et al. (2000) *Nature* 407: 319-320; Smith et al. (2000) *Nature* 407:319-320; Wesley et al. (2001) *Plant J.* 27: 581-590; Wang and Waterhouse (2001) *Curr. Opin. Plant Biol.* 5: 146-150; Waterhouse and Helliwell (2003) *Nat. Rev. Genet.* 4: 29-38; Helliwell and Waterhouse (2003) *Methods* 30: 289-295; Pandolfini et al. *BMC Biotechnology* 3: 7; U.S. Patent Publication No. 20030180945; U.S. Patent Publication No. 20030175965; WO 99/49029; WO 99/53050; WO 99/61631; and WO 00/49035); transcriptional gene silencing (TGS) (Aufsatz et al. (2002) *Proc. Nat'l. Acad. Sci.* 99 (Suppl. 4):16499-16506; Mette et al. (2000) *EMBO J.* 19(19):5194-5201; microRNA (Aukerman & Sakai (2003) Plant Cell 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); methods of using amplicons (Angell and Baulcombe (1997) *EMBO J.* 16: 3675-3684, Angell and Baulcombe (1999) *Plant J.* 20: 357-362, and U.S. Pat. No. 6,646,805); polynucleotides that encode an antibody that binds to protein of interest (Conrad and Sonnewald (2003) *Nature Biotech.* 21: 35-36); transposon tagging (Maes et al. (1999) *Trends Plant Sci.* 4: 90-96; Dharmapuri and Sonti (1999) *FEMS Microbiol. Lett.* 179: 53-59; Meissner et al. (2000) *Plant J.* 22: 265-274; Phogat et al. (2000) *J. Biosci.* 25: 57-63; Walbot (2000) *Curr. Opin. Plant Biol.* 2: 103-107; Gai et al. (2000) *Nucleic Acids Res.* 28: 94-96; Fitzmaurice et al. (1999) *Genetics* 153: 1919-1928; the TUSC process for selecting Mu insertions in selected genes (Bensen et al. (1995) *Plant Cell* 7: 75-84; Mena et al. (1996) *Science* 274: 1537-1540; and U.S. Pat. No. 5,962,764); other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted (Ohshima et al. (1998) *Virology* 243: 472-481; Okubara et al. (1994) *Genetics* 137: 867-874; and Quesada et al. (2000) *Genetics* 154: 421-436; TILLING (Targeting Induced Local Lesions In Genomes) (McCallum et al. (2000) *Nat. Biotechnol.* 18: 455-457) and other methods or combinations of the above methods known to those of skill in the art. Each reference is herein incorporated by reference An expression cassette is designed to reduce activity of the target gene may express an RNA molecule corresponding to all or part of a messenger RNA encoding a target gene in the sense or antisense orientation or a combination of both sense and antisense. Overexpression of the RNA molecule can result in reduced expression of the native gene. Accordingly, multiple plant lines transformed with the sense suppression expression cassette are screened to identify those that show the greatest inhibition of the target gene's expression.

The polynucleotide used for target gene suppression may correspond to all or part of the sequence encoding the target gene, all or part of the 5' and/or 3' untranslated region of a target gene transcript, or all or part of both the coding region and the untranslated regions of a transcript encoding of the target gene or all or part of the promoter sequence responsible for expression of the target gene. A polynucleotide used for sense suppression or other gene silencing methods may share 99%, 98%, 97%, 96%, 95%, 94%, 93%, 92%, 91%, 90%, 89%, 88%, 87%, 85%, 80%, or less sequence identity with the target sequence. When portions of the polynucleotides are used to disrupt the expression of the target gene, generally, sequences of at least 15, 16, 17, 18, 19, 20, 21, 22, 23, 24, 25, 26, 27, 28, 29, 30, 35, 40, 45, 50, 60, 70, 80, 90, 100, 200, 300, 400, 450, 500, 550, 600, 650, 700, 750, 800, or 900 nucleotides or 1 kb or greater may be used.

The present invention includes:

In one embodiment, a transformed plant comprising in its genome: (a) a first recombinant nucleic acid molecule comprising at least one regulatory sequence operably linked to at least one nucleotide sequence selected from the group consisting of: (i) a nucleotide sequence encoding a polypeptide having gamma-tocopherol methyltransferase activity; (ii) a nucleotide sequence set forth in SEQ ID NOs: 11, 13, 15, 17, 19, 21, 23, 25, 27, 29, 31, 33, 35, 37 or 39; (iii) a nucleotide sequence encoding the amino acid sequence set forth in SEQ ID NOs: 12, 14, 16, 18, 20, 22, 24, 26, 28, 30, 32, 34, 36, 38 or 40; (iv) a nucleotide sequence having at least 80% sequence identity to the nucleotide sequence set forth in any one of (i)-(iii), wherein the nucleotide sequence encodes a polypeptide having gamma-tocopherol methyltransferase activity; and (v) a nucleotide sequence that is fully complementary to the nucleotide sequence of any one of (i)-(iv); (b) a second recombinant nucleic acid molecule comprising at least one regulatory sequence operably linked to at least one nucleotide sequence selected from the group consisting of: (vi) a nucleotide sequence encoding a polypeptide having homogentisate geranylgeranyl transferase activity; (vii) a nucleotide sequence set forth in SEQ ID NOs: 1, 3, 5, 7, or 9; (viii) a nucleotide sequence encoding the amino acid sequence set forth in SEQ ID NOs: 2, 4, 6, 8, or 10; (ix) a nucleotide sequence having at least 80% sequence identity to the nucleotide sequence set forth in any one of (vi)-(viii), wherein the nucleotide sequence encodes a polypeptide having homogentisate geranylgeranyl transferase activity; and (x) a nucleotide sequence that is fully complementary to the nucleotide sequence of any one of (vi)-(ix); and (c) a third recombinant nucleic acid molecule comprising at least one regulatory sequence operably linked to at least one nucleotide sequence selected from the group consisting of: (xi) a nucleotide sequence encoding a polypeptide having 2-methyl-6-phytylbenzoquinol methyltransferase activity; (xii) a nucleotide sequence set forth in SEQ ID NO:53; (xiii) a nucleotide sequence encoding the amino acid sequence set forth in SEQ ID NOs: 54, 61, 62, 63, 64, 65, 66, 67, 68, 69 or 70; (xiv) a nucleotide sequence having at least 80% sequence identity to the nucleotide sequence set forth in any one of (xi)-(xii), wherein the nucleotide sequence encodes a polypeptide having 2-methyl-6-phytylbenzoquinol methyltransferase activity; (xv) a nucleotide sequence encoding a polypeptide having 2-methyl-6-phytylbenzoquinol methyltransferase activity, wherein the amino acid sequence of the polypeptide has at least 95% sequence identity to the amino acid sequence set forth in SEQ ID NOs: 54, 61, 62, 63, 64, 65, 66, 67, 68, 69 or 70; and (xvi) a nucleotide sequence that is fully complementary to the nucleotide sequence of any one of (xi)-(xv); wherein the first recombinant nucleic acid molecule, the second recombinant nucleic acid molecule and the third recombinant nucleic acid molecule are stably incorporated into the genome of the transformed plant.

In another embodiment, a transformed plant comprising in its genome at least one recombinant nucleic acid molecule selected from the group consisting of the first recombinant nucleic acid molecule, the second recombinant nucleic acid molecule and the third recombinant nucleic acid molecule of above, wherein the at least one recombinant nucleic acid molecule is stably incorporated into the genome of the transformed plant.

In another embodiment, the transformed plant may be a monocot selected from the group consisting of maize, wheat, rice, sorghum, barley, millet and rye.

In another embodiment, the transformed plant may be a dicot selected from the group consisting of soybean, *Brassica* sp., alfalfa, safflower, sunflower, cotton, peanut, canola, *Arabidopsis*, tobacco and potato.

In another embodiment, the at least one regulatory sequence of the first, second or third recombinant nucleic acid molecule comprises at least one promoter selected from the group consisting of seed-preferred, constitutive, chemically regulated, tissue-preferred, and developmentally regulated promoters.

In another embodiment, the invention includes seed of the transformed plant, wherein said seed comprises in its genome the first recombinant nucleic acid molecule, the second recombinant nucleic acid molecule and the third recombinant nucleic acid molecule.

In another embodiment, the transformed plant of the invention produces a seed with an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, the invention includes a method of increasing the level of alpha-tocotrienol, beta-tocotrienol, or both, in a plant, comprising stably incorporating into a plant genome: (a) a first recombinant nucleic acid molecule comprising at least one regulatory sequence operably linked to at least one nucleotide sequence selected from the group consisting of: (i) a nucleotide sequence encoding a polypeptide having gamma-tocopherol methyltransferase activity; (ii) a nucleotide sequence set forth in SEQ ID NOs: 11, 13, 15, 17, 19, 21, 23, 25, 27, 29, 31, 33, 35, 37 or 39; (iii) a nucleotide sequence encoding the amino acid sequence set forth in SEQ ID NOs: 12, 14, 16, 18, 20, 22, 24, 26, 28, 30, 32, 34, 36, 38 or 40; (iv) a nucleotide sequence having at least 80% sequence identity to the nucleotide sequence set forth in any one of (i)-(iii), wherein the nucleotide sequence encodes a polypeptide having gamma-tocopherol methyltransferase activity; and (v) a nucleotide sequence that is complementary to the nucleotide sequence of any one of (i)-(iv); (b) a second recombinant nucleic acid molecule comprising at least one regulatory sequence operably linked to at least one nucleotide sequence selected from the group consisting of: (vi) a nucleotide sequence encoding a polypeptide having homogentisate geranylgeranyl transferase activity; (vii) a nucleotide sequence set forth in SEQ ID NOs: 1, 3, 5, 7, or 9; (viii) a nucleotide sequence encoding the amino acid sequence set forth in SEQ ID NOs: 2, 4, 6, 8, or 10; (ix) a nucleotide sequence having at least 80% sequence identity to the nucleotide sequence set forth in any one of (vi)-(viii), wherein the nucleotide sequence encodes a polypeptide having homogentisate geranylgeranyl transferase activity; and (x) a nucleotide sequence that is complementary to the nucleotide sequence of any one of (vi)-(ix); and (c) a third recombinant nucleic acid molecule comprising at least one regulatory sequence operably linked to at least one nucleotide sequence selected from the group consisting of: (xi) a nucleotide sequence encoding a polypeptide having 2-methyl-6-phytylbenzoquinol methyltransferase activity; (xii) a nucleotide sequence set forth in SEQ ID NO:53; (xiii) a nucleotide sequence encoding the amino acid sequence set forth in SEQ ID NOs: 54, 61, 62, 63, 64, 65, 66, 67, 68, 69 or 70; (xiv) a nucleotide sequence having at least 80% sequence identity to the nucleotide sequence set forth in any one of (xi)-(xii), wherein the nucleotide sequence encodes a polypeptide having 2-methyl-6-phytylbenzoquinol methyltransferase activity; (xv) a nucleotide sequence encoding a polypeptide having 2-methyl-6-phytylbenzoquinol methyltransferase activity, wherein the amino acid sequence of the polypeptide has at least 95% sequence identity to the amino acid sequence set forth in SEQ ID NOs: 54, 61, 62, 63, 64, 65, 66, 67, 68, 69 or 70; and (xvi) a nucleotide sequence that is fully complementary to the nucleotide sequence of any one of (xi)-(xv); and selecting a transformed plant that has an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, a method in which the first, second and third recombinant nucleic acid molecules are incorporated into the plant genome by co-transformation of a plant cell.

In another embodiment, a method in which at least one of said first, second or third recombinant nucleic acid molecules is incorporated into the plant genome by re-transformation of a transformed plant cell, wherein said transformed plant cell comprises at least one of said first, second or third recombinant nucleic acid molecules.

In another embodiment, a method in which at least one of said first, second or third recombinant nucleic acid molecule is incorporated into the plant genome by breeding.

In another embodiment, a method in which the at least one regulatory sequence of the first, second or third recombinant nucleic acid molecule comprises at least one promoter selected from the group consisting of seed-preferred, constitutive, chemically regulated, tissue-preferred, and developmentally regulated promoters.

In another embodiment, the invention includes methods for transforming plants and plants cells to change the oil content therein comprising transforming a plant with one to three nucleotide sequences alone or in any combination of two or three nucleotide sequences. The method comprises; (a) obtaining a first plant comprising in its genome a first recombinant nucleic acid molecule comprising at least one regulatory sequence operably linked to a nucleotide sequence encoding a polypeptide having gamma-tocopherol methyltransferase activity; (b) crossing the transgenic plant of step (a) with a second plant comprising in its genome a second recombinant nucleic acid molecule comprising at least one regulatory sequence operably linked to a nucleotide sequence encoding a polypeptide having homogentisate geranylgeranyl transferase activity; (c) crossing the transgenic plant of step (b) with a third plant comprising in its genome a third recombinant nucleic acid molecule comprising at least one regulatory sequence operably linked to a nucleotide sequence encoding a polypeptide having 2-methyl-6-phytylbenzoquinol methyltransferase activity; and (d) obtaining a progeny plant from said step (c) crossing, wherein said progeny plant comprises in its genome the first recombinant nucleic acid molecule, the second recombinant nucleic acid molecule and the third recombinant nucleic acid molecule, and wherein said progeny plant exhibits an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, a method of increasing the level of alpha-tocotrienol, beta-tocotrienol, or both, in a plant, comprising: (a) obtaining a first transformed plant comprising in its genome a first recombinant nucleic acid molecule comprising at least one regulatory sequence operably linked to at least one nucleotide sequence selected from the group consisting of: (i) a nucleotide sequence encoding a polypeptide having gamma-tocopherol methyltransferase activity; (ii) a nucleotide sequence set forth in SEQ ID NOs: 11, 13, 15, 17, 19, 21, 23, 25, 27, 29, 31, 33, 35, 37 or 39; (iii) a nucleotide sequence encoding the amino acid sequence set forth in SEQ ID NOs: 12, 14, 16, 18, 20, 22, 24, 26, 28, 30, 32, 34, 36, 38 or 40; (iv) a nucleotide sequence having at least 80% sequence identity to the entire coding sequence of the nucleotide sequence set forth in any one or (i)-(iii), wherein the nucleotide sequence encodes a polypeptide having gamma-tocopherol methyltransferase activity; and (v) a nucleotide sequence that is complementary to the nucleotide sequence of any one of (i)-(iv); (b) crossing the transformed plant of step (a) with a second transformed plant comprising within its genome a second recombinant nucleic acid molecule comprising at least one regulatory sequence operably linked to at least one nucleotide sequence selected from the group consisting of: (vi) a nucleotide sequence encoding a polypeptide having homogentisate geranylgeranyl transferase activity; (vii) a nucleotide sequence set forth in SEQ ID NOs: 1, 3, 5, 7 or 9; (viii) a nucleotide sequence encoding the amino acid sequence set forth in SEQ ID NOs: 2, 4, 6, 8 or 10; (ix) a nucleotide sequence having at least 80% sequence identity to the entire coding sequence of the nucleotide sequence set forth in (vi)-(viii), wherein the nucleotide sequence encodes a polypeptide having homogentisate geranylgeranyl transferase activity; and (x) a nucleotide sequence that is complementary to the nucleotide sequence of any one of (vi)-(ix); and (c) crossing the transformed plant of step (b) with a third transformed plant comprising within its genome a third recombinant nucleic acid molecule comprising at least one regulatory sequence operably linked to at least one nucleotide sequence selected from the group consisting of: (xi) a nucleotide sequence encoding a polypeptide having 2-methyl-6-phytylbenzoquinol methyltransferase activity; (xii) a nucleotide sequence set forth in SEQ ID NO:53; (xiii) a nucleotide sequence encoding the amino acid sequence set forth in SEQ ID NOs: 54 or 70; (xiv) a nucleotide sequence having at least 80% sequence identity to the nucleotide sequence set forth in any one of (xi)-(xii), wherein the nucleotide sequence encodes a polypeptide having 2-methyl-6-phytylbenzoquinol methyltransferase activity; (xv) a nucleotide sequence encoding a polypeptide having 2-methyl-6-phytylbenzoquinol methyltransferase activity, wherein the amino acid sequence of the polypeptide has at least 95% sequence identity to the amino acid sequence set forth in SEQ ID NOs: 54, 61, 62, 63, 64, 65, 66, 67, 68, 69 or 70; and (xvi) a nucleotide sequence that is fully complementary to the nucleotide sequence of any one of (xi)-(xv); and selecting a progeny plant from said step (c) crossing, wherein said progeny plant comprises in its genome the first recombinant nucleic acid molecule, the second recombinant nucleic acid molecule and the third recombinant nucleic acid molecule, and wherein said progeny plant exhibits an increased level of alpha-tocotrienol, beta-tocotrienol, or both, relative to a plant with a similar genetic background but lacking said first recombinant nucleic acid molecule, said second recombinant nucleic acid molecule and said third recombinant nucleic acid molecule.

In another embodiment, any of the methods of the invention wherein the plant is a monocot is selected from the group consisting of maize, wheat, rice, sorghum, barley, millet and rye.

In another embodiment, any of the methods of the invention wherein the plant is a dicot is selected from the group consisting of soybean, *Brassica* sp., alfalfa, safflower, sunflower, cotton, peanut, canola, *Arabidopsis*, tobacco and potato.

In another embodiment, the invention includes transformed seed or byproducts of any of the transformed plants of the invention.

In another embodiment, the transformed seed of the invention has an alpha-tocotrienol level of at least 20 ppm.

In another embodiment, the transformed seed of the invention contains alpha-tocotrienol in an amount of at least 20% of total tocopherol and tocotrienol content in the transformed seed.

In another embodiment, the transformed seed of the invention has an alpha-tocotrienol content of at least 70% of total combined tocopherol and tocotrienol content in the transformed seed.

In another embodiment, the transformed seed of the invention contains a combined level of alpha-tocotrienol and alpha-tocopherol of at least 95% of total tocopherol and tocotrienol content in the transformed seed.

In another embodiment, a method of improving the tissue quality of an animal, comprising feeding the animal the transformed seed of the invention.

In another embodiment, the tissue is meat and the quality of the meat is measured by at least one criteria selected from the group consisting of increased pH, improved food color, improved oxidative stability, increased shelf life and reduced purge.

In another embodiment, the animal is a ruminant, preferably cattle.

In another embodiment, the animal is a non-ruminant, preferably swine or poultry.

In another embodiment, an isolated polynucleotide comprising SEQ ID NO:57.

In another embodiment, an isolated polynucleotide comprising: (a) a nucleotide sequence encoding a polypeptide having 2-methyl-6-phytylbenzoquinol methyltransferase activity, wherein the polypeptide has an amino acid sequence of at least 95% sequence identity, based on the Clustal W method of alignment, when compared to SEQ ID NO:54 or 70, or (b) a complement of the nucleotide sequence, wherein the complement and the nucleotide sequence consist of the same number of nucleotides and are 100% complementary. The amino acid sequence of the polypeptide preferably comprises SEQ ID NO:54 or 70. The nucleotide sequence preferably comprises SEQ ID NO:53.

In another embodiment, the present invention includes a vector comprising any of the isolated polynucleotides of the present invention.

In another embodiment, the present invention includes a recombinant DNA construct comprising any of the isolated polynucleotides of the present invention operably linked to at least one regulatory sequence.

In another embodiment, the present invention concerns a method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterium.

In another embodiment, the present invention includes a method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

In another embodiment, an isolated polypeptide having 2-methyl-6-phytylbenzoquinol methyltransferase activity, wherein the polypeptide has an amino acid sequence of at least 95% sequence identity, based on the Clustal W method of alignment, when compared to one of SEQ ID NO:54 or 70. The amino acid sequence of the polypeptide preferably comprises SEQ ID NO:54 or 70.

In another embodiment, a method for isolating a polypeptide having 2-methyl-6-phytylbenzoquinol methyltransferase activity comprising isolating the polypeptide from a cell or culture medium of the cell, wherein the cell comprises a recombinant DNA construct comprising the polynucleotide of the invention operably linked to at least one regulatory sequence.

In another embodiment, a method of altering the level of expression of a 2-methyl-6-phytylbenzoquinol methyltransferase in a host cell comprising: (a) transforming a host cell with the recombinant DNA construct of the invention; and (b) growing the transformed host cell under conditions that are suitable for expression of the recombinant DNA construct wherein expression of the recombinant DNA construct results in production of altered levels of the 2-methyl-6-phytylbenzoquinol methyltransferase in the transformed host cell.

The following examples are presented by way of illustration, not by way of limitation.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration, not by way of limitation. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Alpha- and Beta-Tocotrienol Production in *Arabidopsis thaliana* by Transgenic Expression of Barley HGGT and Soybean Gamma-Tocopherol Methyltransferase The cDNA for barley homogentisate geranylgeranyl transferase (HGGT) (bdl2c.pk006.o2; SEQ ID NO:2) and soybean gamma-tocopherol methyltransferase (sah1c.pk004.g2; SEQ ID NO:12) were expressed in *Arabidopsis thaliana* to demonstrate the feasability of these cDNA for alpha and beta-tocotrienol production in transgenic plants.

A transformation vector was constructed using standard molecular tools that expressed the barley HGGT gene under the control of the β-conglycinin promoter of soybean (Beachy et al., *EMBO J.* 4:3047-3053 (1985)) and the soybean gamma-tocopherol methyltransferase gene under the control of the Kti promoter (Kunitz Trypsin Inhibitor, Jofuku et. al., (1989) Plant Cell 1:1079-1093).

The 1.1 kb DNA fragment containing the soybean gamma-tocopherol methyltransferase gene was excised from SC1 (see Example 3) using the restriction enzyme NotI, and ligated, in the sense orientation behind the Kti promoter, to DNA of KS126 (PCT Publication No. WO 04/071467) linearized with the restriction enzyme NotI to give KS308 (SEQ ID NO:41).

The 3.1 kb DNA fragment containing β-conglycinin promoter, HGGT gene, and phaseolin terminator was excised from SC38 (see Example 3) using the restriction enzyme AscI, the ends were blunted with the large fragment of DNA polymerase I, and ligated to DNA of KS178 (construction described below) to give KS270 (SEQ ID NO:42). KS178 had previously been linearized with the restriction enzyme Pad followed by filling in of 3' overhangs with the large fragment of DNA polymerase I.

KS178 was constructed as follows. The 4.0 kb DNA fragment containing the SAMS/ALS/ALS3' cassette, was excised from pZSL13LeuB (PCT Publication No. WO 04/071467) using the restriction enzymes PstI and SmaI, the ends were blunted with the large fragment of DNA polymerase I, and ligated to DNA of KS102 (PCT Publication No. WO 04/071467) linearized with the restriction enzyme BamHI, to give KS178. Prior to ligation the ends of the linearized KS102 vector were blunted with the large fragment of DNA polymerase I.

The 3.4 kb DNA fragment containing the gamma-tocopherol methyltransferase expression cassette was excised from KS308 using the restriction enzyme AscI, the ends were blunted with the large fragment of DNA polymerase I, and ligated to DNA of pBLUESCRIPT® II KS—(Stratagene) linearized with the restriction enzyme SmaI. The resulting vector was linearized with the restriction enzyme SnaBI, and ligated to the 3.0 kb DNA fragment containing the HGGT expression cassette removed from KS270 using the restriction enzymes Pad and BamHI to give KS318. Prior to ligation the ends of this fragment were blunted with the large fragment of DNA polymerase I. The 6.4 kb DNA fragment containing the HGGT and gamma-tocopherol methyltransferase expression cassettes was excised from KS318 using the restriction enzyme SalI, and ligated to DNA of the *Agrobacterium tumefaciens* binary vector pZBL120, linearized with SalI, to give KS319. The T-DNA of the plant transformation vector KS319 is set forth as SEQ ID NO:43.

Applicants note that the binary vector pZBL120 is identical to the pZBL1 binary vector (American Type Culture Collection Accession No. 209128) described in U.S. Pat. No. 5,968,793, except the NOS promoter was replaced with a 963 bp 35S promoter (NCBI Accession No. V00141; also known as NCBI General Indentifier No. 58821) from nucleotide 6494 to 7456 in the Nos/P-nptII-OCS 3' gene. The new 35S promoter-nptII-OCS 3' gene serves as a kanamycin (Kan) resistance plant selection marker in pZBL120.

Generation and Analysis of Transgenic Arabidospis Lines:

Plasmid DNA of KS319 was introduced into *Agrobacterium tumefaciens* NTL4 (Luo et al, *Molecular Plant-Microbe Interactions* (2001) 14(1):98-103) by electroporation. Briefly, 1 μg plasmid DNA was mixed with 100 μL of electrocompetent cells on ice. The cell suspension was transferred to a 100 μL electro oration curette (1 mm gap width) and electro orated using a BIORAD electro orator set to 1 kV, 400Ω and 25 μF. Cells were transferred to 1 mL LB medium and incubated for 2 h at 30° C. Cells were plated onto LB medium containing 50 μg/mL kanamycin. Plates were incubated at 30° C. for 60 h. Recombinant *agrobacterium* cultures (500 mL LB, 50 μg/mL kanamycin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 $cm^2$ pot in METRO-MIX® 360 soil mixture for 4 weeks (22° C., 16 h light/8 h dark, 100 $\mu E\ m^{-2}s^{-1}$). Plants were repeatedly dipped into the *agrobacterium* suspension harboring the binary vector KS319 and kept in a dark, high humidity environment for 24 h. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% triton X-100, followed by 45 mL of 30% (V/V) household bleach in water, 0.01% triton X-100 and finally by repeated rinsing in sterile water. Aliquots of 20,000 seeds were transferred to square plates (20×20 cm) containing 150 mL of sterile plant growth medium comprised of 0.5×MS salts, 1.0% (W/V) sucrose, 0.05 MES/KOH (pH 5.8), 200 μg/mL timentin, and 50 μg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown to maturity.

A total of 137 transgenic lines were generated and subjected to HPLC analysis: 5 mg crushed seed were extracted at ambient temperature in 200 μL of heptane. Tocopherols and tocotrienols were quantitated by HPLC as described in Example 3. The highest total tocotrienol content was 2,800 ppm. The highest alpha-tocotrienol content was 400 ppm. In these events, 25% of all tocopherols and tocotrienols comprised of alpha-tocotrienol.

Two events, #58 and #135 were advanced to transgene homozygousity by repeated selfing. T2 seed of both events contained 25% of kanamycin-sensitive seed indicating that both events contained transgene insertion at a single genetic locus. Bulk seed were produced from T3 seed that no longer segregated kanamycin-sensitive progeny. Fifty mg of T4 seed material was extracted in 1 mL of heptane. Tocopherol and tocotrienol were quantitated by HPLC and these results are found in Table 5. As discussed below, event #58 expressed HGGT and gamma-tocopherol methyltransferase genes. Event #135 expressed only HGGT.

TABLE 5

Tocol Composition (% of total tocols) of Homozygous T4 Seed Material of Transgenic *Arabidopsis* Lines

| line | | alpha-tocopherol | beta-tocopherol | gamma-tocopherol | delta-tocopherol | Tocopherol |
|---|---|---|---|---|---|---|
| wild-type | ppm | 6 | 0 | 396 | 9 | 411 |
| | % | 2 | 0 | 96 | 2 | |
| #135 | ppm | 25 | 4 | 326 | 104 | 455 |
| | % | 1 | 0 | 12 | 4 | |
| #58 | ppm | 308 | 58 | 98 | 30 | 495 |
| | % | 15 | 3 | 5 | 1 | |
| | | **alpha-tocotrienol** | **beta-tocotrienol** | **gamma-tocotrienol** | **delta-tocotrienol** | **Tocotrienol** |
| wild-type | ppm | 0 | 0 | 0 | 0 | 0 |
| | % | 0 | 0 | 0 | 0 | |
| #135 | ppm | 13 | 0 | 1754 | 590 | 2358 |
| | % | 0 | 0 | 62 | 21 | |
| #58 | ppm | 419 | 47 | 876 | 273 | 1615 |
| | % | 20 | 2 | 42 | 13 | |

Table 5 indicates that event #135 apparently only expresses the barley HGGT gene. The seed tocotrienol profile of event #135 resembles that of leaves of transgenic *Arabidopsis* plants over-expressing the barley HGGT gene. The leaf profile is dominated by gamma-tocotrienol with alpha-tocotrienol comprising less than 3% of the total tocotrienol fraction (see PCT Publication No. WO 03/082899; U.S. Application No. 2004/0034886; Cahoon et al. (2003) *Nat. Biotechnol.* 21:1082-1087). Applicants note that in line #135 only trace levels of alpha-tocotrienol are detected. Hence, there is very little endogenous enzyme activity present in *Arabidopsis* seed that can convert gamma-tocotrienol to alpha-tocotrienol.

In contrast to the above, the co-expression of the soybean gamma-tocopherol methyltransferase gene with the HGGT gene in event #58 leads to significant accumulation of alpha-tocotrienol with levels of 419 ppm. The oil content of heptane extracts was measured using sodium methoxide derivatization followed by GC analysis (see below). Using this analysis, it was determined that the seed oil of event #58 contained 1,200 ppm alpha-tocotrienol. The alpha-tocotrienol of event #58 makes up about 20% of the total tocopherols and tocotrienols. About 30% of gamma-tocotrienol is converted to alpha-tocotrienol. Applicants note that expression of the gamma-tocopherol methyltransferase gene may be low, because a heterologous promoter was used. Even higher levels of alpha-tocotrienol will very likely be observed if the gamma-tocopherol methyltransferase gene is expressed under control of an endogenous seed-preferred promoter. Nevertheless, the *Arabidopsis* data has demonstrated that the soybean gamma-tocopherol methyltransferase gene is an efficient enzyme catalyst for methylation of tocotrienols for the production of alpha- and beta-tocotrienol.

One skilled in the art understands that the homogentisate geranylgeranyl transferases (HGGT) and gamma-tocopherol methyltransferases found in Table 1 and Table 2, respectively, may also be expressed in *Arabidopsis thaliana* to demonstrate the feasability of using these cDNA to increase alpha and beta-tocotrienol production in transgenic plants.

GC/MS Analysis to Confirm Identity of Tocopherols and Tocotrienols:

Total tocol analysis was performed on an Agilent 6890 gas chromatograph in conjunction with Agilent 5973 Mass Selective Detector (MSD). Four μL samples of heptane extracts of *Arabidopsis* seeds of lines #58 and #135 were injected into a split/splitless injector (2:1 split ratio) held at 300° C. Chromatographic separation was performed on a 30 m×250 μm (ID)×0.25 μm (film thickness) Agilent DB5MS column using helium gas as the carrier (39 cm/sec linear velocity). The oven temperature profile was as follows: 260° C., hold 4 min; 2° C. ramp to 340° C., hold for 12 min. Compounds eluting from the column were directed into the MSD though a heated (325° C.) transfer line and ionized (70 eV). The MSD was tuned using the standard tune protocol and was run in Scan mode (10-500 mass range). Data was analyzed using ChemStation (Agilent) and AMDIS version 2.1 (National Institute of Standards and Technology; NIST).

Compound identity was confirmed by comparing compound elution times with those of authentic samples and by mass spectral comparisons with an electronic database (version 2.0, NIST). The database contained entries for alpha-, beta-, gamma- and delta-tocopherols, as well as the internal standard (alpha-tocopherol acetate). Library entries were not available for any of the tocotrienols. The identity of these compounds was therefore confirmed by comparison of the chromatographic elution and by visual comparison of the mass-spectrum with those of authentic standards run under the same chromatographic conditions.

Example 2

Production of Tocotrienols in Transgenic Soybean Lines: Molecular Stack of Barley HGGT and Soybean Gamma-Tocopherol Methyltransferase To demonstrate the ability to produce increased levels of alpha-tocotrienols, beta-tocotrienols, or both, in transgenic soybean lines, the barley HGGT cDNA (bdl2c.pk006.o2; SEQ ID NO:2) and soybean gamma-tocopherol methyltransferase (sah1c.pk004.g2; SEQ ID NO:12) were used in a molecular stack (progeny with both transgene-related traits).

Transgenic soybean lines were generated with plasmid DNA of KS270 and KS308, see Example 1, using particle bombardment of embryogenic callus.

KS270 provides the barley HGGT gene under control of 617 bp of the soybean β-conglycinin promoter. The polyadenylation signal for the HGGT transcript is derived from the terminator of the phaseolin gene (from the bean *Phaseolus vulgaris*; Doyle et al. (1986) *J. Biol. Chem.* 261:9228-9238). The plasmid also contains the cDNA of a sulfonylurea-resistant variant of the soybean ALS gene that is under control of 1217 bp of the SAMS promoter. The polyadenylation signal for the HGGT transcript is derived from the terminator of the soybean ALS gene.

KS308 provides the gamma-tocopherol methyltransferase gene from soybean under the control of 2090 bp of the soybean Kti promoter. The polyadeylation signal for the gamma-tocopherol methyltransferase transcript is derived from the terminator of the Kti gene. KS308 also provides a hygromycin B phosphotransferase (HPT) resistance gene (Gritz et al. (1983) *Gene* 25:179-188) that is under control of 1408 bp of the 35S promoter from Cauliflower Mosaic Virus (Odell et al. (1985) *Nature* 313:810-812). The polyadenylation signal for the hygromycin resistance gene is derived from the terminator of nopaline synthase gene from the T-DNA of the Ti plasmid of *Agrobacterium tumefaciens.*

Soybean embryogenic suspension cultures were transformed with DNA plasmids KS270 in conjunction with KS308 by the method of particle gun bombardment (Klein et al. (1987) *Nature* (London) 327:70-73, U.S. Pat. No. 4,945,050) using a BIORAD BIOLISTIC™ PDS1000/He instrument. The following stock solutions and media were used for transformation and regeneration of soybean plants:

Stock Solutions:

Sulfate 100× Stock: 37.0 g $MgSO_4.7H_2O$, 1.69 g $MnSO_4.H_2O$, 0.86 g $ZnSO_4.7H_2O$, 0.0025 g $CuSO_4.5H_2O$ Halides 100× Stock: 30.0 g $CaCl_2.2H_2O$, 0.083 g KI, 0.0025 g $CoCl_2.6H_2O$ P, B, Mo 100× Stock: 18.5 g $KH_2PO_4$, 0.62 g $H_3BO_3$, 0.025 g $Na_2MoO_4.2H_2O$ Fe EDTA 100× Stock: 3.724 g $Na_2EDTA$, 2.784 g $FeSO_4.7H_2O$ 2,4-D Stock: 10 mg/mL Vitamin B5 1000× Stock: 10.0 g myo-inositol, 0.10 g nicotinic acid, 0.10 g pyridoxine HCl, 1 g thiamine.

Media (Per Liter):

SB196: 10 mL of each of the above stock solutions, 1 mL B5 Vitamin stock, 0.463 g $(NH_4)_2SO_4$, 2.83 g $KNO_3$, 1 mL 2,4-D stock, 1 g asparagine, 10 g Sucrose, pH 5.7

SB103: 1 pk. Murashige & Skoog salts mixture, 1 mL B5 Vitamin stock, 750 mg $MgCl_2$ hexahydrate, 60 g maltose, 2 g GELRITE®, pH 5.7.

SB166: SB103 supplemented with 5 g per liter activated charcoal.

SB71-4: Gamborg's B5 salts, 1 mL B5 vitamin stock, 30 g sucrose, 5 g TC agar, pH 5.7.

To prepare tissue for transformation, soybean embryogenic suspension cultures were maintained in 35 mL liquid medium (SB196) on a rotary shaker (150 rpm) at 28° C. with fluorescent lights providing a 16 hour day/8 hour night cycle. Cultures were subcultured every 2 weeks by inoculating approximately 35 mg of tissue into 35 mL of fresh liquid media.

In particle gun bombardment procedures it is possible to use purified 1) entire plasmid DNA or, 2) DNA fragments containing only the recombinant DNA expression cassette(s) of interest. For every seventeen bombardment transformations, 85 μL of suspension is prepared containing 1 to 90 picograms (pg) of plasmid DNA per base pair of each DNA plasmid. Both recombinant DNA plasmids were co-precipitated onto gold particles as follows. The DNAs in suspension were added to 50 μL of a 20-60 mg/mL 0.6 μm gold particle suspension and then combined with 50 μL $CaCl_2$ (2.5 M) and 20 μL spermidine (0.1 M). The mixture was vortexed for 5 seconds, spun in a microfuge for 5 seconds, and the supernatant removed. The DNA-coated particles were then washed once with 150 μL of 100% ethanol, vortexed and spun in a microfuge again, then resuspended in 85 μL of anhydrous ethanol. Five μL of the DNA-coated gold particles were then loaded on each macrocarrier disk.

Approximately 150 to 250 mg of two-week-old suspension culture was placed in an empty 60 mm×15 mm petri plate and the residual liquid removed from the tissue using a pipette. The tissue was placed about 3.5 inches away from the retaining screen and each plate of tissue was bombarded once. Membrane rupture pressure was set at 650 psi and the chamber was evacuated to −28 inches of Hg. Three plates were bombarded, and, following bombardment, the tissue from each plate was divided between two flasks, placed back into liquid media, and cultured as described above.

Seven days after bombardment, the liquid medium was exchanged with fresh SB196 medium supplemented with 30-50 mg/L hygromycin. The selective medium was subsequently refreshed weekly or biweekly. Seven weeks post-bombardment, bright green, transformed tissue was observed growing from untransformed, chlorotic or necrotic embryogenic clusters. Isolated green tissue was removed and inoculated into individual wells in six-well culture dishes to generate new, clonally-propagated, transformed embryogenic suspension cultures. Thus, each new line was treated as independent transformation event in an individual well. These suspensions can then be maintained as suspensions of embryos clustered in an immature developmental stage through subculture or they can be regenerated into whole plants by maturation and germination of individual somatic embryos.

After two weeks in individual cell wells, transformed embryogenic clusters were removed from liquid culture and placed on solidified medium (SB166) containing no hormones or antibiotics for one week. Embryos were cultured for at 26° C. with mixed fluorescent and incandescent lights on a 16 hour day/8 hour night schedule. After one week, the cultures were then transferred to SB103 medium and maintained in the same growth conditions for 3 additional weeks.

Somatic embryos became suitable for germination after 4 weeks and were then removed from the maturation medium and dried in empty petri dishes for 1 to 5 days. The dried embryos were then planted in SB71-4 medium where they were allowed to germinate under the same light and temperature conditions as described above. Germinated embryos were transferred to sterile soil and grown to maturity for seed production.

A total of fourteen events were created by co-transformation with KS270 and KS308 plasmids. Tocol composition of T1 seed was assayed as follows. A seed chip (approximately 5-15 mg of tissue) was obtained from the cotyledon tissue of the seed. The chip was extracted with 100 μL of heptane for 2 hours. Tocopherol and tocotrienol was quantitated by HPLC analysis as described in Example 3.

A total of 14 events were generated and analyzed. Seed from five events contained significant levels of tocotrienol. Three of these also contained significant levels (>150 ppm) of alpha- and beta-tocotrienol. One event did not show conversion of gamma- to alpha-tocotrienol and one event did only exhibit low levels of gamma-tocopherol methyltransferase activity (20-150 ppm alpha-tocotrienol). One event 4060.2.5.1 was selected for further work. For event 4060.2.5.1, seven out of ten T1 seed showed the transgenic trait, indicating that these events likely had a single or multiple transgenic insertion at a single genetic locus. Positive-positive T1 seed were planted and T2 seed were selected from individual plants. A total of forty-eight T2 seed was analyzed by HPLC and the results can be found in Table 6.

TABLE 6

Tocol Composition (% of total tocopherols (tocph.) and tocotrienols (toct.)) for T2 Progeny of Event 4060.2.5.1

| No. | alpha-tocph. | beta-tocph. | gamma-tocph. | delta-tocph. | alpha-toct. | beta-toct. | gamma-toct. | delta-toct. | tocph. (ppm) | toct. (ppm) |
|---|---|---|---|---|---|---|---|---|---|---|
| 1 | 8 | 4 | 0 | 0 | 31 | 24 | 12 | 20 | 406 | 2786 |
| 2 | 9 | 5 | 0 | 0 | 31 | 22 | 15 | 19 | 474 | 3100 |
| 3 | 8 | 4 | 0 | 0 | 30 | 24 | 13 | 21 | 453 | 3172 |
| 4 | 9 | 4 | 0 | 0 | 30 | 23 | 14 | 20 | 471 | 2922 |
| 5 | 7 | 4 | 0 | 0 | 30 | 24 | 13 | 21 | 389 | 3059 |
| 6 | 9 | 5 | 0 | 0 | 29 | 22 | 13 | 22 | 479 | 3046 |
| 7 | 9 | 5 | 0 | 0 | 29 | 23 | 12 | 22 | 434 | 2596 |
| 8 | 9 | 5 | 0 | 0 | 29 | 22 | 13 | 22 | 454 | 2693 |
| 9 | 9 | 5 | 0 | 0 | 28 | 22 | 13 | 22 | 442 | 2595 |
| 10 | 10 | 5 | 0 | 0 | 28 | 22 | 13 | 22 | 487 | 2686 |
| 11 | 8 | 5 | 0 | 0 | 28 | 22 | 15 | 21 | 292 | 1846 |
| 12 | 10 | 5 | 0 | 0 | 27 | 22 | 12 | 23 | 401 | 2120 |
| 13 | 10 | 5 | 0 | 0 | 27 | 23 | 12 | 23 | 384 | 2164 |
| 14 | 10 | 5 | 0 | 0 | 27 | 19 | 17 | 23 | 424 | 2481 |
| 15 | 8 | 3 | 0 | 0 | 26 | 14 | 26 | 22 | 382 | 2912 |
| 16 | 8 | 5 | 0 | 0 | 26 | 22 | 14 | 26 | 468 | 3128 |
| 17 | 8 | 5 | 0 | 0 | 26 | 22 | 14 | 26 | 399 | 2692 |
| 18 | 9 | 5 | 0 | 0 | 25 | 21 | 14 | 25 | 477 | 2906 |
| 19 | 7 | 5 | 0 | 0 | 25 | 23 | 13 | 26 | 365 | 2580 |
| 20 | 7 | 5 | 0 | 0 | 25 | 21 | 14 | 27 | 405 | 2826 |
| 21 | 7 | 5 | 0 | 0 | 25 | 22 | 14 | 27 | 442 | 3138 |
| 22 | 11 | 5 | 0 | 0 | 24 | 16 | 19 | 24 | 408 | 2084 |
| 23 | 8 | 6 | 0 | 0 | 24 | 22 | 14 | 27 | 435 | 2818 |
| 24 | 7 | 5 | 0 | 0 | 24 | 20 | 15 | 29 | 411 | 2947 |
| 25 | 9 | 6 | 0 | 0 | 24 | 21 | 13 | 27 | 412 | 2340 |
| 26 | 9 | 6 | 0 | 0 | 24 | 20 | 15 | 27 | 453 | 2624 |
| 27 | 9 | 6 | 0 | 0 | 23 | 21 | 14 | 27 | 392 | 2315 |
| 28 | 9 | 6 | 0 | 0 | 23 | 20 | 14 | 28 | 443 | 2415 |
| 29 | 8 | 2 | 1 | 0 | 22 | 10 | 36 | 21 | 460 | 3873 |
| 30 | 7 | 5 | 0 | 0 | 22 | 21 | 14 | 30 | 386 | 2723 |
| 31 | 9 | 5 | 0 | 0 | 22 | 18 | 17 | 30 | 435 | 2718 |
| 32 | 16 | 1 | 73 | 10 | 0 | 0 | 0 | 0 | 383 | 0 |
| 33 | 51 | 2 | 45 | 2 | 0 | 0 | 0 | 0 | 368 | 0 |
| 34 | 35 | 2 | 59 | 4 | 0 | 0 | 0 | 0 | 362 | 0 |
| 35 | 20 | 1 | 69 | 10 | 0 | 0 | 0 | 0 | 353 | 0 |
| 36 | 36 | 2 | 56 | 5 | 0 | 0 | 0 | 0 | 325 | 0 |
| 37 | 18 | 2 | 71 | 10 | 0 | 0 | 0 | 0 | 357 | 0 |
| 38 | 35 | 3 | 58 | 5 | 0 | 0 | 0 | 0 | 307 | 0 |
| 39 | 13 | 2 | 74 | 11 | 0 | 0 | 0 | 0 | 302 | 0 |
| 40 | 25 | 2 | 64 | 9 | 0 | 0 | 0 | 0 | 353 | 0 |
| 41 | 18 | 1 | 71 | 10 | 0 | 0 | 0 | 0 | 328 | 0 |
| 42 | 25 | 2 | 64 | 9 | 0 | 0 | 0 | 0 | 353 | 0 |
| 43 | 17 | 2 | 70 | 11 | 0 | 0 | 0 | 0 | 384 | 0 |
| 44 | 14 | 1 | 73 | 12 | 0 | 0 | 0 | 0 | 337 | 0 |
| 45 | 20 | 1 | 70 | 8 | 0 | 0 | 0 | 0 | 344 | 0 |
| 46 | 16 | 1 | 73 | 10 | 0 | 0 | 0 | 0 | 335 | 0 |
| 47 | 16 | 1 | 74 | 10 | 0 | 0 | 0 | 0 | 328 | 0 |
| 48 | 18 | 1 | 71 | 8 | 0 | 0 | 0 | 2 | 354 | 0 |

The T2 seed were generated through selfing of a transgenic line that was heterzogous for a single dominant transgenic trait. Accordingly, one would expect to detect 25% (12/48) non-transgenic segregants. Applicants observed 35% (17/48) non-transgenic segregants (see numbers 32-48). Seeds numbers 1 to 31 are transgenic segregants.

T2 progeny with both transgene-related traits were found to contain at least 590 ppm and as much as 1,099 ppm alpha-tocotrienol and at least 401 ppm and as much as 868 ppm beta-tocotrienol. In these T2 lines, alpha-tocotrienol constituted at least 22% and up to 31%, and integers in between, of the total tocopherol and tocotrienol fraction. Oil content of the heptane extracts was determined by derivatization with sodium methoxide followed by GC analysis. Oil could be calculated from that tocotrienol concentrations expressed as ppm. T2 progeny with both transgene-related traits contained an oil with at least 2,618 ppm and as much as 4,891 alpha-tocotrienol and at least 1,732 ppm and as much as 3,804 ppm beta-tocotrienol. Applicants also tested for a possible negative effect of the high alpha- and beta-tocotrienol content on seed weight. To this end, seed weight of the forty-eight T2 seed was plotted against alpha-tocotrienol content. No correlation between seed weight and alpha-tocotrienol content could be detected. Moreover, no unusual seed phenotypes related to seed shape, coloration or germination behaviour were observed in seed with the high alpha- and beta-tocotrienol trait.

One skilled in the art understands that the homogentisate geranylgeranyl transferases (HGGT) and gamma-tocopherol methyltransferases found in Table 1 and Table 2, respectively, may also be expressed in soybean to demonstrate the feasability of these cDNA for alpha- and beta-tocotrienol production in transgenic plants.

In summary, gamma-tocopherol methyltransferase enzyme from soybean can efficiently use tocotrienol substrates, for example, by the foregoing method to generate a seed or an extracted oil with high levels of alpha- and beta-tocotrienol. The alpha-tocotrienol content of soybeans over-expressing barley HGGT and the soybean gamma-tocopherol methyltransferase gene exceeds that of any non-transgenic seed or oil described previously by at least one order of magnitude (Packer et al. (2001) *J. Nutr.* 131:369 S-373S; Bertoli et al. (1998) *JAOCS* 75:1037-1040; PCT Publication No. WO 00/072862). These results further demonstrate the ability to produce alpha- and beta-tocotrienols in a crop plant that does not normally accumulate these antioxidant molecules through the transgenic expression of nucleic acid fragments encoding HGGT and gamma-tocopherol methyltransferase polypeptides.

Example 3

Production of Tocotrienols in Somatic Soybean Embryos and Transgenic Soybean Lines: Genetic Crossing of Barly HGGT and Soybean Gamma-Tocopherol Methyltransferase To demonstrate the ability to produce increased levels of alpha- and beta-tocotrienols in somatic soybean embryos and transgenic soybean lines, the barley HGGT cDNA (bdl2c.pk006.o2; SEQ ID NO:2) and soybean gamma-tocopherol methyltransferase (sah1c.pk004.g2; SEQ ID NO:12) were used in a genetic stack (progeny with both transgene-related traits produced by crossing).

Somatic soybean embryos have been used as model for the prediction of transgenic phenotypes in soybean seeds (Kinney, A. J. (1996) *J. Food Lipids* 3:273-292). Somatic soybean embryos and seeds are enriched in tocopherols, but contain little or no tocotrienols (Coughlan, unpublished result; The Lipid Handbook, 2nd Edition, Gunstone, F. D., et al., Eds., Chapman and Hall, London, 1994, pp. 129-131).

Plasmid DNA from clone sah1c.pk004.g2 was used as a template to prepare a NotI PCR fragment encoding the entire deduced open reading frame using the following PCR primers: forward primer 5'-AGCGCGGCCGCATGGCCACCGTGGTGAGGATCCCA-3' (SEQ ID NO:44), AND reverse primer 5'-AGCGCGGCCGCTTATTCAGGTTTTCGACATGTAATGATG-3' (SEQ ID NO:45).

PCR amplification was achieved using Pfu polymerase, and DNA of EST sah1c.pk004.g2 was used as the template. The product of this PCR reaction was purified by agarose gel electrophoresis and subcloned into pCR-Script-AMP (Stratagene) as described in the manufacturer's protocol. The amplified open-reading frame of the soybean gamma-tocopherol methyltransferase gene was then released as a NotI fragment and cloned into the corresponding site of soybean expression vector pKS67 to generate plasmid pSC1 (SEQ ID NO:50). The plasmid pKS67 was prepared by replacing in pRB20 (described in U.S. Pat. No. 5,846,784, incorporated herein by reference) the 800 bp Nos 3' fragment, with the 285 bp Nos 3' fragment containing the polyadenylation signal sequence and described in Depicker et al. (1982) *J. Mol. Appl. Genet.* 1:561-573. Ligation products were transformed into *E. coli* and recombinant clones were selected using hygromycin B selection.

Restriction digestion of plasmid DNA was used to identify cultures harboring plasmid DNA in which the start codon of the soybean gamma-tocopherol methyltransferase cDNA was in close proximity to the transcription start site of the soybean β-conglycinin promoter. In this plasmid construct, henceforth referred to as SC1, the soybean gamma-tocopherol methyltransferase cDNA is under the control of a 617 bp fragment of the soybean β-conglycinin promoter. The polyadenylation signal for the HGGT transcript is derived from the terminator of the phaseolin gene. Plasmid SC1 (SEQ ID NO:50) contains hygromycin B phosphotransferase gene under control of the cauliflower mosaic 35S promoter, which allows for selection of transformed plant cells by resistance to the antibiotic hygromycin B. Plasmid DNA of SC1 was used to generate transgenic somatic embryos of soybean as described below.

Transformation of Soybean Somatic Embryo Cultures:

The following stock solutions and media were used for transformation and propagation of soybean somatic embryos:

TABLE 7

Stock Solutions and Media for Transformation and Propagation of Soybean Somatic Embryos

| Stock Solutions | (g/L) |
|---|---|
| MS Sulfate 100x stock | |
| $MgSO_4 \cdot 7H_2O$ | 37.0 |
| $MnSO_4 \cdot H_2O$ | 1.69 |
| $ZnSO_4 \cdot 7H_2O$ | 0.86 |
| $CuSO_4 \cdot 5H_2O$ | 0.0025 |
| MS Halides 100x stock | |
| $CaCl_2 \cdot 2H_2O$ | 44.0 |
| KI | 0.083 |
| $CoCl_2 \cdot 6H_2O$ | 0.00125 |
| $KH_2PO_4$ | 17.0 |
| $H_3BO_3$ | 0.62 |

TABLE 7-continued

| Stock Solutions and Media for Transformation and Propagation of Soybean Somatic Embryos | |
|---|---|
| $Na_2MoO_4 \cdot 2H_2O$ | 0.025 |
| $Na_2EDTA$ | 3.724 |
| $FeSO_4 \cdot 7H_2O$ | 2.784 |
| B5 Vitamin stock | |
| myo-inositol | 100.0 |
| nicotinic acid | 1.0 |
| pyridoxine HCl | 1.0 |
| thiamine | 10.0 |
| Media | |
| SB55 (per Liter) | |
| 10 mL of each MS stock | |
| 1 mL of B5 Vitamin stock | |
| 0.8 g $NH_4NO_3$ | |
| 3.033 g $KNO_3$ | |
| 1 mL 2,4-D (10 mg/mL stock) | |
| 0.667 g asparagine | |
| pH 5.7 | |
| SB103 (per Liter) | |
| 1 pk. Murashige & Skoog salt mixture* | |
| 60 g maltose | |
| 2 g GELRITE ® | |
| pH 5.7 | |
| SB148 (per Liter) | |
| 1 pk. Murashige & Skoog salt mixture* | |
| 60 g maltose | |
| 1 mL B5 vitamin stock | |
| 7 g agarose | |
| pH 5.7 | |

*(Gibco BRL)

Soybean embryonic suspension cultures were maintained in 35 mL liquid media (SB55) on a rotary shaker (150 rpm) at 28° C. with a mix of fluorescent and incandescent lights providing a 16 hour day/8 hour night cycle. Cultures were subcultured every 2 to 3 weeks by inoculating approximately 35 mg of tissue into 35 mL of fresh liquid media.

Soybean embryonic suspension cultures were transformed with the plasmid containing the gamma-tocopherol methyltransferase sequence by the method of particle gun bombardment (see Klein et al. (1987) *Nature* 327:70-73) using a DUPONT™ BIOLISTIC™ PDS1000/He instrument. Five μL of pKS93s plastid DNA (1 mg/L), 50 μL $CaI_2$ (2.5 M), and 20 μL spermdine (0.1 M) were added to 50 μL of a 60 mg/mol 1 mm gold particle suspension. The particle preparation was agitated for 3 minutes, spun on a microphage for 10 seconds and the supernatant removed. The DNA-coated particles were then washed once with 400 μL of 70% ethanol and resuspended in 40 μL of anhydrous ethanol. The DNA/particle suspension was sonicated three times for 1 second each. Five μL of the DNA-coated gold particles were then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, containing 0.5% charcoal to begin maturation. After one week, embryos were transferred to SB103 media minus charcoal. After five weeks on SB103 media, maturing embryos were separated and placed onto SB148 media. During maturation embryos were kept at 26° C. with a mix of fluorescent and incandescent lights providing a 16 hour day/8 hour night cycle. After three weeks on SB148 media, embryos were analyzed for the expression of the tocopherols. Each embryonic cluster gave rise to 5 to 20 somatic embryos.

Non-transformed somatic embryos were cultured by the same method as used for the transformed somatic embryos.

Analysis of Transformed Somatic Embryos:

At the end of the sixth week on SB148 medium, somatic embryos were harvested from 25 independently transformed lines. Somatic embryos were collected in pools of five and weighed for fresh weight. Excess embryos were stored in 96-well plates at −80° C. The pooled somatic embryos were lyophilized for 18 hours and the dry weight measured. The lyophilized somatic embryos were briefly pulverized with a hand held Potter homogeniser and then 600 μL of heptane added and the samples incubated for 24 hours in the dark at room temperature to extract oils and tocopherols. The heptane was decanted and a further 300 μL added to the samples. The extracts were combined and centrifuged (5 minutes, 12000 g). The supernatant was stored in amber hulk auto sampler vials at −20° C. prior to analysis.

HPLC analysis of the extracts was carried out using an HP 1100 system (Agilent Technologies) 25 μL of the heptane sample was applied to a Lichrosphere Si 60 column (5 micron, 4×12.5 mm). The column was eluted with heptane/isopropanol (98:2 v/v) at a flow rate of 1 mL/min. After six minutes all four tocopherol isomers were eluted, as detected by a HP1100 fluorescence detector (Excitation wavelength 295 nm, emission wavelength 330 nm). Individual tocopherol standards (Matreya) were diluted with HPLC grade heptane to levels between 1 and 200 ng/μL to construct a 6-point external standard curve. Tocopherols in each oil were quantified using a standard curve run on the same day as the samples. The sum of tocopherol peak areas of samples from a non-transformed control line were compared with those of 25 independent gamma-tocopherol methyltransferase-transformed, hygromycin resistant lines.

Several events were identified that showed over-expression of the soybean gamma-tocopherol methyltransferase gene. In many of the lines 80% of the total tocol fraction was comprised of alpha-tocopherol in contrast to untransformed soybean embryos where gamma-tocopherol constitutes the dominant tocol molecule. Soybean plants were generated from clonal tissue derived from ten independent transgenic soybean events with high levels of alpha-tocopherol. Several plants were generated for each of the ten events. Five T1 seed from each transgenic event were subjected to HPLC analysis to determine the composition of the tocopherol fraction. Briefly, individual dry beans were homogenized using a tissue pulverizer (Genogrinder). Approximately 30 mg of tissue powder were extracted with 600 μL for 2 hours at ambient temperature. The heptane extract was cleared by brief centrifugation. Tocol composition of the heptane extracts was analyzed by HPLC as described previously. Percent alpha-tocopherol of T1 seed is summarized in Table 8.

TABLE 8

Percent Alpha-Tocopherol of T1 Seed

| Event | Seed # 1 | Seed # 2 | Seed # 3 | Seed # 4 | Seed # 5 |
|---|---|---|---|---|---|
| 719/1/1/A | 5.8 | 4.9 | 4.2 | 6.9 | 6.7 |
| 719/1/1/B | 8.4 | 5.6 | 7.0 | 8.8 | 7.6 |
| 719/1/1/C | 6.3 | 2.8 | 2.5 | 4.8 | 5.7 |
| 719/1/2/A | 52.4 | 56.5 | 53.0 | 47.0 | 51.1 |
| 719/1/2/B | 56.7 | 5.0 | 43.9 | 11.4 | 5.4 |
| 719/1/2/C | 41.9 | 44.4 | 2.9 | 42.7 | 5.9 |
| 719/1/3/A | 18.4 | 14.8 | 22.5 | 6.5 | 16.7 |
| 719/1/4/A | 7.0 | 5.3 | 11.7 | 5.6 | 10.6 |
| 719/1/4/B | 2.5 | 4.9 | 2.0 | 5.3 | 1.0 |
| 719/1/5/A | 34.1 | 52.9 | 31.2 | 37.6 | 9.2 |
| 719/1/5/B | 7.7 | 10.4 | 61.7 | 60.9 | 57.8 |
| 719/1/8/A | 30.7 | 15.2 | 33.9 | 42.4 | 53.1 |
| 719/1/10/A | 8.2 | 75.0 | 86.0 | 79.4 | 80.5 |
| 719/1/10/B | 85.3 | 81.2 | 8.0 | 7.4 | 80.1 |
| 719/1/10/C | 80.4 | 79.0 | 80.0 | 83.8 | 86.8 |
| 719/1/13/A | 14.6 | 9.1 | 7.3 | 10.2 | 9.2 |
| 719/1/13/B | 4.5 | 83.0 | 6.0 | 81.3 | 7.2 |
| 719/1/13/C | 78.1 | 9.5 | 9.7 | 9.2 | 10.7 |
| 719/1/13/D | 12.8 | 11.4 | 11.5 | 7.6 | 10.8 |
| 719/1/13/E | 8.5 | 11.5 | 14.2 | 14.0 | 10.9 |
| 720/4/1/A | 16.4 | 6.1 | 7.1 | 5.1 | 8.9 |
| 720/4/2/A | 7.2 | 79.6 | 73.1 | 50.9 | 34.7 |
| 720/4/2/B | 58.3 | 54.6 | 52.9 | 51.7 | 62.6 |
| 720/4/2/C | 7.0 | 53.7 | 59.8 | 79.1 | 42.7 |
| 721/7/1/A | 8.4 | 6.6 | 7.2 | 6.4 | 8.7 |

Event 719.1.10 was selected for advancement. The segregation of the high alpha-tocopherol trait in T1 seed indicated that this event has a single locus insertion of the over-expressed gamma-tocopherol methyltransferase gene. T1 plants were allowed to self and T2 seed selections from individual plants were subjected to HPLC analysis of individual seed. T2 seed selections were identified that no longer segregated seed with the low alpha-tocopherol content (alpha-tocopherol <10% of total tocol). Seed from these selections were planted and bulk seed that were homozygous of the transgene were harvested from these T2 plants.

Quantitative analysis of tocopherols of T3 seed was conducted as follows. Soybeans were ground in a FOSS tecator sample mill (FOSS, USA) using a 1 mm screen. 200 mg of tissue were extracted in 5 mL of heptane for two hours; alpha-tocopherol acetate was added as internal standard at a final concentration of 38 μg $mL^{-1}$. Ten μL of filtered heptane extract was subjected to HPLC using a Lichrospher column (250-4 HPLC cartridge, Si60, 5 μM particle size) using heptane containing 0.75% isopropanol as mobile phase at a flow rate of 1 mL $min^{-1}$. External standards of all four tocopherols and tocotrienols (2.5 μg $mL^{-1}$) separated under identical conditions were used for tocol quantitation. Tocols were detected using a fluorescence detector using excitation and emission wavelengths of 295 nm, 330 nm, respectively. Table 9 indicates that EMSP 719.1.10 expresses high level of gamma-tocopherol methyltransferase activity indicated by the nearly quantitative conversion of gamma- and delta- to alpha- and beta-tocopherol, respectively. Applicants note that no tocotrienols could be detected.

TABLE 9

Tocol Composition of Homozygous T3 Seed of Event EMSP 719.1.10

| | alpha-tocopherol | beta-tocopherol | gamma-tocopherol | delta-tocopherol | tocopherol |
|---|---|---|---|---|---|
| ppm | 148 | 29 | 5 | 3 | 183 |
| % | 77 | 15 | 2 | 1 | |

Generation of a Transgenic Soybean Line with Seed-preferred Expression of the Barley HGGT Gene:

A DNA fragment was generated by PCR. The new DNA fragment contains the complete open reading frame (1224 bp; SEQ ID NO:46) of the barley HGGT cDNA flanked at 5' and 3' position by DNA sequences recognized by the restriction enzyme NotI. Briefly, the modified HGGT cDNA was amplified from a barley developing seed cDNA library (see PCT Publication No. WO 03/082899) using oligonucleotide primers that include NotI sites that start four nucleotides upstream of the start codon and two nucleotides downstream of the stop codon of the HGGT cDNA sequence, respectively. The sequences of the sense and antisense oligonucleotide primers used in this reaction were as follows:

```
                                        (SEQ ID NO: 47)
5'-ttgcggccgcAGGATGCAAGCCGTCACGGCGGCAGCCG-3'
and

                                        (SEQ ID NO: 48)
5'-ttgcggccgcTTCACATCTGCTGGCCCTTGTAC-3'.
```

(Note: The lower case, underlined nucleotide sequences correspond to added NotI restriction sites.) PCR amplification was achieved using Pfu polymerase, and an aliquot of the barley developing seed cDNA library described in PCT Publication No. WO 03/082899 was used as the template. The product of this PCR reaction was purified by agarose gel electrophoresis and subcloned into pCR-Script-AMP (Stratagene) as described in the manufacturer's protocol.

The amplified open-reading frame of the barley HGGT was then released as a NotI fragment and cloned into the corresponding site of soybean expression vector pKS123 (construction described below) to generate plasmid pSC38 (SEQ ID NO:49).

The construction of vector pKS123 was previously described in PCT Publication No. WO 02/008269 (the contents of which are hereby incorporated by reference). Briefly, plasmid pKS123 contains the hygromycin B phosphotransferase gene (HPT) (Gritz, L. and Davies, J. (1983) *Gene* 25:179-188), flanked by the T7 promoter and transcription terminator (T7prom/hpt/T7term cassette), and a bacterial origin of replication (ori) for selection and replication in bacteria (e.g., *E. coli*). In addition, pKS123 also contains the hygromycin B phosphotransferase gene, flanked by the 35S promoter (Odell et al. *Nature* (1985) 313:810-812) and NOS 3' transcription terminator (Depicker et al. *J. Mol. Appl. Genet.* (1982) 1:561:570) (35S/hpt/NOS3' cassette) for selection in plants such as soybean. pKS123 also contains a NotI restriction site, flanked by the promoter for the α' subunit of β-conglycinin (Beachy et al. *EMBO J.* (1985) 4:3047-3053) and the 3' transcription termination region of the phaseolin gene (Doyle, J. J. et al. *J. Biol. Chem.* (1986) 261:9228-9238) thus allowing for strong tissue-preferred expression in the seeds of soybean of genes cloned into the NotI site.

Ligation products were transformed into *E. coli* and recombinant clones were selected using hygromycin B selection. Restriction digestion of plasmid DNA was used to identify cultures harboring plasmid DNA in which the start codon of the HGGT cDNA was in close proximity to the transcription start site of the soybean β-conglycinin promoter. In this plasmid construct henceforth referred to as SC38, the barley HGGT cDNA is under the control of a 617 bp fragment of the β-conglycinin promoter. The polyadenylation signal for the HGGT transcript is derived from the terminator of the phaseolin gene. Plasmid SC38 contains hygromycin B phosphotransferase gene under control of the cauliflower mosaic 35S promoter, which allows for selection of transformed plant cells by resistance to the antibiotic hygromycin B. Plasmid DNA of SC38 was used to generate transgenic somatic embryos of soybean as described above.

A total of 31 independent events were created. Analysis of tocopherols and tocotrienols was performed by HPLC analysis as described above. Eight events could be identified that contained detectable levels of tocotrienols indicating that in these transgenic events the barley HGGT enzyme was expressed. Tocotrienol levels are below detection limits of fluorescence detection in unmodified leaf and seed tissue of soybean. Transgenic soybeans plants were generated from somatic embryo tissue of one event (1052.5.2). A total of eight T1 seed were subjected analysis of tocopherols and tocotrienols by HPLC of these six seed contained detectable levels of tocotrienols. The segregation of the tocotrienol trait in T1 seed indicated that this event contains a single locus insertion of the β-conglycinin::HGGT expression cassette.

Nineteen randomly selected T1 seed were grown and T2 seed were selected from individual plants. Initially, eight seed from each T2 progeny were subjected to HPLC analysis. This analysis allowed Applicants to identify five T2 progeny that did not produce seed lacking tocotrienols. The non-segregating nature of these progeny was further confirmed through analysis of another eight seed by HPLC. One of the homozygous T2 seed selections was used to produce bulked T3 seed. This seed material was used for quantitative tocol analysis and these results are found in Table 10. Table 10 shows that soybeans over-expressing the HGGT gene from barley accumulate only gamma- and delta-tocotrienol. No alpha- or beta-tocotrienol could be detected in these transgenic lines.

TABLE 10

Tocol Composition of Homozygous T3 Seed of Event EMSP 1052.5.2

| | alpha-tocopherol | beta-tocopherol | gamma-tocopherol | delta-tocopherol | tocopherol |
|---|---|---|---|---|---|
| ppm | 12 | 7 | 94 | 82 | 196 |
| % | 0 | 0 | 3 | 3 | |
| | alpha-tocotrienol | beta-tocotrienol | gamma-tocotrienol | delta-tocotrienol | tocotrienol |
| ppm | 0 | 0 | 1329 | 1212 | 2540 |
| % | 0 | 0 | 49 | 44 | |

The tocotrienol profile of soybeans expressing the HGGT protein from barley indicate that there is no detectable activity converting gamma- and delta-tocotrienols to alpha- and beta-tocotrienols, respectively. Although not to be limited by theory, two possible scenarios could explain the lack of conversion of gamma- and delta-tocotrienol to alpha- and beta-tocotrienols in HGGT-expressing seed of dicotyledoneous plants such as soybean. First, gamma-tocopherol methyltransferase enzymes from plants that do not synthesize tocotrienols may not accept tocotrienol substrates. According to this scenario, gamma-tocopherol methyltransferase enzymes from monocotyledoneous plants have evolved into catalysts for tocotrienol methylation and their co-expression with HGGT would be required for biosynthesis of high levels of alpha- and beta-tocotrienols in dicots. Second, gamma-tocopherol methyltransferase enzymes from dicots may be effective enzymes for synthesis of alpha- and beta-tocotrienols, but their endogenous expression level is too low to achieve conversion of tocotrienol substrates (i.e., the gamma-tocopherol methyltransferase enzymes may be saturated with tocopherol substrates from the over-expression of HGGT).

Combination of Traits for Over-expression of HGGT and Gamma-Tocopherol Methyltransferase by Genetic Crossing:

EMSP 719.1.10 was crossed to EMSP 1052.5.2 to test the feasability of the soybean gamma-tocopherol methyltransferase enzyme for biosynthesis of alpha- and beta-tocotrienol. A total of 20 F1 seed was generated. Quantitative analysis of tocol composition of F1 seed was conducted on a total of four F1 seed and the results are found in Table 11.

TABLE 11

Tocol Composition of F1 Seed Containing Transgenes for Seed-Preferred Over-Expression of the HGGT Gene From Barley and the Gamma-Tocopherol Methyltransferase Gene from Soybean

| | | alpha-tocopherol | beta-tocopherol | gamma-tocopherol | delta-tocopherol | tocopherol |
|---|---|---|---|---|---|---|
| EMSP 1052.5.2 | ppm | 11 | 5 | 93 | 74 | 184 |
| | % | 0.8 | 0.4 | 6 | 5 | |
| EMSP 1052.5.2; | ppm | 143 | 81 | 0 | 2 | 226 |
| EMSP 719.1.10 | % | 14 | 8 | 0 | 0 | |
| | | alpha-tocotrienol | beta-tocotrienol | gamma-tocotrienol | delta-tocotrienol | tocotrienol |
| EMSP 1052.5.2 | ppm | 0 | 0 | 581 | 681 | 1261 |
| | % | 0 | 0 | 40 | 47 | |
| EMSP 1052.5.2; | ppm | 274 | 289 | 54 | 146 | 763 |
| EMSP 719.1.10 | % | 28 | 29 | 5 | 15 | |

Comparison of the tocol profile of EMSP 1052.5.2 to that of F1 beans of a cross of EMSP 1052.5.2 to EMSP 719.1.10 reveals dramatic differences. Whereas alpha-tocotrienol is not detectable in the 1052.5.2 parent, it constitutes the second most abundant tocotrienol species in the crossed material. Applicants note that gamma-tocotrienol is almost completely converted to alpha-tocotrienol. The soybean gamma-tocopherol methyltransferase enzyme evidently also converts delta- to beta-tocotrienol. The lower total tocotrienol concentration of the F1 beans (763 ppm compared to 1,261 ppm in the 1052.5.2 parent) may be attributed to the heterozygous state of the HGGT transgene in the F1 seed or could indicate that the two β-conglycinin promoter-driven transcripts are subject to transcriptional or post-transcriptional gene silencing due to identical promoter and/or 5'UTR sequences. F1 seed were germinated in soil and allow to self. A total of forty-eight F2 seed was analyzed by HPLC and the results are found in Table 12.

TABLE 12

Tocol Composition (percent of total tocopherols (tocph.) and tocotrienols (toct.)) for F2 Progeny of a Cross of EMSP 1052.5.2 to EMSP 719.1.10

| No. | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 1 | 10 | 7 | 0 | 0 | 31 | 37 | 5 | 10 | 217 | 1128 |
| 2 | 10 | 7 | 0 | 0 | 31 | 38 | 5 | 9 | 248 | 1220 |
| 3 | 10 | 6 | 0 | 0 | 30 | 36 | 9 | 10 | 196 | 1067 |
| 4 | 13 | 7 | 0 | 0 | 30 | 37 | 5 | 8 | 279 | 1124 |
| 5 | 9 | 6 | 0 | 0 | 30 | 33 | 9 | 13 | 239 | 1366 |
| 6 | 8 | 6 | 0 | 0 | 30 | 39 | 6 | 11 | 229 | 1408 |
| 7 | 12 | 7 | 0 | 0 | 30 | 33 | 8 | 10 | 271 | 1098 |
| 8 | 11 | 7 | 0 | 0 | 30 | 34 | 9 | 9 | 258 | 1158 |
| 9 | 10 | 6 | 0 | 0 | 29 | 34 | 7 | 13 | 227 | 1177 |
| 10 | 15 | 7 | 0 | 0 | 29 | 31 | 8 | 9 | 265 | 903 |
| 11 | 10 | 7 | 0 | 0 | 28 | 29 | 12 | 14 | 199 | 1005 |
| 12 | 8 | 6 | 0 | 0 | 28 | 36 | 8 | 14 | 227 | 1449 |
| 13 | 12 | 6 | 0 | 0 | 28 | 32 | 12 | 10 | 255 | 1144 |
| 14 | 9 | 7 | 0 | 0 | 28 | 35 | 8 | 13 | 227 | 1190 |
| 15 | 10 | 7 | 0 | 0 | 27 | 37 | 7 | 12 | 240 | 1196 |
| 16 | 13 | 8 | 0 | 0 | 27 | 31 | 7 | 14 | 263 | 996 |
| 17 | 11 | 7 | 0 | 0 | 27 | 34 | 8 | 13 | 228 | 1017 |
| 18 | 11 | 8 | 0 | 0 | 27 | 33 | 7 | 14 | 261 | 1095 |
| 19 | 10 | 7 | 0 | 0 | 27 | 36 | 7 | 12 | 256 | 1207 |
| 20 | 13 | 7 | 0 | 0 | 27 | 31 | 10 | 12 | 210 | 822 |
| 21 | 11 | 7 | 0 | 0 | 26 | 39 | 6 | 10 | 250 | 1108 |
| 22 | 8 | 7 | 0 | 0 | 26 | 40 | 7 | 12 | 228 | 1260 |
| 23 | 8 | 6 | 0 | 0 | 26 | 35 | 8 | 17 | 230 | 1409 |
| 24 | 12 | 7 | 0 | 0 | 26 | 28 | 14 | 14 | 193 | 818 |
| 25 | 10 | 8 | 0 | 0 | 26 | 37 | 6 | 13 | 265 | 1155 |
| 26 | 7 | 7 | 0 | 0 | 25 | 41 | 7 | 13 | 237 | 1472 |
| 27 | 8 | 7 | 0 | 0 | 24 | 38 | 7 | 15 | 224 | 1262 |
| 28 | 10 | 7 | 0 | 0 | 24 | 32 | 9 | 17 | 282 | 1385 |
| 29 | 7 | 6 | 0 | 0 | 24 | 37 | 8 | 18 | 176 | 1171 |
| 30 | 9 | 7 | 0 | 0 | 21 | 29 | 13 | 21 | 219 | 1111 |
| 31 | 2 | 1 | 7 | 4 | 1 | 0 | 46 | 40 | 238 | 1554 |
| 32 | 1 | 0 | 4 | 3 | 0 | 0 | 45 | 45 | 232 | 2284 |
| 33 | 1 | 1 | 5 | 3 | 0 | 0 | 47 | 43 | 190 | 1740 |
| 34 | 1 | 1 | 6 | 4 | 0 | 0 | 44 | 44 | 231 | 1784 |
| 35 | 2 | 0 | 6 | 3 | 0 | 0 | 51 | 37 | 225 | 1788 |
| 36 | 2 | 1 | 5 | 4 | 0 | 0 | 41 | 46 | 204 | 1499 |
| 37 | 86 | 14 | 0 | 0 | 0 | 0 | 0 | 0 | 244 | 0 |
| 38 | 84 | 16 | 0 | 0 | 0 | 0 | 0 | 0 | 253 | 0 |
| 39 | 83 | 17 | 0 | 0 | 0 | 0 | 0 | 0 | 183 | 0 |
| 40 | 82 | 18 | 0 | 0 | 0 | 0 | 0 | 0 | 216 | 0 |
| 41 | 81 | 17 | 1 | 1 | 0 | 0 | 0 | 0 | 317 | 0 |
| 42 | 80 | 19 | 1 | 0 | 0 | 0 | 0 | 0 | 221 | 0 |
| 43 | 78 | 19 | 2 | 1 | 0 | 0 | 0 | 0 | 226 | 0 |
| 44 | 34 | 3 | 56 | 7 | 0 | 0 | 0 | 0 | 225 | 0 |
| 45 | 26 | 3 | 59 | 11 | 0 | 0 | 0 | 0 | 337 | 0 |
| 46 | 23 | 2 | 64 | 10 | 0 | 0 | 0 | 0 | 213 | 0 |
| 47 | 13 | 2 | 69 | 17 | 0 | 0 | 0 | 0 | 261 | 0 |
| 48 | 12 | 2 | 70 | 16 | 0 | 0 | 0 | 0 | 216 | 0 |

Tocol analysis of forty-eight F2 seed revealed 30 F2 seed that expressed both transgene-related traits (see numbers 1-30), six and seven seed with only HGGT or gamma-tocopherol methyltransferase traits, (see numbers 31-36 and 37-43, respectively), and five wild-type seed (see numbers 44-48). These findings are very close to the expected segregation of two unlinked, dominant traits in the F2 generation of a cross of two parents that were homozygous for one of each of the dominant traits. The expected frequency of F2s with both transgenic traits is 62.5% (30/48). The expected frequency of F2s with a single transgenic trait or no transgenic trait is 12.5% (6/48).

F2 progeny with both transgene-related traits were found to contain at least 258 ppm and as much as 487 ppm alpha-tocotrienol and at least 278 ppm and as much as 701 ppm beta-tocotrienol. The oil content of the heptane extracts was determined by derivatization with sodium methoxide followed by GC analysis. Oil was calculated from the tocotrienol concentrations expressed as ppm. F2 progeny with both transgene-related traits contained an oil with at least 1,670 ppm and as much as 2,940 alpha-tocotrienol and at least 1,800 ppm and as much as 4,080 ppm beta-tocotrienol. Applicants also tested for a possible negative effect of the high alpha- and beta-tocotrienol content on seed weight. To this end, seed weight of the forty-eight F2 seed was plotted against alpha-tocotrienol content. No correlation between seed weight and alpha-tocotrienol content could be detected.

In summary, gamma-tocopherol methyltransferase enzyme from soybean can efficiently use tocotrienol substrates, and the foregoing is a method to generate a seed or an extracted oil with high levels of alpha- and beta-tocotrienol. The alpha-tocotrienol content of soybeans over-expressing barley HGGT and the soybean gamma-tocopherol methyltransferase gene exceeds that of any non-transgenic seed or oil described previously by at least one order of magnitude (Packer et al. (2001) *J. Nutr.* 131:369 S-373S; Bertoli et al. (1998) *JAOCS* 75:1037-1040; PCT Publication No. WO 00/072862). These results further demonstrate the ability to produce alpha- and beta-tocotrienols in a crop plant that does not normally accumulate these antioxidant molecules through the transgenic expression of nucleic acid fragments encoding HGGT and gamma-tocopherol methyltransferase polypeptides.

Example 4

Production of Alpha- and Beta-Tocotrienols in Maize (*Zea mays*) Seed

Maize oil, which is derived primarily from the embryo of maize seeds, is typically enriched in tocopherols but contains little or no tocotrienols (The Lipid Handbook, 2nd Edition, Gunstone, F. D., et al., Eds., Chapman and Hall, London, 1994, pp. 129-131). Embryo-preferred expression of the barley HGGT gene in maize leads to accumulation of high levels of tococtrienols. 70-80% of the tocotrienols accumulate in the form of gamma-tocotrienol and only 5-10% of the total tocotrienol fraction is represented by alpha-tocotrienol (see PCT Publication No. WO 03/082899; U.S. Application No. 2004/0034886, Cahoon et al. (2003) *Nat. Biotechnol.* 21:1082-1087.

Based on results disclosed in Examples 1, 2 and 3 of the instant application, the barley HGGT cDNA (bdl2c.pk006.o2; SEQ ID NO:2) and soybean gamma-tocopherol methyltransferase (sah1c.pk004.g2; SEQ ID NO:12) can be expressed in seed embryo of maize to increase the tocol antioxidant content of this tissue and the extracted oil to produce a novel tocol composition that is dominated by alpha- and beta-tocotrienols. As described below, this result can be achieved by transforming maize with an expression cassette comprising the soybean gamma-tocopherol methyltransferase open reading frame operably linked on its 5' end to an embryo preferred promoter, such as the promoter for the maize 16 kDa oleosin gene (Lee, K. and Huang, A. H. (1994) *Plant Mol. Biol.* 26:1981-1987) and the barley HGGT open reading frame operably linked to the maize embryo abundant (EAP1) promoter and terminator.

An expression cassette comprising the promoter from the maize 16 kDa oleosin gene (OLE PRO), the coding sequence of soybean gamma-tocopherol methyltransferase (SEQ ID NO:14) derived from cDNA clone sah1c.pk001.k8:fis (SEQ ID NO:13) (PCT Publication No. WO 00/032757) and the polyadenylation signal sequence/terminator from the nopaline synthase (NOS) gene of *Agrobacterium tumefaciens* is constructed using methods and technologies known in the art. A second expression cassette comprises the barley HGGT coding sequence (PCT Publication No. WO 03/082899; U.S. Application No. 2004/0034886) under the transcriptional control of the maize embryo abundant protein (EAP1) promoter and terminator, with the maize ADH1 INTRON1 inserted between the promoter and coding sequence for enhanced expression. The two expression cassettes are linked, together with a gene encoding a selectable marker, in a binary vector suitable for *Agrobacterium*-mediated transformation of maize.

Similarly, a vector may be created as described above, with the maize gamma-tocopherol methyltransferase (SEQ ID NO:16) derived from cDNA clone p0060.coran49r:fis (SEQ ID NO:15) (PCT Publication No. WO 00/032757) used in place of the soybean gamma-tocopherol methyltransferase, using the same promoter/terminator elements and HGGT expression cassette already described. Furthermore, one skilled in the art understands that the homogentisate geranylgeranyl transferases (HGGT) and gamma-tocopherol methyltransferases found in Table 1 and Table 2, respectively, may also be expressed in maize to demonstrate the feasability of these cDNA for alpha and beta-tocotrienol production in transgenic plants.

An *Agrobacterium*-based protocol can be used for the transformation of maize (see below). The resulting binary vector is introduced into *Agrobacterium* LBA4404 (PHP10523) cells, preferably by electroporation. An in vivo recombination generates a cointegrate plasmid between the introduced binary vector and the vir plasmid (PHP10523) resident in the *Agrobacterium* cells. The resulting *Agrobacterium* cells are used to transform maize.

Transformation of Maize Mediated by *Agrobacterium:*

Freshly isolated immature embryos of maize, about ten days after pollination (DAP), can be incubated with the *Agrobacterium*. The preferred genotype for transformation is the highly transformable genotype Hi-II (Armstrong (1991) *Maize Gen. Coop. Newsletter* 65:92-93). An F1 hybrid created by crossing a Hi-II with an elite inbred may also be used. After *Agrobacterium* treatment of immature embryos, the embryos can be cultured on medium containing toxic levels of herbicide. Only those cells that receive the herbicide resistance gene, and the linked gene(s), grow on selective medium. Transgenic events so selected can be propagated and regenerated to whole plants, produce seed, and transmit transgenes to progeny.

Preparation of *Agrobacterium:*

The engineered *Agrobacterium tumefaciens* LBA4404 can be constructed to contain plasmids for seed-preferred expression of HGGT and gamma-tocopherol methyltransferase genes, as disclosed in U.S. Pat. No. 5,591,616 (the contents of which are hereby incorporated by reference). To use the engineered construct in plant transformation, a master plate of a single bacterial colony transformed with plasmids for seed-preferred expression of HGGT and gamma-tocopherol methyltransferase genes can be prepared by inoculating the bacteria on minimal AB medium and allowing incubation at 28° C. for approximately three days. (The composition and preparation of minimal AB medium has been previously described in PCT Publication No. WO 02/009040 (the contents of which are hereby incorporated by reference). A working plate can then be prepared by streaking the transformed *Agrobacterium* on YP medium (0.5% (w/v) yeast extract, 1% (w/v) peptone, 0.5% (w/v) sodium chloride, 1.5% (w/v) agar) that contains 50 μg/mL of spectinomycin.

The transformed *Agrobacterium* for plant transfection and co-cultivation can then be prepared one day prior to maize transformation. Into 30 mL of minimal A medium (prepared as described in PCT Publication No. WO 02/009040) in a flask was placed 50 μg/mL spectinomycin, 100 μM acetosyringone, and about a ⅛ loopful of *Agrobacterium* from a one to two-day-old working plate. The *Agrobacterium* can then be grown at 28° C. with shaking at 200 rpm for approximately fourteen hours. At mid-log phase, the *Agrobacterium* can be harvested and resuspended at a density of 3 to 5×108 CFU/mL in 561Q medium that contains 100 μM acetosyringone using standard microbial techniques. The composition and preparation of 561Q medium was described in PCT Publication No. WO 02/009040.

Immature Embryo Preparation:

Nine to ten days after controlled pollination of a maize plant, developing immature embryos are opaque and 1-1.5 mm long. This length is the optimal size for infection with the PHP18749-transformed *Agrobacterium*. The husked ears can be sterilized in 50% commercial bleach and one drop TWEEN®-20 for thirty minutes, and then rinsed twice with sterile water. The immature embryos can then be aseptically removed from the caryopsis and placed into 2 mL of sterile holding solution consisting of medium 561Q that contains 100 μM of acetosyringone.

*Agrobacterium* Infection and Co-Cultivation of Embryos:

The holding solution can be decanted from the excised immature embryos and replaced with transformed *Agrobacterium*. Following gentle mixing and incubation for about five minutes, the *Agrobacterium* can be decanted from the immature embryos. Immature embryos were then moved to a plate of 562P medium, the composition of which has been previously described in PCT Publication No. WO 02/009040. The immature embryos can be placed on this media scutellum surface pointed upwards and then incubated at 20° C. for three days in darkness. This can be followed by incubation at 28° C. for three days in darkness on medium 562P that contains 100 μg/mL carbenecillin as described in U.S. Pat. No. 5,981,840.

Selection of Transgenic Events:

Following incubation, the immature embryos can be transferred to 5630 medium, which can be prepared as described in PCT Publication No. WO 02/009040. This medium contains Bialaphos for selection of transgenic plant cells as conferred by the BAR gene that is linked to barley HGGT expression cassette. At ten to fourteen-day intervals, embryos were transferred to 5630 medium. Actively growing putative transgenic embryogenic tissue can be after six to eight weeks of incubation on the 5630 medium.

Regeneration of $T_0$ Plants:

Transgenic embryogenic tissue is transferred to 288 W medium and incubated at 28° C. in darkness until somatic embryos matured, or about ten to eighteen days. Individual matured somatic embryos with well-defined scutellum and coleoptile are transferred to 272 embryo germination medium and incubated at 28° C. in the light. After shoots and roots emerge, individual plants are potted in soil and hardened-off using typical horticultural methods.

288 W medium contains the following ingredients: 950 mL of deionized water; 4.3 g of MS Salts (Gibco); 0.1 g of myo-inositol; 5 mL of MS Vitamins Stock Solution (Gibco); 1 mL of zeatin (5 mg/mL solution); 60 g sucrose; 8 g of agar (Sigma A-7049, Purified), 2 mL of indole acetic acid (0.5 mg/mL solution*); 1 mL of 0.1 mM ABA*; 3 mL of Bialaphos (1 mg/mL solution*); and 2 mL of carbenicillin (50 mg/mL solution). The pH of this solution is adjusted to pH 5.6. The solution is autoclaved and ingredients marked with an asterisk (*) are added after the media has cooled to 60° C.

Medium 272 contains the following ingredients: 950 mL of deionized water; 4.3 g of MS salts (Gibco); 0.1 g of myo-inositol; 5 mL of MS vitamins stock solution (Gibco); 40 g of Sucrose; and 1.5 g of GELRITE®. This solution is adjusted to pH 5.6 and then autoclaved.

Example 5

Expression of Chimeric Genes in Microbial Cells

The cDNAs encoding the instant HGGT and gamma-tocopherol methyltransferase polypeptides can be used to produce alpha- and beta-tocotrienols in microbes such as algal and cyanobacterial cells that contain an operable tocopherol biosynthetic pathway. Expression of cDNAs encoding the instant HGGT polypeptides in these cells are expected to result in the condensation of geranylgeranyl pyrophosphate and homogentisate. The product of the HGGT reaction 2-methyl-6-geranylgeranylbenzoquinol can then be converted to alpha- and beta-tocotrienols by tocopherol biosynthetic enzymes native to the host microbial cell and the instant gamma-tocopherol methyltransferase polypeptides. Tocotrienols can be produced in microbes by linking the cDNAs encoding the instant HGGT and gamma-tocopherol methyltransferase polypeptides with promoter elements that are suitable to direct gene expression in the selected host cell. The resulting chimeric genes can be introduced into the host microbial cell using techniques such as homologous recombination (Williams, J. G. K. (1988) *Methods Enzymol.* 167:766-778; Legarde, D. et al. (2000) *App. Environ. Microbiol.* 66:64-72). Host cells transformed with cDNAs for the instant HGGT and gamma-tocopherol methyltransferase polypeptides operably linked to functional promoters can then be analyzed for tocotrienol production using techniques described in Example 1.

Example 6

Production of Alpha- and Beta-Tocotrienol in Plant Cells

The cDNAs encoding the instant HGGT and gamma-tocopherol methyltransferase polypeptides can be used to produce alpha- and beta-tocotrienols in plant cells. Even higher levels of alpha- and beta-tocotrienol production may be achieved when genes encoding the instant HGGT and gamma-tocopherol methyltransferase polypeptides are co-expressed with genes that encode enzymes that participate either in the conversion of plastidic chorismate pools to homogentisate or in the conversion of 2-methyl-6-prenylbenzoquinol to 2,3-methyl-6-prenylbenzoquinol. To this end, transgenic plants are generated with DNA constructs that provide constitutive- or seed-specific expression of bifunctional chorismate mutase-prephenate dehydratase genes (TYRA) of bacterial or fungal origin and p-hydroxyphenylpyruvate dioxygenase genes (HPPD) and 2-methyl-6-prenylbenzoquinol methyltransferase genes (VTE3) from plants or photosynthetic bacteria. The TRYA gene products are targeted to the chloroplast by way of being fused to suitable chloroplast target peptides.

Plant transformations are performed as described above in Examples 1-3. Transgenic lines expressing high levels TYRA, HPPD and VTE3 are identified by measuring tocochromanol content as described above in Examples 1-3. The events with high levels of tocochromanols are crossed to events generated with constructs expressing the instant HGGT and gamma-tocopherol methyltransferase polypeptides. Suitable constructs to generate the latter events are KS319 (Example 1), SC1 and SC38 (Example 2), KS270 and KS308 (Example 3). Alternatively, new DNA constructs are generated using standard methods of molecular biology that provide seed-specific or constitutive expression of five genes comprised of TYRA, HPPD, VTE3 and HGGT and gamma-tocopherol methyltransferase genes of instant invention. Plant transformations are performed as described in Examples 1-3. Transgenic lines expressing high levels of all five gene products are identified by measuring tocochromanol content of plant tissue as described in Examples 1-3.

Example 7

Production of Tocotrienols in Transgenic Soybean Lines: Molecular Stack of Barley HGGT and Maize Gamma-Tocopherol Methyltransferase To demonstrate the ability to produce increased levels of alpha- and beta-tocotrienols in transgenic soybean lines, the barley HGGT cDNA (bdl2c.pk006.o2; SEQ ID NO:2) and maize gamma-tocopherol methyltransferase (p0060.coran49r:fis; SEQ ID NO:15) (PCT Publication No. WO 00/032757) were used in a molecular stack (progeny with both transgene-related traits).

A construct for seed specific expression of maize gamma-tocopherol methyltransferase in soybean was generated as follows. DNA of KS126 (see Example 1) was linearized with NotI. 5' overhangs were completely filled in with T4 polynucleotide kinase and dephosphorylated using calf intestinal phosphatase. A restriction fragment containing the complete ORF of the maize GTMT cDNA was excised from the EST clone using restriction enzymes DraI and SnaBI and ligated to the KS126 vector. Ligation products were introduced into *E coli*. Plasmid DNA was isolated form recombinant clones and subjected to restriction digests with BamHI. Plasmid clones which produced a DNA fragment of 2.8 kb when digested with BamHI contain the maize GTMT gene in an orientation in which the 5' end of the transcript is in proximity to the 3' end of the KTI promoter (sense orientation). This plasmid was named KS325. Its sequence is set forth as SEQ ID NO:51.

Transgenic soybean lines were generated with plasmid DNA of KS270 (see Example 1) and KS325 using particle bombardment of embryogenic callus.

KS270 provides the barley HGGT gene under control of 617 bp of the soybean O-conglycinin promoter. The polyadenylation signal for the HGGT transcript is derived from the terminator of the phaseolin gene (from the bean *Phaseolus vulgaris*; Doyle et al. (1986) *J. Biol. Chem.* 261:9228-9238). The plasmid also contains the cDNA of a sulfonylurea-resistant variant of the soybean ALS gene that is under control of 1217 bp of the SAMS promoter. The polyadenylation signal for the HGGT transcript is derived from the terminator of the soybean ALS gene.

KS325 provides the gamma-tocopherol methyltransferase gene from maize under the control of 2090 bp of the soybean Kti promoter. The polyadeylation signal for the gamma-tocopherol methyltransferase transcript is derived from the terminator of the Kti gene. KS325 also provides a hygromycin B phosphotransferase (HPT) resistance gene (Gritz et al. (1983) *Gene* 25:179-188) that is under control of 1408 bp of the 35S promoter from Cauliflower Mosaic Virus (Odell et al. (1985) *Nature* 313:810-812). The polyadenylation signal for the hygromycin resistance gene is derived from the terminator of nopaline synthase gene from the T-DNA of the Ti plasmid of *Agrobacterium tumefaciens.*

Soybean embryogenic suspension cultures were transformed with DNA plasmids KS270 in conjunction with KS325 by the method of particle gun bombardment (Klein et al. (1987) *Nature* (London) 327:70-73; U.S. Pat. No. 4,945,050) using a BIORAD BIOLISTIC™ PDS1000/He instrument. The following stock solutions and media were used for transformation and regeneration of soybean plants:

Stock Solutions:

Sulfate 100× Stock: 37.0 g $MgSO_4.7H_2O$, 1.69 g $MnSO_4.H_2O$, 0.86 g $ZnSO_4.7H_2O$, 0.0025 g $CuSO_4.5H_2O$ Halides 100× Stock: 30.0 g $CaCl_2.2H_2O$, 0.083 g KI, 0.0025 g $CoCl_2.6H_2O$ P, B, Mo 100× Stock: 18.5 g $KH_2PO_4$, 0.62 g $H_3BO_3$, 0.025 g $Na_2MoO_4.2H_2O$ Fe EDTA 100× Stock: 3.724 g $Na_2EDTA$, 2.784 g $FeSO_4.7H_2O$ 2,4-D Stock: 10 mg/mL Vitamin B5 1000× Stock: 10.0 g myo-inositol, 0.10 g nicotinic acid, 0.10 g pyridoxine HCl, 1 g thiamine.

Media (Per Liter):

SB196: 10 mL of each of the above stock solutions, 1 mL B5 Vitamin stock, 0.463 g $(NH_4)_2SO_4$, 2.83 g $KNO_3$, 1 mL 2,4-D stock, 1 g asparagine, 10 g Sucrose, pH 5.7

SB103: 1 pk. Murashige & Skoog salts mixture, 1 mL B5 Vitamin stock, 750 mg $MgCl_2$ hexahydrate, 60 g maltose, 2 g GELRITE®, pH 5.7.

SB166: SB103 supplemented with 5 g per liter activated charcoal.

SB71-4: Gamborg's B5 salts, 1 mL B5 vitamin stock, 30 g sucrose, 5 g TC agar, pH 5.7.

To prepare tissue for transformation, soybean embryogenic suspension cultures were maintained in 35 mL liquid medium (SB196) on a rotary shaker (150 rpm) at 28° C. with fluorescent lights providing a 16 hour day/8 hour night cycle. Cultures were subcultured every two weeks by inoculating approximately 35 mg of tissue into 35 mL of fresh liquid media.

In particle gun bombardment procedures it is possible to use purified 1) entire plasmid DNA; or 2) DNA fragments containing only the recombinant DNA expression cassette(s) of interest. For every seventeen bombardment transformations, 85 μL of suspension is prepared containing 1 to 90 picograms (pg) of plasmid DNA per base pair of each DNA plasmid. Both recombinant DNA plasmids were co-precipitated onto gold particles as follows. The DNAs in suspension were added to 50 μL of a 20-60 mg/mL 0.6 μm gold particle suspension and then combined with 50 μL $CaCl_2$ (2.5 M) and 20 μL spermidine (0.1 M). The mixture was vortexed for 5 seconds, spun in a microfuge for 5 seconds, and the supernatant removed. The DNA-coated particles were then washed once with 150 μL of 100% ethanol, vortexed and spun in a microfuge again, then resuspended in 85 μL of anhydrous ethanol. Five μL of the DNA-coated gold particles were then loaded on each macrocarrier disk.

Approximately 150 to 250 mg of two-week-old suspension culture was placed in an empty 60 mm×15 mm petri plate and the residual liquid removed from the tissue using a pipette. The tissue was placed about 3.5 inches away from the retaining screen and each plate of tissue was bombarded once. Membrane rupture pressure was set at 650 psi and the chamber was evacuated to −28 inches of Hg. Three plates were bombarded, and, following bombardment, the tissue from each plate was divided between two flasks, placed back into liquid media, and cultured as described above.

Seven days after bombardment, the liquid medium was exchanged with fresh SB196 medium supplemented with 30-50 mg/L hygromycin. The selective medium was subsequently refreshed weekly or biweekly. Seven weeks post-bombardment, bright green, transformed tissue was observed growing from untransformed, chlorotic or necrotic embryogenic clusters. Isolated green tissue was removed and inoculated into individual wells in six-well culture dishes to generate new, clonally-propagated, transformed embryogenic suspension cultures. Thus, each new line was treated as independent transformation event in an individual well. These suspensions can then be maintained as suspensions of embryos clustered in an immature developmental stage through subculture or they can be regenerated into whole plants by maturation and germination of individual somatic embryos.

After two weeks in individual cell wells, transformed embryogenic clusters were removed from liquid culture and placed on solidified medium (SB166) containing no hormones or antibiotics for one week. Embryos were cultured for at 26° C. with mixed fluorescent and incandescent lights on a 16 hour day/8 hour night schedule. After one week, the cultures were then transferred to SB103 medium and maintained in the same growth conditions for 3 additional weeks.

Somatic embryos became suitable for germination after four weeks and were then removed from the maturation medium and dried in empty petri dishes for 1 to 5 days. The dried embryos were then planted in SB71-4 medium where they were allowed to germinate under the same light and temperature conditions as described above. Germinated embryos were transferred to sterile soil and grown to maturity for seed production.

A total of eighteen events were created by co-transformation with KS270 and KS325 plasmids. Tocol composition of five T1 seed was assayed for each events as follows. A seed chip (approximately 5-15 mg of tissue) was obtained from the cotyledon tissue of the seed. The chip was extracted with 100 μL of heptane for 2 hours. Tocopherol and tocotrienol was quantitated by HPLC analysis as described in Example 3.

A total of eighteen events were generated and analyzed (see Table 13).

TABLE 13

Tocol Composition (percent of total tocopherols (tocph.) and tocotrienols (toct.)) for T1 Seed Chips of Events Generated with KS270 and KS325

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 4652.1.10.1A | 1 | 1 | 2 | 3 | 2 | 1 | 44 | 46 | 167 | 2175 |
| 4652.1.10.1B | 17 | 2 | 80 | 0 | 0 | 0 | 0 | 0 | 240 | 0 |
| 4652.1.10.1C | 2 | 1 | 3 | 0 | 2 | 1 | 44 | 47 | 279 | 4711 |
| 4652.1.10.1D | 11 | 1 | 88 | 0 | 0 | 0 | 0 | 0 | 310 | 0 |
| 4652.1.10.1E | 2 | 1 | 4 | 0 | 4 | 2 | 42 | 46 | 317 | 4070 |
| 4652.1.11.1A | 1 | 0 | 3 | 0 | 0 | 0 | 44 | 51 | 156 | 3463 |
| 4652.1.11.1B | 1 | 1 | 4 | 0 | 0 | 0 | 47 | 47 | 127 | 2133 |
| 4652.1.11.1C | 1 | 0 | 4 | 0 | 0 | 0 | 50 | 46 | 96 | 1900 |
| 4652.1.11.1D | 20 | 2 | 78 | 0 | 0 | 0 | 0 | 0 | 270 | 0 |
| 4652.1.11.1E | 1 | 0 | 5 | 0 | 0 | 0 | 53 | 39 | 201 | 2600 |
| 4652.1.2.1A | 1 | 0 | 3 | 0 | 1 | 0 | 42 | 52 | 101 | 2204 |
| 4652.1.2.1B | 1 | 0 | 3 | 0 | 1 | 0 | 46 | 50 | 149 | 3923 |
| 4652.1.2.1C | 11 | 1 | 88 | 0 | 0 | 0 | 0 | 0 | 192 | 0 |
| 4652.1.2.1D | 1 | 0 | 3 | 0 | 1 | 0 | 44 | 51 | 153 | 3310 |
| 4652.1.2.1E | 0 | 0 | 3 | 0 | 1 | 0 | 41 | 54 | 109 | 2831 |
| 4652.1.7.1A | 6 | 4 | 0 | 0 | 38 | 41 | 4 | 7 | 240 | 2051 |
| 4652.1.7.1B | 6 | 4 | 0 | 0 | 42 | 40 | 3 | 5 | 169 | 1597 |
| 4652.1.7.1C | 22 | 2 | 76 | 0 | 0 | 0 | 0 | 0 | 273 | 0 |
| 4652.1.7.1D | 6 | 5 | 0 | 0 | 35 | 45 | 3 | 6 | 214 | 1756 |
| 4652.1.7.1E | 5 | 5 | 0 | 0 | 32 | 52 | 2 | 5 | 400 | 3670 |
| 4652.1.8.1A | 16 | 2 | 83 | 0 | 0 | 0 | 0 | 0 | 175 | 0 |
| 4652.1.8.1B | 0 | 0 | 4 | 0 | 0 | 0 | 47 | 48 | 115 | 2429 |
| 4652.1.8.1C | 17 | 2 | 82 | 0 | 0 | 0 | 0 | 0 | 160 | 0 |
| 4652.1.8.1D | 1 | 0 | 4 | 0 | 0 | 0 | 45 | 50 | 114 | 2277 |
| 4652.1.8.1E | 1 | 0 | 4 | 0 | 0 | 0 | 51 | 44 | 100 | 1962 |
| 4652.2.10.1A | 0 | 0 | 4 | 0 | 0 | 0 | 42 | 53 | 124 | 2292 |
| 4652.2.10.1B | 0 | 0 | 4 | 0 | 0 | 0 | 47 | 47 | 147 | 2767 |
| 4652.2.10.1C | 1 | 0 | 5 | 0 | 0 | 0 | 48 | 46 | 223 | 3502 |
| 4652.2.10.1D | 9 | 1 | 90 | 0 | 0 | 0 | 0 | 0 | 254 | 0 |
| 4652.2.10.1E | 11 | 2 | 87 | 0 | 0 | 0 | 0 | 0 | 267 | 0 |
| 4652.2.11.1A | 11 | 1 | 87 | 0 | 0 | 0 | 0 | 0 | 164 | 0 |
| 4652.2.11.1B | 6 | 5 | 0 | 0 | 37 | 50 | 0 | 1 | 197 | 1604 |
| 4652.2.11.1C | 7 | 6 | 0 | 0 | 36 | 50 | 0 | 0 | 466 | 2950 |
| 4652.2.11.1D | 12 | 1 | 86 | 0 | 0 | 0 | 0 | 0 | 209 | 0 |
| 4652.2.11.1E | 6 | 7 | 0 | 0 | 32 | 55 | 0 | 0 | 440 | 2973 |
| 4652.2.13.1A | 10 | 1 | 88 | 0 | 0 | 0 | 0 | 0 | 243 | 0 |
| 4652.2.13.1B | 10 | 1 | 88 | 0 | 0 | 0 | 0 | 0 | 230 | 0 |
| 4652.2.13.1C | 15 | 2 | 82 | 0 | 0 | 0 | 0 | 0 | 155 | 0 |
| 4652.2.13.1D | 11 | 1 | 88 | 0 | 0 | 0 | 0 | 0 | 284 | 0 |
| 4652.2.13.1E | 11 | 1 | 88 | 0 | 0 | 0 | 0 | 0 | 229 | 0 |
| 4652.2.14.1A | 85 | 14 | 1 | 0 | 0 | 0 | 0 | 0 | 360 | 0 |
| 4652.2.14.1B | 4 | 4 | 0 | 0 | 31 | 43 | 5 | 12 | 267 | 2796 |
| 4652.2.14.1C | 9 | 6 | 0 | 0 | 40 | 44 | 0 | 1 | 342 | 1855 |
| 4652.2.14.1D | 86 | 13 | 0 | 0 | 0 | 0 | 0 | 0 | 254 | 1 |
| 4652.2.14.1E | 5 | 4 | 0 | 0 | 32 | 58 | 0 | 1 | 262 | 2495 |
| 4652.2.6.1A | 6 | 8 | 0 | 0 | 32 | 54 | 0 | 0 | 353 | 2192 |
| 4652.2.6.1B | 65 | 14 | 0 | 0 | 15 | 6 | 0 | 0 | 378 | 102 |
| 4652.2.6.1C | 8 | 7 | 0 | 0 | 33 | 52 | 0 | 0 | 488 | 2762 |
| 4652.2.6.1D | 6 | 6 | 0 | 0 | 33 | 53 | 0 | 1 | 399 | 2905 |
| 4652.2.6.1E | 63 | 16 | 0 | 0 | 15 | 6 | 0 | 0 | 358 | 95 |
| 4652.2.7.1A | 2 | 1 | 4 | 0 | 1 | 1 | 42 | 49 | 205 | 2779 |
| 4652.2.7.1B | 2 | 1 | 4 | 0 | 2 | 1 | 43 | 48 | 176 | 2660 |
| 4652.2.7.1C | 1 | 1 | 3 | 0 | 2 | 1 | 45 | 48 | 110 | 2192 |
| 4652.2.7.1D | 1 | 1 | 4 | 0 | 2 | 1 | 42 | 50 | 170 | 2679 |

TABLE 13-continued

Tocol Composition (percent of total tocopherols (tocph.) and tocotrienols (toct.)) for T1 Seed Chips of Events Generated with KS270 and KS325

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 4652.2.7.1E | 3 | 1 | 6 | 0 | 2 | 1 | 48 | 40 | 199 | 1889 |
| 4652.2.9.1A | 5 | 4 | 0 | 0 | 28 | 31 | 11 | 22 | 252 | 2495 |
| 4652.2.9.1B | 6 | 5 | 0 | 0 | 33 | 40 | 5 | 11 | 214 | 1614 |
| 4652.2.9.1C | 4 | 2 | 3 | 0 | 17 | 8 | 37 | 29 | 212 | 2148 |
| 4652.2.9.1D | 5 | 4 | 0 | 0 | 30 | 33 | 10 | 19 | 245 | 2521 |
| 4652.2.9.1E | 4 | 2 | 1 | 0 | 19 | 14 | 24 | 36 | 194 | 2212 |
| 4652.3.15.1A | 85 | 14 | 1 | 0 | 0 | 0 | 0 | 0 | 213 | 0 |
| 4652.3.15.1B | 76 | 23 | 0 | 0 | 0 | 0 | 0 | 0 | 379 | 0 |
| 4652.3.15.1C | 13 | 2 | 86 | 0 | 0 | 0 | 0 | 0 | 183 | 0 |
| 4652.3.15.1D | 77 | 22 | 0 | 0 | 0 | 0 | 0 | 1 | 167 | 1 |
| 4652.3.15.1E | 78 | 21 | 1 | 0 | 0 | 0 | 0 | 0 | 248 | 0 |
| 4652.3.17.1A | 8 | 7 | 0 | 0 | 36 | 47 | 1 | 1 | 361 | 2029 |
| 4652.3.17.1B | 8 | 5 | 0 | 0 | 42 | 44 | 1 | 1 | 362 | 2419 |
| 4652.3.17.1C | 18 | 10 | 0 | 0 | 34 | 37 | 0 | 1 | 471 | 1198 |
| 4652.3.17.1D | 8 | 6 | 0 | 0 | 38 | 45 | 1 | 1 | 334 | 1941 |
| 4652.3.17.1E | 9 | 7 | 0 | 0 | 38 | 45 | 0 | 1 | 276 | 1392 |
| 4652.3.3.1A | 4 | 4 | 0 | 0 | 37 | 41 | 5 | 9 | 272 | 2905 |
| 4652.3.3.1B | 5 | 4 | 0 | 0 | 37 | 45 | 3 | 6 | 282 | 2714 |
| 4652.3.3.1C | 8 | 6 | 0 | 0 | 36 | 48 | 1 | 2 | 416 | 2608 |
| 4652.3.3.1D | 4 | 4 | 0 | 0 | 36 | 53 | 1 | 2 | 233 | 2390 |
| 4652.3.3.1E | 5 | 5 | 0 | 0 | 31 | 43 | 5 | 12 | 344 | 3319 |
| 4652.3.5.1A | 18 | 2 | 80 | 0 | 0 | 0 | 0 | 0 | 161 | 0 |
| 4652.3.5.1B | 21 | 2 | 77 | 0 | 0 | 0 | 0 | 0 | 192 | 0 |
| 4652.3.5.1C | 4 | 4 | 0 | 0 | 22 | 28 | 13 | 29 | 203 | 2315 |
| 4652.3.5.1D | 18 | 2 | 80 | 0 | 0 | 0 | 0 | 0 | 191 | 0 |
| 4652.3.5.1E | 6 | 4 | 1 | 0 | 28 | 27 | 14 | 20 | 296 | 2450 |
| 4652.3.6.1A | 16 | 2 | 82 | 0 | 0 | 0 | 0 | 0 | 182 | 0 |
| 4652.3.6.1B | 7 | 5 | 0 | 0 | 43 | 43 | 1 | 1 | 328 | 2451 |
| 4652.3.6.1C | 7 | 5 | 0 | 0 | 41 | 44 | 1 | 1 | 292 | 2060 |
| 4652.3.6.1D | 9 | 6 | 0 | 0 | 41 | 42 | 1 | 1 | 288 | 1654 |
| 4652.3.6.1E | 15 | 2 | 84 | 0 | 0 | 0 | 0 | 0 | 244 | 0 |
| 4652.3.8.1A | 30 | 4 | 66 | 0 | 0 | 0 | 0 | 0 | 137 | 0 |
| 4652.3.8.1B | 24 | 3 | 73 | 0 | 0 | 0 | 0 | 0 | 180 | 0 |
| 4652.3.8.1C | 16 | 2 | 82 | 0 | 0 | 0 | 0 | 0 | 196 | 0 |
| 4652.3.8.1D | 30 | 3 | 68 | 0 | 0 | 0 | 0 | 0 | 205 | 0 |
| 4652.3.8.1E | 44 | 6 | 49 | 0 | 0 | 0 | 0 | 0 | 194 | 0 |

Seed chips from fifteen events contained significant levels of tocotrienol. Ten of these also contained significant levels (>150 ppm) of alpha- and beta-tocotrienol. Alpha-tocotrienol content in seed chips reached 1300 ppm in event 4652.1.7.1E (i.e, (400+3670)×0.32=1302). For several events greater than 40% of the total tocopherol and tocotrienol content was alpha-tocotrienol. Seed chips do not provide a comprehensive picture of the oil composition of the entire seed. Therefore, the entire T1 seed from selected events were subjected to tocol analysis as described in Example 2 (see Table 14).

The highest whole seed alpha-tocotrienol level (847 ppm) was reached in event 4652.1.7.1. For the six events subjected to whole seed tocol analysis at least 24% and up to 36% of the total tocopherol and tocotrienol content was derived from alpha-tocotrienol. In all six events gamma- and delta-tocotrienol levels are at very low levels compared to the best transgenic event generated in similar experiments performed with the soybean GTMT sequence (Example 2). The maize GTMT provides an excellent enzyme for methylation of gamma- and delta-tocotrienol in developing soybean seed.

TABLE 14

Tocol Composition (percent of total tocopherols (tocph.) and tocotrienols (toct.)) for T1 Seed of Events Generated with KS270 and KS325

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 4652.1.7.1 A | 5 | 4 | 0 | 0 | 31 | 45 | 3 | 10 | 261 | 2355 |
| 4652.1.7.1 B | 5 | 4 | 0 | 0 | 36 | 44 | 3 | 8 | 214 | 2162 |
| 4652.2.11.1 B | 4 | 5 | 0 | 0 | 29 | 59 | 1 | 2 | 213 | 2028 |
| 4652.2.11.1 C | 6 | 7 | 0 | 0 | 24 | 62 | 0 | 0 | 224 | 1414 |
| 4652.2.14.1 C | 6 | 6 | 0 | 0 | 30 | 53 | 1 | 3 | 245 | 1694 |
| 4652.2.6.1 C | 7 | 9 | 0 | 0 | 25 | 57 | 0 | 2 | 320 | 1636 |
| 4652.2.6.1 D | 7 | 8 | 0 | 0 | 27 | 57 | 0 | 1 | 327 | 1986 |
| 4652.3.17.1 B | 5 | 6 | 0 | 0 | 28 | 54 | 2 | 6 | 210 | 1688 |
| 4652.3.17.1 D | 7 | 6 | 0 | 0 | 31 | 51 | 1 | 4 | 238 | 1612 |
| 4652.3.6.1 B | 5 | 4 | 0 | 0 | 36 | 51 | 1 | 2 | 227 | 2077 |
| 4652.3.6.1 C | 6 | 5 | 0 | 0 | 35 | 50 | 1 | 2 | 238 | 1802 |

Example 8

Alpha-Tocotrienol Production in *Arabidopsis thaliana* by Transgenic Expression of Barley HGGT and Maize Gamma-Tocopherol Methyltransferase A construct for co-expression of barley homogentisate geranylgeranyl transferase and maize gamma-tocopherol methyltransferase in *Arabidopsis thaliana* was generated as follows. The maize GTMT expression cassette comprised of Kti promoter GTMT gene and Kti terminator was excised from KS325 (see Example 7) as a 3.6 kb fragment by complete digestion with AscI. This DNA fragment was ligated to SC38 DNA that had previously been lineraized by partial digestion with AscI. Recombinant clones were recovered and plasmid DNA was isolated using standard techniques. This new plasmid is referred to KS325×SC38. A 6.7 kb DNA fragment containing expression cassettes for barley HGGT and maize GTMT genes was excised from this plasmid by partial digestion with SalI and ligated to pZBL120 (see Example 1) linearized with SalI to give pZBL120×KS325×SC38. The T-DNA of the plant transformation vector pZBL120×KS325×SC38 is set forth as SEQ ID NO:52. Transgenic *Arabidopsis* lines were generated using pZBL20×KS325×SC38 as described in Example 1. A total of 38 lines were generated and tocochromanol content of T2 seed was determined by HPLC analysis as described in Example 1 (see Table 15).

TABLE 15

Tocol Composition (percent of total tocopherols (tocph.) and tocotrienols (toct.)) of T2 Seed Material of Transgenic *Arabidopsis* Lines Expressing Barley HGGT and Maize Gamma-Tocopherol Methyltransferase Genes

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 38 | 24 | 1 | 14 | 1 | 51 | 2 | 7 | 1 | 244 | 382 |
| 17 | 33 | 1 | 12 | 0 | 50 | 0 | 4 | 0 | 327 | 382 |
| 31 | 27 | 1 | 14 | 1 | 49 | 0 | 8 | 1 | 421 | 577 |
| 3 | 30 | 0 | 14 | 0 | 49 | 0 | 7 | 0 | 489 | 626 |
| 34 | 24 | 1 | 12 | 1 | 49 | 3 | 9 | 2 | 180 | 300 |
| 32 | 32 | 1 | 12 | 1 | 49 | 2 | 4 | 0 | 347 | 418 |
| 2 | 28 | 1 | 18 | 1 | 48 | 0 | 3 | 0 | 254 | 271 |
| 35 | 24 | 1 | 15 | 1 | 48 | 2 | 8 | 1 | 245 | 348 |
| 6 | 23 | 0 | 30 | 0 | 47 | 0 | 0 | 0 | 165 | 148 |
| 12 | 17 | 2 | 7 | 1 | 47 | 7 | 16 | 2 | 388 | 987 |
| 29 | 26 | 1 | 13 | 1 | 47 | 2 | 8 | 2 | 318 | 461 |
| 25 | 29 | 1 | 14 | 1 | 47 | 2 | 6 | 1 | 327 | 407 |
| 15 | 25 | 1 | 22 | 1 | 47 | 2 | 2 | 0 | 350 | 374 |
| 18 | 27 | 1 | 16 | 1 | 46 | 0 | 8 | 1 | 344 | 429 |
| 27 | 26 | 1 | 16 | 1 | 45 | 2 | 8 | 1 | 335 | 435 |
| 33 | 28 | 1 | 16 | 1 | 45 | 0 | 7 | 1 | 214 | 246 |
| 20 | 29 | 1 | 16 | 1 | 45 | 0 | 8 | 1 | 330 | 385 |
| 13 | 28 | 0 | 17 | 1 | 44 | 0 | 9 | 1 | 356 | 419 |
| 26 | 27 | 1 | 20 | 1 | 40 | 0 | 11 | 1 | 284 | 312 |
| 30 | 35 | 1 | 17 | 1 | 40 | 0 | 7 | 1 | 400 | 354 |
| 21 | 31 | 0 | 22 | 1 | 38 | 0 | 8 | 1 | 329 | 282 |
| 22 | 14 | 1 | 11 | 1 | 38 | 3 | 29 | 4 | 358 | 965 |
| 1 | 38 | 0 | 21 | 1 | 34 | 0 | 6 | 0 | 422 | 286 |
| 5 | 31 | 0 | 28 | 0 | 33 | 0 | 8 | 0 | 168 | 117 |
| 28 | 49 | 1 | 19 | 0 | 29 | 0 | 2 | 0 | 240 | 108 |
| 10 | 22 | 0 | 39 | 1 | 29 | 0 | 9 | 1 | 260 | 160 |
| 11 | 3 | 0 | 94 | 1 | 2 | 0 | 0 | 0 | 377 | 8 |
| 23 | 69 | 0 | 30 | 1 | 0 | 0 | 0 | 0 | 400 | 2 |
| 4 | 1 | 0 | 98 | 1 | 0 | 0 | 0 | 0 | 291 | 0 |
| 7 | 17 | 0 | 82 | 1 | 0 | 0 | 0 | 0 | 311 | 0 |
| 8 | 1 | 0 | 98 | 1 | 0 | 0 | 0 | 0 | 347 | 0 |
| 9 | 1 | 0 | 98 | 2 | 0 | 0 | 0 | 0 | 417 | 0 |
| 14 | 65 | 0 | 34 | 1 | 0 | 0 | 0 | 0 | 426 | 0 |
| 16 | 1 | 0 | 98 | 2 | 0 | 0 | 0 | 0 | 266 | 0 |
| 19 | 1 | 0 | 98 | 1 | 0 | 0 | 0 | 0 | 379 | 0 |
| 24 | 68 | 1 | 30 | 1 | 0 | 0 | 0 | 0 | 323 | 0 |
| 36 | 69 | 1 | 30 | 1 | 0 | 0 | 0 | 0 | 305 | 0 |
| 37 | 1 | 0 | 97 | 2 | 0 | 0 | 0 | 0 | 262 | 0 |
| wild-type | 1 | 0 | 98 | 1 | 0 | 0 | 0 | 0 | 173 | 0 |

Of the 38 events analyzed 26 showed greater than 100 ppm tocotrienols and reached levels as high as 990 ppm. In these 26 events alpha-tocotrienol represented at least 28% and as much as 51% of the total tocochromanol content. In T2 seed of the best event (Event ID 12) alpha-tocotrienol levels reached 640 ppm (i.e., (388+987)×0.47=646). The T2 material described so far still contains 25% of wild-type seed. Events 3, 12, 29, 31 and 32 were germinated on selective media. When grown on selective media T2 seed of all six events produced 25% of kanamycin-sensitive wild-type seed. For each event 15 kanamycin resistant seedlings were transferred to soil allowed to self-fertilize and grown to maturity. For each event three T3 seed selections were identified that no longer segregated kanamycin-sensitive seedlings. This seed material was subjected to tocochromanol quantitation as described above (see Table 16).

TABLE 16

Tocol Composition (percent of total tocopherols (tocph.) and tocotrienols (toct.)) of Homozygous T3 Seed Material of Transgenic *Arabidopsis* Lines Expressing Barley HGGT and Maize Gamma-Tocopherol Methyltransferase Genes

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 3 | 29 | 1 | 2 | 1 | 61 | 2 | 3 | 1 | 229 | 464 |
| 3 | 33 | 1 | 2 | 1 | 58 | 2 | 3 | 0 | 493 | 849 |
| 3 | 32 | 1 | 2 | 1 | 58 | 2 | 4 | 1 | 307 | 545 |
| 12 | 24 | 2 | 2 | 1 | 59 | 7 | 4 | 1 | 407 | 971 |
| 12 | 19 | 5 | 1 | 1 | 55 | 14 | 4 | 2 | 361 | 1031 |
| 12 | 21 | 3 | 9 | 1 | 53 | 7 | 5 | 1 | 441 | 880 |
| 29 | 23 | 2 | 2 | 0 | 58 | 6 | 7 | 2 | 345 | 943 |
| 29 | 28 | 2 | 3 | 0 | 53 | 4 | 8 | 2 | 320 | 647 |
| 29 | 17 | 2 | 2 | 0 | 51 | 7 | 15 | 5 | 219 | 770 |
| 32 | 21 | 2 | 1 | 0 | 64 | 8 | 4 | 1 | 213 | 675 |
| 32 | 22 | 2 | 1 | 0 | 63 | 6 | 4 | 1 | 291 | 841 |
| 32 | 24 | 2 | 2 | 1 | 61 | 5 | 4 | 1 | 346 | 865 |
| 31 | 21 | 2 | 2 | 2 | 65 | 3 | 4 | 1 | 300 | 795 |
| 31 | 22 | 3 | 1 | 1 | 66 | 4 | 3 | 1 | 213 | 562 |
| 31 | 21 | 3 | 2 | 2 | 63 | 4 | 5 | 1 | 297 | 785 |

In the homozygous T3 seed material of the five events alpha-tocotrienol represented at least 51% and as much as 65% of the total tocochromanol content. In homozygous T3 seed of one event (Event ID 12) alpha-tocotrienol levels reached 810 ppm (i.e., (407+971)×0.59=813). In all five events gamma tocotrienol levels are at very low levels compared to the best transgenic event generated in similar experiments performed with the soybean GTMT sequence (Example 1). The maize GTMT provides an excellent enzyme for methylation of gamma-tocotrienol in developing *Arabidopsis* seed.

Example 9

Preparation of cDNA Libraries and Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBLUESCRIPT®. In addition, the cDNAs may be introduced directly into precut Bluescript® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBLUESCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI PRISM® dye-terminator ReadyReaction mix) outward from the transposition event site, utilizing unique primers specific to the binding sites within the transposon.

Sequence data is collected (ABI PRISM® Collections) and assembled using Phred and Phrap (Ewing et al. (1998) *Genome Res.* 8:175-185; Ewing and Green (1998) *Genome Res.* 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment may correspond to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBLUESCRIPT® vector using a commercial kit and following the manufacturer's protocol. This kit is selected from many available from several vendors including INVITROGEN™ (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 10

Identification of cDNA Clones cDNA clones encoding ferrochelatases can be identified by conducting BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States (1993) *Nat. Genet.* 3:266-272) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST are reported herein as "pLog" values, which represent the negative of the logarithm of the reported P-value or E-value. Accordingly, the greater the pLog value, the greater the likelihood that the cDNA-encoded sequence and the BLAST "hit" represent homologous proteins.

ESTs sequences can be compared to the Genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 11

Characterization of a cDNA Clones Encoding 2-Methyl-6-Phytylbenzoquinol Methyltransferase A cDNA library representing mRNAs from developing seed tissue of balsam pear (*Momordica charantia*) was prepared and a cDNA clone, fds1n.pk003.e5, was identified that encodes 2-methyl-6-phytylbenzoquinol methyltransferase (MC VTE3). The nucleic acid sequence of the protein-coding region of the cDNA insert in fds1n.pk003.e5 is presented as SEQ ID NO:53. The amino acid sequence of the protein encoded by SEQ ID NO:53 is presented as SEQ ID NO:54. The amino acid sequence of the putative mature protein, i.e., minus the transit peptide (amino acids 1-47 of SEQ ID NO:54), is presented as SEQ ID NO:70.

Shown in Table 17 are the BLASTP results, expressed as pLog of the E-value, for SEQ ID NO:54 and each of the indicated polypeptides. Polypeptides in which the putative transit peptide has been removed are indicated as "mature". The amino acid sequence of the mature *Arabidopsis* 2-methyl-6-phytylbenzoquinol methyltransferase polypeptide (SEQ ID NO:67) is taken from Cheng et al. 2003 Plant Cell 15:2343-2356. Also shown in Table 17 are the percent sequence identity values for between SEQ ID NO:54 and each of the indicated amino acid sequences:

TABLE 17

BLAST Results and Percent Sequence Identity for the 2-Methyl-6-Phytylbenzoquinol Methyltransferase From *Momordica charantia* (SEQ ID NO: 54)

| NCBI GI No. or Patent Reference | Plant | SEQ ID NO | BLASTP pLog of E-value | Percent Sequence Identity |
|---|---|---|---|---|
| 108385436 | *Arabidopsis* | 61 | 154 | 80.7 |
| 157348021 | Grape | 62 | 168 | 83.0 |
| 80971672 | Sunflower | 63 | 162 | 81.8 |
| US2007061916 | Cotton | 64 | 171 | 86.0 |
| WO2003034812 | Soybean | 65 | 168 | 84.7 |
| WO2003034812 | Corn | 66 | 141 | 73.1 |
| 108385436-derived | *Arabidopsis* (mature) | 67 | — | 88.9 |
| WO2003034812 | Soybean (mature) | 68 | 162 | 92.4 |
| WO2003034812 | Corn (mature) | 69 | 139 | 80.2 |

SEQ ID NO:70 is the amino acid sequence of the putative mature 2-methyl-6-phytylbenzoquinol methyltransferase from *Momordica charantia*. Shown in Table 18 are the percent sequence identity values between SEQ ID NO:70 and each of the indicated amino acid sequences:

TABLE 18

Percent Sequence Identity with the Mature 2-Methyl-6-Phytylbenzoquinol Methyltransferase From *Momordica charantia* (SEQ ID NO: 70)

| NCBI GI No. or Patent Reference | Plant | SEQ ID NO | Percent Sequence Identity |
|---|---|---|---|
| 108385436 | *Arabidopsis* | 61 | 87.8 |
| 157348021 | Grape | 62 | 88.5 |
| 80971672 | Sunflower | 63 | 89.6 |
| US2007061916 | Cotton | 64 | 92.0 |
| WO2003034812 | Soybean | 65 | 92.4 |
| WO2003034812 | Corn | 66 | 80.2 |
| 108385436-derived | *Arabidopsis* (mature) | 67 | 88.9 |
| WO2003034812 | Soybean (mature) | 68 | 92.4 |
| WO2003034812 | Corn (mature) | 69 | 80.2 |

FIGS. 3A-3C present an alignment of the amino acid sequences of the 2-methyl-6-phytylbenzoquinol methyltransferase proteins set forth in SEQ ID NOs: 54, 61, 62, 63, 64, 65, 66, 67, 68, 69 and 70. FIG. 4 presents the percent sequence identities and divergence values for each sequence pair presented in FIGS. 3A-3C.

Sequence alignments and percent identity calculations were performed using the MEGALIGN® program of the LASERGENE® bioinformatics computing suite (DNASTAR® Inc., Madison, Wis.). Alignment of the sequences was performed using the Clustal W method of alignment with the default parameters. Default parameters for multiple alignments were Gap Penalty=10, Gap Length Penalty=0.20, Delay Divergent Sequence=30%, and DNA Transition Weight=0.50. Default parameters for pairwise alignments were Gap Penalty=10.0 and Gap Length=0.10.

Example 12

Tocol Composition of Soybean Somatic Embryos Transformed with Barley HGGT, Maize Gamma-Tocopherol Methyltransferase and *Momordica charantia* 2-Methyl-6-Phytylbenzoquinol Methyltransferase EST clone fds1n.pk003.e5 is derived from a cDNA library of developing seed tissue of balsam pear (*Momordica charantia*) encodes a protein with 83% sequence identity to the VTE3 gene product of *Arabidopsis* (Plant Cell (2003), 15(10), 2343-2356), using the CLUSTAL W method of alignment. The DNA sequence of the open-reading frame in the cDNA insert is set forth as SEQ ID NO:53. The predicted amino acid sequence of the *Momordica charantia* 2-methyl-6-phytylbenzoquinol methyltransferase, designated "MC VTE3", is set forth as SEQ ID NO:54. A DNA fragment was generated by PCR. The ORF was amplified from plasmid DNA using oligonucleotide primers. The sequences of the sense (forward) and antisense (reverse) oligonucleotide primers used in this reaction were as follows:

```
                                    (SEQ ID NO: 55)
5'-CACCATGGCTTCTGCAATGCTCAATGG -3'
and

                                    (SEQ ID NO: 56)
5'-CTCCCCAACTCAGATTGGTTGCCCTTC-3'.
```

PCR amplification was achieved using TAQ polymerase, and plasmid DNA of the EST clone was used as the template. The product of this PCR reaction was purified by agarose gel electrophoresis and subcloned into pENTR/D-TOPO® (INVITROGEN™) as described in the manufacturer's protocol. A 1042 bp fragment containing the entire open-reading frame of was excised using restriction enzymes AscI and NotI. Ends were completely filled in with T4 polymerase (INVITROGEN™, USA) according to instructions of the manufacturer and ligated to NotI linearized, filled-in pKR561 vector. Recombinant clones were subjected to analysis by restriction enzyme digestion to identify ligation products in which the start codon was in proximity of the annexin promoter in pKR561 (sense orientation). Plasmids with this orientation are henceforth referred to as pKR561-MCVTE3 (SEQ ID NO:57).

Vector pKR561 had previously been constructed as follows. Vector pKR268 (SEQ ID NO:58), which was previously described in U.S. Pat. No. 7,256,033 (the contents of which are hereby incorporated by reference), contains a NotI site flanked by the soybean annexin promoter (U.S. Pat. No. 7,129,089) and the BD30 3' termination region (Ann/NotI/BD30 cassette). Vector pKR145 (SEQ ID NO:59), which was previously described in PCT Publication No. WO 2004/071467 (the contents of which are hereby incorporated by reference), contains the hygromycin B phosphotransferase gene [Gritz, L. and Davies, J. (1983) Gene 25:179-188], flanked by the T7 promoter and transcription terminator (T7prom/hpt/T7term cassette), and a bacterial origin of replication (ori) for selection and replication in *E. coli*. In addition, pKR145 contains the hygromycin B phosphotransferase gene, flanked by the 35S promoter [Odell et al., (1985) Nature 313:810-812] and NOS 3' transcription terminator [Depicker et al., (1982) J. Mol. Appl. Genet. 1:561:570] (35S/hpt/NOS3' cassette) for selection in soybean. The BsiWI fragment of pKR268, containing the Ann/NotI/BD30 cassette, was cloned into the BsiWI fragment of pKR145, containing the 35S/hpt/NOS3' cassette), to produce pKR561 (SEQ ID NO:60).

Generation of Transgenic Somatic Embryos:

For co-expression of HV HGGT, ZM GTMT (VTE4) and MC VTE3 genes in soybean somatic embryos, soybean tissue was co-bombarded as described below with a mixture of KS325×SC38 (see Example 8) and pKR561-MCVTE3. Prior to mixing the DNAs, KS325×SC38 was digested with EcoRI and BglII to inactivate vector components conferring hygromycin resistance. Likewise pKR561-MCVTE3 was linearized with BamHI. KS325×SC38 and pKR561-MCVTE3 were combined in a 10:1 ratio and used for transformation of soybean somatic embryos as described below. In the resulting DNA mixture the linearized pKR561-MCVTE3 DNA fragment provides an intact expression cassette for hygromycin resistance comprised of CaMV 35S promoter hygromycin phosphotransferase gene and nos terminator.

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 h day/night photoperiod at light intensity of 60-85 μE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., Nature 327:70 (1987)) using a DUPONT™ BIOLISTIC™ PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using two 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time, secondary embryos were cut and placed into SB196 liquid media for 7 days.

Preparation of DNA for Bombardment:

Either an intact plasmid or a DNA plasmid fragment containing the genes of interest and the selectable marker gene were used for bombardment.

A 50 μL aliquot of sterile distilled water containing 1 mg of gold particles was added to 5 μL of a 1 μg/μL DNA solution (DNA fragments prepared as described above), 50 μL 2.5M $CaCl_2$ and 20 μL of 0.1 M spermidine. The mixture was pulsed 5 times on level 4 of a vortex shaker and spun for 5 sec in a bench microfuge. After a wash with 150 μL of 100% ethanol, the pellet was suspended by sonication in 85 μL of 100% ethanol. Five μL of DNA suspension was dispensed to each flying disk of the BIOLISTIC™ PDS1000/HE instrument disk. Each 5 μL aliquot contained approximately 0.058 mg gold particles per bombardment (i.e., per disk).

Tissue Preparation and Bombardment with DNA:

Approximately 100-150 mg of 7 day old embryonic suspension cultures were placed in an empty, sterile 60×15 mm petri dish and the dish was placed inside of an empty 150×25 mm Petri dish. Tissue was bombarded 1 shot per plate with membrane rupture pressure set at 650 PSI and the chamber was evacuated to a vacuum of 27-28 inches of mercury. Tissue was placed approximately 2.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six to eight days post-bombardment, the SB196 is exchanged with fresh SB196 containing 30 mg/L hygromycin. The selection media was refreshed weekly. Four to six weeks post-selection, green, transformed tissue was observed growing from untransformed, necrotic embryogenic clusters. Isolated, green tissue was removed and inoculated into multi-well plates to generate new, clonally propagated, transformed embryogenic suspension cultures.

Embryo Maturation:

Transformed embryogenic clusters were cultured for one-three weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 μE/m$^2$s. After this time embryo clusters were removed to a solid agar media, SB166, for 1 week, then subcultured to medium SB103 for 3 weeks. Alternatively, embryo clusters were removed to SB228 (SHaM) liquid media, 35 mL in 250 mL Erlenmeyer flask, for 2-3 weeks. Tissue cultured in SB228 was maintained on a rotary shaker, 130 rpm, 26° C. with cool white fluorescent lights on 16:8 h day/night photoperiod at light intensity of 60-85 μE/m2/s. During this period, individual embryos were removed from the clusters and screened for alterations in their fatty acid compositions as described supra.

Media Recipes:

SB196—FN Lite Liquid Proliferation Medium (per liter) contains the following: 10 mL of MS FeEDTA—100× Stock 1; 10 mL of MS Sulfate—100× Stock 2; 10 mL of FN Lite Halides—100× Stock 3; 10 mL of FN Lite P, B, Mo—100× Stock 4; 1.0 mL of B5 vitamins (1 mL/L); 1.0 mL of 2,4-D (10 mg/L final concentration); 2.83 g of $KNO_3$; 0.463 g of $(NH_4)_2SO_4$; 1.0 g of Asparagine; 10 g of Sucrose (1%); adjust to pH 5.8.

FN Lite Stock Solutions No. 1-4 are prepared as follows:

Stock Number 1—MS Fe EDTA 100× Stock contains (per liter): 3.724 g of $Na_2$ EDTA (Add first, dissolve in dark bottle while stirring); and 2.784 g of $FeSO_4$-$7H_2O$.

Stock Number 2—MS Sulfate 100× stock contains (per liter): 37.0 g of $MgSO_4$-$7H_2O$; 1.69 g of $MnSO_4$—$H_2O$; 0.86 g of $ZnSO_4$-$7H_2O$; and 0.0025 g of $CuSO_4$-$5H_2O$.

Stock Number 3—FN Lite Halides 100× Stock contains (per liter): 30.0 g of $CaCl_2$-$2H_2O$; 0.083 g of KI; and 0.0025 g of $CoCl_2$-$6H_2O$.

Stock Number 4—FN Lite P, B, Mo 100× Stock contains (per liter): 18.5 g of $KH_2PO_4$; 0.62 g of $H_3BO_3$; and 0.025 g of $Na_2MoO_4.2H_2O$.

SB1 Solid Medium contains the following (per liter): 1 package MS salts (Gibco/BRL—Cat. No. 11117-066); 1 mL B5 vitamins 1000× stock; 31.5 g Glucose; 2 mL 2,4-D (20 mg/L final concentration); adjust to pH 5.7; and 8 g TC agar.

SB199 Solid Medium contains the following (per liter): 1 package MS salts (Gibco/BRL—Cat. No. 11117-066); 1 mL B5 vitamins 1000× stock; 30 g Sucrose; 4 mL 2,4-D (40 mg/L final concentration); adjust to pH 7.0; and 2 gm GELRITE®.

SB166 Solid Medium contains the following (per liter): 1 package MS salts (Gibco/BRL—Cat. No. 11117-066); 1 mL B5 vitamins 1000× stock; 60 g maltose; 750 mg $MgCl_2$ hexahydrate; 5 g Activated charcoal; adjust to pH 5.7; and 2 g GELRITE®.

SB103 Solid Medium contains the following (per liter): 1 package MS salts (Gibco/BRL—Cat. No. 11117-066); 1 mL B5 vitamins 1000× stock; 60 g maltose; 750 mg MgCl2 hexahydrate; adjust to pH 5.7; and 2 g GELRITE®.

SB71-4 Solid Medium contains the following (per liter): 1 bottle Gamborg's B5 salts w/sucrose (Gibco/BRL—Cat. No. 21153-036); adjust to pH 5.7; and 5 g TC agar.

2,4-D Stock: Obtain premade from PHYTOTECHNOLOGY LABORATORIES™ Cat. No. D 295—concentration 1 mg/mL.

B5 Vitamins Stock contains the following (per 100 mL): 10 g Myo-inositol; 100 mg Nicotinic acid; 100 mg Pyridoxine HCl; and 1 g Thiamine. If the solution does not dissolve quickly enough, apply a low level of heat via the hot stir plate. Store aliquots at −20° C.

SB228—Soybean Histodifferentiation & Maturation (SHaM) contains the following (per liter): 600 mL DDI $H_2O$; 100 mL FN-Lite Macro Salts for SHaM 10×; 1 mL MS Micro Salts 1000×; 10 mL MS FeEDTA 100×; 6.82 mL CaCl 100×; 1 mL B5 Vitamins 1000×; 0.149 g L-Methionine; 30 g Sucrose; 30 g Sorbitol; adjust volume to 900 mL; adjust to pH 5.8; autoclave. Add to cooled media (≦30° C.): 110 mL 4% glutamine (final conc. 30 mM). Final volume will be 1010 mL after glutamine addition. Because glutamine degrades relatively rapidly, it may be preferable to add immediately prior to using media. Expiration is 2 weeks after glutamine is added; base media can be kept longer without glutamine.

FN-lite Macro for SHAM 10×—Stock #1 contains the following (per liter): 4.63 g $(NH_4)2\text{-}SO_4$ (Ammonium Sulfate); 28.3 g $KNO_3$ (Potassium Nitrate); 3.7 g $MgSO_4{*}7H_20$ (Magnesium Sulfate Heptahydrate); 1.85 g $KH_2PO_4$ (Potassium Phosphate, Monobasic); bring to volume; autoclave.

MS Micro 1000—Stock #2 contains the following (per 1 liter): 6.2 g $H_3BO_3$ (Boric Acid); 16.9 g $MnSO_4{*}H_2O$ (Manganese Sulfate Monohydrate); 8.6 g ZnSO4*7H20 (Zinc Sulfate Heptahydrate); 0.25 g $Na_2MoO_4.2H_2O$ (Sodium Molybdate Dihydrate); 0.025 g $CuSO_4{*}5H_2O$ (Copper Sulfate Pentahydrate); 0.025 g $CoCl_2{*}6H_2O$ (Cobalt Chloride Hexahydrate); 0.8300 g KI (Potassium Iodide); bring to volume and autoclave.

FeEDTA 100×—Stock #3 contains the following (per liter): 3.73 g $Na_2EDTA$ (Sodium EDTA); EDTA must be completely dissolved before adding iron; 2.78 g $FeSO_4{*}7H_2O$ (Iron Sulfate Heptahydrate); bring to volume and autoclave. Solution is photosensitive. Bottle(s) should be wrapped in foil to omit light.

Ca 100×—Stock #4 contains the following (per liter): 44 g $CaCl_2{*}2H_2O$ (Calcium Chloride Dihydrate); bring to volume and autoclave.

B5 Vitamin 1000×—Stock #5 contains the following (per liter): 10 g Thiamine*HCl; 1 g Nicotinic Acid; 1 g Pyridoxine*HCl; 100 g Myo-Inositol; bring to volume; store frozen.

4% Glutamine—Stock #6 contains the following (per liter): 900 mL DDI water heated to 30° C.; 40 g L-Glutamine; gradually add while stirring and applying low heat. Do not exceed 35° C. Bring to Volume. Filter terilize and store frozen. Warm thawed stock in 31° C. bath to fully dissolve crystals.

Tocol and Oil Analysis:

Somatic embryos were harvested after two weeks of culture in the liquid maturation medium SB228 (SHaM) liquid media. Thirty-one events were created. All embryos generated for a given event were harvested in bulk and processed as follows. Embryos were frozen on dry ice or by incubation in a −80° C. freezer for two h followed by lyophilization for 48 h.

Dried embryos were ground to a fine powder using a genogrinder vial (½"×2" polycarbonate) and a steel ball (SPEX Centriprep (Metuchen, N.J., U.S.A.). Grinding time was 30 sec at 1450 oscillations per min. For every event, approximately 30 mg of tissue were weighed into Eppendorf tubes 5 μL of tocopherol acteate (3.79 ng $\mu L^{-1}$) was added to each sample as internal standard. The tissue was extracted using 200 μL heptane at room temperature under continuous shaking for 2 h. Heptane extracts were cleared by centrifugation and filtration and 10 uL of extract were analyzed by HPLC as described in Example 3.

Tocol data are summarized in Table 19.

TABLE 19

Tocol Composition (percent of total tocopherols (tocph.) and tocotrienols (toct.)) of Soybean Somatic Embryos Generated by Co-Transformation with KS325xSC38 and pKR561-MCVTE3

| Event ID | alpha-tocoph. | beta-tocoph. | gamma-tocoph. | delta-tocoph. | alpha-toct. | beta-toct. | gamma-toct. | delta-toct. | tocph. (ppm) | toct. (ppm) |
|---|---|---|---|---|---|---|---|---|---|---|
| 19 | 17 | 1 | 0 | 0 | 78 | 3 | 1 | 0 | 247 | 1123 |
| 11 | 19 | 0 | 0 | 0 | 77 | 2 | 1 | 0 | 317 | 1328 |
| 28 | 27 | 3 | 0 | 0 | 57 | 11 | 1 | 0 | 161 | 370 |
| 29 | 30 | 6 | 1 | 0 | 47 | 16 | 1 | 0 | 262 | 454 |
| 1 | 31 | 7 | 0 | 0 | 42 | 18 | 1 | 1 | 302 | 497 |
| 7 | 17 | 7 | 8 | 1 | 35 | 25 | 2 | 6 | 199 | 411 |
| 23 | 32 | 3 | 8 | 1 | 34 | 10 | 10 | 3 | 244 | 326 |
| 31 | 18 | 3 | 3 | 1 | 34 | 14 | 18 | 9 | 201 | 586 |
| 2 | 56 | 2 | 2 | 0 | 32 | 7 | 1 | 0 | 284 | 190 |
| 12 | 24 | 3 | 29 | 2 | 25 | 8 | 5 | 3 | 225 | 158 |
| 30 | 18 | 4 | 24 | 2 | 24 | 13 | 8 | 7 | 184 | 204 |
| 17 | 5 | 0 | 16 | 0 | 7 | 0 | 70 | 1 | 182 | 669 |
| 15 | 13 | 1 | 12 | 4 | 6 | 2 | 42 | 20 | 186 | 427 |
| 14 | 15 | 1 | 66 | 6 | 4 | 0 | 5 | 1 | 241 | 30 |
| 8 | 5 | 1 | 12 | 5 | 4 | 2 | 50 | 21 | 188 | 642 |
| 5 | 7 | 1 | 15 | 4 | 3 | 0 | 51 | 20 | 189 | 508 |
| 4 | 6 | 1 | 13 | 4 | 2 | 0 | 54 | 19 | 224 | 692 |
| 13 | 2 | 1 | 6 | 5 | 2 | 0 | 45 | 39 | 148 | 941 |
| 27 | 4 | 0 | 13 | 0 | 2 | 0 | 80 | 1 | 175 | 832 |
| 20 | 6 | 0 | 15 | 5 | 1 | 0 | 37 | 35 | 171 | 472 |
| 25 | 52 | 1 | 6 | 2 | 1 | 0 | 23 | 15 | 255 | 162 |
| 9 | 5 | 0 | 38 | 3 | 1 | 0 | 43 | 9 | 210 | 241 |
| 32 | 6 | 0 | 88 | 4 | 1 | 0 | 1 | 0 | 165 | 3 |
| 26 | 7 | 0 | 89 | 3 | 0 | 0 | 1 | 0 | 222 | 2 |
| 18 | 5 | 0 | 89 | 4 | 0 | 0 | 1 | 0 | 300 | 6 |
| 16 | 6 | 0 | 80 | 4 | 0 | 8 | 1 | 0 | 287 | 32 |
| 22 | 11 | 0 | 80 | 6 | 0 | 0 | 2 | 0 | 238 | 7 |
| 10 | 9 | 0 | 84 | 5 | 0 | 0 | 1 | 0 | 266 | 4 |
| 21 | 1 | 0 | 9 | 4 | 0 | 0 | 54 | 32 | 165 | 1002 |
| 3 | 8 | 1 | 86 | 4 | 0 | 0 | 1 | 0 | 225 | 3 |
| 6 | 66 | 5 | 27 | 2 | 0 | 0 | 1 | 0 | 256 | 1 |
| 24 | 98 | 2 | 0 | 0 | 0 | 0 | 0 | 0 | 361 | 0 |

Oil concentration of the heptane extract was measured as follows. 25 μL of extract was derivatized to fatty acid methyl esters as follows. One mL of a 25% sodium methoxide stock solution was added to 24 mL of HPLC grade methanol. Sodium methoxide was stored under an inert gas.

Five μL of a 17:0 TAG (Nu-Chek Prep, Elysian, Minn., USA) stock solution (10 mg/mL) was combined with 25 μL of heptane tissue extract in a glass culture tube 500 μL of 1% sodium methoxide was added. Samples were derivatized in a water bath at 50° C. for 15 min. Samples were allowed to cool to RT and 1 mL of 1M NaCl was added followed by brief mixing. FAMEs were extracted into 1 mL of heptane and 4 μL sample were quantitated by GC analysis.

Two transgenic somatic embryo events (with Event ID numbers 19 and 11) were identified that contained very high levels of alpha tocotrienol (>70% of total tocols). These events contained 1270 and 1060 ppm alpha tocotrienol on a DW basis and 21,590 and 18050 ppm alpha tocotrienol on an oil basis. Co-expression of HV HGGT, ZM GTMT and MC VTE3 allowed for very high level of alpha tocotrienol accumulation. A vitamin E profile was generated that was dominated by alpha tocotrienol and alpha tocopherol; other vitamins represented less than 5% of the total tocols. Moreover, the tocol profile of a significant number of somatic embryo events suggest that only some of the genes present on the two DNA fragments used for transformation were expressed in these. For example, event number 24 very likely only expressed ZM GTMT and MC VTE3 and events 19 and 21 only expressed HV HGGT (see Example 3). Event number 7 very likely only expressed HGGT and ZM GTMT (see Example 7). Its tocol profile is very similar to that of soybeans expressing only these two vitamin E biosynthetic genes. Events 27 and 17 with a profile dominated by gamma tocotrienol very likely only expressed HV HGGT and MC VTE3. Finally, events such as 32, 26, 18 and 10, with a tocol profile dominated by gamma tocopherol and only trace levels of tocotrienol, very likely did not express any transgene-derived Vitamin E biosynthetic genes.

In summary, the data illustrated that by using only three types of vitamin E biosynthetic genes described herein, a wide range of vitamin E profiles can be generated in a combinatorial fashion. Moreover, it was shown that co-expression of HV-HGGT, ZM GTMT (VTE4) and MC VTE3 can lead to an increase of tocol levels of 6.5-fold and an increase of the relative alpha tocochromanol content to >95% of total tocols.

All publications and patent applications mentioned in the specification are indicative of the level of those skilled in the art to which this invention pertains. All publications and patent applications are herein incorporated by reference in their entirety to the same extent as if each individual publication or patent application was specifically and individually indicated to be incorporated by reference in its entirety.

Although the foregoing invention has been described in some detail by way of illustration and example for purposes of clarity of understanding, one of ordinary skill will recognize that certain changes and modifications may be practiced and are included within the scope of the foregoing invention and the appended claims.

What is claimed is:

1. A transformed microbial cell comprising in its genome:

(a) a first recombinant nucleic acid molecule comprising at least one regulatory sequence operably linked to at least one nucleotide sequence selected from the group consisting of:

(i) the nucleotide sequence set forth in SEQ ID NO: 15;

(ii) a nucleotide sequence encoding the amino acid sequence set forth in SEQ ID NO 16; and (iii) a nucleotide sequence encoding a polypeptide having an amino acid sequence of at least 95% sequence identity, based on the Clustal V method of alignment, when compared to SEQ ID NO:16, wherein the polypeptide has gamma-tocopherol methyltransferase activity;

(b) a second recombinant nucleic acid molecule comprising at least one regulatory sequence operably linked to at least one nucleotide sequence selected from the group consisting of:

(iv) the nucleotide sequence set forth in SEQ ID NO:1;

(v) a nucleotide sequence encoding the amino acid sequence set forth in SEQ ID NO:2; and (vi) a nucleotide sequence encoding a polypeptide having an amino acid sequence of at least 95% sequence identity, based on the Clustal V method of alignment, when compared to SEQ ID NO:2, wherein the polypeptide has homogentisate geranylgeranyl transferase activity; and (c) a third recombinant nucleic acid molecule comprising at least one regulatory sequence operably linked to at least one nucleotide sequence selected from the group consisting of:

(vii) the nucleotide sequence set forth in SEQ ID NO:53;

(viii) a nucleotide sequence encoding the amino acid sequence set forth in SEQ ID NO:54; and (ix) a nucleotide sequence encoding a polypeptide having an amino acid sequence of at least 95% sequence identity, based on the Clustal V method of alignment, when compared to SEQ ID NO:54, wherein the polypeptide has 2-methyl-6-phytylbenzoquinol methyltransferase activity;

wherein the first recombinant nucleic acid molecule, the second recombinant nucleic acid molecule and the third recombinant nucleic acid molecule are stably incorporated into the genome of the transformed microbial cell.

2. The transformed microbial cell of claim 1, wherein said microbial cell is an algal cell.

3. The transformed microbial cell of claim 1, wherein the at least one regulatory sequence of the first, second, and third recombinant nucleic acid molecules is a promoter.

* * * * *

SEQUENCE LISTING

```
<160> NUMBER OF SEQ ID NOS: 70

<210> SEQ ID NO 1
<211> LENGTH: 1457
<212> TYPE: DNA
<213> ORGANISM: Hordeum vulgare
<220> FEATURE:
<221> NAME/KEY: misc_feature
<222> LOCATION: (1410)..(1410)
<223> OTHER INFORMATION: n is a, c, g, or t
<220> FEATURE:
<221> NAME/KEY: misc_feature
<222> LOCATION: (1421)..(1421)
<223> OTHER INFORMATION: n is a, c, g, or t

<400> SEQUENCE: 1

cccctccttt acacagatcc gcgggttaac ttcctcctcc ggaggccgcc cggccggcga     60

ggatgcaagc cgtcacggcg gcggccgcgg cggggcagct gctaacagat acgaggagag    120

ggcccagatg tagggctcgg ctgggaacga cgagattatc ctggacaggt cgatttgcag    180

tggaagcttt tgcaggccag tgccaaagtg ctactactgt aatgcataaa ttcagtgcca    240

tttctcaagc tgctaggcct agaagaaaca caaagagaca gtgcagcgat gattatccag    300

ccctccaagc tggatgcagc gaggttaatt gggatcaaaa cggttccaac gccaatcggc    360

ttgaggaaat caggggagat gttttgaaga aattgcgctc tttctatgaa ttttgcaggc    420

cacacacaat ttttggcact ataataggta taacttcagt gtctctcctg ccaatgaaga    480

gcatagatga ttttactgtc acggtactac gaggatatct cgaggctttg actgctgctt    540

tatgtatgaa catttatgtg gtcgggctga atcagctata tgacattcag attgacaaga    600

tcaacaagcc aggtcttcca ttggcatctg gggaattttc agtagcaact ggagttttct    660

tagtactcgc attcctgatc atgagcttta gcataggaat acgttccgga tcggcgccac    720

tgatgtgtgc tttaattgtc agcttccttc ttggaagtgc gtactccatt gaggctccgt    780

tcctccggtg gaaacggcac gcgctcctcg ctgcatcatg tatcctattt gtgagggcta    840
```

```
tcttggtcca gttggctttc tttgcacata tgcagcaaca tgttctgaaa aggccattgg    900

cagcaaccaa atcgctggtg tttgcaacat tgtttatgtg ttgcttctct gccgtcatag    960

cactattcaa ggatattcca gatgttgatg gagatcgaga ctttggtatc caatccttga   1020

gtgtgagatt ggggcctcaa agagtgtatc agctctgcat aagcatattg ttgacagcct   1080

atggcgctgc cactctagta ggagcttcat ccacaaacct atttcaaaag atcatcactg   1140

tgtctggtca tggcctgctt gctttgacac tttggcagag agcgcagcac tttgaggttg   1200

aaaaccaagc gcgtgtcaca tcattttaca tgttcatttg gaagctattc tatgcagagt   1260

atttccttat accatttgtg cagtgaaatt tgtacaaggg ccagcagatg tgaactatat   1320

atacatgtaa aacaaattat attactgatg atactcaatc caatgcttgg attttgcttg   1380

tactgtgcta tctgtaattt catgatctan agaaagagca natgttggat gtgtaaaaaa   1440

aaaaaaaaaa aaaaaaa                                                  1457
```

```
<210> SEQ ID NO 2
<211> LENGTH: 407
<212> TYPE: PRT
<213> ORGANISM: Hordeum vulgare

<400> SEQUENCE: 2

Met Gln Ala Val Thr Ala Ala Ala Ala Ala Gly Gln Leu Leu Thr Asp
1               5                   10                  15

Thr Arg Arg Gly Pro Arg Cys Arg Ala Arg Leu Gly Thr Thr Arg Leu
            20                  25                  30

Ser Trp Thr Gly Arg Phe Ala Val Glu Ala Phe Ala Gly Gln Cys Gln
        35                  40                  45

Ser Ala Thr Thr Val Met His Lys Phe Ser Ala Ile Ser Gln Ala Ala
    50                  55                  60

Arg Pro Arg Arg Asn Thr Lys Arg Gln Cys Ser Asp Asp Tyr Pro Ala
65                  70                  75                  80

Leu Gln Ala Gly Cys Ser Glu Val Asn Trp Asp Gln Asn Gly Ser Asn
                85                  90                  95

Ala Asn Arg Leu Glu Glu Ile Arg Gly Asp Val Leu Lys Lys Leu Arg
            100                 105                 110

Ser Phe Tyr Glu Phe Cys Arg Pro His Thr Ile Phe Gly Thr Ile Ile
        115                 120                 125

Gly Ile Thr Ser Val Ser Leu Leu Pro Met Lys Ser Ile Asp Asp Phe
    130                 135                 140

Thr Val Thr Val Leu Arg Gly Tyr Leu Glu Ala Leu Thr Ala Ala Leu
145                 150                 155                 160

Cys Met Asn Ile Tyr Val Val Gly Leu Asn Gln Leu Tyr Asp Ile Gln
                165                 170                 175

Ile Asp Lys Ile Asn Lys Pro Gly Leu Pro Leu Ala Ser Gly Glu Phe
            180                 185                 190

Ser Val Ala Thr Gly Val Phe Leu Val Leu Ala Phe Leu Ile Met Ser
        195                 200                 205

Phe Ser Ile Gly Ile Arg Ser Gly Ser Ala Pro Leu Met Cys Ala Leu
    210                 215                 220

Ile Val Ser Phe Leu Leu Gly Ser Ala Tyr Ser Ile Glu Ala Pro Phe
225                 230                 235                 240

Leu Arg Trp Lys Arg His Ala Leu Leu Ala Ala Ser Cys Ile Leu Phe
                245                 250                 255

Val Arg Ala Ile Leu Val Gln Leu Ala Phe Phe Ala His Met Gln Gln
```

```
            260                 265                 270

His Val Leu Lys Arg Pro Leu Ala Ala Thr Lys Ser Leu Val Phe Ala
        275                 280                 285

Thr Leu Phe Met Cys Cys Phe Ser Ala Val Ile Ala Leu Phe Lys Asp
    290                 295                 300

Ile Pro Asp Val Asp Gly Asp Arg Asp Phe Gly Ile Gln Ser Leu Ser
305                 310                 315                 320

Val Arg Leu Gly Pro Gln Arg Val Tyr Gln Leu Cys Ile Ser Ile Leu
                325                 330                 335

Leu Thr Ala Tyr Gly Ala Ala Thr Leu Val Gly Ala Ser Ser Thr Asn
            340                 345                 350

Leu Phe Gln Lys Ile Ile Thr Val Ser Gly His Gly Leu Leu Ala Leu
        355                 360                 365

Thr Leu Trp Gln Arg Ala Gln His Phe Glu Val Glu Asn Gln Ala Arg
    370                 375                 380

Val Thr Ser Phe Tyr Met Phe Ile Trp Lys Leu Phe Tyr Ala Glu Tyr
385                 390                 395                 400

Phe Leu Ile Pro Phe Val Gln
                405
```

<210> SEQ ID NO 3
<211> LENGTH: 1365
<212> TYPE: DNA
<213> ORGANISM: Triticum aestivum

<400> SEQUENCE: 3

```
ctttcacaca gatcccaggc cgcttttctc ctccggtggc cgcccggcga ggatgcaagc     60

caccacggcc gcggcggcgg cgcagctgct aacagatacg aggagagggc ccagatgtag    120

tagggctcgg ctgggagcga cgagattatc ctggccaggt cgatttgcag tggaagcttt    180

tgcaggccgg tgccaaagca gtgctactac tgtcacgcat agattcagtg ccatttctca    240

agctacaagc cctagaagaa aggcaaggag gcagtgcagc gatgatcagt cagccctcca    300

agctggatgc agcaaggtta atcgcgatca acatggttac gacgtgaact ggtttgagga    360

aatcagccaa gaagtttcga agaaattgcg cgctttctac cagttctgca gaccacacac    420

aatctttggc actatcatag gcataacttc agtgtctctc ctgccaatga agagcataga    480

tgattttact gcaacggtac taaaagggta tctcgaggct ttggctgctg ctttatgtat    540

gaacatttat gtggtagggc tgaatcagct atatgacatt cagattgaca agatcaacaa    600

gccaggtctt ccattggcag ctggggaatt ttcagtagca actggggtat ttttagtagt    660

cacattcctg atcatgagct ttagcatcgg aatacattcc ggatcggtgc cactgatgta    720

tgctttagtt gtcagcttcc ttcttggaag tgcatactcc attgaggctc cgttgctccg    780

gtggaaacgg cacgcactcc tcgctgcatc ctgtatccta tttgtgaggg ctatcttggt    840

ccagttggct ttctttgcac atatgcagca acatgttctg aaaaggccct tggcagcaac    900

aaaatcactg gtgtttgcaa cattgttcat gtgttgcttc tctgccgtca tagctctatt    960

caaggatata cctgatgttg atggagaccg agattttggc atccaatcct tgagtgtgag   1020

attggggcca caaagagtgt atcagctctg cataagcata ctgttgacag cctatttggc   1080

tgccactgta gtaggagctt catccacaca cctacttcaa aagataatca ctgtgtctgg   1140

tcatggcctg cttgcactaa cactttggca gagagcgcgg caccttgagg ttgaaaatca   1200

agcgcgtgtc acatcatttt acatgttcat ttggaagcta ttctatgcag agtatttcct   1260

tataccattt gtgcagtgaa atttgtacaa gggccagcag atgtgagcta tatatacatg   1320
```

taaaacaaat tatattactg atgataccct atccaatgct tggaa 1365

<210> SEQ ID NO 4
<211> LENGTH: 408
<212> TYPE: PRT
<213> ORGANISM: Triticum aestivum

<400> SEQUENCE: 4

```
Met Gln Ala Thr Thr Ala Ala Ala Ala Ala Gln Leu Leu Thr Asp Thr
1               5                   10                  15

Arg Arg Gly Pro Arg Cys Ser Arg Ala Arg Leu Gly Ala Thr Arg Leu
            20                  25                  30

Ser Trp Pro Gly Arg Phe Ala Val Glu Ala Phe Ala Gly Arg Cys Gln
        35                  40                  45

Ser Ser Ala Thr Thr Val Thr His Arg Phe Ser Ala Ile Ser Gln Ala
    50                  55                  60

Thr Ser Pro Arg Arg Lys Ala Arg Arg Gln Cys Ser Asp Asp Gln Ser
65                  70                  75                  80

Ala Leu Gln Ala Gly Cys Ser Lys Val Asn Arg Asp Gln His Gly Tyr
                85                  90                  95

Asp Val Asn Trp Phe Glu Glu Ile Ser Gln Glu Val Ser Lys Lys Leu
            100                 105                 110

Arg Ala Phe Tyr Gln Phe Cys Arg Pro His Thr Ile Phe Gly Thr Ile
        115                 120                 125

Ile Gly Ile Thr Ser Val Ser Leu Leu Pro Met Lys Ser Ile Asp Asp
    130                 135                 140

Phe Thr Ala Thr Val Leu Lys Gly Tyr Leu Glu Ala Leu Ala Ala Ala
145                 150                 155                 160

Leu Cys Met Asn Ile Tyr Val Val Gly Leu Asn Gln Leu Tyr Asp Ile
                165                 170                 175

Gln Ile Asp Lys Ile Asn Lys Pro Gly Leu Pro Leu Ala Ala Gly Glu
            180                 185                 190

Phe Ser Val Ala Thr Gly Val Phe Leu Val Val Thr Phe Leu Ile Met
        195                 200                 205

Ser Phe Ser Ile Gly Ile His Ser Gly Ser Val Pro Leu Met Tyr Ala
    210                 215                 220

Leu Val Val Ser Phe Leu Leu Gly Ser Ala Tyr Ser Ile Glu Ala Pro
225                 230                 235                 240

Leu Leu Arg Trp Lys Arg His Ala Leu Leu Ala Ala Ser Cys Ile Leu
                245                 250                 255

Phe Val Arg Ala Ile Leu Val Gln Leu Ala Phe Phe Ala His Met Gln
            260                 265                 270

Gln His Val Leu Lys Arg Pro Leu Ala Ala Thr Lys Ser Leu Val Phe
        275                 280                 285

Ala Thr Leu Phe Met Cys Cys Phe Ser Ala Val Ile Ala Leu Phe Lys
    290                 295                 300

Asp Ile Pro Asp Val Asp Gly Asp Arg Asp Phe Gly Ile Gln Ser Leu
305                 310                 315                 320

Ser Val Arg Leu Gly Pro Gln Arg Val Tyr Gln Leu Cys Ile Ser Ile
                325                 330                 335

Leu Leu Thr Ala Tyr Leu Ala Ala Thr Val Val Gly Ala Ser Ser Thr
            340                 345                 350

His Leu Leu Gln Lys Ile Ile Thr Val Ser Gly His Gly Leu Leu Ala
        355                 360                 365
```

```
Leu Thr Leu Trp Gln Arg Ala Arg His Leu Glu Val Glu Asn Gln Ala
    370                 375                 380

Arg Val Thr Ser Phe Tyr Met Phe Ile Trp Lys Leu Phe Tyr Ala Glu
385                 390                 395                 400

Tyr Phe Leu Ile Pro Phe Val Gln
                405
```

<210> SEQ ID NO 5
<211> LENGTH: 1242
<212> TYPE: DNA
<213> ORGANISM: Oryza sativa

<400> SEQUENCE: 5

```
agacgatgca agcctcatcg gcggcggcgg cggcggcgtg ctcggctatc aagccggcgg     60

cgcatcagca caccgtgcaa gtccaggaag ataagagggg atcggaattc agggctcggt    120

ttggaacgag gaaactgtcc tggggaggta aattgtcggt ggaaaattct gctctacacc    180

agtgtcaaag tctcacaaga agcataagga ggcaaaaaag acaacattct ccagtcctcc    240

aagtgagatg ctatgccatt gctggtgatc agcacgaatc catcgccact gagtttgaag    300

aaatttgcaa agaagttccc cagaaactgg gagcttttta tcggttttgc cgaccccaca    360

caatttttgg cactataata ggaatcactt cagtttctct cctgccaatg aggagcctag    420

atgattttac tatgaaagca ttatggggat ttcttgaggc tttatcctct tctttatgta    480

tgaatatcta tgttgtaggc ctgaatcaac tatatgacat ccagattgat aaggtcaata    540

agcccagcct tccgttggcg tcaggagaat tttcagtggc aactggagca gtgttagtac    600

tcacgtcctt gatcatgagc attgccattg gaatcagatc caaatcagct cctttgttat    660

gtgctttgtt tatcagtttc tttcttggaa gtgcatactc tgttgatgct ccgttactcc    720

ggtggaaaag gaacgcgttt ctcgctgcat cttgtatact atttgtaaga gctgtcttag    780

ttcagctagc tttctttgca catatgcagc aacatgttct gaagaggccc ttggcaccaa    840

caaagtcggt ggttttcgca acattattca tgtgttgctt ttcttcagtt atagctttat    900

tcaaggatat tccagatatt gatggtgaca gacattttgg cgtcgaatcc ctgagcgtac    960

gtttgggtcc agaaagagtg tattggctct gcataaacat actattaaca gcatatgggg   1020

ctgccatttt ggctggagca tcatctacaa atctatgtca aatgattatc accgttttcg   1080

gccatggcct gcttgccttt gcactttggc agagagcaca gcactgtgac gttgaaaaca   1140

aggcgtggat cacatcattt tacatgttca tttggaagtt gttctacgct gagtatttcc   1200

ttataccatt tgtgcagtga gcactatata cacaagggca ag                      1242
```

<210> SEQ ID NO 6
<211> LENGTH: 404
<212> TYPE: PRT
<213> ORGANISM: Oryza sativa

<400> SEQUENCE: 6

```
Met Gln Ala Ser Ser Ala Ala Ala Ala Ala Ala Cys Ser Ala Ile Lys
1               5                   10                  15

Pro Ala Ala His Gln His Thr Val Gln Val Gln Glu Asp Lys Arg Gly
            20                  25                  30

Ser Glu Phe Arg Ala Arg Phe Gly Thr Arg Lys Leu Ser Trp Gly Gly
        35                  40                  45

Lys Leu Ser Val Glu Asn Ser Ala Leu His Gln Cys Gln Ser Leu Thr
    50                  55                  60

Arg Ser Ile Arg Arg Gln Lys Arg Gln His Ser Pro Val Leu Gln Val
```

-continued

```
65                  70                  75                  80

Arg Cys Tyr Ala Ile Ala Gly Asp Gln His Glu Ser Ile Ala Thr Glu
                85                  90                  95

Phe Glu Glu Ile Cys Lys Glu Val Pro Gln Lys Leu Gly Ala Phe Tyr
            100                 105                 110

Arg Phe Cys Arg Pro His Thr Ile Phe Gly Thr Ile Ile Gly Ile Thr
        115                 120                 125

Ser Val Ser Leu Leu Pro Met Arg Ser Leu Asp Asp Phe Thr Met Lys
    130                 135                 140

Ala Leu Trp Gly Phe Leu Glu Ala Leu Ser Ser Ser Leu Cys Met Asn
145                 150                 155                 160

Ile Tyr Val Val Gly Leu Asn Gln Leu Tyr Asp Ile Gln Ile Asp Lys
                165                 170                 175

Val Asn Lys Pro Ser Leu Pro Leu Ala Ser Gly Glu Phe Ser Val Ala
            180                 185                 190

Thr Gly Ala Val Leu Val Leu Thr Ser Leu Ile Met Ser Ile Ala Ile
        195                 200                 205

Gly Ile Arg Ser Lys Ser Ala Pro Leu Leu Cys Ala Leu Phe Ile Ser
    210                 215                 220

Phe Phe Leu Gly Ser Ala Tyr Ser Val Asp Ala Pro Leu Leu Arg Trp
225                 230                 235                 240

Lys Arg Asn Ala Phe Leu Ala Ala Ser Cys Ile Leu Phe Val Arg Ala
                245                 250                 255

Val Leu Val Gln Leu Ala Phe Phe Ala His Met Gln Gln His Val Leu
            260                 265                 270

Lys Arg Pro Leu Ala Pro Thr Lys Ser Val Val Phe Ala Thr Leu Phe
        275                 280                 285

Met Cys Cys Phe Ser Ser Val Ile Ala Leu Phe Lys Asp Ile Pro Asp
    290                 295                 300

Ile Asp Gly Asp Arg His Phe Gly Val Glu Ser Leu Ser Val Arg Leu
305                 310                 315                 320

Gly Pro Glu Arg Val Tyr Trp Leu Cys Ile Asn Ile Leu Leu Thr Ala
                325                 330                 335

Tyr Gly Ala Ala Ile Leu Ala Gly Ala Ser Ser Thr Asn Leu Cys Gln
            340                 345                 350

Met Ile Ile Thr Val Phe Gly His Gly Leu Leu Ala Phe Ala Leu Trp
        355                 360                 365

Gln Arg Ala Gln His Cys Asp Val Glu Asn Lys Ala Trp Ile Thr Ser
    370                 375                 380

Phe Tyr Met Phe Ile Trp Lys Leu Phe Tyr Ala Glu Tyr Phe Leu Ile
385                 390                 395                 400

Pro Phe Val Gln


<210> SEQ ID NO 7
<211> LENGTH: 1730
<212> TYPE: DNA
<213> ORGANISM: Zea mays

<400> SEQUENCE: 7

ccttgagccg ttccgctgcc attcgaccac caccgccacg gcggcgccga tgccgactac      60

aaccactcgc agagactacc gcctccagcc ccgccgcttc tcatctccac gcagccgtcc     120

gatggccaag cggctcgccg gtgccgacaa agaggtgctc gtcgaggtgg tgaggttcac     180

gcataagagc ggactgaggg gctgtgacgg cggctggaag gatttcctgg cccagaacga     240
```

```
caggaagttt ggcgcgtcgg tgagcgaccc gaggaagcgc tccagggacg tgctgttcgc    300
cttcctgcag accttcccca aggatttcca gaagaaacac ttgatgccac tagtccgacg    360
agagccaccg gaagacaacg caggcattcc tcagtcccca aagtgagctg ctgggcagct    420
gctcatcacc aacacaattc taacccccag cagtttcagg cgattggcat acgaatcgca    480
aagacgctgc atgccttcta tcagttctgc cgaccacaca caatatttgg aaccataata    540
ggcattactt cggtgtctat cctgccagtg aagagcctgg acgattttac gttgatagct    600
atatggggat ttctcgaggc tttggccgcc gcattatgta tgaacgttta tgtagtaggg    660
ctgaacaagg tcaataagcc aaccctccca ttatcgttcg gagagttttc aatgccaact    720
gcagtattgt tagtagtggc attcttggtc atgagcatta gcatcggaat aagatcaaag    780
tctgctccat tgatgtgtgc tttgcttgtt tgcttccttc ttggaagcgc ataccccatt    840
gacgtcccat tactccggtg gaagcgacat gcttttctag ctgcattctg cataatcttt    900
gtgaggcctg tagtggtcca gttagctttc tttgcacaca tgcagcaaca tgttctgaag    960
aggcccttgg cacctacaag gtcggtggtc tttgcaacat gtttcatgtg ttgcttcgct   1020
gcagtaatag cgctattcaa ggatattcct gatgtcgatg gagatagaga tttcggcatt   1080
cagtccatga ctgtacgatt aggccaacag agagtgcata ggctctgcat taatattctc   1140
atgacagcat acgcagccgc aattttggta ggcgcgtcat ctacgaacct gtatcagaag   1200
attgtcattg tgtctggtca tggcttgctt gcctccacac tctggcaaag agcacaacaa   1260
tttgacattg agaataagga ttgtatcaca caattttata tgttcatttg gaagttattc   1320
tacgccgagt attttcttat accatttgtg tagtaaagaa tcatgcgaag aacaacaccc   1380
ctgctataga catgtgaagg tttattgcta atgttactct accccctgct atagacatgt   1440
gaaggtttat tgctaatgtt actctaccga atggtctgaa tgtctatgcg tcatttgaat   1500
gtaatatgac tatttgttgt atcagggtaa caactggagc aaatgtacca tgtatattaa   1560
gcattaattt aactgcatca tttgtaccat gtatattatg actatgtatg agatattgtc   1620
tcttattagt actggatgtg atgtgtctta ttatgactat ggatgagact tttgtgatgt   1680
aattgatgag actatggttt taaatattgt tatgtgattg tgtgtgagat               1730
```

<210> SEQ ID NO 8
<211> LENGTH: 380
<212> TYPE: PRT
<213> ORGANISM: Zea mays

<400> SEQUENCE: 8

```
Arg Leu Glu Gly Phe Pro Gly Pro Glu Arg Gln Glu Val Trp Arg Val
1               5                   10                  15

Gly Glu Arg Pro Glu Glu Ala Leu Gln Gly Arg Ala Val Arg Leu Pro
            20                  25                  30

Ala Asp Leu Pro Gln Gly Phe Pro Glu Glu Thr Leu Asp Ala Thr Ser
        35                  40                  45

Pro Thr Arg Ala Thr Gly Arg Gln Arg Arg His Ser Ser Val Pro Lys
    50                  55                  60

Val Ser Cys Trp Ala Ala Ala His His Gln His Asn Ser Asn Pro Gln
65                  70                  75                  80

Gln Phe Gln Ala Ile Gly Ile Arg Ile Ala Lys Thr Leu His Ala Phe
                85                  90                  95

Tyr Gln Phe Cys Arg Pro His Thr Ile Phe Gly Thr Ile Ile Gly Ile
            100                 105                 110

Thr Ser Val Ser Ile Leu Pro Val Lys Ser Leu Asp Asp Phe Thr Leu
```

```
        115                 120                 125

Ile Ala Ile Trp Gly Phe Leu Glu Ala Leu Ala Ala Ala Leu Cys Met
    130                 135                 140

Asn Val Tyr Val Val Gly Leu Asn Lys Val Asn Lys Pro Thr Leu Pro
145                 150                 155                 160

Leu Ser Phe Gly Glu Phe Ser Met Pro Thr Ala Val Leu Leu Val Val
                165                 170                 175

Ala Phe Leu Val Met Ser Ile Ser Ile Gly Ile Arg Ser Lys Ser Ala
            180                 185                 190

Pro Leu Met Cys Ala Leu Leu Val Cys Phe Leu Leu Gly Ser Ala Tyr
        195                 200                 205

Pro Ile Asp Val Pro Leu Leu Arg Trp Lys Arg His Ala Phe Leu Ala
    210                 215                 220

Ala Phe Cys Ile Ile Phe Val Arg Pro Val Val Val Gln Leu Ala Phe
225                 230                 235                 240

Phe Ala His Met Gln Gln His Val Leu Lys Arg Pro Leu Ala Pro Thr
                245                 250                 255

Arg Ser Val Val Phe Ala Thr Cys Phe Met Cys Cys Phe Ala Ala Val
            260                 265                 270

Ile Ala Leu Phe Lys Asp Ile Pro Asp Val Asp Gly Asp Arg Asp Phe
        275                 280                 285

Gly Ile Gln Ser Met Thr Val Arg Leu Gly Gln Gln Arg Val His Arg
    290                 295                 300

Leu Cys Ile Asn Ile Leu Met Thr Ala Tyr Ala Ala Ala Ile Leu Val
305                 310                 315                 320

Gly Ala Ser Ser Thr Asn Leu Tyr Gln Lys Ile Val Ile Val Ser Gly
                325                 330                 335

His Gly Leu Leu Ala Ser Thr Leu Trp Gln Arg Ala Gln Gln Phe Asp
            340                 345                 350

Ile Glu Asn Lys Asp Cys Ile Thr Gln Phe Tyr Met Phe Ile Trp Lys
        355                 360                 365

Leu Phe Tyr Ala Glu Tyr Phe Leu Ile Pro Phe Val
    370                 375                 380


<210> SEQ ID NO 9
<211> LENGTH: 1769
<212> TYPE: DNA
<213> ORGANISM: Zea mays
<220> FEATURE:
<221> NAME/KEY: misc_feature
<222> LOCATION: (1206)..(1207)
<223> OTHER INFORMATION: n is a, c, g, or t

<400> SEQUENCE: 9

ccacgcgtcc gcgaccacca ccaccacggt gccgccgacg ccgaccacaa ccactcgtag      60

agactaccgt ctccgccccc gctgcttctc gtctccacgc agccgtccga tggccaagcg     120

gctcgccggc gccaacaaag aggtagggga cggcatgcca acaaagcagc ccacccggac     180

tcggcaggcc gcctcgtttc gctaacccat ttgatctgcg ccgggtgctc gtcgaggtgg     240

tgaggttcac gcagaagagc ggactgaggg gctgtgacgg tggctggaag gatttcctgg     300

cccggaacga caggaagttt ggagcgtcgg tgagcgacca gaggaagcgc tctagggacg     360

tgttgttcgc cttcctacag accttcccca aggatttcca gaagaaacac ttgatgccac     420

tagtccgacg agagccactg gaaggcaaca caggcattcc tcagtcccca aagtgagctg     480

ctgggcagct gctcatcacc aacacaattc taacccccag cagtttcagg cgattggcat     540
```

```
acgaatcgca aagacgctgc atgcctttta tcagttctgc cgaccacaca caatatttgg    600

aaccataata ggcattactt cggtgtctct cctgccagtg aagagcctgg acgattttac    660

gttgatagct atatggggat ttctcgaggc tttggccgcc gcattatgta tgaacgttta    720

tgtagtaggg ctgaaccagc tatttgacat tgagattgac aaggtcaata agccaaccct    780

cccattagcg tccggagagt tttcagtgcc aactgcagta ttgttagtag tggcattctt    840

ggtcatgagc attagcatcg gaataagatc aaagtgtgcg ccattgatgt gtgctttgct    900

tgttagcttc cttcttggaa gcgcatactc cattgacgtt ccattactcc gatggaagcg    960

acatgctttt ctagctgcat tctgcataat ctttgtgagg gctgtagtgg tccggttagc   1020

tttctttgca cacatgcagc aacatgttct gaagaggccc ttggcaccta caaggtcggt   1080

ggtctttgca acatgtttca tgtgttgctt cgctgcagta atagcgctat tcaaggatat   1140

tcctgatgtc gatggagata gagatttcgg cattcagtcc atgactgtac gattaggcca   1200

acaganngag ctctgcatta atattctcat gacagcatac gcagtcacaa ttttggtagg   1260

agcgttgtct acgaacctgt atcagaagat tgtcattgtg tctggtcatg gcttgcttgc   1320

ctccacactc tggcaaagag cacaacaatt tgacattgag aataaggatt gtatcacaca   1380

attttatatg ttcatttgga agttattcta tgccgagtat ttcttatac  catttgtgta   1440

gtaaagaatc atgcgaagaa catcaccctt gctatagaca tgtgaaggtt cattgctaat   1500

gttactctac cgaatggtct gaatgtctat gcgtcatttg tatgtaatat gactttgttg   1560

tatcagggta acaactggag caaatgtacc atgtatatta agcattaatt tagctgtgtc   1620

atttgtacca tgtatattat gactatgtat gagatattgt ctcttattag tactagatgt   1680

gatgtgtctt attatgacta tggatgaaac ttttgtgatg taattgatga gactatggat   1740

ttaaatattg ttaaaaaaaa aaaaaaaaa                                     1769
```

```
<210> SEQ ID NO 10
<211> LENGTH: 361
<212> TYPE: PRT
<213> ORGANISM: Zea mays
<220> FEATURE:
<221> NAME/KEY: misc_feature
<222> LOCATION: (284)..(284)
<223> OTHER INFORMATION: Xaa can be any naturally occurring amino acid

<400> SEQUENCE: 10

Gly Arg Val Val Arg Leu Pro Thr Asp Leu Pro Gln Gly Phe Pro Glu
1               5                   10                  15

Glu Thr Leu Asp Ala Thr Ser Pro Thr Arg Ala Thr Gly Arg Gln His
            20                  25                  30

Arg His Ser Ser Val Pro Lys Val Ser Cys Trp Ala Ala Ala His His
        35                  40                  45

Gln His Asn Ser Asn Pro Gln Gln Phe Gln Ala Ile Gly Ile Arg Ile
    50                  55                  60

Ala Lys Thr Leu His Ala Phe Tyr Gln Phe Cys Arg Pro His Thr Ile
65                  70                  75                  80

Phe Gly Thr Ile Ile Gly Ile Thr Ser Val Ser Leu Leu Pro Val Lys
                85                  90                  95

Ser Leu Asp Asp Phe Thr Leu Ile Ala Ile Trp Gly Phe Leu Glu Ala
            100                 105                 110

Leu Ala Ala Ala Leu Cys Met Asn Val Tyr Val Val Gly Leu Asn Gln
        115                 120                 125

Leu Phe Asp Ile Glu Ile Asp Lys Val Asn Lys Pro Thr Leu Pro Leu
    130                 135                 140
```

```
Ala Ser Gly Glu Phe Ser Val Pro Thr Ala Val Leu Leu Val Val Ala
145                 150                 155                 160

Phe Leu Val Met Ser Ile Ser Ile Gly Ile Arg Ser Lys Cys Ala Pro
                165                 170                 175

Leu Met Cys Ala Leu Leu Val Ser Phe Leu Leu Gly Ser Ala Tyr Ser
            180                 185                 190

Ile Asp Val Pro Leu Leu Arg Trp Lys Arg His Ala Phe Leu Ala Ala
        195                 200                 205

Phe Cys Ile Ile Phe Val Arg Ala Val Val Val Arg Leu Ala Phe Phe
    210                 215                 220

Ala His Met Gln Gln His Val Leu Lys Arg Pro Leu Ala Pro Thr Arg
225                 230                 235                 240

Ser Val Val Phe Ala Thr Cys Phe Met Cys Cys Phe Ala Ala Val Ile
                245                 250                 255

Ala Leu Phe Lys Asp Ile Pro Asp Val Asp Gly Asp Arg Asp Phe Gly
            260                 265                 270

Ile Gln Ser Met Thr Val Arg Leu Gly Gln Gln Xaa Glu Leu Cys Ile
        275                 280                 285

Asn Ile Leu Met Thr Ala Tyr Ala Val Thr Ile Leu Val Gly Ala Leu
    290                 295                 300

Ser Thr Asn Leu Tyr Gln Lys Ile Val Ile Val Ser Gly His Gly Leu
305                 310                 315                 320

Leu Ala Ser Thr Leu Trp Gln Arg Ala Gln Gln Phe Asp Ile Glu Asn
                325                 330                 335

Lys Asp Cys Ile Thr Gln Phe Tyr Met Phe Ile Trp Lys Leu Phe Tyr
            340                 345                 350

Ala Glu Tyr Phe Leu Ile Pro Phe Val
        355                 360
```

<210> SEQ ID NO 11
<211> LENGTH: 1053
<212> TYPE: DNA
<213> ORGANISM: Glycine max

<400> SEQUENCE: 11

```
atggccaccg tggtgaggat cccaacaatc tcatgcatcc acatccacac gttccgttcc      60

caatcccctc gcactttcgc cagaatccgg gtcggaccca ggtcgtgggc tcctattcgg     120

gcatcggcag cgagctcgga gagaggggag atagtattgg agcagaagcc gaagaaggat     180

gacaagaaga agctgcagaa gggaatcgca gagttttacg acgagtcgtc tggcttatgg     240

gagaacattt ggggcgacca catgcaccat ggcttttatg actcggattc cactgtttcg     300

ctttcggatc atcgtgctgc tcagatccga atgatccaag agtctcttcg ctttgcctct     360

gtttctgagg agcgtagtaa atggcccaag agtatagttg atgttgggtg tggcataggt     420

ggcagctcta gatacctggc caagaaattt ggagcaacca gtgtaggcat cactctgagt     480

cctgttcaag ctcaaagagc aaatgctctt gctgctgctc aaggattggc tgataaggtt     540

tcctttcagg ttgctgacgc tctacagcaa ccattctctg acggccagtt tgatctggtg     600

tggtccatgg agagtggaga gcatatgcct gacaaagcta agtttgttgg agagttagct     660

cgggtagcag caccaggtgc cattataata atagtaacat ggtgccacag ggatcttggc     720

cctgacgaac aatccttaca tccatgggag caagatctct taaagaagat ttgcgatgca     780

tattacctcc ctgcctggtg ctcaacttct gattatgtta agttgctcca atccctgtca     840

cttcaggaca tcaagtcaga agattggtct cgctttgttg ctccattttg gccagcagtg     900
```

```
atacgctcag ccttcacatg gaagggtcta tcttcactct tgagcagtgg acaaaaaacg    960

ataaaaggag ctttggctat gccattgatg atagagggat acaagaaaga tctaattaag   1020

tttgccatca ttacatgtcg aaaacctgaa taa                                1053


<210> SEQ ID NO 12
<211> LENGTH: 350
<212> TYPE: PRT
<213> ORGANISM: Glycine max

<400> SEQUENCE: 12

Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ala Ser Ser Glu Arg
        35                  40                  45

Gly Glu Ile Val Leu Glu Gln Lys Pro Lys Lys Asp Asp Lys Lys Lys
    50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His His Gly Phe Tyr Asp Ser Asp
                85                  90                  95

Ser Thr Val Ser Leu Ser Asp His Arg Ala Ala Gln Ile Arg Met Ile
            100                 105                 110

Gln Glu Ser Leu Arg Phe Ala Ser Val Ser Glu Glu Arg Ser Lys Trp
        115                 120                 125

Pro Lys Ser Ile Val Asp Val Gly Cys Gly Ile Gly Gly Ser Ser Arg
    130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Ile Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285

Trp Ser Arg Phe Val Ala Pro Phe Trp Pro Ala Val Ile Arg Ser Ala
    290                 295                 300

Phe Thr Trp Lys Gly Leu Ser Ser Leu Leu Ser Ser Gly Gln Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
            340                 345                 350
```

<210> SEQ ID NO 13
<211> LENGTH: 1331
<212> TYPE: DNA
<213> ORGANISM: Glycine max

<400> SEQUENCE: 13

```
gtgacatggc caccgtggtg aggatcccaa caatctcatg catccacatc cacacgttcc      60
gttcccaatc ccctcgcact ttcgccagaa tccgggtcgg acccaggtcg tgggctccta     120
ttcgggcatc ggcagcgagc tcggagagag gggagatagt attggagcag aagccgaaga     180
aggatgacaa gaagaagctg cagaagggaa tcgcagagtt ttacgacgag tcgtctggct     240
tatgggagaa catttggggc gaccacatgc accatggctt ttatgactcg gattccactg     300
tttcgctttc ggatcatcgt gctgctcaga tccgaatgat ccaagagtct cttcgctttg     360
cctctgtttc tgaggagcgt agtaaatggc ccaagagtat agttgatgtt gggtgtggca     420
taggtggcag ctctagatac ctggccaaga aatttggagc aaccagtgta ggcatcactc     480
tgagtcctgt tcaagctcaa agagcaaatg ctcttgctgc tgctcaagga ttggctgata     540
aggtttcctt tcaggttgct gacgctctac agcaaccatt ctctgacggc cagtttgatc     600
tggtgtggtc catggagagt ggagagcata tgcctgacaa agctaagttt gttggagagt     660
tagctcgggt agcagcacca ggtgccatta taataatagt aacatggtgc cacagggatc     720
ttggccctga cgaacaatcc ttacatccat gggagcaaga tctcttaaag aagatttgcg     780
atgcatatta cctccctgcc tggtgctcaa cttctgatta tgttaagttg ctccaatccc     840
tgtcacttca ggacatcaag tcagaagatt ggtctcgctt tgttgctcca ttttggccag     900
cagtgatacg ctcagccttc acatggaagg gtctatcttc actcttgagc agtggtaagc     960
ttggaattta tattgcattt caaaaacaaa cccccccatc ttctattgca acttgcaagt    1020
cttatgtcac tgatcattat ttccacacta gataaccctt tacaactaag aacgtagtct    1080
tcatgttcag cgaaatagat aaaaatatgc aacagagtca gagacagggt gcatgatatt    1140
tacaagaaaa tatcttttat atatataaat gattcaatca aattacttga tgaggattat    1200
gagtgaaaat gagaggacag tcatagaaac tttatcctac attccttcta tttccacttc    1260
tgtcaaatat tcctttcatc ttagctatgc tacttgactt gagtaaaaaa aaaaaaaaaa    1320
aaaaaaaaaa a                                                         1331
```

<210> SEQ ID NO 14
<211> LENGTH: 349
<212> TYPE: PRT
<213> ORGANISM: Glycine max

<400> SEQUENCE: 14

```
Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ala Ser Ser Glu Arg
        35                  40                  45

Gly Glu Ile Val Leu Glu Gln Lys Pro Lys Lys Asp Asp Lys Lys Lys
    50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His His Gly Phe Tyr Asp Ser Asp
                85                  90                  95
```

```
Ser Thr Val Ser Leu Ser Asp His Arg Ala Ala Gln Ile Arg Met Ile
            100                 105                 110

Gln Glu Ser Leu Arg Phe Ala Ser Val Ser Glu Glu Arg Ser Lys Trp
        115                 120                 125

Pro Lys Ser Ile Val Asp Val Gly Cys Gly Ile Gly Gly Ser Ser Arg
    130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Ile Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285

Trp Ser Arg Phe Val Ala Pro Phe Trp Pro Ala Val Ile Arg Ser Ala
    290                 295                 300

Phe Thr Trp Lys Gly Leu Ser Ser Leu Leu Ser Ser Gly Lys Leu Gly
305                 310                 315                 320

Ile Tyr Ile Ala Phe Gln Lys Gln Thr Pro Pro Ser Ser Ile Ala Thr
                325                 330                 335

Cys Lys Ser Tyr Val Thr Asp His Tyr Phe His Thr Arg
            340                 345

<210> SEQ ID NO 15
<211> LENGTH: 1301
<212> TYPE: DNA
<213> ORGANISM: Zea mays

<400> SEQUENCE: 15

ccacgcgtcc gcctcggcct cttttaaata tcgcgcatcc cggcgccgca aatggctcac      60

gcggcgctgc tccattgctc ccagtcctcc aggagcctcg cagcctgccg ccgcggcagc     120

cactaccgcg ccccttcgca cgtcccgcgc cactcccgcc gtctccgacg cgccgtcgtc     180

agcctgcgtc cgatggcctc gtcgacggct caggcccccg cgacggcgcc gccgggtctg     240

aaggagggca tcgcggggct gtacgacgag tcgtcggggc tgtgggagaa catctggggc     300

gaccacatgc accacggctt ctacgactcg agcgaggccg cctccatggc cgatcaccgc     360

cgcgcccaga tccgcatgat cgaggaggcg ctcgccttcg ccggtgtccc agcctcagat     420

gatccagaga agacaccaaa aacaatagtc gatgtcggat gtggcattgg tggtagctca     480

aggtacttgg cgaagaaata cggagcgcag tgcactggga tcacgttgag ccctgttcaa     540

gccgagagag gaaatgctct cgctgcagcg caggggttgt cggatcaggt tactctgcaa     600

gttgctgatg ctctggagca accgtttcct gacgggcagt tcgatctggt gtggtccatg     660

gagagtggcg agcacatgcc ggacaagaga aagtttgtta gtgagctagc acgcgtggcg     720
```

```
gctcctggag ggacaataat catcgtgaca tggtgccata ggaacctgga tccatccgaa    780

acctcgctaa agcccgatga actgagcctc ctgaggagga tatgcgacgc gtactacctc    840

ccggactggt gctcaccttc agactatgtg gacattgcca agtcactgtc tctcgaggat    900

atcaagacag ctgactggtc ggagaacgtg gccccgtttt ggcccgccgt gataaaatca    960

gcgctaacat ggaagggctt cacctctctg ctgacgaccg gatggaagac gatcagaggc   1020

gcgatggtga tgccgctaat gatccagggc tacaagaagg gcctcatcaa attcaccatc   1080

atcacctgtc gcaagcctgg agccgcgtag gaggaggcca aggagcacaa gttactggca   1140

caggcacagg agtgtcatgt gcaataatgt agattcgtgg ccccatcgcc gtctactcat   1200

ctgtactgca ccaaaatcaa cattctccta ggtgttaaat aattttctgc cactcgtcga   1260

gatatttcaa attcactgtt ccacaaaaaa aaaaaaaaaa g                       1301


<210> SEQ ID NO 16
<211> LENGTH: 352
<212> TYPE: PRT
<213> ORGANISM: Zea mays

<400> SEQUENCE: 16

Met Ala His Ala Ala Leu Leu His Cys Ser Gln Ser Ser Arg Ser Leu
1               5                   10                  15

Ala Ala Cys Arg Arg Gly Ser His Tyr Arg Ala Pro Ser His Val Pro
            20                  25                  30

Arg His Ser Arg Arg Leu Arg Arg Ala Val Val Ser Leu Arg Pro Met
        35                  40                  45

Ala Ser Ser Thr Ala Gln Ala Pro Ala Thr Ala Pro Pro Gly Leu Lys
    50                  55                  60

Glu Gly Ile Ala Gly Leu Tyr Asp Glu Ser Ser Gly Leu Trp Glu Asn
65                  70                  75                  80

Ile Trp Gly Asp His Met His His Gly Phe Tyr Asp Ser Ser Glu Ala
                85                  90                  95

Ala Ser Met Ala Asp His Arg Arg Ala Gln Ile Arg Met Ile Glu Glu
            100                 105                 110

Ala Leu Ala Phe Ala Gly Val Pro Ala Ser Asp Asp Pro Glu Lys Thr
        115                 120                 125

Pro Lys Thr Ile Val Asp Val Gly Cys Gly Ile Gly Gly Ser Ser Arg
    130                 135                 140

Tyr Leu Ala Lys Lys Tyr Gly Ala Gln Cys Thr Gly Ile Thr Leu Ser
145                 150                 155                 160

Pro Val Gln Ala Glu Arg Gly Asn Ala Leu Ala Ala Ala Gln Gly Leu
                165                 170                 175

Ser Asp Gln Val Thr Leu Gln Val Ala Asp Ala Leu Glu Gln Pro Phe
            180                 185                 190

Pro Asp Gly Gln Phe Asp Leu Val Trp Ser Met Glu Ser Gly Glu His
        195                 200                 205

Met Pro Asp Lys Arg Lys Phe Val Ser Glu Leu Ala Arg Val Ala Ala
    210                 215                 220

Pro Gly Gly Thr Ile Ile Ile Val Thr Trp Cys His Arg Asn Leu Asp
225                 230                 235                 240

Pro Ser Glu Thr Ser Leu Lys Pro Asp Glu Leu Ser Leu Leu Arg Arg
                245                 250                 255

Ile Cys Asp Ala Tyr Tyr Leu Pro Asp Trp Cys Ser Pro Ser Asp Tyr
            260                 265                 270
```

```
Val Asp Ile Ala Lys Ser Leu Ser Leu Glu Asp Ile Lys Thr Ala Asp
        275                 280                 285

Trp Ser Glu Asn Val Ala Pro Phe Trp Pro Ala Val Ile Lys Ser Ala
    290                 295                 300

Leu Thr Trp Lys Gly Phe Thr Ser Leu Leu Thr Thr Gly Trp Lys Thr
305                 310                 315                 320

Ile Arg Gly Ala Met Val Met Pro Leu Met Ile Gln Gly Tyr Lys Lys
                325                 330                 335

Gly Leu Ile Lys Phe Thr Ile Ile Thr Cys Arg Lys Pro Gly Ala Ala
            340                 345                 350


<210> SEQ ID NO 17
<211> LENGTH: 1257
<212> TYPE: DNA
<213> ORGANISM: Triticum aestivum
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t

<400> SEQUENCE: 17

gaggctccaa atacaaaatg gcaaactccg nccgccctgc tccactcact cctctccacc      60

gcctggacgc cgcgccgccg cctcgaccga gcctcggcca cgcggctcgc cccgtccccc     120

ggcctgtcct gccgctcctc ccggccagac ngctccgtgc gcccgatggc gtcgtcgacg     180

accgcggccc gggcgacgcg gcgccgccgg ggctgaagga gggcatcgcg gggctctacg     240

acgagtcgtc cggcctgtgg gagagcatct ggggcgagca catgcaccac ggcttctacg     300

actccggcga ggccgcctcc atgtccgacc accgccgcgc ccagatccgc atgatcgagg     360

aggccctcgc cttcgccgcc gtccccgacg atccgacaaa caaacccaaa acgattgttg     420

atgttggatg cggaatcggt ggtagctcaa gatacctggc gaacaaatat ggagcacaat     480

gctctgggat cacattgagc ccagtgcaag ctgagagagg aaatgccctc gcggcagcgc     540

aggggttgtc ggacaaggct tctttccaag ttgctgatgc tctggagcaa ccatttcctg     600

atgggcagtt tgatcttgtc tggtctatgg agagtggtga gcacatgccg aacaaacaga     660

agtttgtaag cgagctggca cgcgtcgcag ctccaggagc aactatcatc atcgtgacct     720

ggtgccatag gaacctcgcg ccgtcggagg actcactgaa acctgacgag ctgaatcttt     780

tgaaaaagat ttgtgatgca tattacctcc cggattggtg ctcgccctcg gattatgtca     840

agattgccga gtcattgtct cttgaggata tcaaaacggc cgactggtca gaaaacgtgg     900

ccccgttctg gcctgctgtc atccaatcag cactgacatg gaaaggcctc acttctctac     960

taaggagtgg atggaagacg ataaagggag cactggtgat gcctctcatg atccaaggct    1020

acaagaaagg cctcattaag ttcagcatca tcacctgccg caaaccccaa gcagccatag    1080

aaggagaacc tgaggccgca tcgcccagtg tagaatagaa cccatgtgat tggaatagac    1140

tcggcttgct gtcgcctcgt agctgaataa ttttgtgtta ccgtgcctct ctatctgcaa    1200

ctggaagtgg cataggaaag tggttcctaa agcaaaaaaa aaaaaaaaaa aaaaaaa       1257


<210> SEQ ID NO 18
<211> LENGTH: 366
<212> TYPE: PRT
<213> ORGANISM: Triticum aestivum
<220> FEATURE:
<221> NAME/KEY: misc_feature
```

<222> LOCATION: (5)..(5)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 18

```
Met Ala Asn Ser Xaa Arg Pro Ala Pro Leu Thr Pro Leu His Arg Leu
1               5                   10                  15

Asp Ala Ala Pro Pro Pro Arg Pro Ser Leu Gly His Ala Ala Arg Pro
            20                  25                  30

Val Pro Arg Pro Val Leu Pro Leu Leu Pro Ala Arg Xaa Leu Arg Ala
        35                  40                  45

Pro Asp Gly Val Val Asp Asp Arg Gly Pro Gly Asp Ala Ala Pro Pro
    50                  55                  60

Gly Leu Lys Glu Gly Ile Ala Gly Leu Tyr Asp Glu Ser Ser Gly Leu
65                  70                  75                  80

Trp Glu Ser Ile Trp Gly Glu His Met His His Gly Phe Tyr Asp Ser
                85                  90                  95

Gly Glu Ala Ala Ser Met Ser Asp His Arg Arg Ala Gln Ile Arg Met
            100                 105                 110

Ile Glu Glu Ala Leu Ala Phe Ala Ala Val Pro Asp Asp Pro Thr Asn
        115                 120                 125

Lys Pro Lys Thr Ile Val Asp Val Gly Cys Gly Ile Gly Gly Ser Ser
    130                 135                 140

Arg Tyr Leu Ala Asn Lys Tyr Gly Ala Gln Cys Ser Gly Ile Thr Leu
145                 150                 155                 160

Ser Pro Val Gln Ala Glu Arg Gly Asn Ala Leu Ala Ala Ala Gln Gly
                165                 170                 175

Leu Ser Asp Lys Ala Ser Phe Gln Val Ala Asp Ala Leu Glu Gln Pro
            180                 185                 190

Phe Pro Asp Gly Gln Phe Asp Leu Val Trp Ser Met Glu Ser Gly Glu
        195                 200                 205

His Met Pro Asn Lys Gln Lys Phe Val Ser Glu Leu Ala Arg Val Ala
    210                 215                 220

Ala Pro Gly Ala Thr Ile Ile Ile Val Thr Trp Cys His Arg Asn Leu
225                 230                 235                 240

Ala Pro Ser Glu Asp Ser Leu Lys Pro Asp Glu Leu Asn Leu Leu Lys
                245                 250                 255

Lys Ile Cys Asp Ala Tyr Tyr Leu Pro Asp Trp Cys Ser Pro Ser Asp
            260                 265                 270

Tyr Val Lys Ile Ala Glu Ser Leu Ser Leu Glu Asp Ile Lys Thr Ala
        275                 280                 285

Asp Trp Ser Glu Asn Val Ala Pro Phe Trp Pro Ala Val Ile Gln Ser
    290                 295                 300

Ala Leu Thr Trp Lys Gly Leu Thr Ser Leu Leu Arg Ser Gly Trp Lys
305                 310                 315                 320

Thr Ile Lys Gly Ala Leu Val Met Pro Leu Met Ile Gln Gly Tyr Lys
                325                 330                 335

Lys Gly Leu Ile Lys Phe Ser Ile Ile Thr Cys Arg Lys Pro Gln Ala
            340                 345                 350

Ala Ile Glu Gly Glu Pro Glu Ala Ala Ser Pro Ser Val Glu
        355                 360                 365
```

<210> SEQ ID NO 19

<211> LENGTH: 1077
<212> TYPE: DNA
<213> ORGANISM: Lotus corniculatus

<400> SEQUENCE: 19

```
atggccacga tgatgatgtc aatttttcca ccaccaccaa gcgtggcttc attatttata      60

ctatcacact gcactcacac aattcgtgta caatcaacaa cgcagttcac aggtttttct     120

ataagaacca gaacacgtga ttgtagtaga attctgttaa cagaagaacg agaaatggcg     180

gtgatggagg agaagaagct tttgcagacc ggaatcgctg agttctacga cgagtcgtcc     240

gggttatggg aagacatgtg gggagaccac atgcatcacg ggttttacga gcaggatgtc     300

accgtctctg tttcagacca ccgtgttgct cagatccgaa tgattgaaga gtctcttcgt     360

tttgctgcac tttctgagga tccagctaaa aagccagaga gtatagtgga tgttgggtgc     420

ggcataggag gcagttctag gtacctagct aagaaatttc aggcaaagag cgttggtatc     480

actctgagtc ctgttcaagc tcagagagca aatgctcttg ctgcttctca aggcttagct     540

gacaaggttt cctttcaagt tgctgatgct ctagagcaac cattccctga tggtcagttt     600

gatctggtgt ggtccatgga gagtggagag catatgcctg acaaacctaa gtttgttggc     660

gagttagctc gggtggcagc accaggtggg accataataa ttgtaacatg gtgccaccgg     720

gatcttggac cagctgaaga atccctgcag ccatgggagc agaatctctt gaagaggata     780

tgcgatgcat tttaccttcc agcatggtgc tcaactgctg attatgtcaa attgctggaa     840

tcccattcac ttcaggacat caaatcagca gattggtctc cctttgttgc tccattttgg     900

ccagctgtga tacgctcagc atttacatgg aagggtctca cttcactgtt gcgcagtgga     960

atgaaaacca taaaaggagc tttggctatg ccattgatga tagaaggatt caagaagggt    1020

gtcatcaagt ttgccattgt tacatgtaga aagcctgaaa atgtggagat agaataa       1077
```

<210> SEQ ID NO 20
<211> LENGTH: 358
<212> TYPE: PRT
<213> ORGANISM: Lotus corniculatus

<400> SEQUENCE: 20

```
Met Ala Thr Met Met Met Ser Ile Phe Pro Pro Pro Pro Ser Val Ala
1               5                   10                  15

Ser Leu Phe Ile Leu Ser His Cys Thr His Thr Ile Arg Val Gln Ser
            20                  25                  30

Thr Thr Gln Phe Thr Gly Phe Ser Ile Arg Thr Arg Thr Arg Asp Cys
        35                  40                  45

Ser Arg Ile Leu Leu Thr Glu Glu Arg Glu Met Ala Val Met Glu Glu
    50                  55                  60

Lys Lys Leu Leu Gln Thr Gly Ile Ala Glu Phe Tyr Asp Glu Ser Ser
65                  70                  75                  80

Gly Leu Trp Glu Asp Met Trp Gly Asp His Met His His Gly Phe Tyr
                85                  90                  95

Glu Gln Asp Val Thr Val Ser Val Ser Asp His Arg Val Ala Gln Ile
            100                 105                 110

Arg Met Ile Glu Glu Ser Leu Arg Phe Ala Ala Leu Ser Glu Asp Pro
        115                 120                 125

Ala Lys Lys Pro Glu Ser Ile Val Asp Val Gly Cys Gly Ile Gly Gly
    130                 135                 140

Ser Ser Arg Tyr Leu Ala Lys Lys Phe Gln Ala Lys Ser Val Gly Ile
145                 150                 155                 160
```

```
Thr Leu Ser Pro Val Gln Ala Gln Arg Ala Asn Ala Leu Ala Ala Ser
                165                 170                 175

Gln Gly Leu Ala Asp Lys Val Ser Phe Gln Val Ala Asp Ala Leu Glu
            180                 185                 190

Gln Pro Phe Pro Asp Gly Gln Phe Asp Leu Val Trp Ser Met Glu Ser
        195                 200                 205

Gly Glu His Met Pro Asp Lys Pro Lys Phe Val Gly Glu Leu Ala Arg
    210                 215                 220

Val Ala Ala Pro Gly Gly Thr Ile Ile Ile Val Thr Trp Cys His Arg
225                 230                 235                 240

Asp Leu Gly Pro Ala Glu Glu Ser Leu Gln Pro Trp Glu Gln Asn Leu
                245                 250                 255

Leu Lys Arg Ile Cys Asp Ala Phe Tyr Leu Pro Ala Trp Cys Ser Thr
            260                 265                 270

Ala Asp Tyr Val Lys Leu Leu Glu Ser His Ser Leu Gln Asp Ile Lys
        275                 280                 285

Ser Ala Asp Trp Ser Pro Phe Val Ala Pro Phe Trp Pro Ala Val Ile
    290                 295                 300

Arg Ser Ala Phe Thr Trp Lys Gly Leu Thr Ser Leu Leu Arg Ser Gly
305                 310                 315                 320

Met Lys Thr Ile Lys Gly Ala Leu Ala Met Pro Leu Met Ile Glu Gly
                325                 330                 335

Phe Lys Lys Gly Val Ile Lys Phe Ala Ile Val Thr Cys Arg Lys Pro
            340                 345                 350

Glu Asn Val Glu Ile Glu
        355
```

<210> SEQ ID NO 21
<211> LENGTH: 1292
<212> TYPE: DNA
<213> ORGANISM: Glycine max

<400> SEQUENCE: 21

```
agcctttatt agtaattgac tattgaaggt tgggcacccg tgagtgacat ggccaccgtg     60

gtgaggatcc caacaatctc atgcatccac atccacacgt tccgttccca atcccctcgc    120

actttcgcca gaatccgggt cggacccagg tcgtgggctc ctattcgggc atcggcagcg    180

agctcggaga gaggggagat agtattggag cagaagccga agaaggatga caagaagaag    240

ctgcagaagg gaatcgcaga gttttacgac gagtcttctg gcttatggga gaacatttgg    300

ggcgaccaca tgcaccatgg cttttatgac tcggattcca ctgtttcgct ttcggatcat    360

cgtgctgctc agatccgaat gatccaagag tctcttcgct ttgcctctgt ttctgaggag    420

cgtagtaaat ggcccaagag tatagttgat gttgggtgtg gcataggtgg cagctctaga    480

tacctggcca agaaatttgg agcaaccagt gtaggcatca ctctgagtcc tgttcaagct    540

caaagagcaa atgctcttgc tgctgctcaa ggattggctg ataaggtttc ctttcaggtt    600

gctgacgctc tacagcaacc attctctgac ggccagtttg atctggtgtg gtccatggag    660

agtggagagc atatgcctga caaagctaag tttgttggag agttagctcg ggtagcagca    720

ccaggtgcca ctataataat agtaacatgg tgccacaggg atcttggccc tgacgaacaa    780

tccttacatc catgggagca agatctctta aagaagattt gcgatgcata ttacctccct    840

gcctggtgct caacttctga ttatgttaag ttgctccaat ccctgtcact tcaggacatc    900

aagtcagaag attggtctcg ctttgttgct ccattttggc cagcagtgat acgctcagcc    960

ttcacatgga agggtctaac ttcactcttg agcagtggac aaaaaacgat aaaaggagct   1020
```

```
ttggctatgc cattgatgat agagggatac aagaaagatc taattaagtt tgccatcatt   1080

acatgtcgaa aacctgaata aatggagagg caggattact tttatagaat gaaccaagtt   1140

tccaacaggt cgtttatttc gatagttgag aaacaagaga aaaaataaat gaaaggggtt   1200

gttcgatttt tattttagtt ttctacatat gcaatatctc ctatgattgg cgaaaatata   1260

ttatctactt aaataaaaaa aaaaaaaaaa aa                                 1292


<210> SEQ ID NO 22
<211> LENGTH: 350
<212> TYPE: PRT
<213> ORGANISM: Glycine max

<400> SEQUENCE: 22

Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ala Ser Ser Glu Arg
        35                  40                  45

Gly Glu Ile Val Leu Glu Gln Lys Pro Lys Lys Asp Asp Lys Lys Lys
    50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His His Gly Phe Tyr Asp Ser Asp
                85                  90                  95

Ser Thr Val Ser Leu Ser Asp His Arg Ala Ala Gln Ile Arg Met Ile
            100                 105                 110

Gln Glu Ser Leu Arg Phe Ala Ser Val Ser Glu Glu Arg Ser Lys Trp
        115                 120                 125

Pro Lys Ser Ile Val Asp Val Gly Cys Gly Ile Gly Gly Ser Ser Arg
    130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Thr Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285

Trp Ser Arg Phe Val Ala Pro Phe Trp Pro Ala Val Ile Arg Ser Ala
    290                 295                 300

Phe Thr Trp Lys Gly Leu Thr Ser Leu Leu Ser Ser Gly Gln Lys Thr
305                 310                 315                 320

Ile Lys Gly Ala Leu Ala Met Pro Leu Met Ile Glu Gly Tyr Lys Lys
```

```
                325                 330                 335

Asp Leu Ile Lys Phe Ala Ile Ile Thr Cys Arg Lys Pro Glu
            340                 345                 350


<210> SEQ ID NO 23
<211> LENGTH: 1301
<212> TYPE: DNA
<213> ORGANISM: Oryza sativa

<400> SEQUENCE: 23

agacgccaga gcgctacaaa atggcccacg ccgccgcggc cacgggcgca ctggcaccgc      60

tgcatccact gctccgctgc acgagccgtc atctctgcgc ctcggcttcc cctcgcgccg     120

gcctctgcct ccaccaccac cgccgccgcc gccgcagcag ccggaggacg aaactcgccg     180

tgcgcgcgat ggcaccgacg ttgtcctcgt cgtcgacggc ggcggcagct cccccggggc     240

tgaaggaggg catcgcgggg ctctacgacg agtcgtccgg cgtgtgggag agcatctggg     300

gcgagcacat gcaccacggc ttctacgacg ccggcgaggc cgcctccatg tccgaccacc     360

gccgcgccca gatccgcatg atcgaggaat ccctcgcctt cgccgccgtc cccgatgatg     420

cggagaagaa acccaaaagt gtagttgatg ttggctgtgg cattggtggt agctcaagat     480

acttggcgaa caaatacgga gcgcaatgct acggcatcac gttgagtccg gtgcaggctg     540

aaagaggaaa tgccctcgcg gcagagcaag ggttatcaga caaggtctcc tttcaagttg     600

gtgatgcatt ggagcagcct tttcctgatg ggcagtttga tcttgtctgg tccatggaga     660

gtggcgagca catgccagac aaacggcagt ttgtaagcga gctggcacgc gtcgcagctc     720

ctggggcgag aataatcatt gtgacctggt gccataggaa cctcgagcca tccgaagagt     780

ccctgaaacc tgatgagctg aatctcctga aaaggatatg cgatgcatat tatctcccag     840

actggtgctc tccttctgat tatgtcaaaa ttgccgagtc actgtctctt gaggatataa     900

ggacagctga ttggtcagag aacgtcgccc cattctggcc tgcggttata aaatcagcat     960

tgacatggaa aggtttaact tctctgctaa gaagtgggtg gaagacgata agaggtgcaa    1020

tggtgatgcc tctgatgatc gaaggataca agaaagggct catcaaattc accatcatca    1080

cctgtcgcaa gcccgaaaca acgcagtagt accctagtag tgaaattacg ctcctgctat    1140

cttctccatc acgaataatg caaattctga cgagttagca cctactgatg gcgatttgtt    1200

gatttgggga acagccagtg cactgttacc acgtcattga ttttgtactc gtcagactta    1260

aaaaaaaaat atccatgaat gtgcactcca aatacgtcaa g                        1301


<210> SEQ ID NO 24
<211> LENGTH: 362
<212> TYPE: PRT
<213> ORGANISM: Oryza sativa

<400> SEQUENCE: 24

Met Ala His Ala Ala Ala Ala Thr Gly Ala Leu Ala Pro Leu His Pro
1               5                   10                  15

Leu Leu Arg Cys Thr Ser Arg His Leu Cys Ala Ser Ala Ser Pro Arg
            20                  25                  30

Ala Gly Leu Cys Leu His His His Arg Arg Arg Arg Arg Ser Ser Arg
        35                  40                  45

Arg Thr Lys Leu Ala Val Arg Ala Met Ala Pro Thr Leu Ser Ser Ser
    50                  55                  60

Ser Thr Ala Ala Ala Ala Pro Pro Gly Leu Lys Glu Gly Ile Ala Gly
65                  70                  75                  80
```

```
Leu Tyr Asp Glu Ser Ser Gly Val Trp Glu Ser Ile Trp Gly Glu His
                85                  90                  95

Met His His Gly Phe Tyr Asp Ala Gly Glu Ala Ala Ser Met Ser Asp
            100                 105                 110

His Arg Arg Ala Gln Ile Arg Met Ile Glu Glu Ser Leu Ala Phe Ala
        115                 120                 125

Ala Val Pro Asp Asp Ala Glu Lys Lys Pro Lys Ser Val Val Asp Val
    130                 135                 140

Gly Cys Gly Ile Gly Gly Ser Ser Arg Tyr Leu Ala Asn Lys Tyr Gly
145                 150                 155                 160

Ala Gln Cys Tyr Gly Ile Thr Leu Ser Pro Val Gln Ala Glu Arg Gly
                165                 170                 175

Asn Ala Leu Ala Ala Glu Gln Gly Leu Ser Asp Lys Val Ser Phe Gln
            180                 185                 190

Val Gly Asp Ala Leu Glu Gln Pro Phe Pro Asp Gly Gln Phe Asp Leu
        195                 200                 205

Val Trp Ser Met Glu Ser Gly Glu His Met Pro Asp Lys Arg Gln Phe
    210                 215                 220

Val Ser Glu Leu Ala Arg Val Ala Ala Pro Gly Ala Arg Ile Ile Ile
225                 230                 235                 240

Val Thr Trp Cys His Arg Asn Leu Glu Pro Ser Glu Glu Ser Leu Lys
                245                 250                 255

Pro Asp Glu Leu Asn Leu Leu Lys Arg Ile Cys Asp Ala Tyr Tyr Leu
            260                 265                 270

Pro Asp Trp Cys Ser Pro Ser Asp Tyr Val Lys Ile Ala Glu Ser Leu
        275                 280                 285

Ser Leu Glu Asp Ile Arg Thr Ala Asp Trp Ser Glu Asn Val Ala Pro
    290                 295                 300

Phe Trp Pro Ala Val Ile Lys Ser Ala Leu Thr Trp Lys Gly Leu Thr
305                 310                 315                 320

Ser Leu Leu Arg Ser Gly Trp Lys Thr Ile Arg Gly Ala Met Val Met
                325                 330                 335

Pro Leu Met Ile Glu Gly Tyr Lys Lys Gly Leu Ile Lys Phe Thr Ile
            340                 345                 350

Ile Thr Cys Arg Lys Pro Glu Thr Thr Gln
        355                 360
```

<210> SEQ ID NO 25
<211> LENGTH: 1265
<212> TYPE: DNA
<213> ORGANISM: Brassica sp.

<400> SEQUENCE: 25

```
tttctccaac caacctctca ttataaatga aagcgactct cgcaccaccc tcctctctca      60

taagcctccc caggcacaaa gtatcttctc tccgttcacc gtcgcttctc cttcagtccc     120

agcggccatc ctcagcctta atgacaacga cggcaacacg tggaagcgta gctgtgacgg     180

ctgctgctac ctcctccgct gaggcgctgc gagaaggaat agcggaattc tacaacgaga     240

cgtcgggatt atgggaggag atttggggag atcatatgca tcacggcttc tacgatcccg     300

attcctctgt tcaactttca gattccggtc accgggaagc tcagatccgg atgattgaag     360

agtctctacg tttcgccggc gttactgaag aggagaaaaa gataaagaga gtggtggatg     420

ttgggtgtgg gatcggagga agctcaaggt atattgcctc taaatttggt gccgaatgca     480

ttggcatcac actcagtccc gttcaagcca agagagccaa tgatctcgcc gccgctcaat     540
```

```
cactctctca taaggtttcc ttccaagttg cagatgcatt ggaccaacca tttgaagatg    600

gtattttcga tcttgtttgg tcaatggaaa gcggtgagca tatgcctgac aaggccaagt    660

tcgtgaagga attggtacgt gtgacggctc caggaggaag gataataata gtgacatggt    720

gccacagaaa tctatcccaa ggggaagaat ctttgcagcc atgggagcag aacctcttgg    780

acagaatctg caaaacattt tatctcccgg cctggtgctc cacctctgat tatgtcgagt    840

tgcttcaatc cctctcgctc caggatatta agtgtgcaga ttggtcagag aacgtagctc    900

ctttctggcc ggcggttata cgaaccgcat taacgtggaa gggccttgtg tctctgcttc    960

gtagtggtat gaagagtata aaaggagcat tgacaatgcc attgatgatt gaagggtaca   1020

agaaaggtgt cattaaattt ggcatcatcg cttgccagaa gcctctctaa gttcaatcta   1080

aacaataaaa ttgtcgtact tttcagcgaa ttgatttcta tctatgatat aggagattga   1140

ataagagtca cgtgagaaat gtggatgcat gaaatccctt aaacgtcatt aatgttcgtt   1200

catggctacg ttgtctattt tagataaata tacaagttga aggtgtcaa aaaaaaaaaa   1260

aaaaa                                                             1265
```

<210> SEQ ID NO 26
<211> LENGTH: 347
<212> TYPE: PRT
<213> ORGANISM: Brassica sp.

<400> SEQUENCE: 26

```
Met Lys Ala Thr Leu Ala Pro Pro Ser Ser Leu Ile Ser Leu Pro Arg
1               5                   10                  15

His Lys Val Ser Ser Leu Arg Ser Pro Ser Leu Leu Leu Gln Ser Gln
            20                  25                  30

Arg Pro Ser Ser Ala Leu Met Thr Thr Thr Ala Thr Arg Gly Ser Val
        35                  40                  45

Ala Val Thr Ala Ala Ala Thr Ser Ser Ala Glu Ala Leu Arg Glu Gly
    50                  55                  60

Ile Ala Glu Phe Tyr Asn Glu Thr Ser Gly Leu Trp Glu Glu Ile Trp
65                  70                  75                  80

Gly Asp His Met His His Gly Phe Tyr Asp Pro Asp Ser Ser Val Gln
                85                  90                  95

Leu Ser Asp Ser Gly His Arg Glu Ala Gln Ile Arg Met Ile Glu Glu
            100                 105                 110

Ser Leu Arg Phe Ala Gly Val Thr Glu Glu Glu Lys Lys Ile Lys Arg
        115                 120                 125

Val Val Asp Val Gly Cys Gly Ile Gly Gly Ser Ser Arg Tyr Ile Ala
    130                 135                 140

Ser Lys Phe Gly Ala Glu Cys Ile Gly Ile Thr Leu Ser Pro Val Gln
145                 150                 155                 160

Ala Lys Arg Ala Asn Asp Leu Ala Ala Ala Gln Ser Leu Ser His Lys
                165                 170                 175

Val Ser Phe Gln Val Ala Asp Ala Leu Asp Gln Pro Phe Glu Asp Gly
            180                 185                 190

Ile Phe Asp Leu Val Trp Ser Met Glu Ser Gly Glu His Met Pro Asp
        195                 200                 205

Lys Ala Lys Phe Val Lys Glu Leu Val Arg Val Thr Ala Pro Gly Gly
    210                 215                 220

Arg Ile Ile Ile Val Thr Trp Cys His Arg Asn Leu Ser Gln Gly Glu
225                 230                 235                 240

Glu Ser Leu Gln Pro Trp Glu Gln Asn Leu Leu Asp Arg Ile Cys Lys
```

```
                245                 250                 255

Thr Phe Tyr Leu Pro Ala Trp Cys Ser Thr Ser Asp Tyr Val Glu Leu
            260                 265                 270

Leu Gln Ser Leu Ser Leu Gln Asp Ile Lys Cys Ala Asp Trp Ser Glu
        275                 280                 285

Asn Val Ala Pro Phe Trp Pro Ala Val Ile Arg Thr Ala Leu Thr Trp
    290                 295                 300

Lys Gly Leu Val Ser Leu Leu Arg Ser Gly Met Lys Ser Ile Lys Gly
305                 310                 315                 320

Ala Leu Thr Met Pro Leu Met Ile Glu Gly Tyr Lys Lys Gly Val Ile
                325                 330                 335

Lys Phe Gly Ile Ile Ala Cys Gln Lys Pro Leu
            340                 345


<210> SEQ ID NO 27
<211> LENGTH: 1369
<212> TYPE: DNA
<213> ORGANISM: Perilla frutescens

<400> SEQUENCE: 27

gtcaaaatca ccaattacct atttccttca atatccgcaa tttccacatg cactgcacat     60

atctttaatt aaataaccgc aaagctcaat ggccgaggcg gtcacgccag gtatctgcac    120

caccgggtgg cgccgcggtg gggtccacgc tcccacttat aatatttcta taaagccagc    180

gacagcgttg ctggttggct gcaccaccaa aaccaaaagc attacttctt tttccacaga    240

ctccctcagg acacgtggca gagcacgtcg cccgacgatg agcctgaacg ccgctgcggc    300

ggagatggag acggagatgg agaccttgcg taaagggatt gcggagttct acgacgagtc    360

gtcgggggtg tgggagaaca tatggggaga ccacatgcac cacggctttt acgagccggc    420

cgccgacgtc tccatctccg accatcgcgc cgcccagatc cgcatgattg aggagtccct    480

ccgattcgct tccttctctc cgataactac gacggagaaa ccgaagaata tagttgatgt    540

gggatgtggt ataggaggca gttctaggta tctggcaaga aaatatgggg ctaaattgtc    600

tagggctatt actctttcca gccctgtgca agcgcagaga gctcaacagc ttgctgatgc    660

tcaaggatta aatggcaagg tttcctttga agttgctgat gcgttgaacc aaccatttcc    720

tgaagggaag tttgatctgg tttggtcgat ggagagtgga gaacacatgc ctgataagaa    780

aaagtttgta aatgagctgg tgcgtgtggc tgctcctggt ggaagaataa tcatcgttac    840

atggtgccac agggacctat caccttctga agaatctctt cgccaagagg agaaagattt    900

gctaaacaaa atatgtagtg cttattatct tccagcatgg tgctctactg ctgactatgt    960

caaattactc gactccctct caatggagga cattaagtct gcagactggt ctgaccatgt   1020

cgctccattt tggccggcag ttataaagtc ggcattgaca tggaagggca taacctcact   1080

gctaaggagc ggatggaaga ctataagagg agcaatggtg atgccattga tgatcgaagg   1140

atataagaag ggcgtgatca aatttgccat cattacatgc cgaaaacctg catcttaata   1200

aatagggcct aacaaatcat tgatggatat agatatagtg ttgcttctgg tattttcaca   1260

tttgatggcc cttatattgt taggtataac gtacttgtca tttcttttat ccgtttataa   1320

attataatga aagaagcttt ccttcaattc acaaaaaaaa aaaaaaaaa               1369


<210> SEQ ID NO 28
<211> LENGTH: 369
<212> TYPE: PRT
<213> ORGANISM: Perilla frutescens
```

<400> SEQUENCE: 28

```
Met Ala Glu Ala Val Thr Pro Gly Ile Cys Thr Thr Gly Trp Arg Arg
1               5                   10                  15

Gly Gly Val His Ala Pro Thr Tyr Asn Ile Ser Ile Lys Pro Ala Thr
            20                  25                  30

Ala Leu Leu Val Gly Cys Thr Thr Lys Thr Lys Ser Ile Thr Ser Phe
        35                  40                  45

Ser Thr Asp Ser Leu Arg Thr Arg Gly Arg Ala Arg Arg Pro Thr Met
    50                  55                  60

Ser Leu Asn Ala Ala Ala Ala Glu Met Glu Thr Glu Met Glu Thr Leu
65                  70                  75                  80

Arg Lys Gly Ile Ala Glu Phe Tyr Asp Glu Ser Ser Gly Val Trp Glu
                85                  90                  95

Asn Ile Trp Gly Asp His Met His His Gly Phe Tyr Glu Pro Ala Ala
            100                 105                 110

Asp Val Ser Ile Ser Asp His Arg Ala Ala Gln Ile Arg Met Ile Glu
        115                 120                 125

Glu Ser Leu Arg Phe Ala Ser Phe Ser Pro Ile Thr Thr Thr Glu Lys
    130                 135                 140

Pro Lys Asn Ile Val Asp Val Gly Cys Gly Ile Gly Gly Ser Ser Arg
145                 150                 155                 160

Tyr Leu Ala Arg Lys Tyr Gly Ala Lys Leu Ser Arg Ala Ile Thr Leu
                165                 170                 175

Ser Ser Pro Val Gln Ala Gln Arg Ala Gln Gln Leu Ala Asp Ala Gln
            180                 185                 190

Gly Leu Asn Gly Lys Val Ser Phe Glu Val Ala Asp Ala Leu Asn Gln
        195                 200                 205

Pro Phe Pro Glu Gly Lys Phe Asp Leu Val Trp Ser Met Glu Ser Gly
    210                 215                 220

Glu His Met Pro Asp Lys Lys Lys Phe Val Asn Glu Leu Val Arg Val
225                 230                 235                 240

Ala Ala Pro Gly Gly Arg Ile Ile Ile Val Thr Trp Cys His Arg Asp
                245                 250                 255

Leu Ser Pro Ser Glu Glu Ser Leu Arg Gln Glu Glu Lys Asp Leu Leu
            260                 265                 270

Asn Lys Ile Cys Ser Ala Tyr Tyr Leu Pro Ala Trp Cys Ser Thr Ala
        275                 280                 285

Asp Tyr Val Lys Leu Leu Asp Ser Leu Ser Met Glu Asp Ile Lys Ser
    290                 295                 300

Ala Asp Trp Ser Asp His Val Ala Pro Phe Trp Pro Ala Val Ile Lys
305                 310                 315                 320

Ser Ala Leu Thr Trp Lys Gly Ile Thr Ser Leu Leu Arg Ser Gly Trp
                325                 330                 335

Lys Thr Ile Arg Gly Ala Met Val Met Pro Leu Met Ile Glu Gly Tyr
            340                 345                 350

Lys Lys Gly Val Ile Lys Phe Ala Ile Ile Thr Cys Arg Lys Pro Ala
        355                 360                 365

Ser
```

<210> SEQ ID NO 29
<211> LENGTH: 1350
<212> TYPE: DNA
<213> ORGANISM: Arabidopsis thaliana

<400> SEQUENCE: 29

```
ccacgcgtcc gcaaataatc cctgacttcg tcacgtttct ttgtatctcc aacgtccaat      60

aaatgaaagc aactctagca gcaccctctt ctctcacaag cctccctat cgaaccaact     120

cttctttcgg ctcaaagtca tcgcttctct ttcggtctcc atcctcctcc tcctcagtct     180

ctatgacgac aacgcgtgga aacgtggctg tggcggctgc tgctacatcc actgaggcgc     240

taagaaaagg aatagcggag ttctacaatg aaacttcggg tttgtgggaa gagatttggg     300

gagatcatat gcatcatggc ttttatgacc ctgattcttc tgttcaactt tctgattctg     360

gtcacaagga agctcagatc cgtatgattg aagagtctct ccgtttcgcc ggtgttactg     420

atgaagagga ggagaaaaag ataaagaaag tagtggatgt tgggtgtggg attggaggaa     480

gctcaagata tcttgcctct aaatttggag ctgaatgcat tggcattact ctcagccctg     540

ttcaggccaa gagagccaat gatctcgcgg ctgctcaatc actctctcat aaggcttcct     600

tccaagttgc ggatgcgttg gatcagccat tcgaagatgg aaaattcgat ctagtgtggt     660

cgatggagag tggtgagcat atgcctgaca aggccaagtt tgtaaaagag ttggtacgtg     720

tggcggctcc aggaggtagg ataataatag tgacatggtg ccatagaaat ctatctgcgg     780

gggaggaagc tttgcagccg tgggagcaaa acatcttgga caaaatctgt aagacgttct     840

atctcccggc ttggtgctcc accgatgatt atgtcaactt gcttcaatcc cattctctcc     900

aggatattaa gtgtgcggat tggtcagaga acgtagctcc tttctggcct gcggttatac     960

ggactgcatt aacatggaag ggccttgtgt ctctgcttcg tagtggtatg aaaagtatta    1020

aaggagcatt gacaatgcca ttgatgattg aaggttacaa gaaaggtgtc attaagtttg    1080

gtatcatcac ttgccagaag ccactctaag tctaaagcta tactaggaga ttcaataaga    1140

ctataagagt agtgtctcat gtgaaagcat gaaattcctt aaaaacgtca atgttaagcc    1200

tatgcttcgt tatttgtttt agataagtat catttcactc ttgtctaagg tagtttctat    1260

aaacaataaa taccatgaat tagctcatgt tatctggtaa attctcggaa gtgattgtca    1320

tggattaact caaaaaaaaa aaaaaaaaaa                                     1350
```

<210> SEQ ID NO 30
<211> LENGTH: 348
<212> TYPE: PRT
<213> ORGANISM: Arabidopsis thaliana

<400> SEQUENCE: 30

```
Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
            20                  25                  30

Pro Ser Ser Ser Ser Ser Val Ser Met Thr Thr Thr Arg Gly Asn Val
        35                  40                  45

Ala Val Ala Ala Ala Ala Thr Ser Thr Glu Ala Leu Arg Lys Gly Ile
    50                  55                  60

Ala Glu Phe Tyr Asn Glu Thr Ser Gly Leu Trp Glu Glu Ile Trp Gly
65                  70                  75                  80

Asp His Met His His Gly Phe Tyr Asp Pro Asp Ser Ser Val Gln Leu
                85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Glu Lys Lys Ile Lys
        115                 120                 125

Lys Val Val Asp Val Gly Cys Gly Ile Gly Gly Ser Ser Arg Tyr Leu
```

```
    130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Ala Gln Ser Leu Ser His
                165                 170                 175

Lys Ala Ser Phe Gln Val Ala Asp Ala Leu Asp Gln Pro Phe Glu Asp
            180                 185                 190

Gly Lys Phe Asp Leu Val Trp Ser Met Glu Ser Gly Glu His Met Pro
        195                 200                 205

Asp Lys Ala Lys Phe Val Lys Glu Leu Val Arg Val Ala Ala Pro Gly
    210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Asp Tyr Val Asn
            260                 265                 270

Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
    290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
            340                 345
```

<210> SEQ ID NO 31
<211> LENGTH: 1330
<212> TYPE: DNA
<213> ORGANISM: Medicago truncatula
<220> FEATURE:
<221> NAME/KEY: misc_feature
<222> LOCATION: (1306)..(1306)
<223> OTHER INFORMATION: n is a, c, g, or t
<220> FEATURE:
<221> NAME/KEY: misc_feature
<222> LOCATION: (1310)..(1310)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t

<400> SEQUENCE: 31

```
aatatttttt atgattgaaa atgaagtaag atctgtggag catgatctta tcatttagtc      60

aggtcaatta tgaaaataac aattcatcac catacgtaca tgtcttgtag caacaaaaga     120

aatcccattt tggtagtagt agtttcgtgc gtacctaaat tacggtttaa tagtaacagc     180

aaaaattgtg ccttgttttt ttgttgtatt gcgcggtgta ccgttgcaag tgataacaca     240

caacacaaca taaccatggt tgttacaaca acgagaatct cttcattatt acactgcaca     300

cacacatttc ctcagcacca cagagacact atcattacta ctacaacaac aacactcaac     360

agtagaagaa gaaaaggttc attgcgtgta tcaatggcgg cggtgaaaga agtgatggtg     420

gtaatggaag aagaagagaa gaagaaactt cagttagagg atcaatcaaa atggccaaag     480

agtgtagttg atgttgggtg tggcataggg ggcagttcaa ggtacctggc caagaaattt     540

ggggcaaact gtgtaggcat cactctcagc cctgttcaag ctgaaagagc taatgctcta     600
```

```
gctgctgctc aaggattagc cgataaggtt tcctttcaag ttgctgacgc tctacaacaa    660

ccattccctg atggccagtt tgatctagtg tggtcaatgg agagcggaga gcatatgcct    720

aacaaaccaa agtttgttgg agagttagct cgggtagcag caccgggtgg caccataata    780

atagtaacat ggtgtcatag ggatcttcgc ccggatgaag aatccctaca acaatgggag    840

aaggatctct tgaagaagat atgtgattca ttttatcttc cggagtggtg ctcaactgct    900

gattatgtca aattacttga aaccatgtcc cttcaggaca tcaaatcagc agattggtct    960

ccctttgttg ctccattttg gccagcagtg atacgttcag cattaacatg gaagggtttc   1020

acctcaatct tgcggagtgg actaaaaact ataaaaggag ctttggctat gccattgatg   1080

atagaaggat ttaggaaggg tgtgattaag tttgccatta tcacatgtcg aaagcctgaa   1140

aacgcagatg gtcaatgatt ttatatgatg aaacagaatt cctacatgtc atttattttg   1200

atagttcaca caaaacaaat aagaaataaa gaatacgtgt ttctgccatg tcagatccaa   1260

ctgtgattga ataattgaag gaaagatgta agctagttcc tgttgngtan cctccaatcn   1320

aaaaaaaaaa                                                          1330


<210> SEQ ID NO 32
<211> LENGTH: 362
<212> TYPE: PRT
<213> ORGANISM: Medicago truncatula

<400> SEQUENCE: 32

Met Lys Ile Thr Ile His His His Thr Tyr Met Ser Cys Ser Asn Lys
1               5                   10                  15

Arg Asn Pro Ile Leu Val Val Val Val Ser Cys Val Pro Lys Leu Arg
            20                  25                  30

Phe Asn Ser Asn Ser Lys Asn Cys Ala Leu Phe Phe Cys Cys Ile Ala
        35                  40                  45

Arg Cys Thr Val Ala Ser Asp Asn Thr Gln His Asn Ile Thr Met Val
    50                  55                  60

Val Thr Thr Thr Arg Ile Ser Ser Leu Leu His Cys Thr His Thr Phe
65                  70                  75                  80

Pro Gln His His Arg Asp Thr Ile Ile Thr Thr Thr Thr Thr Thr Leu
                85                  90                  95

Asn Ser Arg Arg Arg Lys Gly Ser Leu Arg Val Ser Met Ala Ala Val
            100                 105                 110

Lys Glu Val Met Val Val Met Glu Glu Glu Glu Lys Lys Lys Leu Gln
        115                 120                 125

Leu Glu Asp Gln Ser Lys Trp Pro Lys Ser Val Val Asp Val Gly Cys
    130                 135                 140

Gly Ile Gly Gly Ser Ser Arg Tyr Leu Ala Lys Lys Phe Gly Ala Asn
145                 150                 155                 160

Cys Val Gly Ile Thr Leu Ser Pro Val Gln Ala Glu Arg Ala Asn Ala
                165                 170                 175

Leu Ala Ala Ala Gln Gly Leu Ala Asp Lys Val Ser Phe Gln Val Ala
            180                 185                 190

Asp Ala Leu Gln Gln Pro Phe Pro Asp Gly Gln Phe Asp Leu Val Trp
        195                 200                 205

Ser Met Glu Ser Gly Glu His Met Pro Asn Lys Pro Lys Phe Val Gly
    210                 215                 220

Glu Leu Ala Arg Val Ala Ala Pro Gly Gly Thr Ile Ile Ile Val Thr
225                 230                 235                 240
```

```
Trp Cys His Arg Asp Leu Arg Pro Asp Glu Glu Ser Leu Gln Gln Trp
                245                 250                 255

Glu Lys Asp Leu Leu Lys Lys Ile Cys Asp Ser Phe Tyr Leu Pro Glu
            260                 265                 270

Trp Cys Ser Thr Ala Asp Tyr Val Lys Leu Leu Glu Thr Met Ser Leu
        275                 280                 285

Gln Asp Ile Lys Ser Ala Asp Trp Ser Pro Phe Val Ala Pro Phe Trp
    290                 295                 300

Pro Ala Val Ile Arg Ser Ala Leu Thr Trp Lys Gly Phe Thr Ser Ile
305                 310                 315                 320

Leu Arg Ser Gly Leu Lys Thr Ile Lys Gly Ala Leu Ala Met Pro Leu
                325                 330                 335

Met Ile Glu Gly Phe Arg Lys Gly Val Ile Lys Phe Ala Ile Ile Thr
            340                 345                 350

Cys Arg Lys Pro Glu Asn Ala Asp Gly Gln
        355                 360
```

<210> SEQ ID NO 33
<211> LENGTH: 1573
<212> TYPE: DNA
<213> ORGANISM: Chlamydomonas sp.

<400> SEQUENCE: 33

```
agattaaaac aaaaccgctg agaagtttgc caagatgccc agcactgcgc tgcaagggca     60

cacgctgccc tcaagctctg catgcctagg tagagctaca cgccatgtat gcagagtgtc    120

cacacggagc cggcgcgctg tgacggttcg cgcgggaccg ctggagacgc tcgtgaagcc    180

gctcacgacg ctgggaaagg tcagcgacct caaagtcggc atcgccaact tctatgacga    240

gtcttcggag ctgtgggaga acatgtgggg ggagcacatg catcacggct actatcccaa    300

gggtgccccc gtcaagagca accagcaggc acagatcgat atgattgagg agacgctcaa    360

ggtggctggt gtgacacaag ccaagaagat ggtggacgtg ggctgcggca tcggcggcag    420

ctcgcgctac atcagccgca agttcggctg cacctccaac ggcatcacgc tcagccccaa    480

gcaggctgct cgcgccaatg cgctgagcaa ggagcagggc tttggcgaca agctgcagtt    540

ccaggtgggc gacgcgctgg cgcagccgtt cgaggccggc gccttcgacc tggtgtggtc    600

catggagagc ggcgagcaca tgcccgacaa gaagaagttt gtgtcggagc tggcgcgcgt    660

gtgtgcgccc ggcggcaccg tgattgtggt gacgtggtgc caccgcgtgt tgggtccggg    720

cgaggcgggc ttgcgcgagg acgagaaggc gctgctggac cgcatcaacg aggcctacta    780

cctgcccgac tggtgctccg tggcagacta ccagaaactg ttcgaggcac aaggcctgac    840

tgacatccag acccgcgact ggagccagga ggtgtcgccc ttctggggcg ccgtgatcgc    900

cacggccctg accagcgagg gtctggcggg tctggccaag gcgggctgga ccaccatcaa    960

gggcgccctg gtgatgccgc tcatggccga gggcttcaga cgcggcctca tcaagttcaa   1020

cctcatcagc ggccgcaagc tgcagcagta gtagcagtgc ggcggcaatg cggctgtagc   1080

agcagtggta gtggtagcag ggggccagcg gggctgcaga ctatggaggg agcgcccaat   1140

cgccgcggag ctcttgcttg tgtttgtcgt tgtgatgagg tcagtggcgc gatggcgcaa   1200

gaagccaggg acggaccggc tcgcgaggag tggtggcaac tgcattcatg gtgggtgtga   1260

ccgcgtgggc gtgagcgcgt gagggtcagg tgagaacgaa cgggccaggc aagaggacat   1320

ggattgcggg gctgcaggat gggggactgt catcgtatcg ctgtgagctg gtgacagagc   1380

tggtgaccgg acaagcagct gtgaggaccc ggcgcggcat agcgtcgccg gtgtgaccgc   1440
```

```
cgtttctctt tgggcaacgc aaaccaggtg actcaggggg cacccccttt cttgtcttcg   1500

ggctgcatca cgcatggtgc cacgcatgtc atgtgcacct gaggctattg caagttggct   1560

ggttgggcat gtc                                                      1573


<210> SEQ ID NO 34
<211> LENGTH: 338
<212> TYPE: PRT
<213> ORGANISM: Chlamydomonas sp.

<400> SEQUENCE: 34

Met Pro Ser Thr Ala Leu Gln Gly His Thr Leu Pro Ser Ser Ser Ala
1               5                   10                  15

Cys Leu Gly Arg Ala Thr Arg His Val Cys Arg Val Ser Thr Arg Ser
            20                  25                  30

Arg Arg Ala Val Thr Val Arg Ala Gly Pro Leu Glu Thr Leu Val Lys
        35                  40                  45

Pro Leu Thr Thr Leu Gly Lys Val Ser Asp Leu Lys Val Gly Ile Ala
    50                  55                  60

Asn Phe Tyr Asp Glu Ser Ser Glu Leu Trp Glu Asn Met Trp Gly Glu
65                  70                  75                  80

His Met His His Gly Tyr Tyr Pro Lys Gly Ala Pro Val Lys Ser Asn
                85                  90                  95

Gln Gln Ala Gln Ile Asp Met Ile Glu Glu Thr Leu Lys Val Ala Gly
            100                 105                 110

Val Thr Gln Ala Lys Lys Met Val Asp Val Gly Cys Gly Ile Gly Gly
        115                 120                 125

Ser Ser Arg Tyr Ile Ser Arg Lys Phe Gly Cys Thr Ser Asn Gly Ile
    130                 135                 140

Thr Leu Ser Pro Lys Gln Ala Ala Arg Ala Asn Ala Leu Ser Lys Glu
145                 150                 155                 160

Gln Gly Phe Gly Asp Lys Leu Gln Phe Gln Val Gly Asp Ala Leu Ala
                165                 170                 175

Gln Pro Phe Glu Ala Gly Ala Phe Asp Leu Val Trp Ser Met Glu Ser
            180                 185                 190

Gly Glu His Met Pro Asp Lys Lys Lys Phe Val Ser Glu Leu Ala Arg
        195                 200                 205

Val Cys Ala Pro Gly Gly Thr Val Ile Val Val Thr Trp Cys His Arg
    210                 215                 220

Val Leu Gly Pro Gly Glu Ala Gly Leu Arg Glu Asp Glu Lys Ala Leu
225                 230                 235                 240

Leu Asp Arg Ile Asn Glu Ala Tyr Tyr Leu Pro Asp Trp Cys Ser Val
                245                 250                 255

Ala Asp Tyr Gln Lys Leu Phe Glu Ala Gln Gly Leu Thr Asp Ile Gln
            260                 265                 270

Thr Arg Asp Trp Ser Gln Glu Val Ser Pro Phe Trp Gly Ala Val Ile
        275                 280                 285

Ala Thr Ala Leu Thr Ser Glu Gly Leu Ala Gly Leu Ala Lys Ala Gly
    290                 295                 300

Trp Thr Thr Ile Lys Gly Ala Leu Val Met Pro Leu Met Ala Glu Gly
305                 310                 315                 320

Phe Arg Arg Gly Leu Ile Lys Phe Asn Leu Ile Ser Gly Arg Lys Leu
                325                 330                 335

Gln Gln
```

<210> SEQ ID NO 35
<211> LENGTH: 954
<212> TYPE: DNA
<213> ORGANISM: Synechocystis sp.

<400> SEQUENCE: 35

```
atggtttacc atgttaggcc taagcacgcc ctgttcttag cattctattg ttatttctct     60
ttgcttacca tggccagcgc caccattgcc agtgcagacc tctacgaaaa aattaaaaat    120
ttctacgacg actccagcgg tctctgggaa gacgtttggg gtgagcatat gcaccacggc    180
tactacggtc cccacggcac ctatcggatc gatcgccgcc aggctcaaat tgatctgatc    240
aaagaactat tggcctgggc agtgccccaa aatagcgcca aaccacgaaa aattctcgat    300
ttaggctgtg gcattggcgg cagtagtttg tacttggccc agcaacacca agcagaagtg    360
atgggggcta gtctttcccc agtgcaggtg gaacgggcgg gggaaagggc cagggccctg    420
gggttgggct caacctgcca gtttcaggtg gccaatgcct tggatttgcc ctttgcttcc    480
gattcctttg actgggtttg gtcgttggaa agtggggagc acatgcccaa caaagctcag    540
tttttacaag aagcttggcg ggtacttaaa ccaggtggcc gtctgatttt agcgacctgg    600
tgtcatcgtc ccattgatcc cggcaatggc cccctgactg ccgatgaacg tcgccatctc    660
caagccatct atgacgttta ctgtttgccc tatgtggttt ccctgccgga ctacgaggcg    720
atcgccaggg aatgtgggtt tggggaaatt aagactgccg attggtcagt ggcggtggca    780
ccttttttggg accgggtgat tgagtctgcg ttcgatcccc gggtgttgtg ggccttgggg    840
caagcggggc caaaaattat caatgccgcc ctgtgtttac gattaatgaa atggggctat    900
gaacggggat tagtgcgttt tggcttatta acggggataa agcctttagt ttga          954
```

<210> SEQ ID NO 36
<211> LENGTH: 317
<212> TYPE: PRT
<213> ORGANISM: Synechocystis sp.

<400> SEQUENCE: 36

```
Met Val Tyr His Val Arg Pro Lys His Ala Leu Phe Leu Ala Phe Tyr
1               5                   10                  15

Cys Tyr Phe Ser Leu Leu Thr Met Ala Ser Ala Thr Ile Ala Ser Ala
            20                  25                  30

Asp Leu Tyr Glu Lys Ile Lys Asn Phe Tyr Asp Asp Ser Ser Gly Leu
        35                  40                  45

Trp Glu Asp Val Trp Gly Glu His Met His His Gly Tyr Tyr Gly Pro
    50                  55                  60

His Gly Thr Tyr Arg Ile Asp Arg Arg Gln Ala Gln Ile Asp Leu Ile
65                  70                  75                  80

Lys Glu Leu Leu Ala Trp Ala Val Pro Gln Asn Ser Ala Lys Pro Arg
                85                  90                  95

Lys Ile Leu Asp Leu Gly Cys Gly Ile Gly Gly Ser Ser Leu Tyr Leu
            100                 105                 110

Ala Gln Gln His Gln Ala Glu Val Met Gly Ala Ser Leu Ser Pro Val
        115                 120                 125

Gln Val Glu Arg Ala Gly Glu Arg Ala Arg Ala Leu Gly Leu Gly Ser
    130                 135                 140

Thr Cys Gln Phe Gln Val Ala Asn Ala Leu Asp Leu Pro Phe Ala Ser
145                 150                 155                 160

Asp Ser Phe Asp Trp Val Trp Ser Leu Glu Ser Gly Glu His Met Pro
                165                 170                 175
```

```
Asn Lys Ala Gln Phe Leu Gln Glu Ala Trp Arg Val Leu Lys Pro Gly
            180                 185                 190

Gly Arg Leu Ile Leu Ala Thr Trp Cys His Arg Pro Ile Asp Pro Gly
        195                 200                 205

Asn Gly Pro Leu Thr Ala Asp Glu Arg Arg His Leu Gln Ala Ile Tyr
    210                 215                 220

Asp Val Tyr Cys Leu Pro Tyr Val Val Ser Leu Pro Asp Tyr Glu Ala
225                 230                 235                 240

Ile Ala Arg Glu Cys Gly Phe Gly Glu Ile Lys Thr Ala Asp Trp Ser
                245                 250                 255

Val Ala Val Ala Pro Phe Trp Asp Arg Val Ile Glu Ser Ala Phe Asp
            260                 265                 270

Pro Arg Val Leu Trp Ala Leu Gly Gln Ala Gly Pro Lys Ile Ile Asn
        275                 280                 285

Ala Ala Leu Cys Leu Arg Leu Met Lys Trp Gly Tyr Glu Arg Gly Leu
    290                 295                 300

Val Arg Phe Gly Leu Leu Thr Gly Ile Lys Pro Leu Val
305                 310                 315
```

<210> SEQ ID NO 37
<211> LENGTH: 843
<212> TYPE: DNA
<213> ORGANISM: Anabaena sp.

<400> SEQUENCE: 37

```
atgagtgcaa cactttacca acaaattcag caattttacg atgcttcctc tgggctgtgg      60

gaagagattt ggggcgaaca tatgcaccac ggctattatg gtgcagacgg tactgaacaa     120

aaaaaccgcc gtcaggcgca aattgattta attgaagaat tactcacttg ggcaggagta     180

caaacagcag aaaatatact agatgtgggt tgtggtattg gtggtagttc tctgtatttg     240

gcaggaaagt tgaatgctaa agctacagga attaccctga gtccagtgca agccgctaga     300

gccacagaaa gagccaagga agctggttta agtggtagaa gtcagttttt agtggcaaat     360

gcccaagcaa tgccttttga tgataattct tttgacttgg tgtggtcgct agaaagtggc     420

gaacatatgc cagataaaac caagtttttg caagagtgtt atcgagtctt gaaaccgggc     480

ggtaagttaa tcatggtgac atggtgtcat cgtcccactg ataaaaacacc actgacggct     540

gatgaaaaaa aacacctaga agatatttat cgggtgtatt gtttgcctta tgtaatttcg     600

ttgccggagt atgaagcgat cgcacgtcaa ctaccattaa ataatatccg caccgccgac     660

tggtcgcaat ccgtcgccca attttggaac atagtcatcg attccgcctt tacccccccaa     720

gcaatattcg gcttactccg cgcaggttgg actaccatcc aaggagcctt atcactaggc     780

ttaatgcgtc gcggctatga gcgcgggtta attcggtttg ggttgctttg tggggataag     840

tga                                                                   843
```

<210> SEQ ID NO 38
<211> LENGTH: 280
<212> TYPE: PRT
<213> ORGANISM: Anabaena sp.

<400> SEQUENCE: 38

```
Met Ser Ala Thr Leu Tyr Gln Gln Ile Gln Gln Phe Tyr Asp Ala Ser
1               5                   10                  15

Ser Gly Leu Trp Glu Glu Ile Trp Gly Glu His Met His His Gly Tyr
            20                  25                  30

Tyr Gly Ala Asp Gly Thr Glu Gln Lys Asn Arg Arg Gln Ala Gln Ile
```

```
        35                  40                  45

Asp Leu Ile Glu Glu Leu Leu Thr Trp Ala Gly Val Gln Thr Ala Glu
    50                  55                  60

Asn Ile Leu Asp Val Gly Cys Gly Ile Gly Gly Ser Ser Leu Tyr Leu
65                  70                  75                  80

Ala Gly Lys Leu Asn Ala Lys Ala Thr Gly Ile Thr Leu Ser Pro Val
                85                  90                  95

Gln Ala Ala Arg Ala Thr Glu Arg Ala Lys Glu Ala Gly Leu Ser Gly
            100                 105                 110

Arg Ser Gln Phe Leu Val Ala Asn Ala Gln Ala Met Pro Phe Asp Asp
        115                 120                 125

Asn Ser Phe Asp Leu Val Trp Ser Leu Glu Ser Gly Glu His Met Pro
    130                 135                 140

Asp Lys Thr Lys Phe Leu Gln Glu Cys Tyr Arg Val Leu Lys Pro Gly
145                 150                 155                 160

Gly Lys Leu Ile Met Val Thr Trp Cys His Arg Pro Thr Asp Lys Thr
                165                 170                 175

Pro Leu Thr Ala Asp Glu Lys Lys His Leu Glu Asp Ile Tyr Arg Val
            180                 185                 190

Tyr Cys Leu Pro Tyr Val Ile Ser Leu Pro Glu Tyr Glu Ala Ile Ala
        195                 200                 205

Arg Gln Leu Pro Leu Asn Asn Ile Arg Thr Ala Asp Trp Ser Gln Ser
    210                 215                 220

Val Ala Gln Phe Trp Asn Ile Val Ile Asp Ser Ala Phe Thr Pro Gln
225                 230                 235                 240

Ala Ile Phe Gly Leu Leu Arg Ala Gly Trp Thr Thr Ile Gln Gly Ala
                245                 250                 255

Leu Ser Leu Gly Leu Met Arg Arg Gly Tyr Glu Arg Gly Leu Ile Arg
            260                 265                 270

Phe Gly Leu Leu Cys Gly Asp Lys
        275                 280
```

<210> SEQ ID NO 39
<211> LENGTH: 846
<212> TYPE: DNA
<213> ORGANISM: Gloeobacter violaceus

<400> SEQUENCE: 39

```
atgggcgagc gaacggttct caacgaaaat atccggcggt tctacgacgc gtcctccggg     60

ttgtgggagg aggtctgggg cgagcacatg caccacggcc actgggaagt gggggaagcg    120

gacaaagatc gccgcgtcgc ccaggtggat ttggtcgtca ggctcctcga ctgggcgggg    180

atcgaccggg ccgagtcgat cgtcgatgtc ggctgcggca tcggcggcag cagtctgttt    240

ctggcggagc gcttcggcgc ccgggtggag gggatcaccc tcagccccgt gcagtgtaag    300

cgcgccgccg agcgcgcccg cgagcaccat ctggacgggc gcgcgcactt tcaggtggcc    360

gacgcccacc ggatgccctt cgccgacggc cggttcgacc tggtctggtc gctcgaaagc    420

ggtgagcaca tggccgacaa ggcccaattt ttgcgcgaat gccaccgggt gctcaggccc    480

ggcggccgct tcgtgtttgt gacttggtgc tgtcgccacg gcgccttgga cgcgcgggat    540

caaaaatggc tcggggcgat ctaccggatc taccacctgc cctacatcct ctcgatcgag    600

agctacacgc agttgcttgg tgagacgggg ttctcgggca ttcggaccac cgactggtcc    660

gatcgggtgg cccgcttctg gtcgctggtc atcgattcgg ccctcgaacc ggcggtgctg    720

tggaaggtga tcgcccaggg accgacggta atcaaaggcg cgctcgccat gcagttgatg    780
```

```
cggcgcagct acgcgcgggg gctggtgcgc ttcggcgtgt tcgcggccca aaaggcggag    840

ggataa                                                                846


<210> SEQ ID NO 40
<211> LENGTH: 281
<212> TYPE: PRT
<213> ORGANISM: Gloeobacter violaceus

<400> SEQUENCE: 40

Met Gly Glu Arg Thr Val Leu Asn Glu Asn Ile Arg Arg Phe Tyr Asp
1               5                   10                  15

Ala Ser Ser Gly Leu Trp Glu Glu Val Trp Gly Glu His Met His His
            20                  25                  30

Gly His Trp Glu Val Gly Glu Ala Asp Lys Asp Arg Arg Val Ala Gln
        35                  40                  45

Val Asp Leu Val Val Arg Leu Leu Asp Trp Ala Gly Ile Asp Arg Ala
    50                  55                  60

Glu Ser Ile Val Asp Val Gly Cys Gly Ile Gly Gly Ser Ser Leu Phe
65                  70                  75                  80

Leu Ala Glu Arg Phe Gly Ala Arg Val Glu Gly Ile Thr Leu Ser Pro
                85                  90                  95

Val Gln Cys Lys Arg Ala Ala Glu Arg Ala Arg Glu His His Leu Asp
            100                 105                 110

Gly Arg Ala His Phe Gln Val Ala Asp Ala His Arg Met Pro Phe Ala
        115                 120                 125

Asp Gly Arg Phe Asp Leu Val Trp Ser Leu Glu Ser Gly Glu His Met
    130                 135                 140

Ala Asp Lys Ala Gln Phe Leu Arg Glu Cys His Arg Val Leu Arg Pro
145                 150                 155                 160

Gly Gly Arg Phe Val Phe Val Thr Trp Cys Cys Arg His Gly Ala Leu
                165                 170                 175

Asp Ala Arg Asp Gln Lys Trp Leu Gly Ala Ile Tyr Arg Ile Tyr His
            180                 185                 190

Leu Pro Tyr Ile Leu Ser Ile Glu Ser Tyr Thr Gln Leu Leu Gly Glu
        195                 200                 205

Thr Gly Phe Ser Gly Ile Arg Thr Thr Asp Trp Ser Asp Arg Val Ala
    210                 215                 220

Arg Phe Trp Ser Leu Val Ile Asp Ser Ala Leu Glu Pro Ala Val Leu
225                 230                 235                 240

Trp Lys Val Ile Ala Gln Gly Pro Thr Val Ile Lys Gly Ala Leu Ala
                245                 250                 255

Met Gln Leu Met Arg Arg Ser Tyr Ala Arg Gly Leu Val Arg Phe Gly
            260                 265                 270

Val Phe Ala Ala Gln Lys Ala Glu Gly
        275                 280


<210> SEQ ID NO 41
<211> LENGTH: 8615
<212> TYPE: DNA
<213> ORGANISM: Artificial Sequence
<220> FEATURE:
<223> OTHER INFORMATION: plasmid KS308
<220> FEATURE:
<221> NAME/KEY: misc_feature
<222> LOCATION: (6642)..(6642)
<223> OTHER INFORMATION: n is a, c, g, or t

<400> SEQUENCE: 41
```

```
ggccgcgaca caagtgtgag agtactaaat aaatgctttg gttgtacgaa atcattacac     60
taaataaaat aatcaaagct tatatatgcc ttccgctaag gccgaatgca aagaaattgg    120
ttctttctcg ttatcttttg ccacttttac tagtacgtat taattactac ttaatcatct    180
ttgtttacgg ctcattatat ccgtcgacgg cgcgcccgat catccggata tagttcctcc    240
tttcagcaaa aaacccctca agacccgttt agaggcccca aggggttatg ctagttattg    300
ctcagcggtg gcagcagcca actcagcttc ctttcgggct ttgttagcag ccggatcgat    360
ccaagctgta cctcactatt cctttgccct cggacgagtg ctggggcgtc ggtttccact    420
atcggcgagt acttctacac agccatcggt ccagacggcc gcgcttctgc gggcgatttg    480
tgtacgcccg acagtcccgg ctccggatcg gacgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc cgcgtgcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct   1020
aagatcggcc gcagcgatcg catccatagc ctccgcgacc ggctgcagaa cagcgggcag   1080
ttcggtttca ggcaggtctt gcaacgtgac accctgtgca cggcgggaga tgcaataggt   1140
caggctctcg ctgaattccc caatgtcaag cacttccgga atcgggagcg cggccgatgc   1200
aaagtgccga taaacataac gatctttgta gaaaccatcg gcgcagctat ttacccgcag   1260
gacatatcca cgccctccta catcgaagct gaaagcacga gattcttcgc cctccgagag   1320
ctgcatcagg tcggagacgc tgtcgaactt ttcgatcaga aacttctcga cagacgtcgc   1380
ggtgagttca ggcttttcca tgggtatatc tccttcttaa agttaaacaa aattatttct   1440
agagggaaac cgttgtggtc tccctatagt gagtcgtatt aatttcgcgg gatcgagatc   1500
gatccaattc caatcccaca aaaatctgag cttaacagca cagttgctcc tctcagagca   1560
gaatcgggta ttcaacaccc tcatatcaac tactacgttg tgtataacgg tccacatgcc   1620
ggtatatacg atgactgggg ttgtacaaag gcggcaacaa acggcgttcc cggagttgca   1680
cacaagaaat ttgccactat tacagaggca agagcagcag ctgacgcgta cacaacaagt   1740
cagcaaacag acaggttgaa cttcatcccc aaaggagaag ctcaactcaa gcccaagagc   1800
tttgctaagg ccctaacaag cccaccaaag caaaaagccc actggctcac gctaggaacc   1860
aaaaggccca gcagtgatcc agccccaaaa gagatctcct ttgccccgga gattacaatg   1920
gacgatttcc tctatcttta cgatctagga aggaagttcg aaggtgaagg tgacgacact   1980
atgttcacca ctgataatga gaaggttagc ctcttcaatt tcagaaagaa tgctgaccca   2040
cagatggtta gagaggccta cgcagcaggt ctcatcaaga cgatctaccc gagtaacaat   2100
ctccaggaga tcaaatacct tcccaagaag gttaaagatg cagtcaaaag attcaggact   2160
aattgcatca agaacacaga gaaagacata tttctcaaga tcagaagtac tattccagta   2220
tggacgattc aaggcttgct tcataaacca aggcaagtaa tagagattgg agtctctaaa   2280
aaggtagttc ctactgaatc taaggccatg catggagtct aagattcaaa tcgaggatct   2340
aacagaactc gccgtgaaga ctggcgaaca gttcatacag agtcttttac gactcaatga   2400
```

```
caagaagaaa atcttcgtca acatggtgga gcacgacact ctggtctact ccaaaaatgt   2460
caaagataca gtctcagaag accaaagggc tattgagact tttcaacaaa ggataatttc   2520
gggaaacctc ctcggattcc attgcccagc tatctgtcac ttcatcgaaa ggacagtaga   2580
aaaggaaggt ggctcctaca aatgccatca ttgcgataaa ggaaaggcta tcattcaaga   2640
tgcctctgcc gacagtggtc ccaaagatgg acccccaccc acgaggagca tcgtggaaaa   2700
agaagacgtt ccaaccacgt cttcaaagca agtggattga tgtgacatct ccactgacgt   2760
aagggatgac gcacaatccc actatccttc gcaagaccct tcctctatat aaggaagttc   2820
atttcatttg gagaggacac gctcgagctc atttctctat tacttcagcc ataacaaaag   2880
aactcttttc tcttcttatt aaaccatgaa aaagcctgaa ctcaccgcga cgtctgtcga   2940
gaagtttctg atcgaaaagt tcgacagcgt ctccgacctg atgcagctct cggagggcga   3000
agaatctcgt gctttcagct tcgatgtagg agggcgtgga tatgtcctgc gggtaaatag   3060
ctgcgccgat ggtttctaca aagatcgtta tgtttatcgg cactttgcat cggccgcgct   3120
cccgattccg gaagtgcttg acattgggga attcagcgag agcctgacct attgcatctc   3180
ccgccgtgca cagggtgtca cgttgcaaga cctgcctgaa accgaactgc ccgctgttct   3240
gcagccggtc gcggaggcca tggatgcgat cgctgcggcc gatcttagcc agacgagcgg   3300
gttcggccca ttcggaccgc aaggaatcgg tcaatacact acatggcgtg atttcatatg   3360
cgcgattgct gatccccatg tgtatcactg gcaaactgtg atggacgaca ccgtcagtgc   3420
gtccgtcgcg caggctctcg atgagctgat gctttgggcc gaggactgcc ccgaagtccg   3480
gcacctcgtg cacgcggatt tcggctccaa caatgtcctg acggacaatg gccgcataac   3540
agcggtcatt gactggagcg aggcgatgtt cggggattcc caatacgagg tcgccaacat   3600
cttcttctgg aggccgtggt tggcttgtat ggagcagcag acgcgctact tcgagcggag   3660
gcatccggag cttgcaggat cgccgcggct ccgggcgtat atgctccgca ttggtcttga   3720
ccaactctat cagagcttgg ttgacggcaa tttcgatgat gcagcttggg cgcagggtcg   3780
atgcgacgca atcgtccgat ccggagccgg gactgtcggg cgtacacaaa tcgcccgcag   3840
aagcgcggcc gtctggaccg atggctgtgt agaagtactc gccgatagtg gaaaccgacg   3900
ccccagcact cgtccgaggg caaaggaata gtgaggtacc taaagaagga gtgcgtcgaa   3960
gcagatcgtt caaacatttg gcaataaagt ttcttaagat tgaatcctgt tgccggtctt   4020
gcgatgatta tcatataatt tctgttgaat tacgttaagc atgtaataat taacatgtaa   4080
tgcatgacgt tatttatgag atgggttttt atgattagag tcccgcaatt atacatttaa   4140
tacgcgatag aaaacaaaat atagcgcgca aactaggata aattatcgcg cgcggtgtca   4200
tctatgttac tagatcgatg tcgaatctga tcaacctgca ttaatgaatc ggccaacgcg   4260
cggggagagg cggtttgcgt attgggcgct cttccgcttc ctcgctcact gactcgctgc   4320
gctcggtcgt tcggctgcgg cgagcggtat cagctcactc aaaggcggta atacggttat   4380
ccacagaatc aggggataac gcaggaaaga acatgtgagc aaaaggccag caaaaggcca   4440
ggaaccgtaa aaaggccgcg ttgctggcgt ttttccatag gctccgcccc cctgacgagc   4500
atcacaaaaa tcgacgctca agtcagaggt ggcgaaaccc gacaggacta taaagatacc   4560
aggcgtttcc ccctggaagc tccctcgtgc gctctcctgt tccgaccctg ccgcttaccg   4620
gatacctgtc cgcctttctc ccttcgggaa gcgtggcgct ttctcaatgc tcacgctgta   4680
ggtatctcag ttcggtgtag gtcgttcgct ccaagctggg ctgtgtgcac gaaccccccg   4740
ttcagcccga ccgctgcgcc ttatccggta actatcgtct tgagtccaac ccggtaagac   4800
```

```
acgacttatc gccactggca gcagccactg gtaacaggat tagcagagcg aggtatgtag   4860
gcggtgctac agagttcttg aagtggtggc ctaactacgg ctacactaga aggacagtat   4920
ttggtatctg cgctctgctg aagccagtta ccttcggaaa aagagttggt agctcttgat   4980
ccggcaaaca aaccaccgct ggtagcggtg gtttttttgt ttgcaagcag cagattacgc   5040
gcagaaaaaa aggatctcaa gaagatcctt tgatcttttc tacggggtct gacgctcagt   5100
ggaacgaaaa ctcacgttaa gggattttgg tcatgacatt aacctataaa aataggcgta   5160
tcacgaggcc ctttcgtctc gcgcgtttcg gtgatgacgg tgaaaacctc tgacacatgc   5220
agctcccgga gacggtcaca gcttgtctgt aagcggatgc cgggagcaga caagcccgtc   5280
agggcgcgtc agcgggtgtt ggcgggtgtc ggggctggct taactatgcg gcatcagagc   5340
agattgtact gagagtgcac catatggaca tattgtcgtt agaacgcggc tacaattaat   5400
acataacctt atgtatcata cacatacgat ttaggtgaca ctatagaacg gcgcgccaag   5460
cttggatcct cgaagagaag ggttaataac acactttttt aacattttta acacaaattt   5520
tagttattta aaaatttatt aaaaaattta aaataagaag aggaactctt taaataaatc   5580
taacttacaa aatttatgat ttttaataag ttttcaccaa taaaaaatgt cataaaaata   5640
tgttaaaaag tatattatca atattctctt tatgataaat aaaaagaaaa aaaaaataaa   5700
agttaagtga aaatgagatt gaagtgactt taggtgtgta taaatatatc aaccccgcca   5760
acaatttatt taatccaaat atattgaagt atattattcc atagccttta tttatttata   5820
tatttattat ataaaagctt tatttgttct aggttgttca tgaaatattt ttttggtttt   5880
atctccgttg taagaaaatc atgtgctttg tgtcgccact cactattgca gctttttcat   5940
gcattggtca gattgacggt tgattgtatt tttgtttttt atggttttgt gttatgactt   6000
aagtcttcat ctctttatct cttcatcagg tttgatggtt acctaatatg gtccatgggt   6060
acatgcatgg ttaaattagg tggccaactt tgttgtgaac gatagaattt tttttatatt   6120
aagtaaacta tttttatatt atgaaataat aataaaaaaa atattttatc attattaaca   6180
aaatcatatt agttaatttg ttaactctat aataaaagaa atactgtaac attcacatta   6240
catggtaaca tctttccacc ctttcatttg tttttgttt gatgactttt tttcttgttt   6300
aaatttattt cccttctttt aaatttggaa tacattatca tcatatataa actaaaatac   6360
taaaaacagg attacacaaa tgataaataa taacacaaat atttataaat ctagctgcaa   6420
tatatttaaa ctagctatat cgatattgta aaataaaact agctgcattg atactgataa   6480
aaaaatatca tgtgctttct ggactgatga tgcagtatac ttttgacatt gcctttattt   6540
tatttttcag aaaagctttc ttagttctgg gttcttcatt atttgtttcc catctccatt   6600
gtgaattgaa tcatttgctt cgtgtcacaa atacaattta gntaggtaca tgcattggtc   6660
agattcacgg tttattatgt catgacttaa gttcatggta gtacattacc tgccacgcat   6720
gcattatatt ggttagattt gataggcaaa tttggttgtc aacaatataa atataaataa   6780
tgtttttata ttacgaaata acagtgatca aaacaaacag ttttatcttt attaacaaga   6840
ttttgttttt gtttgatgac gttttttaat gtttacgctt tccccctct tttgaattta   6900
gaacacttta tcatcataaa atcaaatact aaaaaaatta catatttcat aaataataac   6960
acaaatattt ttaaaaaatc tgaaataata atgaacaata ttacatatta tcacgaaaat   7020
tcattaataa aaatattata taaataaaat gtaatagtag ttatatgtag gaaaaaagta   7080
ctgcacgcat aatatataca aaaagattaa aatgaactat tataaataat aacactaaat   7140
taatggtgaa tcatatcaaa ataatgaaaa agtaaataaa atttgtaatt aacttctata   7200
```

```
tgtattacac acacaaataa taaataatag taaaaaaaat tatgataaat atttaccatc   7260

tcataagata tttaaaataa tgataaaaat atagattatt ttttatgcaa ctagctagcc   7320

aaaaagagaa cacgggtata tataaaaaga gtacctttaa attctactgt acttccttta   7380

ttcctgacgt ttttatatca agtggacata cgtgaagatt ttaattatca gtctaaatat   7440

ttcattagca cttaatactt ttctgtttta ttcctatcct ataagtagtc ccgattctcc   7500

caacattgct tattcacaca actaactaag aaagtcttcc atagcccccc aagcggccgc   7560

atggccaccg tggtgaggat cccaacaatc tcatgcatcc acatccacac gttccgttcc   7620

caatcccctc gcactttcgc cagaatccgg gtcggaccca ggtcgtgggc tcctattcgg   7680

gcatcggcag cgagctcgga gagaggggag atagtattgg agcagaagcc gaagaaggat   7740

gacaagaaga agctgcagaa gggaatcgca gagttttacg acgagtcgtc tggcttatgg   7800

gagaacattt ggggcgacca catgcaccat ggcttttatg actcggattc cactgtttcg   7860

ctttcggatc atcgtgctgc tcagatccga atgatccaag agtctcttcg ctttgcctct   7920

gtttctgagg agcgtagtaa atggcccaag agtatagttg atgttgggtg tggcataggt   7980

ggcagctcta gatacctggc caagaaattt ggagcaacca gtgtaggcat cactctgagt   8040

cctgttcaag ctcaaagagc aaatgctctt gctgctgctc aaggattggc tgataaggtt   8100

tcctttcagg ttgctgacgc tctacagcaa ccattctctg acggccagtt tgatctggtg   8160

tggtccatgg agagtggaga gcatatgcct gacaaagcta agtttgttgg agagttagct   8220

cgggtagcag caccaggtgc cattataata atagtaacat ggtgccacag ggatcttggc   8280

cctgacgaac aatccttaca tccatgggag caagatctct taaagaagat ttgcgatgca   8340

tattacctcc ctgcctggtg ctcaacttct gattatgtta agttgctcca atccctgtca   8400

cttcaggaca tcaagtcaga agattggtct cgctttgttg ctccattttg gccagcagtg   8460

atacgctcag ccttcacatg gaagggtcta tcttcactct tgagcagtgg acaaaaaacg   8520

ataaaaggag ctttggctat gccattgatg atagagggat acaagaaaga tctaattaag   8580

tttgccatca ttacatgtcg aaaacctgaa taagc                              8615
```

<210> SEQ ID NO 42
<211> LENGTH: 9571
<212> TYPE: DNA
<213> ORGANISM: Artificial Sequence
<220> FEATURE:
<223> OTHER INFORMATION: plasmid KS270

<400> SEQUENCE: 42

```
taatatctta aaaataatga ttaatattta acccaaaata attagtatga ttggtaagga     60

agatatccat gttatgtttg gatgtgagtt tgatctagag caaagcttac tagagtcgac    120

cgatccgtcg acggcgcgcc cgatcatccg gatatagttc ctcctttcag caaaaaaccc    180

ctcaagaccc gtttagaggc cccaaggggt tatgctagtt attgctcagc ggtggcagca    240

gccaactcag cttcctttcg ggctttgtta gcagccggat cgatccaagc tgtacctcac    300

tattcctttg ccctcggacg agtgctgggg cgtcggtttc cactatcggc gagtacttct    360

acacagccat cggtccagac ggccgcgctt ctgcgggcga tttgtgtacg cccgacagtc    420

ccggctccgg atcggacgat tgcgtcgcat cgaccctgcg cccaagctgc atcatcgaaa    480

ttgccgtcaa ccaagctctg atagagttgg tcaagaccaa tgcggagcat atacgcccgg    540

agccgcggcg atcctgcaag ctccggatgc ctccgctcga agtagcgcgt ctgctgctcc    600

atacaagcca accacggcct ccagaagaag atgttggcga cctcgtattg ggaatccccg    660
```

```
aacatcgcct cgctccagtc aatgaccgct gttatgcggc cattgtccgt caggacattg    720
ttggagccga aatccgcgtg cacgaggtgc cggacttcgg ggcagtcctc ggcccaaagc    780
atcagctcat cgagagcctg cgcgacggac gcactgacgg tgtcgtccat cacagtttgc    840
cagtgataca catggggatc agcaatcgcg catatgaaat cacgccatgt agtgtattga    900
ccgattcctt gcggtccgaa tgggccgaac ccgctcgtct ggctaagatc ggccgcagcg    960
atcgcatcca tagcctccgc gaccggctgc agaacagcgg gcagttcggt ttcaggcagg   1020
tcttgcaacg tgacaccctg tgcacggcgg gagatgcaat aggtcaggct ctcgctgaat   1080
tccccaatgt caagcacttc cggaatcggg agcgcggccg atgcaaagtg ccgataaaca   1140
taacgatctt tgtagaaacc atcggcgcag ctatttaccc gcaggacata tccacgccct   1200
cctacatcga agctgaaagc acgagattct tcgccctccg agagctgcat caggtcggag   1260
acgctgtcga acttttcgat cagaaacttc tcgacagacg tcgcggtgag ttcaggcttt   1320
tccatgggta tatctccttc ttaaagttaa acaaaattat ttctagaggg aaaccgttgt   1380
ggtctcccta tagtgagtcg tattaatttc gcgggatcga gatctgatca acctgcatta   1440
atgaatcggc caacgcgcgg ggagaggcgg tttgcgtatt gggcgctctt ccgcttcctc   1500
gctcactgac tcgctgcgct cggtcgttcg gctgcggcga gcggtatcag ctcactcaaa   1560
ggcggtaata cggttatcca cagaatcagg ggataacgca ggaaagaaca tgtgagcaaa   1620
aggccagcaa aaggccagga accgtaaaaa ggccgcgttg ctggcgtttt tccataggct   1680
ccgcccccct gacgagcatc acaaaaatcg acgctcaagt cagaggtggc gaaacccgac   1740
aggactataa agataccagg cgtttccccc tggaagctcc ctcgtgcgct ctcctgttcc   1800
gaccctgccg cttaccggat acctgtccgc ctttctccct tcgggaagcg tggcgctttc   1860
tcaatgctca cgctgtaggt atctcagttc ggtgtaggtc gttcgctcca agctgggctg   1920
tgtgcacgaa ccccccgttc agcccgaccg ctgcgcctta tccggtaact atcgtcttga   1980
gtccaacccg gtaagacacg acttatcgcc actggcagca gccactggta acaggattag   2040
cagagcgagg tatgtaggcg gtgctacaga gttcttgaag tggtggccta actacggcta   2100
cactagaagg acagtatttg gtatctgcgc tctgctgaag ccagttacct tcggaaaaag   2160
agttggtagc tcttgatccg gcaaacaaac caccgctggt agcggtggtt tttttgtttg   2220
caagcagcag attacgcgca gaaaaaaagg atctcaagaa gatcctttga tcttttctac   2280
ggggtctgac gctcagtgga acgaaaactc acgttaaggg attttggtca tgacattaac   2340
ctataaaaat aggcgtatca cgaggccctt tcgtctcgcg cgtttcggtg atgacggtga   2400
aaacctctga cacatgcagc tcccggagac ggtcacagct tgtctgtaag cggatgccgg   2460
gagcagacaa gcccgtcagg gcgcgtcagc gggtgttggc gggtgtcggg gctggcttaa   2520
ctatgcggca tcagagcaga ttgtactgag agtgcaccat atggacatat tgtcgttaga   2580
acgcggctac aattaataca taaccttatg tatcatacac atacgattta ggtgacacta   2640
tagaacggcg cgccaagctt ggatcctaga actagaaacg tgatgccact tgttattgaa   2700
gtcgattaca gcatctattc tgttttacta tttataactt tgccatttct gacttttgaa   2760
aactatctct ggatttcggt atcgctttgt gaagatcgag caaaagagac gttttgtgga   2820
cgcaatggtc caaatccgtt ctacatgaac aaattggtca caatttccac taaaagtaaa   2880
taaatggcaa gttaaaaaag gaatatgcat tttactgatt gcctaggtga gctccaagag   2940
aagttgaatc tacacgtcta ccaaccgcta aaaaaagaaa aacattgata tgtaacctga   3000
ttccattagc ttttgacttc ttcaacagat tctctactta gatttctaac agaaatatta   3060
```

```
ttactagcac atcattttca gtctcactac agcaaaaaat ccaacggcac aatacagaca   3120
acaggagata tcagactaca gagatagata gatgctactg catgtagtaa gttaaataaa   3180
aggaaaataa aatgtcttgc taccaaaact actacagact atgatgctca ccacaggcca   3240
aatcctgcaa ctaggacagc attatcttat atatattgta caaaacaagc atcaaggaac   3300
atttggtcta ggcaatcagt acctcgttct accatcaccc tcagttatca catccttgaa   3360
ggatccatta ctgggaatca tcggcaacac atgctcctga tggggcacaa tgacatcaag   3420
aaggtagggg ccaggggtgt ccaacattct ctgaattgcc gctctaagct cttccttctt   3480
cgtcactcgc gctgccggta tcccacaagc atcagcaaac ttgagcatgt ttgggaatat   3540
ctcgctctcg ctagacggat ctccaagata ggtgtgagct ctattggact tgtagaacct   3600
atcctccaac tgaaccacca tacccaaatg ctgattgttc aacaacaata tcttaactgg   3660
gagattctcc actcttatag tggccaactc ctgaacattc atgatgaaac taccatcccc   3720
atcaatgtca accacaacag ccccagggtt agcaacagca gcaccaatag ccgcaggcaa   3780
tccaaaaccc atggctccaa gaccccctga ggtcaaccac tgcctcggtc tcttgtactt   3840
gtaaaactgc gcagcccaca tttgatgctg cccaacccca gtactaacaa tagcatctcc   3900
attagtcaac tcatcaagaa cctcgatagc atgctgcgga gaaatcgcgt cctggaatgt   3960
cttgtaaccc aatggaaact tgtgtttctg cacattaatc tcttctctcc aacctccaag   4020
atcaaactta ccctccactc ctttctcctc caaaatcata ttaattccct tcaaggccaa   4080
cttcaaatcc gcgcaaaccg acacgtgcgc ctgcttgttc ttcccaatct cggcagaatc   4140
aatatcaatg tgaacaatct tagccctact agcaaaagcc tcaagcttcc cagtaacacg   4200
gtcatcaaac cttaccccaa aggcaagcaa caaatcacta ttgtcaacag catagttagc   4260
ataaacagta ccatgcatac ccagcatctg aagggaatat tcatcaccaa taggaaaagt   4320
tccaagaccc attaaagtgc tagcaacggg aataccagtg agttcaacaa agcgcctcaa   4380
ttcagcactg gaattcaaac tgccaccgcc gacgtagaga acgggctttt gggcctccat   4440
gatgagtctg acaatgtgtt ccaattgggc ctcggcgggg ggcctgggca gcctggcgag   4500
gtaaccgggg aggttaacgg gctcgtccca attaggcacg gcgagttgct gctgaacgtc   4560
tttgggaatg tcgatgagga ccggaccggg gcggccggag gtggcgacga agaaagcctc   4620
ggcgacgacg cgggggatgt cgtcgacgtc gaggatgagg tagttgtgct tcgtgatgga   4680
tctgctcacc tccacgatcg gggtttcttg gaaggcgtcg gtgccgatca tccggcgggc   4740
gacctggccg gtgatggcga cgactgggac gctgtccatt aaagcgtcgg cgaggccgct   4800
cacgaggttg gtggcgccgg ggccggaggt ggcaatgcag acgccgggga ggccggagga   4860
acgcgcgtag ccttcggcgg cgaagacgcc gccctgctcg tggcgcggga gcacgttgcg   4920
gatggcggcg gagcgcgtga gcgcctggtg gatctccatc gacgcaccgc cggggtacgc   4980
gaacaccgtc gtcacgccct gcctctccag cgcctccaca aggatgtccg cgcccttgcg   5040
aggttcgccg gaggcgaacc gtgacacgaa gggctccgtg gtcggcgctt ccttggtgaa   5100
gggcgccgcc gtgggggggtt tggagatgga acatttgatt ttgagagcgt ggttgggttt   5160
ggtgagggtt tgatgagaga gagggagggt ggatctagta atgcgtttgg ggaaggtggg   5220
gtgtgaagag gaagaagaga atcgggtggt tctggaagcg gtggccgcca ttgtgttgtg   5280
tggcatggtt atacttcaaa aactgcacaa caagcctaga gttagtacct aaacagtaaa   5340
tttacaacag agagcaaaga cacatgcaaa aatttcagcc ataaaaaaag ttataataga   5400
atttaaagca aaagtttcat tttttaaaca tatatacaaa caaactggat ttgaaggaag   5460
```

```
ggattaattc ccctgctcaa agtttgaatt cctattgtga cctatactcg aataaaattg   5520
aagcctaagg aatgtatgag aaacaagaaa acaaaacaaa actacagaca aacaagtaca   5580
attacaaaat tcgctaaaat tctgtaatca ccaaacccca tctcagtcag cacaaggccc   5640
aaggtttatt ttgaaataaa aaaaaagtga ttttatttct cataagctaa aagaaagaaa   5700
ggcaattatg aaatgatttc gactagatct gaaagtccaa cgcgtattcc gcagatatta   5760
aagaaagagt agagtttcac atggatccta gatggaccca gttgaggaaa aagcaaggca   5820
aagcaaacca gaagtgcaag atccgaaatt gaaccacgga atctaggatt tggtagaggg   5880
agaagaaaag taccttgaga ggtagaagag aagagaagag cagagagata tatgaacgag   5940
tgtgtcttgg tctcaactct gaagcgatac gagtttagag gggagcattg agttccaatt   6000
tatagggaaa ccgggtggca ggggtgagtt aatgacggaa aagcccctaa gtaacgagat   6060
tggattgtgg gttagattca accgtttgca tccgcggctt agattgggga agtcagagtg   6120
aatctcaacc gttgactgag ttgaaaattg aatgtagcaa ccaattgagc caaccccagc   6180
ctttgccctt tgattttgat ttgtttgttg catacttttt atttgtcttc tggttctgac   6240
tctctttctc tcgtttcaat gccaggttgc ctactcccac accactcaca agaagattct   6300
actgttagta ttaaatattt tttaatgtat taaatgatga atgcttttgt aaacagaaca   6360
agactatgtc taataagtgt cttgcaacat tttttaagaa attaaaaaaa atatatttat   6420
tatcaaaatc aaatgtatga aaaatcatga ataatataat tttatacatt tttttaaaaa   6480
atcttttaat ttcttacgcg ccaagctttt gatccatgcc cttcatttgc cgcttattaa   6540
ttaatttggt aacagtccgt actaatcagt tacttatcct tcccccatca taattaatct   6600
tggtagtctc gaatgccaca acactgacta gtctcttgga tcataagaaa aagccaagga   6660
acaaaagaag acaaaacaca atgagagtat cctttgcata gcaatgtcta agttcataaa   6720
attcaaacaa aaacgcaatc acacacagtg gacatcactt atccactagc tgatcaggat   6780
cgccgcgtca agaaaaaaaa actggacccc aaaagccatg cacaacaaca cgtactcaca   6840
aaggtgtcaa tcgagcagcc caaaacattc accaactcaa cccatcatga gccctcacat   6900
ttgttgtttc taacccaacc tcaaactcgt attctcttcc gccacctcat ttttgtttat   6960
ttcaacaccc gtcaaactgc atgccacccc gtggccaaat gtccatgcat gttaacaaga   7020
cctatgacta taaatagctg caatctcggc ccaggttttc atcatcaaga accagttcaa   7080
tatcctagta caccgtatta aagaatttaa gatatactgc ggccgcagga tgcaagccgt   7140
cacggcggcg gccgcggcgg ggcagctgct aacagatacg aggagagggc ccagatgtag   7200
ggctcggctg ggaacgacga gattatcctg gacaggtcga tttgcagtgg aagcttttgc   7260
aggccagtgc caaagtgcta ctactgtaat gcataaattc agtgccattt ctcaagctgc   7320
taggcctaga agaaacacaa agagacagtg cagcgatgat tatccagccc tccaagctgg   7380
atgcagcgag gttaattggg atcaaaacgg ttccaacgcc aatcggcttg aggaaatcag   7440
gggagatgtt ttgaagaaat tgcgctcttt ctatgaattt tgcaggccac acacaatttt   7500
tggcactata ataggtataa cttcagtgtc tctcctgcca atgaagagca tagatgattt   7560
tactgtcacg gtactacgag gatatctcga ggctttgact gctgctttat gtatgaacat   7620
ttatgtggtc gggctgaatc agctatatga cattcagatt gacaagatca acaagccagg   7680
tcttccattg gcatctgggg aattttcagt agcaactgga gttttcttag tactcgcatt   7740
cctgatcatg agctttagca taggaatacg ttccggatcg gcgccactga tgtgtgcttt   7800
aattgtcagc ttccttcttg gaagtgcgta ctccattgag gctccgttcc tccggtggaa   7860
```

```
acggcacgcg ctcctcgctg catcatgtat cctatttgtg agggctatct tggtccagtt   7920
ggctttcttt gcacatatgc agcaacatgt tctgaaaagg ccattggcag caaccaaatc   7980
gctggtgttt gcaacattgt ttatgtgttg cttctctgcc gtcatagcac tattcaagga   8040
tattccagat gttgatggag atcgagactt tggtatccaa tccttgagtg tgagattggg   8100
gcctcaaaga gtgtatcagc tctgcataag catattgttg acagcctatg gcgctgccac   8160
tctagtagga gcttcatcca caaacctatt tcaaaagatc atcactgtgt ctggtcatgg   8220
cctgcttgct ttgacacttt ggcagagagc gcagcacttt gaggttgaaa accaagcgcg   8280
tgtcacatca ttttacatgt tcatttggaa gctattctat gcagagtatt tccttatacc   8340
atttgtgcag tgaaatttgt acaagggcca gcagatgtga agcggccgca agtatgaact   8400
aaaatgcatg taggtgtaag agctcatgga gagcatggaa tattgtatcc gaccatgtaa   8460
cagtataata actgagctcc atctcacttc ttctatgaat aaacaaagga tgttatgata   8520
tattaacact ctatctatgc accttattgt tctatgataa atttcctctt attattataa   8580
atcatctgaa tcgtgacggc ttatggaatg cttcaaatag tacaaaaaca aatgtgtact   8640
ataagacttt ctaaacaatt ctaaccttag cattgtgaac gagacataag tgttaagaag   8700
acataacaat tataatggaa gaagtttgtc tccatttata tattatatat tacccactta   8760
tgtattatat taggatgtta aggagacata acaattataa agagagaagt ttgtatccat   8820
ttatatatta tatactaccc atttatatat tatacttatc cacttattta atgtctttat   8880
aaggtttgat ccatgatatt tctaatattt tagttgatat gtatatgaaa gggtactatt   8940
tgaactctct tactctgtat aaaggttgga tcatccttaa agtgggtcta tttaatttta   9000
ttgcttctta cagataaaaa aaaaattatg agttggtttg ataaaatatt gaaggattta   9060
aaataataat aaataacata taatatatgt atataaattt attataatat aacatttatc   9120
tataaaaaag taaatattgt cataaatcta tacaatcgtt tagccttgct ggacgaatct   9180
caattattta aacgagagta aacatatttg actttttggt tatttaacaa attattattt   9240
aacactatat gaaatttttt tttttatcag caaagaataa aattaaatta agaaggacaa   9300
tggtgtccca atccttatac aaccaacttc cacaagaaag tcaagtcaga gacaacaaaa   9360
aaacaagcaa aggaaatttt ttaatttgag ttgtcttgtt tgctgcataa tttatgcagt   9420
aaaacactac acataaccct tttagcagta gagcaatggt tgaccgtgtg cttagcttct   9480
tttattttat ttttttatca gcaaagaata aataaaataa aatgagacac ttcagggatg   9540
tttcaacaag cttggatccg tcgacggcgc g                                  9571
```

<210> SEQ ID NO 43
<211> LENGTH: 9522
<212> TYPE: DNA
<213> ORGANISM: Artificial Sequence
<220> FEATURE:
<223> OTHER INFORMATION: plasmid KS319
<220> FEATURE:
<221> NAME/KEY: misc_feature
<222> LOCATION: (1257)..(1257)
<223> OTHER INFORMATION: n is a, c, g, or t

<400> SEQUENCE: 43

```
aattacaacg gtatatatcc tgccgtcgac ggtatcgata agcttgatat cgaattcctg     60
cagccccgcg ccaagcttgg atcctcgaag agaagggtta ataacacact tttttaacat    120
ttttaacaca aattttagtt atttaaaaat ttattaaaaa atttaaaata agaagaggaa    180
ctctttaaat aaatctaact tacaaaattt atgattttta ataagttttc accaataaaa    240
```

```
aatgtcataa aaatatgtta aaaagtatat tatcaatatt ctctttatga taaataaaaa    300
gaaaaaaaaa ataaaagtta agtgaaaatg agattgaagt gactttaggt gtgtataaat    360
atatcaaccc cgccaacaat ttatttaatc caaatatatt gaagtatatt attccatagc    420
ctttatttat ttatatattt attatataaa agctttattt gttctaggtt gttcatgaaa    480
tatttttttg gttttatctc cgttgtaaga aaatcatgtg ctttgtgtcg ccactcacta    540
ttgcagcttt ttcatgcatt ggtcagattg acggttgatt gtatttttgt tttttatggt    600
tttgtgttat gacttaagtc ttcatctctt tatctcttca tcaggtttga tggttaccta    660
atatggtcca tgggtacatg catggttaaa ttaggtggcc aactttgttg tgaacgatag    720
aatttttttt atattaagta aactattttt atattatgaa ataataataa aaaaaatatt    780
ttatcattat taacaaaatc atattagtta atttgttaac tctataataa aagaaatact    840
gtaacattca cattacatgg taacatcttt ccaccctttc atttgttttt tgtttgatga    900
cttttttttct tgtttaaatt tatttccctt cttttaaatt tggaatacat tatcatcata    960
tataaactaa aatactaaaa acaggattac acaaatgata aataataaca caaatattta   1020
taaatctagc tgcaatatat ttaaactagc tatatcgata ttgtaaaata aaactagctg   1080
cattgatact gataaaaaaa tatcatgtgc tttctggact gatgatgcag tatacttttg   1140
acattgcctt tattttattt ttcagaaaag ctttcttagt tctgggttct tcattatttg   1200
tttcccatct ccattgtgaa ttgaatcatt tgcttcgtgt cacaaataca atttagntag   1260
gtacatgcat tggtcagatt cacggtttat tatgtcatga cttaagttca tggtagtaca   1320
ttacctgcca cgcatgcatt atattggtta gatttgatag gcaaatttgg ttgtcaacaa   1380
tataaatata aataatgttt ttatattacg aaataacagt gatcaaaaca aacagtttta   1440
tctttattaa caagatttttg tttttgtttg atgacgtttt ttaatgttta cgctttcccc   1500
cttcttttga atttagaaca ctttatcatc ataaaatcaa atactaaaaa aattacatat   1560
ttcataaata ataacacaaa tatttttaaa aaatctgaaa taataatgaa caatattaca   1620
tattatcacg aaaattcatt aataaaaata ttatataaat aaaatgtaat agtagttata   1680
tgtaggaaaa aagtactgca cgcataatat atacaaaaag attaaaatga actattataa   1740
ataataacac taaattaatg gtgaatcata tcaaaataat gaaaaagtaa ataaaatttg   1800
taattaactt ctatatgtat tacacacaca aataataaat aatagtaaaa aaaattatga   1860
taaatattta ccatctcata agatatttaa aataatgata aaaatataga ttattttttta   1920
tgcaactagc tagccaaaaa gagaacacgg gtatatataa aaagagtacc tttaaattct   1980
actgtacttc ctttattcct gacgttttta tatcaagtgg acatacgtga agattttaat   2040
tatcagtcta aatatttcat tagcacttaa tacttttctg ttttattcct atcctataag   2100
tagtcccgat tctcccaaca ttgcttattc acacaactaa ctaagaaagt cttccatagc   2160
cccccaagcg gccgcatggc caccgtggtg aggatcccaa caatctcatg catccacatc   2220
cacacgttcc gttcccaatc ccctcgcact ttcgccagaa tccgggtcgg acccaggtcg   2280
tgggctccta ttcgggcatc ggcagcgagc tcggagagag gggagatagt attggagcag   2340
aagccgaaga aggatgacaa gaagaagctg cagaagggaa tcgcagagtt ttacgacgag   2400
tcgtctggct tatgggagaa catttggggc gaccacatgc accatggctt ttatgactcg   2460
gattccactg tttcgctttc ggatcatcgt gctgctcaga tccgaatgat ccaagagtct   2520
cttcgctttg cctctgtttc tgaggagcgt agtaaatggc ccaagagtat agttgatgtt   2580
gggtgtggca taggtggcag ctctagatac ctggccaaga aatttggagc aaccagtgta   2640
```

```
ggcatcactc tgagtcctgt tcaagctcaa agagcaaatg ctcttgctgc tgctcaagga   2700
ttggctgata aggtttcctt tcaggttgct gacgctctac agcaaccatt ctctgacggc   2760
cagtttgatc tggtgtggtc catggagagt ggagagcata tgcctgacaa agctaagttt   2820
gttggagagt tagctcgggt agcagcacca ggtgccatta taataatagt aacatggtgc   2880
cacagggatc ttggccctga cgaacaatcc ttacatccat gggagcaaga tctcttaaag   2940
aagatttgcg atgcatatta cctccctgcc tggtgctcaa cttctgatta tgttaagttg   3000
ctccaatccc tgtcacttca ggacatcaag tcagaagatt ggtctcgctt tgttgctcca   3060
ttttggccag cagtgatacg ctcagccttc acatggaagg gtctatcttc actcttgagc   3120
agtggacaaa aaacgataaa aggagctttg gctatgccat tgatgataga gggatacaag   3180
aaagatctaa ttaagtttgc catcattaca tgtcgaaaac ctgaataagc ggccgcgaca   3240
caagtgtgag agtactaaat aaatgctttg gttgtacgaa atcattacac taaataaaat   3300
aatcaaagct tatatatgcc ttccgctaag gccgaatgca aagaaattgg ttctttctcg   3360
ttatcttttg ccacttttac tagtacgatc caagcttgtt gaaacatccc tgaagtgtct   3420
cattttattt tatttattct ttgctgataa aaaaataaaa taaaagaagc taagcacacg   3480
gtcaaccatt gctctactgc taaaagggtt atgtgtagtg ttttactgca taaattatgc   3540
agcaaacaag acaactcaaa ttaaaaaatt tcctttgctt gttttttttgt tgtctctgac   3600
ttgactttct tgtggaagtt ggttgtataa ggattgggac accattgtcc ttcttaattt   3660
aattttattc tttgctgata aaaaaaaaaa tttcatatag tgttaaataa taatttgtta   3720
aataaccaaa aagtcaaata tgtttactct cgtttaaata attgagattc gtccagcaag   3780
gctaaacgat tgtatagatt tatgacaata tttacttttt tatagataaa tgttatatta   3840
taataaattt atatacatat attatatgtt atttattatt attttaaatc cttcaatatt   3900
ttatcaaacc aactcataat ttttttttta tctgtaagaa gcaataaaat taaatagacc   3960
cactttaagg atgatccaac ctttatacag agtaagagag ttcaaatagt accctttcat   4020
atacatatca actaaaatat tagaaatatc atggatcaaa ccttataaag acattaaata   4080
agtggataag tataatatat aaatgggtag tatataatat ataaatggat acaaacttct   4140
ctctttataa ttgttatgtc tccttaacat cctaatataa tacataagtg ggtaatatat   4200
aatatataaa tggagacaaa cttcttccat tataattgtt atgtcttctt aacacttatg   4260
tctcgttcac aatgctaagg ttagaattgt ttagaaagtc ttatagtaca catttgtttt   4320
tgtactattt gaagcattcc ataagccgtc acgattcaga tgatttataa taataagagg   4380
aaatttatca tagaacaata aggtgcatag atagagtgtt aatatatcat aacatccttt   4440
gtttattcat agaagaagtg agatggagct cagttattat actgttacat ggtcggatac   4500
aatattccat gctctccatg agctcttaca cctacatgca ttttagttca tacttgcggc   4560
cgcttcacat ctgctggccc ttgtacaaat ttcactgcac aaatggtata aggaaatact   4620
ctgcatagaa tagcttccaa atgaacatgt aaaatgatgt gacacgcgct tggttttcaa   4680
cctcaaagtg ctgcgctctc tgccaaagtg tcaaagcaag caggccatga ccagacacag   4740
tgatgatctt ttgaaatagg tttgtggatg aagctcctac tagagtggca gcgccatagg   4800
ctgtcaacaa tatgcttatg cagagctgat acactctttg aggccccaat ctcacactca   4860
aggattggat accaaagtct cgatctccat caacatctgg aatatccttg aatagtgcta   4920
tgacggcaga gaagcaacac ataaacaatg ttgcaaacac cagcgatttg gttgctgcca   4980
atggcctttt cagaacatgt tgctgcatat gtgcaaagaa agccaactgg accaagatag   5040
```

```
ccctcacaaa taggatacat gatgcagcga ggagcgcgtg ccgtttccac cggaggaacg   5100
gagcctcaat ggagtacgca cttccaagaa ggaagctgac aattaaagca cacatcagtg   5160
gcgccgatcc ggaacgtatt cctatgctaa agctcatgat caggaatgcg agtactaaga   5220
aaactccagt tgctactgaa aattccccag atgccaatgg aagacctggc ttgttgatct   5280
tgtcaatctg aatgtcatat agctgattca gcccgaccac ataaatgttc atacataaag   5340
cagcagtcaa agcctcgaga tatcctcgta gtaccgtgac agtaaaatca tctatgctct   5400
tcattggcag gagagacact gaagttatac ctattatagt gccaaaaatt gtgtgtggcc   5460
tgcaaaattc atagaaagag cgcaatttct tcaaaacatc tcccctgatt tcctcaagcc   5520
gattggcgtt ggaaccgttt tgatcccaat taacctcgct gcatccagct tggagggctg   5580
gataatcatc gctgcactgt ctctttgtgt ttcttctagg cctagcagct tgagaaatgg   5640
cactgaattt atgcattaca gtagtagcac tttggcactg gcctgcaaaa gcttccactg   5700
caaatcgacc tgtccaggat aatctcgtcg ttcccagccg agccctacat ctgggccctc   5760
tcctcgtatc tgttagcagc tgccccgccg cggccgccgc cgtgacggct tgcatcctgc   5820
ggccgcagta tatcttaaat tctttaatac ggtgtactag gatattgaac tggttcttga   5880
tgatgaaaac ctgggccgag attgcagcta tttatagtca taggtcttgt taacatgcat   5940
ggacatttgg ccacggggtg gcatgcagtt tgacgggtgt tgaaataaac aaaaatgagg   6000
tggcggaaga gaatacgagt ttgaggttgg gttagaaaca acaaatgtga gggctcatga   6060
tgggttgagt tggtgaatgt tttgggctgc tcgattgaca cctttgtgag tacgtgttgt   6120
tgtgcatggc ttttggggtc cagttttttt ttcttgacgc ggcgatcctg atcagctagt   6180
ggataagtga tgtccactgt gtgtgattgc gtttttgttt gaattttatg aacttagaca   6240
ttgctatgca aaggatactc tcattgtgtt ttgtcttctt ttgttccttg gctttttctt   6300
atgatccaag agactagtca gtgttgtggc attcgagact accaagatta attatgatgg   6360
gggaaggata agtaactgat tagtacggac tgttaccaaa ttagtattaa ttactactta   6420
atcatctttg tttacggctc attatatccg tcgactctag aggatccccg ggtaccgagc   6480
tcgaattcac tggccgtcgt tttacaacgt cgtgactggg aaaaccctgg cgttacccaa   6540
cttaatcgcc ttgcagcaca tccccctttc gccagctggc gtaatagcga agaggcccgc   6600
accgatcgcc cttcccaaca gttgcgcagc ctgaatggcg aatggatcga tccgtcgatc   6660
gaccaaagcg gccatcgtgc ctccccactc ctgcagttcg gggcatgga tgcgcggata   6720
gccgctgctg gtttcctgga tgccgacgga tttgcactgc cggtagaact ccgcgaggtc   6780
gtccagcctc aggcagcagc tgaaccaact cgcgagggga tcgagcccct gctgagcctc   6840
gacatgttgt cgcaaaattc gccctggacc cgcccaacga tttgtcgtca ctgtcaaggt   6900
ttgacctgca cttcatttgg ggcccacata caccaaaaaa atgctgcata attctcgggg   6960
cagcaagtcg gttacccggc cgccgtgctg gaccgggttg aatggtgccc gtaactttcg   7020
gtagagcgga cggccaatac tcaacttcaa ggaatctcac ccatgcgcgc cggcggggaa   7080
ccggagttcc cttcagtgaa cgttattagt tcgccgctcg gtgtgtcgta gatactagcc   7140
cctggggcct tttgaaattt gaataagatt tatgtaatca gtcttttagg tttgaccggt   7200
tctgccgctt tttttaaaat tggatttgta ataataaaac gcaattgttt gttattgtgg   7260
cgctctatca tagatgtcgc tataaaccta ttcagcacaa tatattgttt tcattttaat   7320
attgtacata taagtagtag ggtacaatca gtaaattgaa cggagaatat tattcataaa   7380
aatacgatag taacgggtga tatattcatt agaatgaacc gaaaccggcg gtaaggatct   7440
```

```
gagctacaca tgctcaggtt ttttacaacg tgcacaacag aattgaaagc aaatatcatg   7500

cgatcatagg cgtctcgcat atctcattaa agcagggggt gggcgaagaa ctccagcatg   7560

agatccccgc gctggaggat catccagccg gcgtcccgga aaacgattcc gaagcccaac   7620

ctttcataga aggcggcggt ggaatcgaaa tctcgtgatg gcaggttggg cgtcgcttgg   7680

tcggtcattt cgaaccccag agtcccgctc agaagaactc gtcaagaagg cgatagaagg   7740

cgatgcgctg cgaatcggga gcggcgatac cgtaaagcac gaggaagcgg tcagcccatt   7800

cgccgccaag ctcttcagca atatcacggg tagccaacgc tatgtcctga tagcggtccg   7860

ccacacccag ccggccacag tcgatgaatc cagaaaagcg gccattttcc accatgatat   7920

tcggcaagca ggcatcgcca tgggtcacga cgagatcctc gccgtcgggc atgcgcgcct   7980

tgagcctggc gaacagttcg gctggcgcga gcccctgatg ctcttcgtcc agatcatcct   8040

gatcgacaag accggcttcc atccgagtac gtgctcgctc gatgcgatgt ttcgcttggt   8100

ggtcgaatgg gcaggtagcc ggatcaagcg tatgcagccg ccgcattgca tcagccatga   8160

tggatacttt ctcggcagga gcaaggtgag atgacaggag atcctgcccc ggcacttcgc   8220

ccaatagcag ccagtccctt cccgcttcag tgacaacgtc gagcacagct gcgcaaggaa   8280

cgcccgtcgt ggccagccac gatagccgcg ctgcctcgtc ctgcagttca ttcagggcac   8340

cggacaggtc ggtcttgaca aaaagaaccg ggcgcccctg cgctgacagc cggaacacgg   8400

cggcatcaga gcagccgatt gtctgttgtg cccagtcata gccgaatagc ctctccaccc   8460

aagcggccgg agaacctgcg tgcaatccat cttgttcaat catgcgaaac gatccccgca   8520

agcttggaga ctggtgattt cagcgtgtcc tctccaaatg aaatgaactt ccttatatag   8580

aggaagggtc ttgcgaagga tagtgggatt gtgcgtcatc ccttacgtca gtggagatat   8640

cacatcaatc cacttgcttt gaagacgtgg ttggaacgtc ttcttttttcc acgatgctcc   8700

tcgtgggtgg gggtccatct ttgggaccac tgtcggcaga ggcatcttca acgatggcct   8760

ttcctttatc gcaatgatgg catttgtagg agccaccttc cttttccact atcttcacaa   8820

taaagtgaca gatagctggg caatggaatc cgaggaggtt tccggatatt accctttgtt   8880

gaaaagtctc aattgccctt tggtcttctg agactgtatc tttgatattt ttggagtaga   8940

caagcgtgtc gtgctccacc atgttgacga agattttctt cttgtcattg agtcgtaaga   9000

gactctgtat gaactgttcg ccagtcttta cggcgagttc tgttaggtcc tctatttgaa   9060

tctttgactc catggccttt gattcagtgg gaactacctt tttagagact ccaatctcta   9120

ttacttgcct tggtttgtga agcaagcctt gaatcgtcca tactggaata gtacttctga   9180

tcttgagaaa tatatctttc tctgtgttct tgatgcagtt agtcctgaat cttttgactg   9240

catctttaac cttcttggga aggtatttga tctcctggag attattgctc gggtagatcg   9300

tcttgatgag acctgctgcg taagcctctc taaccatctg tgggttagca ttctttctga   9360

aattgaaaag gctaatcttc tcattatcag tggtgaacat ggtatcgtca ccttctccgt   9420

cgaacttcct gactagatcg tagagataga ggaagtcgtc cattgtgatc tctggggcaa   9480

aggagatctg aattatcatt tacaattgaa tatatcctgc ca                      9522
```

```
<210> SEQ ID NO 44
<211> LENGTH: 35
<212> TYPE: DNA
<213> ORGANISM: Artificial Sequence
<220> FEATURE:
<223> OTHER INFORMATION: primer

<400> SEQUENCE: 44
```

```
agcgcggccg catggccacc gtggtgagga tccca                              35


<210> SEQ ID NO 45
<211> LENGTH: 39
<212> TYPE: DNA
<213> ORGANISM: Artificial Sequence
<220> FEATURE:
<223> OTHER INFORMATION: primer

<400> SEQUENCE: 45

agcgcggccg cttattcagg ttttcgacat gtaatgatg                          39


<210> SEQ ID NO 46
<211> LENGTH: 1224
<212> TYPE: DNA
<213> ORGANISM: Artificial
<220> FEATURE:
<223> OTHER INFORMATION: open reading frame from barley HGGT cDNA (SEQ
      ID NO:1)

<400> SEQUENCE: 46

atgcaagccg tcacggcggc ggccgcggcg gggcagctgc taacagatac gaggagaggg     60

cccagatgta gggctcggct gggaacgacg agattatcct ggacaggtcg atttgcagtg    120

gaagcttttg caggccagtg ccaaagtgct actactgtaa tgcataaatt cagtgccatt    180

tctcaagctg ctaggcctag aagaaacaca aagagacagt gcagcgatga ttatccagcc    240

ctccaagctg gatgcagcga ggttaattgg gatcaaaacg gttccaacgc caatcggctt    300

gaggaaatca ggggagatgt tttgaagaaa ttgcgctctt tctatgaatt ttgcaggcca    360

cacacaattt ttggcactat aataggtata acttcagtgt ctctcctgcc aatgaagagc    420

atagatgatt ttactgtcac ggtactacga ggatatctcg aggctttgac tgctgcttta    480

tgtatgaaca tttatgtggt cgggctgaat cagctatatg acattcagat tgacaagatc    540

aacaagccag gtcttccatt ggcatctggg gaattttcag tagcaactgg agttttctta    600

gtactcgcat tcctgatcat gagctttagc ataggaatac gttccggatc ggcgccactg    660

atgtgtgctt taattgtcag cttccttctt ggaagtgcgt actccattga ggctccgttc    720

ctccggtgga aacggcacgc gctcctcgct gcatcatgta tcctatttgt gagggctatc    780

ttggtccagt tggctttctt tgcacatatg cagcaacatg ttctgaaaag gccattggca    840

gcaaccaaat cgctggtgtt tgcaacattg tttatgtgtt gcttctctgc cgtcatagca    900

ctattcaagg atattccaga tgttgatgga gatcgagact ttggtatcca atccttgagt    960

gtgagattgg ggcctcaaag agtgtatcag ctctgcataa gcatattgtt gacagcctat   1020

ggcgctgcca ctctagtagg agcttcatcc acaaacctat ttcaaaagat catcactgtg   1080

tctggtcatg gcctgcttgc tttgacactt tggcagagag cgcagcactt tgaggttgaa   1140

aaccaagcgc gtgtcacatc attttacatg ttcatttgga agctattcta tgcagagtat   1200

ttccttatac catttgtgca gtga                                          1224


<210> SEQ ID NO 47
<211> LENGTH: 38
<212> TYPE: DNA
<213> ORGANISM: Artificial Sequence
<220> FEATURE:
<223> OTHER INFORMATION: primer

<400> SEQUENCE: 47

ttgcggccgc aggatgcaag ccgtcacggc ggcagccg                           38
```

<210> SEQ ID NO 48
<211> LENGTH: 33
<212> TYPE: DNA
<213> ORGANISM: Artificial Sequence
<220> FEATURE:
<223> OTHER INFORMATION: primer

<400> SEQUENCE: 48
ttgcggccgc ttcacatctg ctggcccttg tac 33

<210> SEQ ID NO 49
<211> LENGTH: 8312
<212> TYPE: DNA
<213> ORGANISM: Artificial Sequence
<220> FEATURE:
<223> OTHER INFORMATION: plasmid SC38

<400> SEQUENCE: 49
ggccgcaagt atgaactaaa atgcatgtag gtgtaagagc tcatggagag catggaatat 60
tgtatccgac catgtaacag tataataact gagctccatc tcacttcttc tatgaataaa 120
caaaggatgt tatgatatat taacactcta tctatgcacc ttattgttct atgataaatt 180
tcctcttatt attataaatc atctgaatcg tgacggctta tggaatgctt caaatagtac 240
aaaaacaaat gtgtactata agactttcta aacaattcta accttagcat tgtgaacgag 300
acataagtgt taagaagaca taacaattat aatggaagaa gtttgtctcc atttatatat 360
tatatattac ccacttatgt attatattag gatgttaagg agacataaca attataaaga 420
gagaagtttg tatccattta tatattatat actacccatt tatatattat acttatccac 480
ttatttaatg tctttataag gtttgatcca tgatatttct aatattttag ttgatatgta 540
tatgaaaggg tactatttga actctcttac tctgtataaa ggttggatca tccttaaagt 600
gggtctattt aattttattg cttcttacag ataaaaaaaa aattatgagt tggtttgata 660
aaatattgaa ggatttaaaa taataataaa taacatataa tatatgtata taaatttatt 720 ataaatataac atttatctat aaaaaagtaa atattgtcat aaatctatac aatcgtttag 780
ccttgctgga cgaatctcaa ttatttaaac gagagtaaac atatttgact ttttggttat 840
ttaacaaatt attatttaac actatatgaa attttttttt ttatcagcaa agaataaaat 900
taaattaaga aggacaatgg tgtcccaatc cttatacaac caacttccac aagaaagtca 960
agtcagagac aacaaaaaaa caagcaaagg aaatttttta atttgagttg tcttgtttgc 1020
tgcataattt atgcagtaaa acactacaca taaccctttt agcagtagag caatggttga 1080
ccgtgtgctt agcttctttt attttatttt tttatcagca aagaataaat aaaataaaat 1140
gagacacttc agggatgttt caacaagctt ggatccgtcg acggcgcgcc cgatcatccg 1200
gatatagttc ctcctttcag caaaaaaccc ctcaagaccc gtttagaggc cccaaggggt 1260
tatgctagtt attgctcagc ggtggcagca gccaactcag cttcctttcg ggctttgtta 1320
gcagccggat cgatccaagc tgtacctcac tattcctttg ccctcggacg agtgctgggg 1380
cgtcggtttc cactatcggc gagtacttct acacagccat cggtccagac ggccgcgctt 1440
ctgcgggcga tttgtgtacg cccgacagtc ccggctccgg atcggacgat tgcgtcgcat 1500
cgaccctgcg cccaagctgc atcatcgaaa ttgccgtcaa ccaagctctg atagagttgg 1560
tcaagaccaa tgcggagcat atacgcccgg agccgcggcg atcctgcaag ctccggatgc 1620
ctccgctcga agtagcgcgt ctgctgctcc atacaagcca accacggcct ccagaagaag 1680
atgttggcga cctcgtattg ggaatccccg aacatcgcct cgctccagtc aatgaccgct 1740

```
gttatgcggc cattgtccgt caggacattg ttggagccga aatccgcgtg cacgaggtgc   1800
cggacttcgg ggcagtcctc ggcccaaagc atcagctcat cgagagcctg cgcgacggac   1860
gcactgacgg tgtcgtccat cacagtttgc cagtgataca catggggatc agcaatcgcg   1920
catatgaaat cacgccatgt agtgtattga ccgattcctt gcggtccgaa tgggccgaac   1980
ccgctcgtct ggctaagatc ggccgcagcg atcgcatcca tagcctccgc gaccggctgc   2040
agaacagcgg gcagttcggt ttcaggcagg tcttgcaacg tgacaccctg tgcacggcgg   2100
gagatgcaat aggtcaggct ctcgctgaat tccccaatgt caagcacttc cggaatcggg   2160
agcgcggccg atgcaaagtg ccgataaaca taacgatctt tgtagaaacc atcggcgcag   2220
ctatttaccc gcaggacata tccacgccct cctacatcga agctgaaagc acgagattct   2280
tcgccctccg agagctgcat caggtcggag acgctgtcga acttttcgat cagaaacttc   2340
tcgacagacg tcgcggtgag ttcaggcttt tccatgggta tatctccttc ttaaagttaa   2400
acaaaattat ttctagaggg aaaccgttgt ggtctcccta tagtgagtcg tattaatttc   2460
gcgggatcga gatcgatcca attccaatcc cacaaaaatc tgagcttaac agcacagttg   2520
ctcctctcag agcagaatcg ggtattcaac accctcatat caactactac gttgtgtata   2580
acggtccaca tgccggtata tacgatgact ggggttgtac aaaggcggca acaaacggcg   2640
ttcccggagt tgcacacaag aaatttgcca ctattacaga ggcaagagca gcagctgacg   2700
cgtacacaac aagtcagcaa acagacaggt tgaacttcat ccccaaagga gaagctcaac   2760
tcaagcccaa gagctttgct aaggccctaa caagcccacc aaagcaaaaa gcccactggc   2820
tcacgctagg aaccaaaagg cccagcagtg atccagcccc aaaagagatc tcctttgccc   2880
cggagattac aatggacgat ttcctctatc tttacgatct aggaaggaag ttcgaaggtg   2940
aaggtgacga cactatgttc accactgata atgagaaggt tagcctcttc aatttcagaa   3000
agaatgctga cccacagatg gttagagagg cctacgcagc aggtctcatc aagacgatct   3060
acccgagtaa caatctccag gagatcaaat accttcccaa gaaggttaaa gatgcagtca   3120
aaagattcag gactaattgc atcaagaaca cagagaaaga catatttctc aagatcagaa   3180
gtactattcc agtatggacg attcaaggct tgcttcataa accaaggcaa gtaatagaga   3240
ttggagtctc taaaaaggta gttcctactg aatctaaggc catgcatgga gtctaagatt   3300
caaatcgagg atctaacaga actcgccgtg aagactggcg aacagttcat acagagtctt   3360
ttacgactca atgacaagaa gaaaatcttc gtcaacatgg tggagcacga cactctggtc   3420
tactccaaaa atgtcaaaga tacagtctca gaagaccaaa gggctattga gacttttcaa   3480
caaaggataa tttcgggaaa cctcctcgga ttccattgcc cagctatctg tcacttcatc   3540
gaaaggacag tagaaaagga aggtggctcc tacaaatgcc atcattgcga taaaggaaag   3600
gctatcattc aagatgcctc tgccgacagt ggtcccaaag atggaccccc acccacgagg   3660
agcatcgtgg aaaaagaaga cgttccaacc acgtcttcaa agcaagtgga ttgatgtgac   3720
atctccactg acgtaaggga tgacgcacaa tcccactatc cttcgcaaga cccttcctct   3780
atataaggaa gttcatttca tttggagagg acacgctcga gctcatttct ctattacttc   3840
agccataaca aaagaactct tttctcttct tattaaacca tgaaaaagcc tgaactcacc   3900
gcgacgtctg tcgagaagtt tctgatcgaa aagttcgaca gcgtctccga cctgatgcag   3960
ctctcggagg gcgaagaatc tcgtgctttc agcttcgatg taggagggcg tggatatgtc   4020
ctgcgggtaa atagctgcgc cgatggtttc tacaaagatc gttatgttta tcggcacttt   4080
gcatcggccg cgctcccgat tccggaagtg cttgacattg gggaattcag cgagagcctg   4140
```

```
acctattgca tctcccgccg tgcacagggt gtcacgttgc aagacctgcc tgaaaccgaa   4200
ctgcccgctg ttctgcagcc ggtcgcggag gccatggatg cgatcgctgc ggccgatctt   4260
agccagacga gcgggttcgg cccattcgga ccgcaaggaa tcggtcaata cactacatgg   4320
cgtgatttca tatgcgcgat tgctgatccc catgtgtatc actggcaaac tgtgatggac   4380
gacaccgtca gtgcgtccgt cgcgcaggct ctcgatgagc tgatgctttg ggccgaggac   4440
tgccccgaag tccggcacct cgtgcacgcg gatttcggct ccaacaatgt cctgacggac   4500
aatggccgca taacagcggt cattgactgg agcgaggcga tgttcgggga ttcccaatac   4560
gaggtcgcca acatcttctt ctggaggccg tggttggctt gtatggagca gcagacgcgc   4620
tacttcgagc ggaggcatcc ggagcttgca ggatcgccgc ggctccgggc gtatatgctc   4680
cgcattggtc ttgaccaact ctatcagagc ttggttgacg gcaatttcga tgatgcagct   4740
tgggcgcagg gtcgatgcga cgcaatcgtc cgatccggag ccgggactgt cgggcgtaca   4800
caaatcgccc gcagaagcgc ggccgtctgg accgatggct gtgtagaagt actcgccgat   4860
agtggaaacc gacgccccag cactcgtccg agggcaaagg aatagtgagg tacctaaaga   4920
aggagtgcgt cgaagcagat cgttcaaaca tttggcaata aagtttctta agattgaatc   4980
ctgttgccgg tcttgcgatg attatcatat aatttctgtt gaattacgtt aagcatgtaa   5040
taattaacat gtaatgcatg acgttattta tgagatgggt ttttatgatt agagtcccgc   5100
aattatacat ttaatacgcg atagaaaaca aaatatagcg cgcaaactag gataaattat   5160
cgcgcgcggt gtcatctatg ttactagatc gatgtcgaat ctgatcaacc tgcattaatg   5220
aatcggccaa cgcgcgggga gaggcggttt gcgtattggg cgctcttccg cttcctcgct   5280
cactgactcg ctgcgctcgg tcgttcggct gcggcgagcg gtatcagctc actcaaaggc   5340
ggtaatacgg ttatccacag aatcagggga taacgcagga aagaacatgt gagcaaaagg   5400
ccagcaaaag gccaggaacc gtaaaaaggc cgcgttgctg gcgtttttcc ataggctccg   5460
cccccctgac gagcatcaca aaaatcgacg ctcaagtcag aggtggcgaa acccgacagg   5520
actataaaga taccaggcgt ttccccctgg aagctccctc gtgcgctctc ctgttccgac   5580
cctgccgctt accggatacc tgtccgcctt tctcccttcg ggaagcgtgg cgctttctca   5640
atgctcacgc tgtaggtatc tcagttcggt gtaggtcgtt cgctccaagc tgggctgtgt   5700
gcacgaaccc cccgttcagc ccgaccgctg cgccttatcc ggtaactatc gtcttgagtc   5760
caacccggta agacacgact tatcgccact ggcagcagcc actggtaaca ggattagcag   5820
agcgaggtat gtaggcggtg ctacagagtt cttgaagtgg tggcctaact acggctacac   5880
tagaaggaca gtatttggta tctgcgctct gctgaagcca gttaccttcg gaaaaagagt   5940
tggtagctct tgatccggca aacaaaccac cgctggtagc ggtggttttt ttgtttgcaa   6000
gcagcagatt acgcgcagaa aaaaaggatc tcaagaagat cctttgatct tttctacggg   6060
gtctgacgct cagtggaacg aaaactcacg ttaagggatt ttggtcatga cattaaccta   6120
taaaaatagg cgtatcacga ggccctttcg tctcgcgcgt ttcggtgatg acggtgaaaa   6180
cctctgacac atgcagctcc cggagacggt cacagcttgt ctgtaagcgg atgccgggag   6240
cagacaagcc cgtcagggcg cgtcagcggg tgttggcggg tgtcggggct ggcttaacta   6300
tgcggcatca gagcagattg tactgagagt gcaccatatg gacatattgt cgttagaacg   6360
cggctacaat taatacataa ccttatgtat catacacata cgatttaggt gacactatag   6420
aacggcgcgc caagcttttg atccatgccc ttcatttgcc gcttattaat taatttggta   6480
acagtccgta ctaatcagtt acttatcctt cccccatcat aattaatctt ggtagtctcg   6540
```

```
aatgccacaa cactgactag tctcttggat cataagaaaa agccaaggaa caaaagaaga   6600

caaaacacaa tgagagtatc ctttgcatag caatgtctaa gttcataaaa ttcaaacaaa   6660

aacgcaatca cacacagtgg acatcactta tccactagct gatcaggatc gccgcgtcaa   6720

gaaaaaaaaa ctggacccca aaagccatgc acaacaacac gtactcacaa aggtgtcaat   6780

cgagcagccc aaaacattca ccaactcaac ccatcatgag ccctcacatt tgttgtttct   6840

aacccaacct caaactcgta ttctcttccg ccacctcatt tttgtttatt tcaacacccg   6900

tcaaactgca tgccaccccg tggccaaatg tccatgcatg ttaacaagac ctatgactat   6960

aaatagctgc aatctcggcc caggttttca tcatcaagaa ccagttcaat atcctagtac   7020

accgtattaa agaatttaag atatactgcg gccgcaggat gcaagccgtc acggcggcgg   7080

ccgcggcggg gcagctgcta acagatacga ggagagggcc cagatgtagg gctcggctgg   7140

gaacgacgag attatcctgg acaggtcgat ttgcagtgga agcttttgca ggccagtgcc   7200

aaagtgctac tactgtaatg cataaattca gtgccatttc tcaagctgct aggcctagaa   7260

gaaacacaaa gagacagtgc agcgatgatt atccagccct ccaagctgga tgcagcgagg   7320

ttaattggga tcaaaacggt tccaacgcca atcggcttga ggaaatcagg ggagatgttt   7380

tgaagaaatt gcgctctttc tatgaatttt gcaggccaca cacaattttt ggcactataa   7440

taggtataac ttcagtgtct ctcctgccaa tgaagagcat agatgatttt actgtcacgg   7500

tactacgagg atatctcgag gctttgactg ctgctttatg tatgaacatt tatgtggtcg   7560

ggctgaatca gctatatgac attcagattg acaagatcaa caagccaggt cttccattgg   7620

catctgggga attttcagta gcaactggag ttttcttagt actcgcattc ctgatcatga   7680

gctttagcat aggaatacgt tccggatcgg cgccactgat gtgtgcttta attgtcagct   7740

tccttcttgg aagtgcgtac tccattgagg ctccgttcct ccggtggaaa cggcacgcgc   7800

tcctcgctgc atcatgtatc ctatttgtga gggctatctt ggtccagttg gctttctttg   7860

cacatatgca gcaacatgtt ctgaaaaggc cattggcagc aaccaaatcg ctggtgtttg   7920

caacattgtt tatgtgttgc ttctctgccg tcatagcact attcaaggat attccagatg   7980

ttgatggaga tcgagacttt ggtatccaat ccttgagtgt gagattgggg cctcaaagag   8040

tgtatcagct ctgcataagc atattgttga cagcctatgg cgctgccact ctagtaggag   8100

cttcatccac aaacctattt caaaagatca tcactgtgtc tggtcatggc ctgcttgctt   8160

tgacactttg gcagagagcg cagcactttg aggttgaaaa ccaagcgcgt gtcacatcat   8220

tttacatgtt catttggaag ctattctatg cagagtattt ccttatacca tttgtgcagt   8280

gaaatttgta caagggccag cagatgtgaa gc                                 8312
```

<210> SEQ ID NO 50
<211> LENGTH: 8137
<212> TYPE: DNA
<213> ORGANISM: Artificial
<220> FEATURE:
<223> OTHER INFORMATION: plasmid SC1

<400> SEQUENCE: 50

```
cgcgtacaca acaagtcagc aaacagacag gttgaacttc atccccaaag gagaagctca     60

actcaagccc aagagctttg ctaaggccct aacaagccca ccaaagcaaa aagcccactg    120

gctcacgcta ggaaccaaaa ggcccagcag tgatccagcc ccaaaagaga tctcctttgc    180

cccggagatt acaatggacg atttcctcta tctttacgat ctaggaagga agttcgaagg    240

tgaaggtgac gacactatgt tcaccactga taatgagaag gttagcctct tcaatttcag    300
```

-continued

```
aaagaatgct gacccacaga tggttagaga ggcctacgca gcaggtctca tcaagacgat    360
ctacccgagt aacaatctcc aggagatcaa ataccttccc aagaaggtta aagatgcagt    420
caaaagattc aggactaatt gcatcaagaa cacagagaaa gacatatttc tcaagatcag    480
aagtactatt ccagtatgga cgattcaagg cttgcttcat aaaccaaggc aagtaataga    540
gattggagtc tctaaaaagg tagttcctac tgaatctaag gccatgcatg gagtctaaga    600
ttcaaatcga ggatctaaca gaactcgccg tgaagactgg cgaacagttc atacagagtc    660
ttttacgact caatgacaag aagaaaatct tcgtcaacat ggtggagcac gacactctgg    720
tctactccaa aaatgtcaaa gatacagtct cagaagacca aagggctatt gagacttttc    780
aacaaaggat aatttcggga aacctcctcg gattccattg cccagctatc tgtcacttca    840
tcgaaaggac agtagaaaag gaaggtggct cctacaaatg ccatcattgc gataaaggaa    900
aggctatcat tcaagatgcc tctgccgaca gtggtcccaa agatggaccc ccacccacga    960
ggagcatcgt ggaaaaagaa gacgttccaa ccacgtcttc aaagcaagtg gattgatgtg   1020
acatctccac tgacgtaagg gatgacgcac aatcccacta tccttcgcaa gacccttcct   1080
ctatataagg aagttcattt catttggaga ggacacgctc gagctcattt ctctattact   1140
tcagccataa caaaagaact cttttctctt cttattaaac catgaaaaag cctgaactca   1200
ccgcgacgtc tgtcgagaag tttctgatcg aaaagttcga cagcgtctcc gacctgatgc   1260
agctctcgga gggcgaagaa tctcgtgctt tcagcttcga tgtaggaggg cgtggatatg   1320
tcctgcgggt aaatagctgc gccgatggtt tctacaaaga tcgttatgtt tatcggcact   1380
ttgcatcggc cgcgctcccg attccggaag tgcttgacat tggggaattc agcgagagcc   1440
tgacctattg catctcccgc cgtgcacagg gtgtcacgtt gcaagacctg cctgaaaccg   1500
aactgcccgc tgttctgcag ccggtcgcgg aggccatgga tgcgatcgct gcggccgatc   1560
ttagccagac gagcgggttc ggcccattcg gaccgcaagg aatcggtcaa tacactacat   1620
ggcgtgattt catatgcgcg attgctgatc cccatgtgta tcactggcaa actgtgatgg   1680
acgacaccgt cagtgcgtcc gtcgcgcagg ctctcgatga gctgatgctt tgggccgagg   1740
actgccccga agtccggcac ctcgtgcacg cggatttcgg ctccaacaat gtcctgacgg   1800
acaatggccg cataacagcg gtcattgact ggagcgaggc gatgttcggg gattcccaat   1860
acgaggtcgc caacatcttc ttctggaggc cgtggttggc ttgtatggag cagcagacgc   1920
gctacttcga gcggaggcat ccggagcttg caggatcgcc gcggctccgg gcgtatatgc   1980
tccgcattgg tcttgaccaa ctctatcaga gcttggttga cggcaatttc gatgatgcag   2040
cttgggcgca gggtcgatgc gacgcaatcg tccgatccgg agccgggact gtcgggcgta   2100
cacaaatcgc ccgcagaagc gcggccgtct ggaccgatgg ctgtgtagaa gtactcgccg   2160
atagtggaaa ccgacgcccc agcactcgtc cgagggcaaa ggaatagtga ggtacctaaa   2220
gaaggagtgc gtcgaagcag atcgttcaaa catttggcaa taaagtttct taagattgaa   2280
tcctgttgcc ggtcttgcga tgattatcat ataatttctg ttgaattacg ttaagcatgt   2340
aataattaac atgtaatgca tgacgttatt tatgagatgg gtttttatga ttagagtccc   2400
gcaattatac atttaatacg cgatagaaaa caaaatatag cgcgcaaact aggataaatt   2460
atcgcgcgcg gtgtcatcta tgttactaga tcgatgtcga cgatcatccg gatatagttc   2520
ctcctttcag caaaaaaccc ctcaagaccc gtttagaggc cccaaggggt tatgctagtt   2580
attgctcagc ggtggcagca gccaactcag cttcctttcg ggctttgtta gcagccggat   2640
cgatccaagc tgtacctcac tattcctttg ccctcggacg agtgctgggg cgtcggtttc   2700
```

```
cactatcggc gagtacttct acacagccat cggtccagac ggccgcgctt ctgcgggcga   2760
tttgtgtacg cccgacagtc ccggctccgg atcggacgat tgcgtcgcat cgaccctgcg   2820
cccaagctgc atcatcgaaa ttgccgtcaa ccaagctctg atagagttgg tcaagaccaa   2880
tgcggagcat atacgcccgg agccgcggcg atcctgcaag ctccggatgc ctccgctcga   2940
agtagcgcgt ctgctgctcc atacaagcca accacggcct ccagaagaag atgttggcga   3000
cctcgtattg ggaatccccg aacatcgcct cgctccagtc aatgaccgct gttatgcggc   3060
cattgtccgt caggacattg ttggagccga aatccgcgtg cacgaggtgc cggacttcgg   3120
ggcagtcctc ggcccaaagc atcagctcat cgagagcctg cgcgacggac gcactgacgg   3180
tgtcgtccat cacagtttgc cagtgataca catggggatc agcaatcgcg catatgaaat   3240
cacgccatgt agtgtattga ccgattcctt gcggtccgaa tgggccgaac ccgctcgtct   3300
ggctaagatc ggccgcagcg atcgcatcca tagcctccgc gaccggctgc agaacagcgg   3360
gcagttcggt ttcaggcagg tcttgcaacg tgacaccctg tgcacggcgg gagatgcaat   3420
aggtcaggct ctcgctgaat tccccaatgt caagcacttc cggaatcggg agcgcggccg   3480
atgcaaagtg ccgataaaca taacgatctt tgtagaaacc atcggcgcag ctatttaccc   3540
gcaggacata tccacgccct cctacatcga agctgaaagc acgagattct tcgccctccg   3600
agagctgcat caggtcggag acgctgtcga acttttcgat cagaaacttc tcgacagacg   3660
tcgcggtgag ttcaggcttt tccatgggta tatctccttc ttaaagttaa acaaaattat   3720
ttctagaggg aaaccgttgt ggtctcccta tagtgagtcg tattaatttc gcgggatcga   3780
gatctgatca acctgcatta atgaatcggc caacgcgcgg ggagaggcgg tttgcgtatt   3840
gggcgctctt ccgcttcctc gctcactgac tcgctgcgct cggtcgttcg gctgcggcga   3900
gcggtatcag ctcactcaaa ggcggtaata cggttatcca cagaatcagg ggataacgca   3960
ggaaagaaca tgtgagcaaa aggccagcaa aaggccagga accgtaaaaa ggccgcgttg   4020
ctggcgtttt tccataggct ccgcccccct gacgagcatc acaaaaatcg acgctcaagt   4080
cagaggtggc gaaacccgac aggactataa agataccagg cgtttccccc tggaagctcc   4140
ctcgtgcgct ctcctgttcc gaccctgccg cttaccggat acctgtccgc ctttctccct   4200
tcgggaagcg tggcgctttc tcaatgctca cgctgtaggt atctcagttc ggtgtaggtc   4260
gttcgctcca agctgggctg tgtgcacgaa ccccccgttc agcccgaccg ctgcgcctta   4320
tccggtaact atcgtcttga gtccaacccg gtaagacacg acttatcgcc actggcagca   4380
gccactggta acaggattag cagagcgagg tatgtaggcg gtgctacaga gttcttgaag   4440
tggtggccta actacggcta cactagaagg acagtatttg gtatctgcgc tctgctgaag   4500
ccagttacct tcggaaaaag agttggtagc tcttgatccg gcaaacaaac caccgctggt   4560
agcggtggtt tttttgtttg caagcagcag attacgcgca gaaaaaaagg atctcaagaa   4620
gatcctttga tcttttctac ggggtctgac gctcagtgga acgaaaactc acgttaaggg   4680
attttggtca tgacattaac ctataaaaat aggcgtatca cgaggccctt tcgtctcgcg   4740
cgtttcggtg atgacggtga aaacctctga cacatgcagc tcccggagac ggtcacagct   4800
tgtctgtaag cggatgccgg gagcagacaa gcccgtcagg gcgcgtcagc gggtgttggc   4860
gggtgtcggg gctggcttaa ctatgcggca tcagagcaga ttgtactgag agtgcaccat   4920
atggacatat tgtcgttaga acgcggctac aattaataca taaccttatg tatcatacac   4980
atacgattta ggtgacacta tagaactcga gcagctgaag cttgatccat gcccttcatt   5040
tgccgctatt aattaatttg gtaacagtag tccgtactaa tcagttactt atccttcctc   5100
```

-continued

```
catcataatt aatcttggta gtctcgaatg ccacaacact gactagtctc ttggatcata   5160
agaaaaagcc aaggaacaaa agaagacaaa acacaatgag agtatccttt gcatagcaat   5220
gtctaagttc ataaaattca aacaaaaacg caatcacaca cagtggacat cacttatcca   5280
ctagctgaat caggatcgcc gcgtcaagaa aaaaaaactg gaccccaaaa gccatgcaca   5340
acaacacgta ctcacaaagg tgtcaatcga gcagcccaaa acattcacca actcaaccca   5400
tcatgagccc tcacatttgt tgtttctaac ccaacctcaa actcgtattc tcttccgcca   5460
cctcattttt gtttatttca acacccgtca aactgcatgc caccccgtgg ccaaatgtcc   5520
atgcatgtta acaagaccta tgactataaa tatctgcaat ctcggcccag gttttcatca   5580
tcaagaacca gttcaatatc ctagtacacc gtattaaaga atttaagata tactaacagc   5640
ggccgcatgg ccaccgtggt gaggatccca acaatctcat gcatccacat ccacacgttc   5700
cgttcccaat cccctcgcac tttcgccaga atccgggtcg gacccaggtc gtgggctcct   5760
attcgggcat cggcagcgag ctcggagaga ggggagatag tattggagca gaagccgaag   5820
aaggatgaca agaagaagct gcagaaggga atcgcagagt tttacgacga gtcgtctggc   5880
ttatgggaga acatttgggg cgaccacatg caccatggct tttatgactc ggattccact   5940
gtttcgcttt cggatcatcg tgctgctcag atccgaatga tccaagagtc tcttcgcttt   6000
gcctctgttt ctgaggagcg tagtaaatgg cccaagagta tagttgatgt tgggtgtggc   6060
ataggtggca gctctagata cctggccaag aaatttggag caaccagtgt aggcatcact   6120
ctgagtcctg ttcaagctca aagagcaaat gctcttgctg ctgctcaagg attggctgat   6180
aaggtttcct ttcaggttgc tgacgctcta cagcaaccat tctctgacgg ccagtttgat   6240
ctggtgtggt ccatggagag tggagagcat atgcctgaca aagctaagtt tgttggagag   6300
ttagctcggg tagcagcacc aggtgccatt ataataatag taacatggtg ccacagggat   6360
cttggccctg acgaacaatc cttacatcca tgggagcaag atctcttaaa gaagatttgc   6420
gatgcatatt acctccctgc ctggtgctca acttctgatt atgttaagtt gctccaatcc   6480
ctgtcacttc aggacatcaa gtcagaagat tggtctcgct ttgttgctcc attttggcca   6540
gcagtgatac gctcagcctt cacatggaag ggtctatctt cactcttgag cagtggacaa   6600
aaaacgataa aggagctttt ggctatgcca ttgatgatag agggatacaa gaaagatcta   6660
attaagtttg ccatcattac atgtcgaaaa cctgaataag cggccgctac atggccacgt   6720
gcatgaagta tgaactaaaa tgcatgtagg tgtaagagct catggagagc atggaatatt   6780
gtatccgacc atgtaacagt ataataactg agctccatct cacttcttct atgaataaac   6840
aaaggatgtt atgatatatt aacactctat ctatgcacct tattgttcta tgataaattt   6900
cctcttatta ttataaatca tctgaatcgt gacggcttat ggaatgcttc aaatagtaca   6960
aaaacaaatg tgtactataa gactttctaa acaattctaa ctttagcatt gtgaacgaga   7020
cataagtgtt aagaagacat aacaattata atggaagaag tttgtctcca tttatatatt   7080
atatattacc cacttatgta ttatattagg atgttaagga gacataacaa ttataaagag   7140
agaagtttgt atccatttat atattatata ctacccattt atatattata cttatccact   7200
tatttaatgt ctttataagg tttgatccat gatatttcta atattttagt tgatatgtat   7260
atgaaagggt actatttgaa ctctcttact ctgtataaag gttggatcat ccttaaagtg   7320
ggtctattta attttattgc ttcttacaga taaaaaaaaa attatgagtt ggtttgataa   7380
aatattgaag gatttaaaat aataataaat aataaataac atataatata tgtatataaa   7440
tttattataa tataacattt atctataaaa aagtaaatat tgtcataaat ctatacaatc   7500
```

```
gtttagcctt gctggacgac tctcaattat ttaaacgaga gtaaacatat ttgacttttt   7560

ggttatttaa caaattatta tttaacacta tatgaaattt ttttttttta tcagcaaaga   7620

aataaaatta aattaagaag gacaatggtg tgtcccaatc cttatacaac caacttccac   7680

aagaaagtca agtcagagac aacaaaaaaa caagcaaagg aaattttta atttgagttg   7740

tcttgtttgc tgcataattt atgcagtaaa acactacaca taaccctttt agcagtagag   7800

caatggttga ccgtgtgctt agcttctttt attttatttt tttatcagca aagaataaat   7860

aaaataaaat gagacacttc agggatgttt caacaagctt cccgggtcta gaggatccaa   7920

ttccaatccc acaaaaatct gagcttaaca gcacagttgc tcctctcaga gcagaatcgg   7980

gtattcaaca ccctcatatc aactactacg ttgtgtataa cggtccacat gccggtatat   8040

acgatgactg ggttgtaca aaggcggcaa caaacggcgt tcccggagtt gcacacaaga   8100

aatttgccac tattacagag gcaagagcag cagctga                            8137
```

<210> SEQ ID NO 51
<211> LENGTH: 11934
<212> TYPE: DNA
<213> ORGANISM: Artificial Sequence
<220> FEATURE:
<223> OTHER INFORMATION: sequence of plasmid KS325
<220> FEATURE:
<221> NAME/KEY: misc_feature
<222> LOCATION: (10748)..(10748)
<223> OTHER INFORMATION: n is a, c, g, or t

<400> SEQUENCE: 51

```
cgcgccaagc ttttgatcca tgcccttcat ttgccgctta ttaattaatt tggtaacagt     60

ccgtactaat cagttactta tccttccccc atcataatta atcttggtag tctcgaatgc    120

cacaacactg actagtctct tggatcataa gaaaaagcca aggaacaaaa gaagacaaaa    180

cacaatgaga gtatcctttg catagcaatg tctaagttca taaaattcaa acaaaaacgc    240

aatcacacac agtggacatc acttatccac tagctgatca ggatcgccgc gtcaagaaaa    300

aaaaactgga ccccaaaagc catgcacaac aacacgtact cacaaaggtg tcaatcgagc    360

agcccaaaac attcaccaac tcaacccatc atgagccctc acatttgttg tttctaaccc    420

aacctcaaac tcgtattctc ttccgccacc tcatttttgt ttatttcaac acccgtcaaa    480

ctgcatgcca ccccgtggcc aaatgtccat gcatgttaac aagacctatg actataaata    540

gctgcaatct cggcccaggt tttcatcatc aagaaccagt tcaatatcct agtacaccgt    600

attaaagaat ttaagatata ctgcggccgc aggatgcaag ccgtcacggc ggcggccacg    660

gcggggcagc tgctaacaga tacgaggaga gggcccagat gtagggctcg gctgggaacg    720

acgagattat cctggacagg tcgatttgca gtggaagctt ttgcaggcca gtgccaaagt    780

gctactactg taatgcataa attcagtgcc atttctcaag ctgctaggcc tagaagaaac    840

acaaagagac agtgcagcga tgattatcca gccctccaag ctggatgcag cgaggttaat    900

tgggatcaaa acggttccaa cgccaatcgg cttgaggaaa tcaggggaga tgttttgaag    960

aaattgcgct ctttctatga attttgcagg ccacacacaa tttttggcac tataataggt   1020

ataacttcag tgtctctcct gccaatgaag agcatagatg attttactgt cacggtacta   1080

cgaggatatc tcgaggcttt gactgctgct ttatgtatga acatttatgt ggtcgggctg   1140

aatcagctat atgacattca gattgacaag atcaacaagc caggtcttcc attggcatct   1200

ggggaatttt cagtagcaac tggagttttc ttagtactcg cattcctgat catgagcttt   1260

agcataggaa tacgttccgg atcggcgcca ctgatgtgtg ctttaattgt cagcttcctt   1320
```

-continued

```
cttggaagtg cgtactccat tgaggctccg ttcctccggt ggaaacggca cgcgctcctc   1380

gctgcatcat gtatcctatt tgtgagggct atcttggtcc agttggcttt ctttgcacat   1440

atgcagcaac atgttctgaa aaggccattg gcagcaacca aatcgctggt gtttgcaaca   1500

ttgtttatgt gttgcttctc tgccgtcata gcactattca aggatattcc agatgttgat   1560

ggagatcgag actttggtat ccaatccttg agtgtgagat tggggcctca aagagtgtat   1620

cagctctgca taagcatatt gttgacagcc tatggcgctg ccactctagt aggagcttca   1680

tccacaaacc tatttcaaaa gatcatcact gtgtctggtc atggcctgct tgctttgaca   1740

ctttggcaga gagcgcagca ctttgaggtt gaaaaccaag cgcgtgtcac atcattttac   1800

atgttcattt ggaagctatt ctatgcagag tatttcctta taccatttgt gcagtgaaat   1860

ttgtacaagg gccagcagat gtgaagcggc cgcaagtatg aactaaaatg catgtaggtg   1920

taagagctca tggagagcat ggaatattgt atccgaccat gtaacagtat aataactgag   1980

ctccatctca cttcttctat gaataaacaa aggatgttat gatatattaa cactctatct   2040

atgcacctta ttgttctatg ataaatttcc tcttattatt ataaatcatc tgaatcgtga   2100

cggcttatgg aatgcttcaa atagtacaaa aacaaatgtg tactataaga ctttctaaac   2160

aattctaacc ttagcattgt gaacgagaca taagtgttaa gaagacataa caattataat   2220

ggaagaagtt tgtctccatt tatatattat atattaccca cttatgtatt atattaggat   2280

gttaaggaga cataacaatt ataaagagag aagtttgtat ccatttatat attatatact   2340

acccatttat atattatact tatccactta tttaatgtct ttataaggtt tgatccatga   2400

tatttctaat attttagttg atatgtatat gaaagggtac tatttgaact ctcttactct   2460

gtataaaggt tggatcatcc ttaaagtggg tctatttaat tttattgctt cttacagata   2520

aaaaaaaaat tatgagttgg tttgataaaa tattgaagga tttaaaataa taataaataa   2580

catataatat atgtatataa atttattata atataacatt tatctataaa aaagtaaata   2640

ttgtcataaa tctatacaat cgtttagcct tgctggacga atctcaatta tttaaacgag   2700

agtaaacata tttgactttt tggttattta acaaattatt atttaacact atatgaaatt   2760

ttttttttta tcagcaaaga ataaaattaa attaagaagg acaatggtgt cccaatcctt   2820

atacaaccaa cttccacaag aaagtcaagt cagagacaac aaaaaaacaa gcaaaggaaa   2880

ttttttaatt tgagttgtct tgtttgctgc ataatttatg cagtaaaaca ctacacataa   2940

ccctttttagc agtagagcaa tggttgaccg tgtgcttagc ttcttttatt ttattttttt   3000

atcagcaaag aataaataaa ataaaatgag acacttcagg gatgtttcaa caagcttgga   3060

tccgtcgacg gcgcgcccga tcatccggat atagttcctc ctttcagcaa aaaacccctc   3120

aagacccgtt tagaggcccc aaggggttat gctagttatt gctcagcggt ggcagcagcc   3180

aactcagctt cctttcgggc tttgttagca gccggatcga tccaagctgt acctcactat   3240

tcctttgccc tcggacgagt gctggggcgt cggtttccac tatcggcgag tacttctaca   3300

cagccatcgg tccagacggc cgcgcttctg cgggcgattt gtgtacgccc gacagtcccg   3360

gctccggatc ggacgattgc gtcgcatcga ccctgcgccc aagctgcatc atcgaaattg   3420

ccgtcaacca agctctgata gagttggtca agaccaatgc ggagcatata cgcccggagc   3480

cgcggcgatc ctgcaagctc cggatgcctc cgctcgaagt agcgcgtctg ctgctccata   3540

caagccaacc acggcctcca gaagaagatg ttggcgacct cgtattggga atccccgaac   3600

atcgcctcgc tccagtcaat gaccgctgtt atgcggccat tgtccgtcag gacattgttg   3660

gagccgaaat ccgcgtgcac gaggtgccgg acttcggggc agtcctcggc ccaaagcatc   3720
```

-continued

```
agctcatcga gagcctgcgc gacggacgca ctgacggtgt cgtccatcac agtttgccag   3780
tgatacacat ggggatcagc aatcgcgcat atgaaatcac gccatgtagt gtattgaccg   3840
attccttgcg gtccgaatgg gccgaacccg ctcgtctggc taagatcggc cgcagcgatc   3900
gcatccatag cctccgcgac cggctgcaga acagcgggca gttcggtttc aggcaggtct   3960
tgcaacgtga caccctgtgc acggcgggag atgcaatagg tcaggctctc gctgaattcc   4020
ccaatgtcaa gcacttccgg aatcgggagc gcggccgatg caaagtgccg ataaacataa   4080
cgatctttgt agaaaccatc ggcgcagcta tttacccgca ggacatatcc acgccctcct   4140
acatcgaagc tgaaagcacg agattcttcg ccctccgaga gctgcatcag gtcggagacg   4200
ctgtcgaact tttcgatcag aaacttctcg acagacgtcg cggtgagttc aggctttttcc   4260
atgggtatat ctccttctta aagttaaaca aaattatttc tagagggaaa ccgttgtggt   4320
ctccctatag tgagtcgtat taatttcgcg ggatcgagat cgatccaatt ccaatcccac   4380
aaaaatctga gcttaacagc acagttgctc ctctcagagc agaatcgggt attcaacacc   4440
ctcatatcaa ctactacgtt gtgtataacg gtccacatgc cggtatatac gatgactggg   4500
gttgtacaaa ggcggcaaca aacggcgttc ccggagttgc acacaagaaa tttgccacta   4560
ttacagaggc aagagcagca gctgacgcgt acacaacaag tcagcaaaca gacaggttga   4620
acttcatccc caaaggagaa gctcaactca agcccaagag ctttgctaag gccctaacaa   4680
gcccaccaaa gcaaaaagcc cactggctca cgctaggaac caaaaggccc agcagtgatc   4740
cagccccaaa agagatctcc tttgccccgg agattacaat ggacgatttc ctctatcttt   4800
acgatctagg aaggaagttc gaaggtgaag gtgacgacac tatgttcacc actgataatg   4860
agaaggttag cctcttcaat ttcagaaaga atgctgaccc acagatggtt agagaggcct   4920
acgcagcagg tctcatcaag acgatctacc cgagtaacaa tctccaggag atcaaatacc   4980
ttcccaagaa ggttaaagat gcagtcaaaa gattcaggac taattgcatc aagaacacag   5040
agaaagacat atttctcaag atcagaagta ctattccagt atggacgatt caaggcttgc   5100
ttcataaacc aaggcaagta atagagattg gagtctctaa aaaggtagtt cctactgaat   5160
ctaaggccat gcatggagtc taagattcaa atcgaggatc taacagaact cgccgtgaag   5220
actggcgaac agttcataca gagtctttta cgactcaatg acaagaagaa aatcttcgtc   5280
aacatggtgg agcacgacac tctggtctac tccaaaaatg tcaaagatac agtctcagaa   5340
gaccaaaggg ctattgagac ttttcaacaa aggataattt cgggaaacct cctcggattc   5400
cattgcccag ctatctgtca cttcatcgaa aggacagtag aaaaggaagg tggctcctac   5460
aaatgccatc attgcgataa aggaaaggct atcattcaag atgcctctgc cgacagtggt   5520
cccaaagatg gacccccacc cacgaggagc atcgtggaaa aagaagacgt tccaaccacg   5580
tcttcaaagc aagtggattg atgtgacatc tccactgacg taagggatga cgcacaatcc   5640
cactatcctt cgcaagaccc ttcctctata taaggaagtt catttcattt ggagaggaca   5700
cgctcgagct catttctcta ttacttcagc cataacaaaa gaactctttt ctcttcttat   5760
taaaccatga aaaagcctga actcaccgcg acgtctgtcg agaagtttct gatcgaaaag   5820
ttcgacagcg tctccgacct gatgcagctc tcggagggcg aagaatctcg tgctttcagc   5880
ttcgatgtag gagggcgtgg atatgtcctg cgggtaaata gctgcgccga tggtttctac   5940
aaagatcgtt atgtttatcg gcactttgca tcggccgcgc tcccgattcc ggaagtgctt   6000
gacattgggg aattcagcga gagcctgacc tattgcatct cccgccgtgc acagggtgtc   6060
acgttgcaag acctgcctga aaccgaactg cccgctgttc tgcagccggt cgcggaggcc   6120
```

-continued

```
atggatgcga tcgctgcggc cgatcttagc cagacgagcg ggttcggccc attcggaccg   6180
caaggaatcg gtcaatacac tacatggcgt gatttcatat gcgcgattgc tgatccccat   6240
gtgtatcact ggcaaactgt gatggacgac accgtcagtg cgtccgtcgc gcaggctctc   6300
gatgagctga tgctttgggc cgaggactgc cccgaagtcc ggcacctcgt gcacgcggat   6360
ttcggctcca acaatgtcct gacggacaat ggccgcataa cagcggtcat tgactggagc   6420
gaggcgatgt tcggggattc ccaatacgag gtcgccaaca tcttcttctg gaggccgtgg   6480
ttggcttgta tggagcagca gacgcgctac ttcgagcgga ggcatccgga gcttgcagga   6540
tcgccgcggc tccgggcgta tatgctccgc attggtcttg accaactcta tcagagcttg   6600
gttgacggca atttcgatga tgcagcttgg gcgcagggtc gatgcgacgc aatcgtccga   6660
tccggagccg ggactgtcgg gcgtacacaa atcgcccgca gaagcgcggc cgtctggacc   6720
gatggctgtg tagaagtact cgccgatagt ggaaaccgac gccccagcac tcgtccgagg   6780
gcaaaggaat agtgaggtac ctaaagaagg agtgcgtcga agcagatcgt tcaaacattt   6840
ggcaataaag tttcttaaga ttgaatcctg ttgccggtct tgcgatgatt atcatataat   6900
ttctgttgaa ttacgttaag catgtaataa ttaacatgta atgcatgacg ttatttatga   6960
gatgggtttt tatgattaga gtcccgcaat tatacattta atacgcgata gaaaacaaaa   7020
tatagcgcgc aaactaggat aaattatcgc gcgcggtgtc atctatgtta ctagatcgat   7080
gtcgaatctg atcaacctgc attaatgaat cggccaacgc gcggggagag gcggtttgcg   7140
tattgggcgc tcttccgctt cctcgctcac tgactcgctg cgctcggtcg ttcggctgcg   7200
gcgagcggta tcagctcact caaaggcggt aatacggtta tccacagaat caggggataa   7260
cgcaggaaag aacatgtgag caaaaggcca gcaaaaggcc aggaaccgta aaaaggccgc   7320
gttgctggcg tttttccata ggctccgccc ccctgacgag catcacaaaa atcgacgctc   7380
aagtcagagg tggcgaaacc cgacaggact ataaagatac caggcgtttc cccctggaag   7440
ctccctcgtg cgctctcctg ttccgaccct gccgcttacc ggatacctgt ccgcctttct   7500
cccttcggga agcgtggcgc tttctcaatg ctcacgctgt aggtatctca gttcggtgta   7560
ggtcgttcgc tccaagctgg gctgtgtgca cgaacccccc gttcagcccg accgctgcgc   7620
cttatccggt aactatcgtc ttgagtccaa cccggtaaga cacgacttat cgccactggc   7680
agcagccact ggtaacagga ttagcagagc gaggtatgta ggcggtgcta cagagttctt   7740
gaagtggtgg cctaactacg gctacactag aaggacagta tttggtatct gcgctctgct   7800
gaagccagtt accttcggaa aaagagttgg tagctcttga tccggcaaac aaaccaccgc   7860
tggtagcggt ggtttttttg tttgcaagca gcagattacg cgcagaaaaa aaggatctca   7920
agaagatcct ttgatctttt ctacggggtc tgacgctcag tggaacgaaa actcacgtta   7980
agggattttg gtcatgacat taacctataa aaataggcgt atcacgaggc cctttcgtct   8040
cgcgcgtttc ggtgatgacg gtgaaaacct ctgacacatg cagctcccgg agacggtcac   8100
agcttgtctg taagcggatg ccgggagcag acaagcccgt cagggcgcgt cagcgggtgt   8160
tggcgggtgt cggggctggc ttaactatgc ggcatcagag cagattgtac tgagagtgca   8220
ccatatggac atattgtcgt tagaacgcgg ctacaattaa tacataacct tatgtatcat   8280
acacatacga tttaggtgac actatagaac ggcgcgccgt cgacggatat aatgagccgt   8340
aaacaaagat gattaagtag taattaatac gtactagtaa aagtggcaaa agataacgag   8400
aaagaaccaa tttctttgca ttcggcctta gcggaaggca tatataagct ttgattattt   8460
tatttagtgt aatgatttcg tacaaccaaa gcatttattt agtactctca cacttgtgtc   8520
```

-continued

```
gcggccgtaa gcttggatcc tctagagcgg ccgccctttt tttttttttt ttgtggaaca    8580
gtgaatttga aatatctcga cgagtggcag aaaattattt aacacctagg agaatgttga    8640
ttttggtgca gtacagatga gtagacggcg atggggccac gaatctacat tattgcacat    8700
gacactcctg tgcctgtgcc agtaacttgt gctccttggc ctcctcctac gcggctccag    8760
gcttgcgaca ggtgatgatg gtgaatttga tgaggccctt cttgtagccc tggatcatta    8820
gcggcatcac catcgcgcct ctgatcgtct tccatccggt cgtcagcaga gaggtgaagc    8880
ccttccatgt tagcgctgat tttatcacgg cgggccaaaa cggggccacg ttctccgacc    8940
agtcagctgt cttgatatcc tcgagagaca gtgacttggc aatgtccaca tagtctgaag    9000
gtgagcacca gtccgggagg tagtacgcgt cgcatatcct cctcaggagg ctcagttcat    9060
cgggctttag cgaggtttcg gatggatcca ggttcctatg gcaccatgtc acgatgatta    9120
ttgtccctcc aggagccgcc acgcgtgcta gctcactaac aaactttctc ttgtccggca    9180
tgtgctcgcc actctccatg gaccacacca gatcgaactg cccgtcagga aacggttgct    9240
ccagagcatc agcaacttgc agagtaacct gatccgacaa cccctgcgct gcagcgagag    9300
catttcctct ctcggcttga acagggctca acgtgatccc agtgcactgc gctccgtatt    9360
tcttcgccaa gtaccttgag ctaccaccaa tgccacatcc gacatcgact attgtttttg    9420
gtgtcttctc tggatcatct gaggctggga caccggcgaa ggcgagcgcc tcctcgatca    9480
tgcggatctg ggcgcggcgg tgatcggcca tggaggcggc ctcgctcgag tcgtagaagc    9540
cgtggtgcat gtggtcgccc cagatgttct cccacagccc cgacgactcg tcgtacagcc    9600
ccgcgatgcc ctccttcaga cccggcggcg ccgtcgcggg ggcctgagcc gtcgacgagg    9660
ccatcggacg caggctgacg acggcgcgtc ggagacggcg ggagtggcgc gggacgtgcg    9720
aaggggcgcg gtagtggctg ccgcggcggc aggctgcgag gctcctggag gactgggagc    9780
aatggagcag cgccgcgtga gccatttgcg gcgccgggat gcgcgatatt tggccgcttg    9840
gggggctatg gaagactttc ttagttagtt gtgtgaataa gcaatgttgg gagaatcggg    9900
actacttata ggataggaat aaaacagaaa agtattaagt gctaatgaaa tatttagact    9960
gataattaaa atcttcacgt atgtccactt gatataaaaa cgtcaggaat aaaggaagta   10020
cagtagaatt taaaggtact ctttttatat atacccgtgt tctcttttttg gctagctagt   10080
tgcataaaaa ataatctata tttttatcat tattttaaat atcttatgag atggtaaata   10140
tttatcataa tttttttac tattatttat tatttgtgtg tgtaatacat atagaagtta   10200
attacaaatt ttatttactt tttcattatt ttgatatgat tcaccattaa tttagtgtta   10260
ttatttataa tagttcattt taatcttttt gtatatatta tgcgtgcagt actttttcc   10320
tacatataac tactattaca ttttatttat ataatatttt tattaatgaa ttttcgtgat   10380
aatatgtaat attgttcatt attatttcag attttttaaa aatatttgtg ttattattta   10440
tgaaatatgt aatttttttta gtatttgatt ttatgatgat aaagtgttct aaattcaaaa   10500
gaagggggaa agcgtaaaca ttaaaaaacg tcatcaaaca aaaacaaaat cttgttaata   10560
aagataaaac tgtttgtttt gatcactgtt atttcgtaat ataaaaacat tatttatatt   10620
tatattgttg acaaccaaat ttgcctatca aatctaacca atataatgca tgcgtggcag   10680
gtaatgtact accatgaact taagtcatga cataataaac cgtgaatctg accaatgcat   10740
gtacctanct aaattgtatt tgtgacacga agcaaatgat tcaattcaca atggagatgg   10800
gaaacaaata atgaagaacc cagaactaag aaagcttttc tgaaaaataa aataaaggca   10860
atgtcaaaag tatactgcat catcagtcca gaaagcacat gatatttttt tatcagtatc   10920
```

```
aatgcagcta gttttatttt acaatatcga tatagctagt ttaaatatat tgcagctaga  10980

tttataaata tttgtgttat tatttatcat ttgtgtaatc ctgtttttag tattttagtt  11040

tatatatgat gataatgtat tccaaattta aaagaaggga aataaattta aacaagaaaa  11100

aaagtcatca aacaaaaaac aaatgaaagg gtggaaagat gttaccatgt aatgtgaatg  11160

ttacagtatt tcttttatta tagagttaac aaattaacta atatgatttt gttaataatg  11220

ataaaatatt ttttttatta ttatttcata atataaaaat agtttactta atataaaaaa  11280

aattctatcg ttcacaacaa agttggccac ctaatttaac catgcatgta cccatggacc  11340

atattaggta accatcaaac ctgatgaaga gataaagaga tgaagactta agtcataaca  11400

caaaaccata aaaaacaaaa atacaatcaa ccgtcaatct gaccaatgca tgaaaaagct  11460

gcaatagtga gtggcgacac aaagcacatg attttcttac aacggagata aaaccaaaaa  11520

aatatttcat gaacaaccta gaacaaataa agcttttata taataaatat ataaataaat  11580

aaaggctatg gaataatata cttcaatata tttggattaa ataaattgtt ggcggggttg  11640

atatatttat acacacctaa agtcacttca atctcatttt cacttaactt ttattttttt  11700

tttcttttta tttatcataa agagaatatt gataatatac tttttaacat atttttatga  11760

catttttat  tggtgaaaac ttattaaaaa tcataaattt tgtaagttag atttatttaa  11820

agagttcctc ttcttatttt aaatttttta ataaattttt aaataactaa aatttgtgtt  11880

aaaaatgtta aaaaagtgtg ttattaaccc ttctcttcga ggatccaagc ttgg        11934
```

```
<210> SEQ ID NO 52
<211> LENGTH: 9779
<212> TYPE: DNA
<213> ORGANISM: Artificial Sequence
<220> FEATURE:
<223> OTHER INFORMATION: sequence of the T-DNA of the plant
      transformation vector pZBL120xKS325xSC38
<220> FEATURE:
<221> NAME/KEY: misc_feature
<222> LOCATION: (4282)..(4282)
<223> OTHER INFORMATION: n is a, c, g, or t

<400> SEQUENCE: 52
```

```
aattacaacg gtatatatcc tgccgcgtcg acggatccaa gcttgttgaa acatccctga     60

agtgtctcat tttattttat ttattctttg ctgataaaaa aataaaaataa aagaagctaa   120

gcacacggtc aaccattgct ctactgctaa aagggttatg tgtagtgttt tactgcataa    180

attatgcagc aaacaagaca actcaaatta aaaaatttcc tttgcttgtt tttttgttgt    240

ctctgacttg actttcttgt ggaagttggt tgtataagga ttgggacacc attgtccttc    300

ttaatttaat tttattcttt gctgataaaa aaaaaaattt catatagtgt taaataataa    360

tttgttaaat aaccaaaaag tcaaatatgt ttactctcgt ttaaataatt gagattcgtc    420

cagcaaggct aaacgattgt atagatttat gacaatattt actttttttat agataaatgt   480

tatattataa taaatttata tacatatatt atatgttatt tattattatt ttaaatcctt    540

caatatttta tcaaaccaac tcataatttt ttttttatct gtaagaagca ataaaattaa    600

atagacccac tttaaggatg atccaacctt tatacagagt aagagagttc aaatagtacc    660

ctttcatata catatcaact aaaatattag aaatatcatg gatcaaacct tataaagaca    720

ttaaataagt ggataagtat aatatataaa tgggtagtat ataatatata aatggataca    780

aacttctctc tttataattg ttatgtctcc ttaacatcct aatataatac ataagtgggt    840

aatatataat atataaatgg agacaaactt cttccattat aattgttatg tcttcttaac    900

acttatgtct cgttcacaat gctaaggtta gaattgttta gaaagtctta tagtacacat    960
```

-continued

```
ttgtttttgt actatttgaa gcattccata agccgtcacg attcagatga tttataataa   1020
taagaggaaa tttatcatag aacaataagg tgcatagata gagtgttaat atatcataac   1080
atcctttgtt tattcataga agaagtgaga tggagctcag ttattatact gttacatggt   1140
cggatacaat attccatgct ctccatgagc tcttacacct acatgcattt tagttcatac   1200
ttgcggccgc ttcacatctg ctggcccttg tacaaatttc actgcacaaa tggtataagg   1260
aaatactctg catagaatag cttccaaatg aacatgtaaa atgatgtgac acgcgcttgg   1320
ttttcaacct caaagtgctg cgctctctgc caaagtgtca aagcaagcag gccatgacca   1380
gacacagtga tgatcttttg aaataggttt gtggatgaag ctcctactag agtggcagcg   1440
ccataggctg tcaacaatat gcttatgcag agctgataca ctctttgagg ccccaatctc   1500
acactcaagg attggatacc aaagtctcga tctccatcaa catctggaat atccttgaat   1560
agtgctatga cggcagagaa gcaacacata aacaatgttg caaacaccag cgatttggtt   1620
gctgccaatg gccttttcag aacatgttgc tgcatatgtg caaagaaagc caactggacc   1680
aagatagccc tcacaaatag gatacatgat gcagcgagga gcgcgtgccg tttccaccgg   1740
aggaacggag cctcaatgga gtacgcactt ccaagaagga agctgacaat taaagcacac   1800
atcagtggcg ccgatccgga acgtattcct atgctaaagc tcatgatcag gaatgcgagt   1860
actaagaaaa ctccagttgc tactgaaaat tccccagatg ccaatggaag acctggcttg   1920
ttgatcttgt caatctgaat gtcatatagc tgattcagcc cgaccacata aatgttcata   1980
cataaagcag cagtcaaagc ctcgagatat cctcgtagta ccgtgacagt aaaatcatct   2040
atgctcttca ttggcaggag agacactgaa gttataccta ttatagtgcc aaaaattgtg   2100
tgtggcctgc aaaattcata gaaagagcgc aatttcttca aaacatctcc cctgatttcc   2160
tcaagccgat tggcgttgga accgttttga tcccaattaa cctcgctgca tccagcttgg   2220
agggctggat aatcatcgct gcactgtctc tttgtgtttc ttctaggcct agcagcttga   2280
gaaatggcac tgaatttatg cattacagta gtagcacttt ggcactggcc tgcaaaagct   2340
tccactgcaa atcgacctgt ccaggataat ctcgtcgttc ccagccgagc cctacatctg   2400
ggccctctcc tcgtatctgt tagcagctgc cccgccgtgg ccgccgccgt gacggcttgc   2460
atcctgcggc cgcagtatat cttaaattct ttaatacggt gtactaggat attgaactgg   2520
ttcttgatga tgaaaacctg ggccgagatt gcagctattt atagtcatag gtcttgttaa   2580
catgcatgga catttggcca cggggtggca tgcagtttga cgggtgttga aataaacaaa   2640
aatgaggtgg cggaagagaa tacgagtttg aggttgggtt agaaacaaca aatgtgaggg   2700
ctcatgatgg gttgagttgg tgaatgtttt gggctgctcg attgacacct ttgtgagtac   2760
gtgttgttgt gcatggcttt tggggtccag tttttttttc ttgacgcggc gatcctgatc   2820
agctagtgga taagtgatgt ccactgtgtg tgattgcgtt tttgtttgaa ttttatgaac   2880
ttagacattg ctatgcaaag gatactctca ttgtgttttg tcttcttttg ttccttggct   2940
ttttcttatg atccaagaga ctagtcagtg ttgtggcatt cgagactacc aagattaatt   3000
atgatggggg aaggataagt aactgattag tacggactgt taccaaatta attaataagc   3060
ggcaaatgaa gggcatggat caaaagcttg gcgcgccaag cttggatcct cgaagagaag   3120
ggttaataac acactttttt aacattttta acacaaattt tagttattta aaaatttatt   3180
aaaaaattta aaataagaag aggaactctt taaataaatc taacttacaa aatttatgat   3240
ttttaataag ttttcaccaa taaaaaatgt cataaaaata tgttaaaaag tatattatca   3300
atattctctt tatgataaat aaaaagaaaa aaaaaataaa agttaagtga aaatgagatt   3360
```

-continued

```
gaagtgactt taggtgtgta taaatatatc aaccccgcca acaatttatt taatccaaat   3420
atattgaagt atattattcc atagccttta tttatttata tatttattat ataaaagctt   3480
tatttgttct aggttgttca tgaaatattt ttttggtttt atctccgttg taagaaaatc   3540
atgtgctttg tgtcgccact cactattgca gctttttcat gcattggtca gattgacggt   3600
tgattgtatt tttgtttttt atggttttgt gttatgactt aagtcttcat ctctttatct   3660
cttcatcagg tttgatggtt acctaatatg gtccatgggt acatgcatgg ttaaattagg   3720
tggccaactt tgttgtgaac gatagaattt tttttatatt aagtaaacta tttttatatt   3780
atgaaataat aataaaaaaa atattttatc attattaaca aaatcatatt agttaatttg   3840
ttaactctat aataaaagaa atactgtaac attcacatta catggtaaca tctttccacc   3900
ctttcatttg tttttttgttt gatgactttt tttcttgttt aaatttattt cccttctttt   3960
aaatttggaa tacattatca tcatatataa actaaaatac taaaaacagg attacacaaa   4020
tgataaataa taacacaaat atttataaat ctagctgcaa tatatttaaa ctagctatat   4080
cgatattgta aaataaaact agctgcattg atactgataa aaaaatatca tgtgctttct   4140
ggactgatga tgcagtatac ttttgacatt gcctttattt tatttttcag aaaagctttc   4200
ttagttctgg gttcttcatt atttgtttcc catctccatt gtgaattgaa tcatttgctt   4260
cgtgtcacaa atacaattta gntaggtaca tgcattggtc agattcacgg tttattatgt   4320
catgacttaa gttcatggta gtacattacc tgccacgcat gcattatatt ggttagattt   4380
gataggcaaa tttggttgtc aacaatataa atataaataa tgtttttata ttacgaaata   4440
acagtgatca aaacaaacag ttttatcttt attaacaaga ttttgttttt gtttgatgac   4500
gttttttaat gtttacgctt tccccccttct tttgaattta gaacacttta tcatcataaa   4560
atcaaatact aaaaaaatta catatttcat aaataataac acaaatattt ttaaaaaatc   4620
tgaaataata atgaacaata ttacatatta tcacgaaaat tcattaataa aaatattata   4680
taaataaaat gtaatagtag ttatatgtag gaaaaaagta ctgcacgcat aatatataca   4740
aaaagattaa aatgaactat tataaataat aacactaaat taatggtgaa tcatatcaaa   4800
ataatgaaaa agtaaataaa atttgtaatt aacttctata tgtattacac acacaaataa   4860
taaataatag taaaaaaaat tatgataaat atttaccatc tcataagata tttaaaataa   4920
tgataaaaat atagattatt ttttatgcaa ctagctagcc aaaaagagaa cacgggtata   4980
tataaaaaga gtacctttaa attctactgt acttccttta ttcctgacgt ttttatatca   5040
agtggacata cgtgaagatt ttaattatca gtctaaatat ttcattagca cttaatactt   5100
ttctgtttta ttcctatcct ataagtagtc ccgattctcc caacattgct tattcacaca   5160
actaactaag aaagtcttcc atagcccccc aagcggccaa atatcgcgca tcccggcgcc   5220
gcaaatggct cacgcggcgc tgctccattg ctcccagtcc tccaggagcc tcgcagcctg   5280
ccgccgcggc agccactacc gcgccccttc gcacgtcccg cgccactccc gccgtctccg   5340
acgcgccgtc gtcagcctgc gtccgatggc ctcgtcgacg gctcaggccc ccgcgacggc   5400
gccgccgggt ctgaaggagg gcatcgcggg gctgtacgac gagtcgtcgg ggctgtggga   5460
gaacatctgg ggcgaccaca tgcaccacgg cttctacgac tcgagcgagg ccgcctccat   5520
ggccgatcac cgccgcgccc agatccgcat gatcgaggag gcgctcgcct tcgccggtgt   5580
cccagcctca gatgatccag agaagacacc aaaaacaata gtcgatgtcg gatgtggcat   5640
tggtggtagc tcaaggtact tggcgaagaa atacggagcg cagtgcactg ggatcacgtt   5700
gagccctgtt caagccgaga gaggaaatgc tctcgctgca gcgcaggggt tgtcggatca   5760
```

```
ggttactctg caagttgctg atgctctgga gcaaccgttt cctgacgggc agttcgatct   5820
ggtgtggtcc atggagagtg gcgagcacat gccggacaag agaaagtttg ttagtgagct   5880
agcacgcgtg gcggctcctg gagggacaat aatcatcgtg acatggtgcc ataggaacct   5940
ggatccatcc gaaacctcgc taaagcccga tgaactgagc ctcctgagga ggatatgcga   6000
cgcgtactac ctcccggact ggtgctcacc ttcagactat gtggacattg ccaagtcact   6060
gtctctcgag gatatcaaga cagctgactg gtcggagaac gtggccccgt tttggcccgc   6120
cgtgataaaa tcagcgctaa catggaaggg cttcacctct ctgctgacga ccggatggaa   6180
gacgatcaga ggcgcgatgg tgatgccgct aatgatccag ggctacaaga agggcctcat   6240
caaattcacc atcatcacct gtcgcaagcc tggagccgcg taggaggagg ccaaggagca   6300
caagttactg gcacaggcac aggagtgtca tgtgcaataa tgtagattcg tggccccatc   6360
gccgtctact catctgtact gcaccaaaat caacattctc ctaggtgtta aataattttc   6420
tgccactcgt cgagatattt caaattcact gttccacaaa aaaaaaaaaa aaagggcggc   6480
cgctctagag gatccaagct tacggccgcg acacaagtgt gagagtacta aataaatgct   6540
ttggttgtac gaaatcatta cactaaataa aataatcaaa gcttatatat gccttccgct   6600
aaggccgaat gcaaagaaat tggttctttc tcgttatctt ttgccacttt tactagtacg   6660
tattaattac tacttaatca tctttgttta cggctcatta tatccgtcga ctctagagga   6720
tccccgggta ccgagctcga attcactggc cgtcgtttta caacgtcgtg actgggaaaa   6780
ccctggcgtt acccaactta atcgccttgc agcacatccc cctttcgcca gctggcgtaa   6840
tagcgaagag gcccgcaccg atcgcccttc ccaacagttg cgcagcctga atggcgaatg   6900
gatcgatccg tcgatcgacc aaagcggcca tcgtgcctcc ccactcctgc agttcggggg   6960
catggatgcg cggatagccg ctgctggttt cctggatgcc gacggatttg cactgccggt   7020
agaactccgc gaggtcgtcc agcctcaggc agcagctgaa ccaactcgcg aggggatcga   7080
gcccctgctg agcctcgaca tgttgtcgca aaattcgccc tggacccgcc caacgatttg   7140
tcgtcactgt caaggtttga cctgcacttc atttggggcc cacatacacc aaaaaaatgc   7200
tgcataattc tcggggcagc aagtcggtta cccggccgcc gtgctggacc gggttgaatg   7260
gtgcccgtaa ctttcggtag agcggacggc caatactcaa cttcaaggaa tctcacccat   7320
gcgcgccggc ggggaaccgg agttcccttc agtgaacgtt attagttcgc cgctcggtgt   7380
gtcgtagata ctagcccctg gggccttttg aaatttgaat aagatttatg taatcagtct   7440
tttaggtttg accggttctg ccgctttttt taaaattgga tttgtaataa taaaacgcaa   7500
ttgtttgtta ttgtggcgct ctatcataga tgtcgctata aacctattca gcacaatata   7560
ttgttttcat tttaatattg tacatataag tagtagggta caatcagtaa attgaacgga   7620
gaatattatt cataaaaata cgatagtaac gggtgatata ttcattagaa tgaaccgaaa   7680
ccggcggtaa ggatctgagc tacacatgct caggtttttt acaacgtgca caacagaatt   7740
gaaagcaaat atcatgcgat cataggcgtc tcgcatatct cattaaagca gggggtgggc   7800
gaagaactcc agcatgagat ccccgcgctg gaggatcatc cagccggcgt cccggaaaac   7860
gattccgaag cccaaccttt catagaaggc ggcggtggaa tcgaaatctc gtgatggcag   7920
gttgggcgtc gcttggtcgg tcatttcgaa ccccagagtc ccgctcagaa gaactcgtca   7980
agaaggcgat agaaggcgat gcgctgcgaa tcgggagcgg cgataccgta aagcacgagg   8040
aagcggtcag cccattcgcc gccaagctct tcagcaatat cacgggtagc caacgctatg   8100
tcctgatagc ggtccgccac acccagccgg ccacagtcga tgaatccaga aaagcggcca   8160
```

```
ttttccacca tgatattcgg caagcaggca tcgccatggg tcacgacgag atcctcgccg   8220
tcgggcatgc gcgccttgag cctggcgaac agttcggctg gcgcgagccc ctgatgctct   8280
tcgtccagat catcctgatc gacaagaccg gcttccatcc gagtacgtgc tcgctcgatg   8340
cgatgtttcg cttggtggtc gaatgggcag gtagccggat caagcgtatg cagccgccgc   8400
attgcatcag ccatgatgga tactttctcg gcaggagcaa ggtgagatga caggagatcc   8460
tgccccggca cttcgcccaa tagcagccag tcccttcccg cttcagtgac aacgtcgagc   8520
acagctgcgc aaggaacgcc cgtcgtggcc agccacgata gccgcgctgc ctcgtcctgc   8580
agttcattca gggcaccgga caggtcggtc ttgacaaaaa gaaccgggcg cccctgcgct   8640
gacagccgga acacggcggc atcagagcag ccgattgtct gttgtgccca gtcatagccg   8700
aatagcctct ccacccaagc ggccggagaa cctgcgtgca atccatcttg ttcaatcatg   8760
cgaaacgatc cccgcaagct tggagactgg tgatttcagc gtgtcctctc caaatgaaat   8820
gaacttcctt atatagagga agggtcttgc gaaggatagt gggattgtgc gtcatccctt   8880
acgtcagtgg agatatcaca tcaatccact tgctttgaag acgtggttgg aacgtcttct   8940
ttttccacga tgctcctcgt gggtgggggt ccatctttgg gaccactgtc ggcagaggca   9000
tcttcaacga tggcctttcc tttatcgcaa tgatggcatt tgtaggagcc accttccttt   9060
tccactatct tcacaataaa gtgacagata gctgggcaat ggaatccgag gaggtttccg   9120
gatattaccc tttgttgaaa agtctcaatt gccctttggt cttctgagac tgtatctttg   9180
atatttttgg agtagacaag cgtgtcgtgc tccaccatgt tgacgaagat tttcttcttg   9240
tcattgagtc gtaagagact ctgtatgaac tgttcgccag tctttacggc gagttctgtt   9300
aggtcctcta tttgaatctt tgactccatg gcctttgatt cagtgggaac tacctttta    9360
gagactccaa tctctattac ttgccttggt ttgtgaagca agccttgaat cgtccatact   9420
ggaatagtac ttctgatctt gagaaatata tctttctctg tgttcttgat gcagttagtc   9480
ctgaatcttt tgactgcatc tttaaccttc ttgggaaggt atttgatctc ctggagatta   9540
ttgctcgggt agatcgtctt gatgagacct gctgcgtaag cctctctaac catctgtggg   9600
ttagcattct ttctgaaatt gaaaaggcta atcttctcat tatcagtggt gaacatggta   9660
tcgtcacctt ctccgtcgaa cttcctgact agatcgtaga gatagaggaa gtcgtccatt   9720
gtgatctctg gggcaaagga gatctgaatt atcatttaca attgaatata tcctgccat    9779
```

```
<210> SEQ ID NO 53
<211> LENGTH: 1005
<212> TYPE: DNA
<213> ORGANISM: Momordica charantia
<220> FEATURE:
<221> NAME/KEY: CDS
<222> LOCATION: (1)..(1005)

<400> SEQUENCE: 53

atg gct tct gca atg ctc aat gga gct gaa agc ctc aag ctc acc aga       48
Met Ala Ser Ala Met Leu Asn Gly Ala Glu Ser Leu Lys Leu Thr Arg
1               5                   10                  15

gga ttg gcc ccc aag ggc ttg ggt ttt tcg ggt tcg aat ttt ccc aga       96
Gly Leu Ala Pro Lys Gly Leu Gly Phe Ser Gly Ser Asn Phe Pro Arg
            20                  25                  30

ttg ggt att gtt tcc acc tat aga tgt tcc aag gcc gcg ccc atg gcg      144
Leu Gly Ile Val Ser Thr Tyr Arg Cys Ser Lys Ala Ala Pro Met Ala
        35                  40                  45

cct aag tgc agt ctt tct gct tcc agg cca gct tct cag cct agg ttc      192
Pro Lys Cys Ser Leu Ser Ala Ser Arg Pro Ala Ser Gln Pro Arg Phe
```

```
    50                  55                  60

att caa cac aag aag gag gca ttc tgg ttc tat agg ttt ctc tca atc      240
Ile Gln His Lys Lys Glu Ala Phe Trp Phe Tyr Arg Phe Leu Ser Ile
65                  70                  75                  80

gtg tac gac cac atc ata aac cct ggg cat tgg acc gag gac atg agg      288
Val Tyr Asp His Ile Ile Asn Pro Gly His Trp Thr Glu Asp Met Arg
                85                  90                  95

gat gaa gct ctc gag cct gca gat ctc agc gat agg aat atg att gtg      336
Asp Glu Ala Leu Glu Pro Ala Asp Leu Ser Asp Arg Asn Met Ile Val
            100                 105                 110

gta gat gtt ggt ggt ggt act ggt ttt act act tta ggg ata gtc aag      384
Val Asp Val Gly Gly Gly Thr Gly Phe Thr Thr Leu Gly Ile Val Lys
        115                 120                 125

cac gtg gat gcc aaa aat gtg acc atc ctg gac caa tcg cct cat cag      432
His Val Asp Ala Lys Asn Val Thr Ile Leu Asp Gln Ser Pro His Gln
    130                 135                 140

ctt gcc aag gct aag cag aag gag ccc ttg aag gat tgc aaa atc att      480
Leu Ala Lys Ala Lys Gln Lys Glu Pro Leu Lys Asp Cys Lys Ile Ile
145                 150                 155                 160

gaa ggg gat gct gag gat ctc cca ttt cgt act gat tat gca gat aga      528
Glu Gly Asp Ala Glu Asp Leu Pro Phe Arg Thr Asp Tyr Ala Asp Arg
                165                 170                 175

tat gta tct gct gga agt att gaa tac tgg cca gat cca cag cgt ggc      576
Tyr Val Ser Ala Gly Ser Ile Glu Tyr Trp Pro Asp Pro Gln Arg Gly
            180                 185                 190

atc acg gaa gca tat agg gtc ctg aaa ctt ggt gga aaa gca tgt cta      624
Ile Thr Glu Ala Tyr Arg Val Leu Lys Leu Gly Gly Lys Ala Cys Leu
        195                 200                 205

att ggt ccg gtg tac cca acg ttt tgg ctg tct cgc ttc ttt gca gat      672
Ile Gly Pro Val Tyr Pro Thr Phe Trp Leu Ser Arg Phe Phe Ala Asp
    210                 215                 220

gtg tgg atg ctt ttc cca aag gaa gaa gag tat att gag tgg ttc aaa      720
Val Trp Met Leu Phe Pro Lys Glu Glu Glu Tyr Ile Glu Trp Phe Lys
225                 230                 235                 240

aat gct gga ttt aaa gat gtc caa ttg aaa agg att ggt cca aaa tgg      768
Asn Ala Gly Phe Lys Asp Val Gln Leu Lys Arg Ile Gly Pro Lys Trp
                245                 250                 255

tac cga gga gtt cgc cgg cat ggg cta atc atg gga tgt tct gtg act      816
Tyr Arg Gly Val Arg Arg His Gly Leu Ile Met Gly Cys Ser Val Thr
            260                 265                 270

gga gtg aag cct tat tct ggt gaa tct cct ttg cag ctc ggt ccc aag      864
Gly Val Lys Pro Tyr Ser Gly Glu Ser Pro Leu Gln Leu Gly Pro Lys
        275                 280                 285

gaa gag gat gtg tcg aaa cct gta aat cca ttt gtg ttc ctg gct cgc      912
Glu Glu Asp Val Ser Lys Pro Val Asn Pro Phe Val Phe Leu Ala Arg
    290                 295                 300

ttc ctt ctg gga gcc atg gca gct aca tac tat gtg ctg gtt ccc ata      960
Phe Leu Leu Gly Ala Met Ala Ala Thr Tyr Tyr Val Leu Val Pro Ile
305                 310                 315                 320

tac atg tgg atg aaa gat cag att gtt cca gaa ggg caa cca atc         1005
Tyr Met Trp Met Lys Asp Gln Ile Val Pro Glu Gly Gln Pro Ile
                325                 330                 335


<210> SEQ ID NO 54
<211> LENGTH: 335
<212> TYPE: PRT
<213> ORGANISM: Momordica charantia

<400> SEQUENCE: 54

Met Ala Ser Ala Met Leu Asn Gly Ala Glu Ser Leu Lys Leu Thr Arg
1               5                   10                  15
```

```
Gly Leu Ala Pro Lys Gly Leu Gly Phe Ser Gly Ser Asn Phe Pro Arg
            20                  25                  30

Leu Gly Ile Val Ser Thr Tyr Arg Cys Ser Lys Ala Ala Pro Met Ala
        35                  40                  45

Pro Lys Cys Ser Leu Ser Ala Ser Arg Pro Ala Ser Gln Pro Arg Phe
    50                  55                  60

Ile Gln His Lys Lys Glu Ala Phe Trp Phe Tyr Arg Phe Leu Ser Ile
65                  70                  75                  80

Val Tyr Asp His Ile Ile Asn Pro Gly His Trp Thr Glu Asp Met Arg
                85                  90                  95

Asp Glu Ala Leu Glu Pro Ala Asp Leu Ser Asp Arg Asn Met Ile Val
            100                 105                 110

Val Asp Val Gly Gly Gly Thr Gly Phe Thr Thr Leu Gly Ile Val Lys
        115                 120                 125

His Val Asp Ala Lys Asn Val Thr Ile Leu Asp Gln Ser Pro His Gln
    130                 135                 140

Leu Ala Lys Ala Lys Gln Lys Glu Pro Leu Lys Asp Cys Lys Ile Ile
145                 150                 155                 160

Glu Gly Asp Ala Glu Asp Leu Pro Phe Arg Thr Asp Tyr Ala Asp Arg
                165                 170                 175

Tyr Val Ser Ala Gly Ser Ile Glu Tyr Trp Pro Asp Pro Gln Arg Gly
            180                 185                 190

Ile Thr Glu Ala Tyr Arg Val Leu Lys Leu Gly Gly Lys Ala Cys Leu
        195                 200                 205

Ile Gly Pro Val Tyr Pro Thr Phe Trp Leu Ser Arg Phe Phe Ala Asp
    210                 215                 220

Val Trp Met Leu Phe Pro Lys Glu Glu Glu Tyr Ile Glu Trp Phe Lys
225                 230                 235                 240

Asn Ala Gly Phe Lys Asp Val Gln Leu Lys Arg Ile Gly Pro Lys Trp
                245                 250                 255

Tyr Arg Gly Val Arg Arg His Gly Leu Ile Met Gly Cys Ser Val Thr
            260                 265                 270

Gly Val Lys Pro Tyr Ser Gly Glu Ser Pro Leu Gln Leu Gly Pro Lys
        275                 280                 285

Glu Glu Asp Val Ser Lys Pro Val Asn Pro Phe Val Phe Leu Ala Arg
    290                 295                 300

Phe Leu Leu Gly Ala Met Ala Ala Thr Tyr Tyr Val Leu Val Pro Ile
305                 310                 315                 320

Tyr Met Trp Met Lys Asp Gln Ile Val Pro Glu Gly Gln Pro Ile
                325                 330                 335
```

<210> SEQ ID NO 55
<211> LENGTH: 27
<212> TYPE: DNA
<213> ORGANISM: Artificial
<220> FEATURE:
<223> OTHER INFORMATION: Forward primer for PCR of MC-VTE3

<400> SEQUENCE: 55
caccatggct tctgcaatgc tcaatgg 27

<210> SEQ ID NO 56
<211> LENGTH: 27
<212> TYPE: DNA
<213> ORGANISM: Artificial
<220> FEATURE:
<223> OTHER INFORMATION: Reverse primer for PCR of MC-VTE3

<400> SEQUENCE: 56
ctccccaact cagattggtt gcccttc 27

<210> SEQ ID NO 57
<211> LENGTH: 8547
<212> TYPE: DNA
<213> ORGANISM: Artificial
<220> FEATURE:
<223> OTHER INFORMATION: Expression plasmid pKR561-MCVTE3

<400> SEQUENCE: 57
ggccgctgaa gtattgcttc ttagttaacc tttcctttct ctctcagcta tgtgaattca 60
ttttgctttc gtcacaattt atatagtgaa attggatctt tggagttaac gccttcacag 120
gattatcgtg ttagaacaat gctttttcat gttctaatta gtagtacatt acaaatgtgc 180
actctattca ataagcatct tttggcacgt taataaatca tgtgaaaaaa aaatactact 240
atttcaaaga aagtgttgta aaaagaaacg gaaagagagc tggcttcagt tgttgagact 300
tgtttgctag taaaaatggt gtgaagagtg attcatggtg aggtggtttt tcgtcccttt 360
ctgtttgcat gaaaaacaaa tggcaagaga tgacgtagga ttccttccct taacgattat 420
ctgtttttaa tttcaaatat acatatagga atttatgaat tactaaggtt gtaaaatatg 480
ctggtcattt atttatggct aaaatatttt tttttctcgt aaatataaaa atatttaaaa 540
tttattttta tcatattttt tatccttata aaattatgtg tacaacctat ataaaaaaat 600
atcatattta atattgatta tatgtttaat caatataaaa aatcattatc atatatttag 660
atttattcga atatacatct aaacaaaaaa taacatattt taattttatg aagaaaaaaa 720
aatattttat cctttattta tttaagatta attaatagtt atgtattgtg gaaagacttt 780
tacacatgca atagatatac tgaatcaatt agatgccaat gctgagttgg aaatcacttg 840
aggaggggag gagacttgcc aatgcttttc agtttcattt aaatgattta gtggaggaga 900
tagagtagtg ataaaggcat gccccaattt tggagtgtat atatgagtgg aaataagaga 960
gggatagaga gaaaaaataa agagagtaaa aataattaat gtgaaatgat atgataaaaa 1020
aataaagaaa gagataaaga gaaaaatgaa atgagagata gatgaaatag agagtagata 1080
catgtttgtt taggtttttt ttaggaaata acacattttt ttctcatcac ttattactca 1140
ctgtcaattt cctctctttc aatcataatg atatgatttg tttaacaaaa atgtgaaaaa 1200
acatataaag taaaatattt ttataaattg ataaataaaa atttacaaaa tttatttctt 1260
attaaattga atagaaaatg aaagaaaaga aaagaaaaag tatatataaa atgatatagc 1320
tttaaaaaga ataaattttt catatcagtc ttttttaat aatttagaaa tatttaagta 1380
tatagcaaaa atataatgta ctttacatat gcataaataa taatttgaaa atagaactaa 1440
tagaatagag aaaaaagtaa tataataatt aactatatga aaatttagaa gggacaatat 1500
ttttaattaa gaatataaac aatatttctt ttcatgtaat gagggacgga tgtacggggc 1560
cagtgttgga gtcaaagcca aaatagtcac ggggaaatta atgcactgca tgactattcg 1620
aaaaaattca ctagccttac ttagatgtta gattaatagc tagggggtgc agataatttt 1680
gaaaggcatg aaaaacatta atttgtacat tgcaagcttt tgatgacaag ctttgcaatt 1740
gttcacacta ccttatgcca tttataaata gagtgattgg catatgaagg aaatcatgag 1800
agtcgaagcg aaaaacaaag cttgagagtg taggaaaaat acagtttttt tggtaaaaat 1860
acagtatttg aataggagcg aaaaatatcc tttcaaaatg atccttttct tttttttttt 1920
ttttcttgtt gttcttggtc agttattcaa aggaaaaggg attgaaataa aaacttgcat 1980

```
gtgggatcgt acgtcgagtc gacggcgcgc ccgatcatcc ggatatagtt cctcctttca   2040
gcaaaaaacc cctcaagacc cgtttagagg ccccaagggg ttatgctagt tattgctcag   2100
cggtggcagc agccaactca gcttcctttc gggctttgtt agcagccgga tcgatccaag   2160
ctgtacctca ctattccttt gccctcggac gagtgctggg gcgtcggttt ccactatcgg   2220
cgagtacttc tacacagcca tcggtccaga cggccgcgct tctgcgggcg atttgtgtac   2280
gcccgacagt cccggctccg gatcggacga ttgcgtcgca tcgaccctgc gcccaagctg   2340
catcatcgaa attgccgtca accaagctct gatagagttg gtcaagacca atgcggagca   2400
tatacgcccg gagccgcggc gatcctgcaa gctccggatg cctccgctcg aagtagcgcg   2460
tctgctgctc catacaagcc aaccacggcc tccagaagaa gatgttggcg acctcgtatt   2520
gggaatcccc gaacatcgcc tcgctccagt caatgaccgc tgttatgcgg ccattgtccg   2580
tcaggacatt gttggagccg aaatccgcgt gcacgaggtg ccggacttcg gggcagtcct   2640
cggcccaaag catcagctca tcgagagcct gcgcgacgga cgcactgacg gtgtcgtcca   2700
tcacagtttg ccagtgatac acatggggat cagcaatcgc gcatatgaaa tcacgccatg   2760
tagtgtattg accgattcct tgcggtccga atgggccgaa cccgctcgtc tggctaagat   2820
cggccgcagc gatcgcatcc atagcctccg cgaccggctg cagaacagcg ggcagttcgg   2880
tttcaggcag gtcttgcaac gtgacaccct gtgcacggcg ggagatgcaa taggtcaggc   2940
tctcgctgaa ttccccaatg tcaagcactt ccggaatcgg gagcgcggcc gatgcaaagt   3000
gccgataaac ataacgatct ttgtagaaac catcggcgca gctatttacc cgcaggacat   3060
atccacgccc tcctacatcg aagctgaaag cacgagattc ttcgccctcc gagagctgca   3120
tcaggtcgga gacgctgtcg aacttttcga tcagaaactt ctcgacagac gtcgcggtga   3180
gttcaggctt ttccatgggt atatctcctt cttaaagtta aacaaaatta tttctagagg   3240
gaaaccgttg tggtctccct atagtgagtc gtattaattt cgcgggatcg agatcgatcc   3300
aattccaatc ccacaaaaat ctgagcttaa cagcacagtt gctcctctca gagcagaatc   3360
gggtattcaa caccctcata tcaactacta cgttgtgtat aacggtccac atgccggtat   3420
atacgatgac tggggttgta caaaggcggc aacaaacggc gttcccggag ttgcacacaa   3480
gaaatttgcc actattacag aggcaagagc agcagctgac gcgtacacaa caagtcagca   3540
aacagacagg ttgaacttca tccccaaagg agaagctcaa ctcaagccca agagctttgc   3600
taaggcccta acaagcccac caaagcaaaa agcccactgg ctcacgctag gaaccaaaag   3660
gcccagcagt gatccagccc caaaagagat ctcctttgcc ccggagatta caatggacga   3720
tttcctctat ctttacgatc taggaaggaa gttcgaaggt gaaggtgacg acactatgtt   3780
caccactgat aatgagaagg ttagcctctt caatttcaga aagaatgctg acccacagat   3840
ggttagagag gcctacgcag caggtctcat caagacgatc tacccgagta acaatctcca   3900
ggagatcaaa taccttccca agaaggttaa agatgcagtc aaaagattca ggactaattg   3960
catcaagaac acagagaaag acatatttct caagatcaga agtactattc cagtatggac   4020
gattcaaggc ttgcttcata aaccaaggca agtaatagag attggagtct ctaaaaaggt   4080
agttcctact gaatctaagg ccatgcatgg agtctaagat tcaaatcgag gatctaacag   4140
aactcgccgt gaagactggc gaacagttca tacagagtct tttacgactc aatgacaaga   4200
agaaaatctt cgtcaacatg gtggagcacg acactctggt ctactccaaa aatgtcaaag   4260
atacagtctc agaagaccaa agggctattg agacttttca acaaaggata atttcgggaa   4320
acctcctcgg attccattgc ccagctatct gtcacttcat cgaaaggaca gtagaaaagg   4380
```

```
aaggtggctc ctacaaatgc catcattgcg ataaaggaaa ggctatcatt caagatgcct   4440
ctgccgacag tggtcccaaa gatggacccc cacccacgag gagcatcgtg gaaaaagaag   4500
acgttccaac cacgtcttca aagcaagtgg attgatgtga catctccact gacgtaaggg   4560
atgacgcaca atcccactat ccttcgcaag acccttcctc tatataagga agttcatttc   4620
atttggagag gacacgctcg agctcatttc tctattactt cagccataac aaaagaactc   4680
ttttctcttc ttattaaacc atgaaaaagc ctgaactcac cgcgacgtct gtcgagaagt   4740
ttctgatcga aaagttcgac agcgtctccg acctgatgca gctctcggag ggcgaagaat   4800
ctcgtgcttt cagcttcgat gtaggagggc gtggatatgt cctgcgggta aatagctgcg   4860
ccgatggttt ctacaaagat cgttatgttt atcggcactt tgcatcggcc gcgctcccga   4920
ttccggaagt gcttgacatt ggggaattca gcgagagcct gacctattgc atctcccgcc   4980
gtgcacaggg tgtcacgttg caagacctgc ctgaaaccga actgcccgct gttctgcagc   5040
cggtcgcgga ggccatggat gcgatcgctg cggccgatct tagccagacg agcgggttcg   5100
gcccattcgg accgcaagga atcggtcaat acactacatg gcgtgatttc atatgcgcga   5160
ttgctgatcc ccatgtgtat cactggcaaa ctgtgatgga cgacaccgtc agtgcgtccg   5220
tcgcgcaggc tctcgatgag ctgatgcttt gggccgagga ctgccccgaa gtccggcacc   5280
tcgtgcacgc ggatttcggc tccaacaatg tcctgacgga caatggccgc ataacagcgg   5340
tcattgactg gagcgaggcg atgttcgggg attcccaata cgaggtcgcc aacatcttct   5400
tctggaggcc gtggttggct tgtatggagc agcagacgcg ctacttcgag cggaggcatc   5460
cggagcttgc aggatcgccg cggctccggg cgtatatgct ccgcattggt cttgaccaac   5520
tctatcagag cttggttgac ggcaatttcg atgatgcagc ttgggcgcag ggtcgatgcg   5580
acgcaatcgt ccgatccgga gccgggactg tcgggcgtac acaaatcgcc cgcagaagcg   5640
cggccgtctg gaccgatggc tgtgtagaag tactcgccga tagtggaaac cgacgcccca   5700
gcactcgtcc gagggcaaag gaatagtgag gtacctaaag aaggagtgcg tcgaagcaga   5760
tcgttcaaac atttggcaat aaagtttctt aagattgaat cctgttgccg gtcttgcgat   5820
gattatcata taatttctgt tgaattacgt taagcatgta ataattaaca tgtaatgcat   5880
gacgttattt atgagatggg tttttatgat tagagtcccg caattataca tttaatacgc   5940
gatagaaaac aaaatatagc gcgcaaacta ggataaatta tcgcgcgcgg tgtcatctat   6000
gttactagat cgatgtcgaa tctgatcaac ctgcattaat gaatcggcca acgcgcgggg   6060
agaggcggtt tgcgtattgg gcgctcttcc gcttcctcgc tcactgactc gctgcgctcg   6120
gtcgttcggc tgcggcgagc ggtatcagct cactcaaagg cggtaatacg gttatccaca   6180
gaatcagggg ataacgcagg aaagaacatg tgagcaaaag gccagcaaaa ggccaggaac   6240
cgtaaaaagg ccgcgttgct ggcgtttttc cataggctcc gcccccctga cgagcatcac   6300
aaaaatcgac gctcaagtca gaggtggcga aacccgacag gactataaag ataccaggcg   6360
tttccccctg gaagctccct cgtgcgctct cctgttccga ccctgccgct taccggatac   6420
ctgtccgcct ttctcccttc gggaagcgtg gcgctttctc aatgctcacg ctgtaggtat   6480
ctcagttcgg tgtaggtcgt tcgctccaag ctgggctgtg tgcacgaacc ccccgttcag   6540
cccgaccgct gcgccttatc cggtaactat cgtcttgagt ccaacccggt aagacacgac   6600
ttatcgccac tggcagcagc cactggtaac aggattagca gagcgaggta tgtaggcggt   6660
gctacagagt tcttgaagtg gtggcctaac tacggctaca ctagaaggac agtatttggt   6720
atctgcgctc tgctgaagcc agttaccttc ggaaaaagag ttggtagctc ttgatccggc   6780
```

```
aaacaaacca ccgctggtag cggtggtttt tttgtttgca agcagcagat tacgcgcaga   6840
aaaaaaggat ctcaagaaga tcctttgatc ttttctacgg ggtctgacgc tcagtggaac   6900
gaaaactcac gttaagggat tttggtcatg acattaacct ataaaaatag gcgtatcacg   6960
aggccctttc gtctcgcgcg tttcggtgat gacggtgaaa acctctgaca catgcagctc   7020
ccggagacgg tcacagcttg tctgtaagcg gatgccggga gcagacaagc ccgtcagggc   7080
gcgtcagcgg gtgttggcgg gtgtcggggc tggcttaact atgcggcatc agagcagatt   7140
gtactgagag tgcaccatat ggacatattg tcgttagaac gcggctacaa ttaatacata   7200
accttatgta tcatacacat acgatttagg tgacactata gaacggcgcg ccaagcttgg   7260
atcctctaga cgtacggtac catctgctaa tattttaaat cacatgcaag agaggaggca   7320
tggttccatt ttctaccttc acattatttg agaaaaacga acttgttctg tgttttattt   7380
ttgcccttca cattagtaca acgtggaaga ctcatggtta cacagaatca tacataagta   7440
caatgcttgt ccctaagaaa acaagcactc gttgtattga acctttacgg ctcatgcggc   7500
ccgcgcccac ccttctcccc aactcagatt ggttgccctt ctggaacaat ctgatctttc   7560
atccacatgt atatgggaac cagcacatag tatgtagctg ccatggctcc cagaaggaag   7620
cgagccagga acacaaatgg atttacaggt ttcgacacat cctcttcctt gggaccgagc   7680
tgcaaaggag attcaccaga ataaggcttc actccagtca cagaacatcc catgattagc   7740
ccatgccggc gaactcctcg gtaccatttt ggaccaatcc ttttcaattg gacatcttta   7800
aatccagcat tttgaacca ctcaatatac tcttcttcct ttgggaaaag catccacaca   7860
tctgcaaaga agcgagacag ccaaaacgtt gggtacaccg gaccaattag acatgctttt   7920
ccaccaagtt tcaggaccct atatgcttcc gtgatgccac gctgtggatc tggccagtat   7980
tcaatacttc cagcagatac atatctatct gcataatcag tacgaaatgg gagatcctca   8040
gcatcccctt caatgatttt gcaatccttc aagggctcct tctgcttagc cttggcaagc   8100
tgatgaggcg attggtccag gatggtcaca tttttggcat ccacgtgctt gactatccct   8160
aaagtagtaa aaccagtacc accaccaaca tctaccacaa tcatattcct atcgctgaga   8220
tctgcaggct cgagagcttc atccctcatg tcctcggtcc aatgcccagg gtttatgatg   8280
tggtcgtaca cgattgagag aaacctatag aaccagaatg cctccttctt gtgttgaatg   8340
aacctaggct gagaagctgg cctggaagca gaaagactgc acttaggcgc catgggcgcg   8400
gccttggaac atctataggt ggaaacaata cccaatctgg gaaaattcga acccgaaaaa   8460
cccaagccct tgggggccaa tcctctggtg agcttgaggc tttcagctcc attgagcatt   8520
gcagaagcca tggtgaaggg ggcggcc                                        8547
```

<210> SEQ ID NO 58
<211> LENGTH: 4906
<212> TYPE: DNA
<213> ORGANISM: Artificial
<220> FEATURE:
<223> OTHER INFORMATION: Vector pKR268

<400> SEQUENCE: 58

```
ggccgcatga gccgtaaagg ttcaatacaa cgagtgcttg ttttcttagg gacaagcatt     60
gtacttatgt atgattctgt gtaaccatga gtcttccacg ttgtactaat gtgaagggca    120
aaaataaaac acagaacaag ttcgtttttc tcaaataatg tgaaggtaga aaatggaacc    180
atgcctcctc tcttgcatgt gatttaaaat attagcagat ggtaccgtac gtgggcggat    240
cccccgggct gcaggaattc actggccgtc gttttacaac gtcgtgactg ggaaaaccct    300
```

```
ggcgttaccc aacttaatcg ccttgcagca catccccctt tcgccagctg gcgtaatagc    360

gaagaggccc gcaccgatcg cccttcccaa cagttgcgca gcctgaatgg cgaatggcgc    420

ctgatgcggt attttctcct tacgcatctg tgcggtattt cacaccgcat atggtgcact    480

ctcagtacaa tctgctctga tgccgcatag ttaagccagc cccgacaccc gccaacaccc    540

gctgacgcgc cctgacgggc ttgtctgctc ccggcatccg cttacagaca agctgtgacc    600

gtctccggga gctgcatgtg tcagaggttt tcaccgtcat caccgaaacg cgcgagacga    660

aagggcctcg tgatacgcct atttttatag gttaatgtca tgataataat ggtttcttag    720

acgtcaggtg gcacttttcg gggaaatgtg cgcggaaccc ctatttgttt atttttctaa    780

atacattcaa atatgtatcc gctcatgaga caataaccct gataaatgct tcaataatat    840

tgaaaaagga agagtatgag tattcaacat ttccgtgtcg cccttattcc cttttttgcg    900

gcattttgcc ttcctgtttt tgctcaccca gaaacgctgg tgaaagtaaa agatgctgaa    960

gatcagttgg gtgcacgagt gggttacatc gaactggatc tcaacagcgg taagatcctt   1020

gagagttttc gccccgaaga acgttttcca atgatgagca cttttaaagt tctgctatgt   1080

ggcgcggtat tatcccgtat tgacgccggg caagagcaac tcggtcgccg catacactat   1140

tctcagaatg acttggttga gtactcacca gtcacagaaa agcatcttac ggatggcatg   1200

acagtaagag aattatgcag tgctgccata accatgagtg ataacactgc ggccaactta   1260

cttctgacaa cgatcggagg accgaaggag ctaaccgctt ttttgcacaa catgggggat   1320

catgtaactc gccttgatcg ttgggaaccg gagctgaatg aagccatacc aaacgacgag   1380

cgtgacacca cgatgcctgt agcaatggca acaacgttgc gcaaactatt aactggcgaa   1440

ctacttactc tagcttcccg gcaacaatta atagactgga tggaggcgga taaagttgca   1500

ggaccacttc tgcgctcggc ccttccggct ggctggttta ttgctgataa atctggagcc   1560

ggtgagcgtg ggtctcgcgg tatcattgca gcactggggc cagatggtaa gccctcccgt   1620

atcgtagtta tctacacgac ggggagtcag gcaactatgg atgaacgaaa tagacagatc   1680

gctgagatag gtgcctcact gattaagcat tggtaactgt cagaccaagt ttactcatat   1740

atactttaga ttgatttaaa acttcatttt taatttaaaa ggatctaggt gaagatcctt   1800

tttgataatc tcatgaccaa aatcccttaa cgtgagtttt cgttccactg agcgtcagac   1860

cccgtagaaa agatcaaagg atcttcttga gatccttttt ttctgcgcgt aatctgctgc   1920

ttgcaaacaa aaaaaccacc gctaccagcg gtggtttgtt tgccggatca agagctacca   1980

actctttttc cgaaggtaac tggcttcagc agagcgcaga taccaaatac tgtccttcta   2040

gtgtagccgt agttaggcca ccacttcaag aactctgtag caccgcctac atacctcgct   2100

ctgctaatcc tgttaccagt ggctgctgcc agtggcgata agtcgtgtct taccgggttg   2160

gactcaagac gatagttacc ggataaggcg cagcggtcgg gctgaacggg gggttcgtgc   2220

acacagccca gcttggagcg aacgacctac accgaactga gatacctaca gcgtgagcta   2280

tgagaaagcg ccacgcttcc cgaagggaga aaggcggaca ggtatccggt aagcggcagg   2340

gtcggaacag gagagcgcac gagggagctt ccagggggaa acgcctggta tctttatagt   2400

cctgtcgggt ttcgccacct ctgacttgag cgtcgatttt tgtgatgctc gtcagggggg   2460

cggagcctat ggaaaaacgc cagcaacgcg gcctttttac ggttcctggc cttttgctgg   2520

ccttttgctc acatgttctt tcctgcgtta tcccctgatt ctgtggataa ccgtattacc   2580

gcctttgagt gagctgatac cgctcgccgc agccgaacga ccgagcgcag cgagtcagtg   2640

agcgaggaag cggaagagcg cccaatacgc aaaccgcctc tccccgcgcg ttggccgatt   2700
```

```
cattaatgca gctggcacga caggtttccc gactggaaag cgggcagtga gcgcaacgca   2760

attaatgtga gttagctcac tcattaggca ccccaggctt tacactttat gcttccggct   2820

cgtatgttgt gtggaattgt gagcggataa caatttcaca caggaaacag ctatgaccat   2880

gattacgcca agcttgcatg cctgcaggtc gactcgacgt acgatcccac atgcaagttt   2940

ttatttcaat ccccttttcct ttgaataact gaccaagaac aacaagaaaa aaaaaaaaaa   3000

agaaaaggat cattttgaaa ggatattttt cgctcctatt caaatactgt atttttacca   3060

aaaaaactgt atttttccta cactctcaag ctttgttttt cgcttcgact ctcatgattt   3120

ccttcatatg ccaatcactc tatttataaa tggcataagg tagtgtgaac aattgcaaag   3180

cttgtcatca aaagcttgca atgtacaaat taatgttttt catgcctttc aaaattatct   3240

gcacccccta gctattaatc taacatctaa gtaaggctag tgaatttttt cgaatagtca   3300

tgcagtgcat taatttcccc gtgactattt tggctttgac tccaacactg gccccgtaca   3360

tccgtccctc attacatgaa aagaaatatt gtttatattc ttaattaaaa atattgtccc   3420

ttctaaattt tcatatagtt aattattata ttactttttt ctctattcta ttagttctat   3480

tttcaaatta ttatttatgc atatgtaaag tacattatat ttttgctata tacttaaata   3540

tttctaaatt attaaaaaaa gactgatatg aaaaatttat tctttttaaa gctatatcat   3600

tttatatata ctttttcttt tcttttcttt catttttctat tcaatttaat aagaaataaa   3660

ttttgtaaat ttttatttat caatttataa aaatatttta ctttatatgt tttttcacat   3720

ttttgttaaa caaatcatat cattatgatt gaaagagagg aaattgacag tgagtaataa   3780

gtgatgagaa aaaaatgtgt tatttcctaa aaaaaaccta aacaaacatg tatctactct   3840

ctatttcatc tatctctcat ttcatttttc tctttatctc tttctttatt tttttatcat   3900

atcatttcac attaattatt tttactctct ttattttttc tctctatccc tctcttattt   3960

ccactcatat atacactcca aaattggggc atgcctttat cactactcta tctcctccac   4020

taaatcattt aaatgaaact gaaaagcatt ggcaagtctc ctcccctcct caagtgattt   4080

ccaactcagc attggcatct aattgattca gtatatctat tgcatgtgta aaagtctttc   4140

cacaatacat aactattaat taatcttaaa taaataaagg ataaaatatt ttttttttctt   4200

cataaaatta aaatatgtta tttttttgttt agatgtatat tcgaataaat ctaaatatat   4260

gataatgatt ttttatattg attaaacata taatcaatat taaatatgat atttttttat   4320

ataggttgta cacataattt tataaggata aaaaatatga taaaaataaa ttttaaatat   4380

ttttatattt acgagaaaaa aaaatatttt agccataaat aaatgaccag catattttac   4440

aaccttagta attcataaat tcctatatgt atatttgaaa ttaaaaacag ataatcgtta   4500

agggaaggaa tcctacgtca tctcttgcca tttgtttttc atgcaaacag aaagggacga   4560

aaaaccacct caccatgaat cactcttcac accattttta ctagcaaaca agtctcaaca   4620

actgaagcca gctctctttc cgtttctttt tacaacactt tctttgaaat agtagtattt   4680

tttttcaca tgatttatta acgtgccaaa agatgcttat tgaatagagt gcacatttgt   4740

aatgtactac taattagaac atgaaaaagc attgttctaa cacgataatc ctgtgaaggc   4800

gttaactcca aagatccaat ttcactatat aaattgtgac gaaagcaaaa tgaattcaca   4860

tagctgagag agaaaggaaa ggttaactaa gaagcaatac ttcagc                  4906
```

<210> SEQ ID NO 59
<211> LENGTH: 7096
<212> TYPE: DNA
<213> ORGANISM: Artificial
<220> FEATURE:
<223> OTHER INFORMATION: Vector pKR145

<400> SEQUENCE: 59

```
gatcctctag acgtacgtga aggttaaaca tggtgaatat gttaccacta gctgggatgc     60
ccattagatc aaaactgtaa aattctcccg tttcccttct attcacatgt gagccccctc    120
ccttttcttt ctttctcaat tttgattgag ttaaagtcac cagcaatgca tcactcaccc    180
tccaaaaaat ttcttgtaca acttctcgga ctatcccaaa gctccttttc ctgagatgga    240
tggtcctgtc tcttgccctt gatgtcttcc ttgttcgatt ttggcttcct ctaatgtctt    300
tcttgctagg aatcaccacc tcactcatct atgttgtcgt agcttctgaa agtctcatac    360
atatccttag tgttgcactc atcttgtatt gaagtgaaaa agaatgttgt tctcctatcc    420
aaatctccat tgaatctctt tctcccaatg ttgtcccatc ggttggtcct cctctccaac    480
caattgtaag gtgtttaaca taaacatggt acaattaaga tttttcattt cattaagaaa    540
agattgagat ttgtggttct aaagtttcaa ttagagtttg atgatattga aacaaccgta    600
gaacacatta agtattacta acttatacat agagcattgg aatttcacct tttatttatt    660
ctgtttccgc caaaggtaca tgactcaagt tattttacac aagtaacaaa ggcatctaag    720
cctaagtatt cttattcaga cttttcatta ttactttcat tgatttggtg cgaaatgcgg    780
ccgcagttgg atagaatata tgtttgtgac gcgaagaacc ttaatctggc atagggattt    840
atagtgaaac ataggaaagt ataggaggga cacatcggct ccaagaagat acatgagttg    900
ctgaccattc gacattcttc atcttgcatg gttatggaag ccttgtgtgt tacacctcat    960
aaaatcaaat gtctcattac agcagaggtg gcttcaagtg agagttgagt aattagatag   1020
ctagctgaaa tcggtggtgt tggggaccat gtatagtata taattgattt ctctttttac   1080
atatgtacgt gagtttgatc attactgtct tgtaatatct agatatatga acctgattca   1140
ctttcaagct agttaatgtc tgtatattgt atgttggata ggatttagtt catggtctgt   1200
acaaattttt aaagtttaat ggtaaagcac aattttgtgt agttgaatat aggtggacga   1260
taacaacttc aaattaaagt gcttgaatta caatttacaa tatagtcata tatgttatat   1320
aaaatcacac aaattatttg gatcaataac aattgatttg ctttaaattt gatgatgatt   1380
gtttaagttc tttaatactt atttaagaaa agttagccat cacattcgta atcataaccc   1440
ttacttgact attttctttt taaattgatt tgggaccgct tccgtaatca taatccttaa   1500
ttgatcatta ctttttaaac tgatttgcaa tgctagtgat tacgaacttg aagtcaataa   1560
aataaaataa aatccatact atatattatg tgaacaaatc ttgaatgaaa agtaaactag   1620
actaccatta agaaggaatt actcgtcata atatttgtat tgggacattt ttgctcttat   1680
ctaactagtt ccaaagttat tgtgtttaca tatcatcgta caacgctcag acacttagtt   1740
gaattaagga gagtcaaaac ctatttgtta atatgagtta tttttcttta aaactttgac   1800
ctggagatca aagataagaa gggacgtacg tcgagtcgac ggcgcgcccg atcatccgga   1860
tatagttcct cctttcagca aaaaacccct caagacccgt ttagaggccc caaggggtta   1920
tgctagttat tgctcagcgg tggcagcagc caactcagct tcctttcggg ctttgttagc   1980
agccggatcg atccaagctg tacctcacta ttcctttgcc ctcggacgag tgctggggcg   2040
tcggtttcca ctatcggcga gtacttctac acagccatcg gtccagacgg ccgcgcttct   2100
gcgggcgatt tgtgtacgcc cgacagtccc ggctccggat cggacgattg cgtcgcatcg   2160
accctgcgcc caagctgcat catcgaaatt gccgtcaacc aagctctgat agagttggtc   2220
aagaccaatg cggagcatat acgcccggag ccgcggcgat cctgcaagct ccggatgcct   2280
```

```
ccgctcgaag tagcgcgtct gctgctccat acaagccaac cacggcctcc agaagaagat   2340
gttggcgacc tcgtattggg aatccccgaa catcgcctcg ctccagtcaa tgaccgctgt   2400
tatgcggcca ttgtccgtca ggacattgtt ggagccgaaa tccgcgtgca cgaggtgccg   2460
gacttcgggg cagtcctcgg cccaaagcat cagctcatcg agagcctgcg cgacggacgc   2520
actgacggtg tcgtccatca cagtttgcca gtgatacaca tggggatcag caatcgcgca   2580
tatgaaatca cgccatgtag tgtattgacc gattccttgc ggtccgaatg ggccgaaccc   2640
gctcgtctgg ctaagatcgg ccgcagcgat cgcatccata gcctccgcga ccggctgcag   2700
aacagcgggc agttcggttt caggcaggtc ttgcaacgtg acaccctgtg cacggcggga   2760
gatgcaatag gtcaggctct cgctgaattc cccaatgtca agcacttccg gaatcgggag   2820
cgcggccgat gcaaagtgcc gataaacata acgatctttg tagaaaccat cggcgcagct   2880
atttacccgc aggacatatc cacgccctcc tacatcgaag ctgaaagcac gagattcttc   2940
gccctccgag agctgcatca ggtcggagac gctgtcgaac ttttcgatca gaaacttctc   3000
gacagacgtc gcggtgagtt caggcttttc catgggtata tctccttctt aaagttaaac   3060
aaaattattt ctagagggaa accgttgtgg tctccctata gtgagtcgta ttaatttcgc   3120
gggatcgaga tcgatccaat tccaatccca caaaaatctg agcttaacag cacagttgct   3180
cctctcagag cagaatcggg tattcaacac cctcatatca actactacgt tgtgtataac   3240
ggtccacatg ccggtatata cgatgactgg ggttgtacaa aggcggcaac aaacggcgtt   3300
cccggagttg cacacaagaa atttgccact attacagagg caagagcagc agctgacgcg   3360
tacacaacaa gtcagcaaac agacaggttg aacttcatcc ccaaaggaga agctcaactc   3420
aagcccaaga gctttgctaa ggccctaaca agcccaccaa agcaaaaagc ccactggctc   3480
acgctaggaa ccaaaaggcc cagcagtgat ccagccccaa aagagatctc ctttgccccg   3540
gagattacaa tggacgattt cctctatctt tacgatctag gaaggaagtt cgaaggtgaa   3600
ggtgacgaca ctatgttcac cactgataat gagaaggtta gcctcttcaa tttcagaaag   3660
aatgctgacc cacagatggt tagagaggcc tacgcagcag gtctcatcaa gacgatctac   3720
ccgagtaaca atctccagga gatcaaatac cttcccaaga aggttaaaga tgcagtcaaa   3780
agattcagga ctaattgcat caagaacaca gagaaagaca tatttctcaa gatcagaagt   3840
actattccag tatggacgat tcaaggcttg cttcataaac caaggcaagt aatagagatt   3900
ggagtctcta aaaaggtagt tcctactgaa tctaaggcca tgcatggagt ctaagattca   3960
aatcgaggat ctaacagaac tcgccgtgaa gactggcgaa cagttcatac agagtctttt   4020
acgactcaat gacaagaaga aaatcttcgt caacatggtg gagcacgaca ctctggtcta   4080
ctccaaaaat gtcaaagata cagtctcaga agaccaaagg gctattgaga cttttcaaca   4140
aaggataatt tcgggaaacc tcctcggatt ccattgccca gctatctgtc acttcatcga   4200
aaggacagta gaaaaggaag gtggctccta caaatgccat cattgcgata aaggaaaggc   4260
tatcattcaa gatgcctctg ccgacagtgg tcccaaagat ggacccccac ccacgaggag   4320
catcgtggaa aaagaagacg ttccaaccac gtcttcaaag caagtggatt gatgtgacat   4380
ctccactgac gtaagggatg acgcacaatc ccactatcct tcgcaagacc cttcctctat   4440
ataaggaagt tcatttcatt tggagaggac acgctcgagc tcatttctct attacttcag   4500
ccataacaaa agaactcttt tctcttctta ttaaaccatg aaaaagcctg aactcaccgc   4560
gacgtctgtc gagaagtttc tgatcgaaaa gttcgacagc gtctccgacc tgatgcagct   4620
ctcggagggc gaagaatctc gtgctttcag cttcgatgta ggagggcgtg gatatgtcct   4680
```

```
gcgggtaaat agctgcgccg atggtttcta caaagatcgt tatgtttatc ggcactttgc   4740
atcggccgcg ctcccgattc cggaagtgct tgacattggg gaattcagcg agagcctgac   4800
ctattgcatc tcccgccgtg cacagggtgt cacgttgcaa gacctgcctg aaaccgaact   4860
gcccgctgtt ctgcagccgg tcgcggaggc catggatgcg atcgctgcgg ccgatcttag   4920
ccagacgagc gggttcggcc cattcggacc gcaaggaatc ggtcaataca ctacatggcg   4980
tgatttcata tgcgcgattg ctgatcccca tgtgtatcac tggcaaactg tgatggacga   5040
caccgtcagt gcgtccgtcg cgcaggctct cgatgagctg atgctttggg ccgaggactg   5100
ccccgaagtc cggcacctcg tgcacgcgga tttcggctcc aacaatgtcc tgacggacaa   5160
tggccgcata acagcggtca ttgactggag cgaggcgatg ttcggggatt cccaatacga   5220
ggtcgccaac atcttcttct ggaggccgtg gttggcttgt atggagcagc agacgcgcta   5280
cttcgagcgg aggcatccgg agcttgcagg atcgccgcgg ctccgggcgt atatgctccg   5340
cattggtctt gaccaactct atcagagctt ggttgacggc aatttcgatg atgcagcttg   5400
ggcgcagggt cgatgcgacg caatcgtccg atccggagcc gggactgtcg ggcgtacaca   5460
aatcgcccgc agaagcgcgg ccgtctggac cgatggctgt gtagaagtac tcgccgatag   5520
tggaaaccga cgccccagca ctcgtccgag ggcaaaggaa tagtgaggta cctaaagaag   5580
gagtgcgtcg aagcagatcg ttcaaacatt tggcaataaa gtttcttaag attgaatcct   5640
gttgccggtc ttgcgatgat tatcatataa tttctgttga attacgttaa gcatgtaata   5700
attaacatgt aatgcatgac gttatttatg agatgggttt ttatgattag agtcccgcaa   5760
ttatacattt aatacgcgat agaaaacaaa atatagcgcg caaactagga taaattatcg   5820
cgcgcggtgt catctatgtt actagatcga tgtcgaatct gatcaacctg cattaatgaa   5880
tcggccaacg cgcggggaga ggcggtttgc gtattgggcg ctcttccgct tcctcgctca   5940
ctgactcgct gcgctcggtc gttcggctgc ggcgagcggt atcagctcac tcaaaggcgg   6000
taatacggtt atccacagaa tcaggggata acgcaggaaa gaacatgtga gcaaaaggcc   6060
agcaaaaggc caggaaccgt aaaaaggccg cgttgctggc gtttttccat aggctccgcc   6120
cccctgacga gcatcacaaa aatcgacgct caagtcagag gtggcgaaac ccgacaggac   6180
tataaagata ccaggcgttt ccccctggaa gctccctcgt gcgctctcct gttccgaccc   6240
tgccgcttac cggatacctg tccgcctttc tcccttcggg aagcgtggcg ctttctcaat   6300
gctcacgctg taggtatctc agttcggtgt aggtcgttcg ctccaagctg ggctgtgtgc   6360
acgaaccccc cgttcagccc gaccgctgcg ccttatccgg taactatcgt cttgagtcca   6420
acccggtaag acacgactta tcgccactgg cagcagccac tggtaacagg attagcagag   6480
cgaggtatgt aggcggtgct acagagttct tgaagtggtg gcctaactac ggctacacta   6540
gaaggacagt atttggtatc tgcgctctgc tgaagccagt taccttcgga aaaagagttg   6600
gtagctcttg atccggcaaa caaaccaccg ctggtagcgg tggttttttt gtttgcaagc   6660
agcagattac gcgcagaaaa aaaggatctc aagaagatcc tttgatcttt tctacggggt   6720
ctgacgctca gtggaacgaa aactcacgtt aagggatttt ggtcatgaca ttaacctata   6780
aaaataggcg tatcacgagg ccctttcgtc tcgcgcgttt cggtgatgac ggtgaaaacc   6840
tctgacacat gcagctcccg gagacggtca cagcttgtct gtaagcggat gccgggagca   6900
gacaagcccg tcagggcgcg tcagcgggtg ttggcgggtg tcggggctgg cttaactatg   6960
cggcatcaga gcagattgta ctgagagtgc accatatgga catattgtcg ttagaacgcg   7020
gctacaatta atacataacc ttatgtatca tacacatacg atttaggtga cactatagaa   7080
```

cggcgcgcca agcttg 7096

<210> SEQ ID NO 60
<211> LENGTH: 7497
<212> TYPE: DNA
<213> ORGANISM: Artificial
<220> FEATURE:
<223> OTHER INFORMATION: Vector pKR561

<400> SEQUENCE: 60
gtacgtcgag tcgacggcgc gcccgatcat ccggatatag ttcctccttt cagcaaaaaa 60
cccctcaaga cccgtttaga ggccccaagg ggttatgcta gttattgctc agcggtggca 120
gcagccaact cagcttcctt tcgggctttg ttagcagccg gatcgatcca agctgtacct 180
cactattcct ttgccctcgg acgagtgctg gggcgtcggt ttccactatc ggcgagtact 240
tctacacagc catcggtcca gacggccgcg cttctgcggg cgatttgtgt acgcccgaca 300
gtcccggctc cggatcggac gattgcgtcg catcgaccct gcgcccaagc tgcatcatcg 360
aaattgccgt caaccaagct ctgatagagt tggtcaagac caatgcggag catatacgcc 420
cggagccgcg gcgatcctgc aagctccgga tgcctccgct cgaagtagcg cgtctgctgc 480
tccatacaag ccaaccacgg cctccagaag aagatgttgg cgacctcgta ttgggaatcc 540
ccgaacatcg cctcgctcca gtcaatgacc gctgttatgc ggccattgtc cgtcaggaca 600
ttgttggagc cgaaatccgc gtgcacgagg tgccggactt cggggcagtc ctcggcccaa 660
agcatcagct catcgagagc ctgcgcgacg gacgcactga cggtgtcgtc catcacagtt 720
tgccagtgat acacatgggg atcagcaatc gcgcatatga aatcacgcca tgtagtgtat 780
tgaccgattc cttgcggtcc gaatgggccg aacccgctcg tctggctaag atcggccgca 840
gcgatcgcat ccatagcctc cgcgaccggc tgcagaacag cgggcagttc ggtttcaggc 900
aggtcttgca acgtgacacc ctgtgcacgg cgggagatgc aataggtcag gctctcgctg 960
aattccccaa tgtcaagcac ttccggaatc gggagcgcgg ccgatgcaaa gtgccgataa 1020
acataacgat ctttgtagaa accatcggcg cagctattta cccgcaggac atatccacgc 1080
cctcctacat cgaagctgaa agcacgagat tcttcgccct ccgagagctg catcaggtcg 1140
gagacgctgt cgaacttttc gatcagaaac ttctcgacag acgtcgcggt gagttcaggc 1200
ttttccatgg gtatatctcc ttcttaaagt taaacaaaat tatttctaga gggaaaccgt 1260
tgtggtctcc ctatagtgag tcgtattaat ttcgcgggat cgagatcgat ccaattccaa 1320
tcccacaaaa atctgagctt aacagcacag ttgctcctct cagagcagaa tcgggtattc 1380
aacaccctca tatcaactac tacgttgtgt ataacggtcc acatgccggt atatacgatg 1440
actggggttg tacaaaggcg gcaacaaacg gcgttcccgg agttgcacac aagaaatttg 1500
ccactattac agaggcaaga gcagcagctg acgcgtacac aacaagtcag caaacagaca 1560
ggttgaactt catccccaaa ggagaagctc aactcaagcc caagagcttt gctaaggccc 1620
taacaagccc accaaagcaa aaagcccact ggctcacgct aggaaccaaa aggcccagca 1680
gtgatccagc cccaaaagag atctcctttg ccccggagat tacaatggac gatttcctct 1740
atctttacga tctaggaagg aagttcgaag gtgaaggtga cgacactatg ttcaccactg 1800
ataatgagaa ggttagcctc ttcaatttca gaaagaatgc tgacccacag atggttagag 1860
aggcctacgc agcaggtctc atcaagacga tctacccgag taacaatctc caggagatca 1920
aataccttcc caagaaggtt aaagatgcag tcaaaagatt caggactaat tgcatcaaga 1980
acacagagaa agacatattt ctcaagatca gaagtactat tccagtatgg acgattcaag 2040

```
gcttgcttca taaaccaagg caagtaatag agattggagt ctctaaaaag gtagttccta   2100
ctgaatctaa ggccatgcat ggagtctaag attcaaatcg aggatctaac agaactcgcc   2160
gtgaagactg gcgaacagtt catacagagt cttttacgac tcaatgacaa gaagaaaatc   2220
ttcgtcaaca tggtggagca cgacactctg gtctactcca aaaatgtcaa agatacagtc   2280
tcagaagacc aaagggctat tgagactttt caacaaagga taatttcggg aaacctcctc   2340
ggattccatt gcccagctat ctgtcacttc atcgaaagga cagtagaaaa ggaaggtggc   2400
tcctacaaat gccatcattg cgataaagga aaggctatca ttcaagatgc ctctgccgac   2460
agtggtccca aagatggacc cccacccacg aggagcatcg tggaaaaaga agacgttcca   2520
accacgtctt caaagcaagt ggattgatgt gacatctcca ctgacgtaag ggatgacgca   2580
caatcccact atccttcgca agacccttcc tctatataag gaagttcatt tcatttggag   2640
aggacacgct cgagctcatt tctctattac ttcagccata acaaaagaac tcttttctct   2700
tcttattaaa ccatgaaaaa gcctgaactc accgcgacgt ctgtcgagaa gtttctgatc   2760
gaaaagttcg acagcgtctc cgacctgatg cagctctcgg agggcgaaga atctcgtgct   2820
ttcagcttcg atgtaggagg gcgtggatat gtcctgcggg taaatagctg cgccgatggt   2880
ttctacaaag atcgttatgt ttatcggcac tttgcatcgg ccgcgctccc gattccggaa   2940
gtgcttgaca ttggggaatt cagcgagagc ctgacctatt gcatctcccg ccgtgcacag   3000
ggtgtcacgt tgcaagacct gcctgaaacc gaactgcccg ctgttctgca gccggtcgcg   3060
gaggccatgg atgcgatcgc tgcggccgat cttagccaga cgagcgggtt cggcccattc   3120
ggaccgcaag gaatcggtca atacactaca tggcgtgatt tcatatgcgc gattgctgat   3180
ccccatgtgt atcactggca aactgtgatg gacgacaccg tcagtgcgtc cgtcgcgcag   3240
gctctcgatg agctgatgct ttgggccgag gactgccccg aagtccggca cctcgtgcac   3300
gcggatttcg gctccaacaa tgtcctgacg gacaatggcc gcataacagc ggtcattgac   3360
tggagcgagg cgatgttcgg ggattcccaa tacgaggtcg ccaacatctt cttctggagg   3420
ccgtggttgg cttgtatgga gcagcagacg cgctacttcg agcggaggca tccggagctt   3480
gcaggatcgc cgcggctccg ggcgtatatg ctccgcattg gtcttgacca actctatcag   3540
agcttggttg acggcaattt cgatgatgca gcttgggcgc agggtcgatg cgacgcaatc   3600
gtccgatccg gagccgggac tgtcgggcgt acacaaatcg cccgcagaag cgcggccgtc   3660
tggaccgatg gctgtgtaga agtactcgcc gatagtggaa accgacgccc cagcactcgt   3720
ccgagggcaa aggaatagtg aggtacctaa agaaggagtg cgtcgaagca gatcgttcaa   3780
acatttggca ataaagtttc ttaagattga atcctgttgc cggtcttgcg atgattatca   3840
tataatttct gttgaattac gttaagcatg taataattaa catgtaatgc atgacgttat   3900
ttatgagatg ggtttttatg attagagtcc cgcaattata catttaatac gcgatagaaa   3960
acaaaatata gcgcgcaaac taggataaat tatcgcgcgc ggtgtcatct atgttactag   4020
atcgatgtcg aatctgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
```

```
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt ggatcctcta   5280
gacgtacggt accatctgct aatattttaa atcacatgca agagaggagg catggttcca   5340
ttttctacct tcacattatt tgagaaaaac gaacttgttc tgtgttttat ttttgccctt   5400
cacattagta caacgtggaa gactcatggt tacacagaat catacataag tacaatgctt   5460
gtccctaaga aaacaagcac tcgttgtatt gaacctttac ggctcatgcg gccgctgaag   5520
tattgcttct tagttaacct ttcctttctc tctcagctat gtgaattcat tttgctttcg   5580
tcacaattta tatagtgaaa ttggatcttt ggagttaacg ccttcacagg attatcgtgt   5640
tagaacaatg ctttttcatg ttctaattag tagtacatta caaatgtgca ctctattcaa   5700
taagcatctt ttggcacgtt aataaatcat gtgaaaaaaa aatactacta tttcaaagaa   5760
agtgttgtaa aaagaaacgg aaagagagct ggcttcagtt gttgagactt gtttgctagt   5820
aaaaatggtg tgaagagtga ttcatggtga ggtggttttt cgtccctttc tgtttgcatg   5880
aaaaacaaat ggcaagagat gacgtaggat tccttccctt aacgattatc tgtttttaat   5940
ttcaaatata catataggaa tttatgaatt actaaggttg taaaatatgc tggtcattta   6000
tttatggcta aaatattttt ttttctcgta aatataaaaa tatttaaaat ttatttttat   6060
catatttttt atccttataa aattatgtgt acaacctata taaaaaaata tcatatttaa   6120
tattgattat atgtttaatc aatataaaaa atcattatca tatatttaga tttattcgaa   6180
tatacatcta aacaaaaaat aacatatttt aattttatga agaaaaaaaa atattttatc   6240
ctttatttat ttaagattaa ttaatagtta tgtattgtgg aaagactttt acacatgcaa   6300
tagatatact gaatcaatta gatgccaatg ctgagttgga aatcacttga ggaggggagg   6360
agacttgcca atgcttttca gtttcattta aatgatttag tggaggagat agagtagtga   6420
taaaggcatg ccccaatttt ggagtgtata tatgagtgga aataagagag ggatagagag   6480
aaaaaataaa gagagtaaaa ataattaatg tgaaatgata tgataaaaaa ataaagaaag   6540
agataaagag aaaaatgaaa tgagagatag atgaaataga gagtagatac atgtttgttt   6600
aggttttttt taggaaataa cacatttttt tctcatcact tattactcac tgtcaatttc   6660
ctctctttca atcataatga tatgatttgt ttaacaaaaa tgtgaaaaaa catataaagt   6720
aaaatatttt tataaattga taaataaaaa tttacaaaat ttatttctta ttaaattgaa   6780
tagaaaatga aagaaaagaa aagaaaaagt atatataaaa tgatatagct ttaaaaagaa   6840
```

```
taaatttttc atatcagtct ttttttaata atttagaaat atttaagtat atagcaaaaa   6900

tataatgtac tttacatatg cataaataat aatttgaaaa tagaactaat agaatagaga   6960

aaaaagtaat ataataatta actatatgaa aatttagaag ggacaatatt tttaattaag   7020

aatataaaca atatttcttt tcatgtaatg agggacggat gtacggggcc agtgttggag   7080

tcaaagccaa aatagtcacg gggaaattaa tgcactgcat gactattcga aaaaattcac   7140

tagccttact tagatgttag attaatagct agggggtgca gataattttg aaaggcatga   7200

aaaacattaa tttgtacatt gcaagctttt gatgacaagc tttgcaattg ttcacactac   7260

cttatgccat ttataaatag agtgattggc atatgaagga aatcatgaga gtcgaagcga   7320

aaaacaaagc ttgagagtgt aggaaaaata cagttttttt ggtaaaaata cagtatttga   7380

ataggagcga aaaatatcct ttcaaaatga tccttttctt tttttttttt tttcttgttg   7440

ttcttggtca gttattcaaa ggaaaaggga ttgaaataaa aacttgcatg tgggatc      7497


<210> SEQ ID NO 61
<211> LENGTH: 338
<212> TYPE: PRT
<213> ORGANISM: Arabidopsis thaliana

<400> SEQUENCE: 61

Met Ala Ser Leu Met Leu Asn Gly Ala Ile Thr Phe Pro Lys Gly Leu
1               5                   10                  15

Gly Ser Pro Val Ser Asn Leu His Ala Arg Ser Ile Pro Arg Pro Thr
            20                  25                  30

Leu Leu Ser Val Thr Arg Thr Ser Thr Pro Arg Leu Ser Val Ala Thr
        35                  40                  45

Arg Cys Ser Ser Ser Ser Val Ser Ser Ser Arg Pro Ser Ala Gln Pro
    50                  55                  60

Arg Phe Ile Gln His Lys Lys Glu Ala Tyr Trp Phe Tyr Arg Phe Leu
65                  70                  75                  80

Ser Ile Val Tyr Asp His Val Ile Asn Pro Gly His Trp Thr Glu Asp
                85                  90                  95

Met Arg Asp Asp Ala Leu Glu Pro Ala Asp Leu Ser His Pro Asp Met
            100                 105                 110

Arg Val Val Asp Val Gly Gly Gly Thr Gly Phe Thr Thr Leu Gly Ile
        115                 120                 125

Val Lys Thr Val Lys Ala Lys Asn Val Thr Ile Leu Asp Gln Ser Pro
    130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
                165                 170                 175

Asp Arg Tyr Val Ser Ala Gly Ser Ile Glu Tyr Trp Pro Asp Pro Gln
            180                 185                 190

Arg Gly Ile Arg Glu Ala Tyr Arg Val Leu Lys Ile Gly Gly Lys Ala
        195                 200                 205

Cys Leu Ile Gly Pro Val Tyr Pro Thr Phe Trp Leu Ser Arg Phe Phe
    210                 215                 220

Ser Asp Val Trp Met Leu Phe Pro Lys Glu Glu Glu Tyr Ile Glu Trp
225                 230                 235                 240

Phe Lys Asn Ala Gly Phe Lys Asp Val Gln Leu Lys Arg Ile Gly Pro
                245                 250                 255

Lys Trp Tyr Arg Gly Val Arg Arg His Gly Leu Ile Met Gly Cys Ser
```

```
            260                 265                 270

Val Thr Gly Val Lys Pro Ala Ser Gly Asp Ser Pro Leu Gln Leu Gly
        275                 280                 285

Pro Lys Glu Glu Asp Val Glu Lys Pro Val Asn Asn Pro Phe Ser Phe
    290                 295                 300

Leu Gly Arg Phe Leu Leu Gly Thr Leu Ala Ala Ala Trp Phe Val Leu
305                 310                 315                 320

Ile Pro Ile Tyr Met Trp Ile Lys Asp Gln Ile Val Pro Lys Asp Gln
                325                 330                 335

Pro Ile


<210> SEQ ID NO 62
<211> LENGTH: 340
<212> TYPE: PRT
<213> ORGANISM: Vitis vinifera

<400> SEQUENCE: 62

Met Ala Ser Ser Met Leu Thr Gly Ala Glu Asn Leu Lys Leu Ile Arg
1               5                   10                  15

Gly Ile Ser Pro Asn Gly Leu Gly Phe Leu Gly Ser Asp Val His Gly
            20                  25                  30

Lys His Phe Pro Lys Leu Gly Leu Val Ser Trp Ser Arg Asn Tyr Arg
        35                  40                  45

Leu Lys Thr Leu Lys Ala Arg Cys Asn Ala Ser Val Ser Arg Pro Ala
    50                  55                  60

Ser Gln Leu Arg Phe Ile Gln His Lys Lys Glu Ala Phe Trp Phe Tyr
65                  70                  75                  80

Arg Phe Leu Ser Ile Val Tyr Asp His Ile Ile Asn Pro Gly His Trp
                85                  90                  95

Thr Glu Asp Met Arg Asp Asp Ala Leu Glu Pro Ala Asp Leu Asn Asp
            100                 105                 110

Arg Asn Leu Val Val Val Asp Val Gly Gly Gly Thr Gly Phe Thr Thr
        115                 120                 125

Leu Gly Ile Val Lys His Val Asp Ala Lys Asn Val Thr Leu Leu Asp
    130                 135                 140

Gln Ser Pro His Gln Leu Ala Lys Ala Lys Lys Lys Glu Pro Leu Lys
145                 150                 155                 160

Asp Cys Arg Ile Ile Glu Gly Asp Ala Glu Asp Leu Pro Phe Pro Thr
                165                 170                 175

Asp Tyr Ala Asp Arg Tyr Val Ser Ala Gly Ser Ile Glu Tyr Trp Pro
            180                 185                 190

Glu Pro Gln Arg Gly Ile Lys Glu Ala Tyr Arg Val Leu Lys Gln Gly
        195                 200                 205

Gly Lys Ala Cys Met Ile Gly Pro Val Tyr Pro Thr Phe Trp Leu Ser
    210                 215                 220

Arg Phe Phe Ala Asp Val Trp Met Leu Phe Pro Lys Glu Glu Glu Tyr
225                 230                 235                 240

Ile Glu Trp Phe Glu Lys Ala Gly Phe Thr Asp Val Gln Leu Lys Arg
                245                 250                 255

Ile Gly Pro Lys Trp Tyr Arg Gly Val Arg Arg His Gly Leu Ile Met
            260                 265                 270

Gly Cys Ser Val Thr Gly Val Lys Pro Ala Ser Gly Asp Ser Pro Leu
        275                 280                 285

Gln Leu Gly Pro Lys Ala Glu Asp Val Ser Lys Pro Thr Asn Pro Phe
    290                 295                 300
```

```
Val Phe Phe Leu Arg Phe Ile Leu Gly Ala Leu Ala Gly Thr Tyr Tyr
305                 310                 315                 320

Val Leu Val Pro Ile Tyr Met Trp Leu Lys Asp Gln Leu Val Pro Glu
                325                 330                 335

Gly Gln Pro Ile
            340


<210> SEQ ID NO 63
<211> LENGTH: 343
<212> TYPE: PRT
<213> ORGANISM: Helianthus annuus

<400> SEQUENCE: 63

Met Thr Ser Ser Met Leu Tyr Gly Ala Glu Asn Leu Ala Ile Ile Arg
1               5                   10                  15

Gly Arg Val Ala Ala Asn Gly Leu Gly Phe Asn Gly Ser Glu Leu Asn
            20                  25                  30

Gly Arg Lys Phe Pro Leu Lys Val Asn Leu Ala Cys Gly Asn Ser Ile
        35                  40                  45

Ser Arg Gly Lys Thr Leu Val Val Pro Lys Cys Ser Val Ser Leu Pro
    50                  55                  60

Arg Pro Ala Ser Gln Pro Arg Phe Ile Gln His Lys Lys Glu Ala Phe
65                  70                  75                  80

Trp Phe Tyr Arg Phe Leu Ser Ile Val Tyr Asp His Val Ile Asn Pro
                85                  90                  95

Gly His Trp Thr Glu Asp Met Arg Asp Glu Ala Leu Glu Pro Ala Asp
            100                 105                 110

Leu Tyr Ser Arg Asn Met Leu Val Val Asp Val Gly Gly Gly Thr Gly
        115                 120                 125

Phe Thr Thr Leu Gly Ile Val Lys Ser Val Asp Ala Lys Asn Val Thr
    130                 135                 140

Ile Leu Asp Gln Ser Pro His Gln Leu Ala Lys Ala Lys Gln Lys Glu
145                 150                 155                 160

Pro Leu Lys Glu Cys Lys Ile Ile Glu Gly Asp Ala Glu Asp Leu Pro
                165                 170                 175

Phe Lys Thr Asp Tyr Ala Asp Arg Tyr Ile Ser Ala Gly Ser Ile Glu
            180                 185                 190

Tyr Trp Pro Glu Pro Gln Arg Gly Ile Lys Glu Ala Tyr Arg Val Leu
        195                 200                 205

Lys Ile Gly Gly Lys Ala Cys Val Ile Gly Pro Val Tyr Pro Thr His
    210                 215                 220

Trp Leu Ser Arg Phe Phe Ala Asp Ala Trp Met Leu Phe Pro Lys Glu
225                 230                 235                 240

Glu Glu Tyr Ile Glu Trp Phe Thr Lys Ala Gly Phe Lys Asp Val Lys
                245                 250                 255

Ile Lys Arg Ile Gly Pro Lys Trp Tyr Arg Gly Val Arg Arg His Gly
            260                 265                 270

Leu Ile Met Gly Cys Ser Val Thr Gly Val Lys Pro Ala Ser Gly Asp
        275                 280                 285

Ser Pro Leu Gln Leu Gly Pro Lys Glu Glu Asp Val Ser Lys Pro Val
    290                 295                 300

Asn Pro Phe Val Phe Leu Ala Arg Phe Leu Leu Gly Ala Leu Ala Gly
305                 310                 315                 320

Val Tyr Tyr Val Leu Val Pro Val Tyr Met Trp Leu Lys Asp Gln Ile
                325                 330                 335
```

```
Val Pro Lys Gly Gln Pro Ile
            340

<210> SEQ ID NO 64
<211> LENGTH: 341
<212> TYPE: PRT
<213> ORGANISM: Gossypium hirsutum

<400> SEQUENCE: 64

Met Ala Ser Ser Met Leu Asn Gly Ala Glu Ser Phe Thr Leu Ile Arg
1               5                   10                  15

Gly Val Thr Pro Arg Arg Val Asp Phe Phe Gly Ser Gly Phe His Gly
            20                  25                  30

Lys His Leu Ser Asn Leu Gly Leu Ala Phe Ser Val Arg Ile Ser Arg
        35                  40                  45

Pro Gly Thr Thr Met Ala Pro Lys Cys Gly Leu Ser Ala Ser Arg Pro
    50                  55                  60

Ala Ser Gln Pro Arg Phe Ile Gln His Lys Lys Glu Ala Phe Trp Phe
65                  70                  75                  80

Tyr Arg Phe Leu Ser Ile Ile Tyr Asp His Val Ile Asn Pro Gly His
                85                  90                  95

Trp Thr Glu Asp Met Arg Asn Asp Ala Leu Glu Pro Ala Asp Leu Asn
            100                 105                 110

Asn Arg Asn Met Ile Val Val Asp Val Gly Gly Gly Thr Gly Phe Thr
        115                 120                 125

Thr Leu Gly Ile Val Lys His Val Asp Ala Lys Asn Val Thr Ile Leu
    130                 135                 140

Asp Gln Ser Pro His Gln Leu Ala Lys Ala Lys Gln Lys Glu Pro Leu
145                 150                 155                 160

Lys Glu Cys Arg Ile Ile Glu Gly Asp Ala Glu Asp Leu Pro Phe Arg
                165                 170                 175

Thr Asp Tyr Ala Asp Arg Tyr Val Ser Ala Gly Ser Ile Glu Tyr Trp
            180                 185                 190

Pro Asp Pro Gln Arg Gly Ile Lys Glu Ala Tyr Arg Val Leu Lys Leu
        195                 200                 205

Gly Gly Lys Ala Cys Leu Ile Gly Pro Val Tyr Pro Thr Phe Trp Leu
    210                 215                 220

Ser Arg Phe Phe Ala Asp Val Trp Met Leu Phe Pro Lys Glu Glu Glu
225                 230                 235                 240

Tyr Ile Asp Trp Phe Glu Lys Ala Gly Phe Lys Asp Val Gln Leu Lys
                245                 250                 255

Arg Ile Gly Pro Lys Trp Tyr Arg Gly Val Arg Arg His Gly Leu Ile
            260                 265                 270

Met Gly Cys Ser Val Thr Gly Val Lys Pro Ala Ser Gly Asp Ser Pro
        275                 280                 285

Leu Gln Leu Gly Pro Lys Ala Glu Asp Val Ser Lys Pro Ile Asn Pro
    290                 295                 300

Leu Thr Phe Leu Leu Arg Phe Ile Leu Gly Thr Met Ala Ala Thr Tyr
305                 310                 315                 320

Tyr Val Leu Val Pro Ile Tyr Met Trp Leu Lys Asp Gln Ile Val Pro
                325                 330                 335

Glu Gly Gln Pro Ile
            340

<210> SEQ ID NO 65
```

<211> LENGTH: 342
<212> TYPE: PRT
<213> ORGANISM: Glycine max

<400> SEQUENCE: 65

```
Met Gly Ser Val Met Leu Ser Gly Thr Glu Lys Leu Thr Leu Arg Thr
1               5                   10                  15

Leu Thr Gly Asn Gly Leu Gly Phe Thr Gly Ser Asp Leu His Gly Lys
            20                  25                  30

Asn Phe Pro Arg Val Ser Phe Ala Ala Thr Thr Ser Ala Lys Val Pro
        35                  40                  45

Asn Phe Arg Ser Ile Val Val Pro Lys Cys Ser Val Ser Ala Ser Arg
    50                  55                  60

Pro Ser Ser Gln Pro Arg Phe Ile Gln His Lys Lys Glu Ala Phe Trp
65                  70                  75                  80

Phe Tyr Arg Phe Leu Ser Ile Val Tyr Asp His Val Ile Asn Pro Gly
                85                  90                  95

His Trp Thr Glu Asp Met Arg Asp Asp Ala Leu Glu Pro Ala Asp Leu
            100                 105                 110

Asn Asp Arg Asn Met Ile Val Val Asp Val Gly Gly Gly Thr Gly Phe
        115                 120                 125

Thr Thr Leu Gly Ile Val Lys His Val Asp Ala Lys Asn Val Thr Ile
    130                 135                 140

Leu Asp Gln Ser Pro His Gln Leu Ala Lys Ala Lys Gln Lys Glu Pro
145                 150                 155                 160

Leu Lys Glu Cys Lys Ile Ile Glu Gly Asp Ala Glu Asp Leu Pro Phe
                165                 170                 175

Arg Thr Asp Tyr Ala Asp Arg Tyr Val Ser Ala Gly Ser Ile Glu Tyr
            180                 185                 190

Trp Pro Asp Pro Gln Arg Gly Ile Lys Glu Ala Tyr Arg Val Leu Lys
        195                 200                 205

Leu Gly Gly Lys Ala Cys Leu Ile Gly Pro Val Tyr Pro Thr Phe Trp
    210                 215                 220

Leu Ser Arg Phe Phe Ala Asp Val Trp Met Leu Phe Pro Lys Glu Glu
225                 230                 235                 240

Glu Tyr Ile Glu Trp Phe Gln Lys Ala Gly Phe Lys Asp Val Gln Leu
                245                 250                 255

Lys Arg Ile Gly Pro Lys Trp Tyr Arg Gly Val Arg Arg His Gly Leu
            260                 265                 270

Ile Met Gly Cys Ser Val Thr Gly Val Lys Pro Ala Ser Gly Asp Ser
        275                 280                 285

Pro Leu Gln Leu Gly Pro Lys Glu Glu Asp Val Glu Lys Pro Val Asn
    290                 295                 300

Pro Phe Val Phe Ala Leu Arg Phe Val Leu Gly Ala Leu Ala Ala Thr
305                 310                 315                 320

Trp Phe Val Leu Val Pro Ile Tyr Met Trp Leu Lys Asp Gln Val Val
                325                 330                 335

Pro Lys Gly Gln Pro Ile
            340
```

<210> SEQ ID NO 66
<211> LENGTH: 352
<212> TYPE: PRT
<213> ORGANISM: Zea mays

<400> SEQUENCE: 66

```
Met Ala Met Ala Ser Thr Tyr Ala Pro Gly Gly Gly Ala Arg Ala Leu
1               5                   10                  15

Ala Gln Gly Arg Cys Arg Val Arg Gly Pro Ala Gly Leu Gly Phe Leu
            20                  25                  30

Gly Pro Ser Lys Ala Ala Gly Leu Pro Arg Pro Leu Ala Leu Ala Leu
        35                  40                  45

Ala Arg Arg Met Ser Ser Pro Val Ala Val Gly Ala Arg Leu Arg Cys
    50                  55                  60

Ala Ala Ser Ser Ser Pro Ala Ala Ala Arg Pro Ala Thr Ala Pro Arg
65                  70                  75                  80

Phe Ile Gln His Lys Lys Glu Ala Phe Trp Phe Tyr Arg Phe Leu Ser
                85                  90                  95

Ile Val Tyr Asp His Val Ile Asn Pro Gly His Trp Thr Glu Asp Met
            100                 105                 110

Arg Asp Asp Ala Leu Glu Pro Ala Asp Leu Phe Ser Arg His Leu Thr
        115                 120                 125

Val Val Asp Val Gly Gly Gly Thr Gly Phe Thr Thr Leu Gly Ile Val
    130                 135                 140

Lys His Val Asn Pro Glu Asn Val Thr Leu Leu Asp Gln Ser Pro His
145                 150                 155                 160

Gln Leu Asp Lys Ala Arg Gln Lys Glu Ala Leu Lys Gly Val Thr Ile
                165                 170                 175

Met Glu Gly Asp Ala Glu Asp Leu Pro Phe Pro Thr Asp Ser Phe Asp
            180                 185                 190

Arg Tyr Ile Ser Ala Gly Ser Ile Glu Tyr Trp Pro Asp Pro Gln Arg
        195                 200                 205

Gly Ile Lys Glu Ala Tyr Arg Val Leu Arg Phe Gly Gly Leu Ala Cys
    210                 215                 220

Val Ile Gly Pro Val Tyr Pro Thr Phe Trp Leu Ser Arg Phe Phe Ala
225                 230                 235                 240

Asp Met Trp Met Leu Phe Pro Lys Glu Glu Glu Tyr Ile Glu Trp Phe
                245                 250                 255

Lys Lys Ala Gly Phe Arg Asp Val Lys Leu Lys Arg Ile Gly Pro Lys
            260                 265                 270

Trp Tyr Arg Gly Val Arg Arg His Gly Leu Ile Met Gly Cys Ser Val
        275                 280                 285

Thr Gly Val Lys Arg Glu Arg Gly Asp Ser Pro Leu Glu Leu Gly Pro
    290                 295                 300

Lys Ala Glu Asp Val Ser Lys Pro Val Asn Pro Ile Thr Phe Leu Phe
305                 310                 315                 320

Arg Phe Leu Val Gly Thr Ile Cys Ala Ala Tyr Tyr Val Leu Val Pro
                325                 330                 335

Ile Tyr Met Trp Ile Lys Asp Gln Ile Val Pro Lys Gly Met Pro Ile
            340                 345                 350
```

<210> SEQ ID NO 67
<211> LENGTH: 280
<212> TYPE: PRT
<213> ORGANISM: Arabidopsis thaliana

<400> SEQUENCE: 67

```
Arg Pro Ser Ala Gln Pro Arg Phe Ile Gln His Lys Lys Glu Ala Tyr
1               5                   10                  15

Trp Phe Tyr Arg Phe Leu Ser Ile Val Tyr Asp His Val Ile Asn Pro
            20                  25                  30
```

```
Gly His Trp Thr Glu Asp Met Arg Asp Asp Ala Leu Glu Pro Ala Asp
        35                  40                  45

Leu Ser His Pro Asp Met Arg Val Val Asp Val Gly Gly Gly Thr Gly
    50                  55                  60

Phe Thr Thr Leu Gly Ile Val Lys Thr Val Lys Ala Lys Asn Val Thr
65                  70                  75                  80

Ile Leu Asp Gln Ser Pro His Gln Leu Ala Lys Ala Lys Gln Lys Glu
                85                  90                  95

Pro Leu Lys Glu Cys Lys Ile Val Glu Gly Asp Ala Glu Asp Leu Pro
            100                 105                 110

Phe Pro Thr Asp Tyr Ala Asp Arg Tyr Val Ser Ala Gly Ser Ile Glu
        115                 120                 125

Tyr Trp Pro Asp Pro Gln Arg Gly Ile Arg Glu Ala Tyr Arg Val Leu
    130                 135                 140

Lys Ile Gly Gly Lys Ala Cys Leu Ile Gly Pro Val Tyr Pro Thr Phe
145                 150                 155                 160

Trp Leu Ser Arg Phe Phe Ser Asp Val Trp Met Leu Phe Pro Lys Glu
                165                 170                 175

Glu Glu Tyr Ile Glu Trp Phe Lys Asn Ala Gly Phe Lys Asp Val Gln
            180                 185                 190

Leu Lys Arg Ile Gly Pro Lys Trp Tyr Arg Gly Val Arg Arg His Gly
        195                 200                 205

Leu Ile Met Gly Cys Ser Val Thr Gly Val Lys Pro Ala Ser Gly Asp
    210                 215                 220

Ser Pro Leu Gln Leu Gly Pro Lys Glu Glu Asp Val Glu Lys Pro Val
225                 230                 235                 240

Asn Asn Pro Phe Ser Phe Leu Gly Arg Phe Leu Leu Gly Thr Leu Ala
                245                 250                 255

Ala Ala Trp Phe Val Leu Ile Pro Ile Tyr Met Trp Ile Lys Asp Gln
            260                 265                 270

Ile Val Pro Lys Asp Gln Pro Ile
        275                 280


<210> SEQ ID NO 68
<211> LENGTH: 288
<212> TYPE: PRT
<213> ORGANISM: Glycine max

<400> SEQUENCE: 68

Val Pro Lys Cys Ser Val Ser Ala Ser Arg Pro Ser Ser Gln Pro Arg
1               5                   10                  15

Phe Ile Gln His Lys Lys Glu Ala Phe Trp Phe Tyr Arg Phe Leu Ser
            20                  25                  30

Ile Val Tyr Asp His Val Ile Asn Pro Gly His Trp Thr Glu Asp Met
        35                  40                  45

Arg Asp Asp Ala Leu Glu Pro Ala Asp Leu Asn Asp Arg Asn Met Ile
    50                  55                  60

Val Val Asp Val Gly Gly Gly Thr Gly Phe Thr Thr Leu Gly Ile Val
65                  70                  75                  80

Lys His Val Asp Ala Lys Asn Val Thr Ile Leu Asp Gln Ser Pro His
                85                  90                  95

Gln Leu Ala Lys Ala Lys Gln Lys Glu Pro Leu Lys Glu Cys Lys Ile
            100                 105                 110

Ile Glu Gly Asp Ala Glu Asp Leu Pro Phe Arg Thr Asp Tyr Ala Asp
        115                 120                 125
```

```
Arg Tyr Val Ser Ala Gly Ser Ile Glu Tyr Trp Pro Asp Pro Gln Arg
    130                 135                 140

Gly Ile Lys Glu Ala Tyr Arg Val Leu Lys Leu Gly Gly Lys Ala Cys
145                 150                 155                 160

Leu Ile Gly Pro Val Tyr Pro Thr Phe Trp Leu Ser Arg Phe Phe Ala
                165                 170                 175

Asp Val Trp Met Leu Phe Pro Lys Glu Glu Glu Tyr Ile Glu Trp Phe
            180                 185                 190

Gln Lys Ala Gly Phe Lys Asp Val Gln Leu Lys Arg Ile Gly Pro Lys
        195                 200                 205

Trp Tyr Arg Gly Val Arg Arg His Gly Leu Ile Met Gly Cys Ser Val
    210                 215                 220

Thr Gly Val Lys Pro Ala Ser Gly Asp Ser Pro Leu Gln Leu Gly Pro
225                 230                 235                 240

Lys Glu Glu Asp Val Glu Lys Pro Val Asn Pro Phe Val Phe Ala Leu
                245                 250                 255

Arg Phe Val Leu Gly Ala Leu Ala Ala Thr Trp Phe Val Leu Val Pro
            260                 265                 270

Ile Tyr Met Trp Leu Lys Asp Gln Val Val Pro Lys Gly Gln Pro Ile
        275                 280                 285


<210> SEQ ID NO 69
<211> LENGTH: 292
<212> TYPE: PRT
<213> ORGANISM: Zea mays

<400> SEQUENCE: 69

Arg Leu Arg Cys Ala Ala Ser Ser Ser Pro Ala Ala Ala Arg Pro Ala
1               5                   10                  15

Thr Ala Pro Arg Phe Ile Gln His Lys Lys Glu Ala Phe Trp Phe Tyr
            20                  25                  30

Arg Phe Leu Ser Ile Val Tyr Asp His Val Ile Asn Pro Gly His Trp
        35                  40                  45

Thr Glu Asp Met Arg Asp Asp Ala Leu Glu Pro Ala Asp Leu Phe Ser
    50                  55                  60

Arg His Leu Thr Val Val Asp Val Gly Gly Gly Thr Gly Phe Thr Thr
65                  70                  75                  80

Leu Gly Ile Val Lys His Val Asn Pro Glu Asn Val Thr Leu Leu Asp
                85                  90                  95

Gln Ser Pro His Gln Leu Asp Lys Ala Arg Gln Lys Glu Ala Leu Lys
            100                 105                 110

Gly Val Thr Ile Met Glu Gly Asp Ala Glu Asp Leu Pro Phe Pro Thr
        115                 120                 125

Asp Ser Phe Asp Arg Tyr Ile Ser Ala Gly Ser Ile Glu Tyr Trp Pro
    130                 135                 140

Asp Pro Gln Arg Gly Ile Lys Glu Ala Tyr Arg Val Leu Arg Phe Gly
145                 150                 155                 160

Gly Leu Ala Cys Val Ile Gly Pro Val Tyr Pro Thr Phe Trp Leu Ser
                165                 170                 175

Arg Phe Phe Ala Asp Met Trp Met Leu Phe Pro Lys Glu Glu Glu Tyr
            180                 185                 190

Ile Glu Trp Phe Lys Lys Ala Gly Phe Arg Asp Val Lys Leu Lys Arg
        195                 200                 205

Ile Gly Pro Lys Trp Tyr Arg Gly Val Arg Arg His Gly Leu Ile Met
    210                 215                 220
```

```
Gly Cys Ser Val Thr Gly Val Lys Arg Glu Arg Gly Asp Ser Pro Leu
225                 230                 235                 240

Glu Leu Gly Pro Lys Ala Glu Asp Val Ser Lys Pro Val Asn Pro Ile
                245                 250                 255

Thr Phe Leu Phe Arg Phe Leu Val Gly Thr Ile Cys Ala Ala Tyr Tyr
            260                 265                 270

Val Leu Val Pro Ile Tyr Met Trp Ile Lys Asp Gln Ile Val Pro Lys
        275                 280                 285

Gly Met Pro Ile
    290


<210> SEQ ID NO 70
<211> LENGTH: 288
<212> TYPE: PRT
<213> ORGANISM: Momordica charantia

<400> SEQUENCE: 70

Ala Pro Lys Cys Ser Leu Ser Ala Ser Arg Pro Ala Ser Gln Pro Arg
1               5                   10                  15

Phe Ile Gln His Lys Lys Glu Ala Phe Trp Phe Tyr Arg Phe Leu Ser
            20                  25                  30

Ile Val Tyr Asp His Ile Ile Asn Pro Gly His Trp Thr Glu Asp Met
        35                  40                  45

Arg Asp Glu Ala Leu Glu Pro Ala Asp Leu Ser Asp Arg Asn Met Ile
    50                  55                  60

Val Val Asp Val Gly Gly Gly Thr Gly Phe Thr Thr Leu Gly Ile Val
65                  70                  75                  80

Lys His Val Asp Ala Lys Asn Val Thr Ile Leu Asp Gln Ser Pro His
                85                  90                  95

Gln Leu Ala Lys Ala Lys Gln Lys Glu Pro Leu Lys Asp Cys Lys Ile
            100                 105                 110

Ile Glu Gly Asp Ala Glu Asp Leu Pro Phe Arg Thr Asp Tyr Ala Asp
        115                 120                 125

Arg Tyr Val Ser Ala Gly Ser Ile Glu Tyr Trp Pro Asp Pro Gln Arg
    130                 135                 140

Gly Ile Thr Glu Ala Tyr Arg Val Leu Lys Leu Gly Gly Lys Ala Cys
145                 150                 155                 160

Leu Ile Gly Pro Val Tyr Pro Thr Phe Trp Leu Ser Arg Phe Phe Ala
                165                 170                 175

Asp Val Trp Met Leu Phe Pro Lys Glu Glu Glu Tyr Ile Glu Trp Phe
            180                 185                 190

Lys Asn Ala Gly Phe Lys Asp Val Gln Leu Lys Arg Ile Gly Pro Lys
        195                 200                 205

Trp Tyr Arg Gly Val Arg Arg His Gly Leu Ile Met Gly Cys Ser Val
    210                 215                 220

Thr Gly Val Lys Pro Tyr Ser Gly Glu Ser Pro Leu Gln Leu Gly Pro
225                 230                 235                 240

Lys Glu Glu Asp Val Ser Lys Pro Val Asn Pro Phe Val Phe Leu Ala
                245                 250                 255

Arg Phe Leu Leu Gly Ala Met Ala Ala Thr Tyr Tyr Val Leu Val Pro
            260                 265                 270

Ile Tyr Met Trp Met Lys Asp Gln Ile Val Pro Glu Gly Gln Pro Ile
        275                 280                 285
```